US010941210B2

(12) United States Patent
Sleeman et al.

(10) Patent No.: US 10,941,210 B2
(45) Date of Patent: Mar. 9, 2021

(54) ANTI-PCSK9 ANTIBODIES

(71) Applicant: REGENERON PHARMACEUTICALS, INC., Tarrytown, NY (US)

(72) Inventors: Mark W. Sleeman, Victoria (AU); Joel H. Martin, Putnam Valley, NY (US); Tammy T. Huang, Cross River, NY (US); Douglas Macdonald, New York, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 49 days.

(21) Appl. No.: 15/996,773

(22) Filed: Jun. 4, 2018

(65) Prior Publication Data

US 2019/0135941 A1 May 9, 2019

Related U.S. Application Data

(60) Continuation of application No. 15/377,364, filed on Dec. 13, 2016, now Pat. No. 10,023,654, which is a continuation of application No. 14/737,488, filed on Jun. 12, 2015, now Pat. No. 9,550,837, which is a continuation of application No. 13/690,585, filed on Nov. 30, 2012, now abandoned, which is a continuation of application No. 12/949,846, filed on Nov. 19, 2010, now Pat. No. 8,501,184, which is a division of application No. 12/637,942, filed on Dec. 15, 2009, now Pat. No. 8,062,640.

(60) Provisional application No. 61/122,482, filed on Dec. 15, 2008, provisional application No. 61/210,566, filed on Mar. 18, 2009, provisional application No. 61/168,753, filed on Apr. 13, 2009, provisional application No. 61/218,136, filed on Jun. 18, 2009, provisional application No. 61/249,135, filed on Oct. 6, 2009, provisional application No. 61/261,776, filed on Nov. 17, 2009.

(51) Int. Cl.

| | |
|---|---|
| ***C07K 16/00*** | (2006.01) |
| ***C07H 21/04*** | (2006.01) |
| ***C12P 21/06*** | (2006.01) |
| ***C12N 15/87*** | (2006.01) |
| ***C12N 5/02*** | (2006.01) |
| ***C12N 5/20*** | (2006.01) |
| ***C12N 1/20*** | (2006.01) |
| ***C12N 15/00*** | (2006.01) |
| ***C07K 16/40*** | (2006.01) |
| ***A61K 39/08*** | (2006.01) |
| ***G01N 33/569*** | (2006.01) |
| ***C07K 16/12*** | (2006.01) |
| *A61K 39/00* | (2006.01) |

(52) U.S. Cl.

CPC .............. *C07K 16/40* (2013.01); *A61K 39/08* (2013.01); *C07K 16/1282* (2013.01); *C12Y 304/21061* (2013.01); *G01N 33/56911* (2013.01); *A61K 2039/505* (2013.01); *A61K 2039/507* (2013.01); *C07K 2317/21* (2013.01); *C07K 2317/33* (2013.01); *C07K 2317/34* (2013.01); *C07K 2317/56* (2013.01); *C07K 2317/565* (2013.01); *C07K 2317/76* (2013.01); *C07K 2317/92* (2013.01); *G01N 2333/33* (2013.01); *Y10S 424/809* (2013.01)

(58) Field of Classification Search

None

See application file for complete search history.

(56) References Cited

U.S. PATENT DOCUMENTS

| | | | |
|---|---|---|---|
| 5,260,440 | A | 11/1993 | Hirai |
| 5,273,995 | A | 12/1993 | Roth |
| 5,399,670 | A | 3/1995 | Bhattacharya |
| 5,851,999 | A | 12/1998 | Ulrich |
| 5,939,598 | A | 8/1999 | Kucherlapati |
| 6,011,003 | A | 1/2000 | Charmock-Jones |
| 6,171,586 | B1 | 1/2001 | Lam |
| 6,267,958 | B1 | 7/2001 | Andya |
| 6,270,993 | B1 | 8/2001 | Shibuya |
| 6,596,541 | B2 | 7/2003 | Murphy |

(Continued)

FOREIGN PATENT DOCUMENTS

| | | |
|---|---|---|
| CN | 101489565 | 7/2009 |
| EP | 0409281 | 1/1991 |

(Continued)

OTHER PUBLICATIONS

Arai, Hidenori, "Dyslipidemia of diabetic patients" from new "Guidelines for prevention of arteriosclerostic diseases 2012 edition", Seasonal Post, (Diabetes network editorial department (SOUSINSYA)), Sep. 1, 2012, vol. 4, No. 3, pp. 1-3. (with English Abstract translation).

(Continued)

*Primary Examiner* — Maher M Haddad

(74) *Attorney, Agent, or Firm* — Lathrop GPM LLP; James H. Velema, Esq.

(57) ABSTRACT

An human antibody or antigen-binding fragment of a human antibody that specifically binds and inhibits human proprotein convertase subtilisin/kexin type 9 (hPCSK9) characterized by the ability to reduce serum LDL cholesterol by 40-80% over a 24, 60 or 90 day period relative to predose levels, with little or no reduction in serum HDL cholesterol and/or with little or no measurable effect on liver function, as determined by ALT and AST measurements.

8 Claims, 14 Drawing Sheets

Specification includes a Sequence Listing.

(56) References Cited

U.S. PATENT DOCUMENTS

| | | | | |
|---|---|---|---|---|
| 6,629,949 | B1 | 10/2003 | Douglas | |
| 6,659,982 | B2 | 12/2003 | Douglas | |
| 6,875,432 | B2 | 4/2005 | Liu | |
| 7,001,892 | B1 | 2/2006 | Chmielweski | |
| 7,029,895 | B2 | 4/2006 | Glucksmann | |
| 7,060,268 | B2 | 6/2006 | Andya | |
| 7,129,338 | B1 | 10/2006 | Ota | |
| 7,300,754 | B2 | 11/2007 | Fadel | |
| 7,482,147 | B2 | 1/2009 | Glucksmann | |
| 7,572,618 | B2 | 8/2009 | Mintier | |
| 7,608,693 | B2 | 10/2009 | Martin | |
| 7,754,208 | B2 | 7/2010 | Ledbetter | |
| 8,030,457 | B2 | 10/2011 | Jackson | |
| 8,062,640 | B2 * | 11/2011 | Sleeman | A61K 39/08 424/158.1 |
| 8,080,243 | B2 | 12/2011 | Liang | |
| 8,092,803 | B2 | 1/2012 | Furfine | |
| 8,168,762 | B2 | 5/2012 | Jackson | |
| 8,188,233 | B2 | 5/2012 | Condra | |
| 8,188,234 | B2 | 5/2012 | Condra | |
| 8,357,371 | B2 | 1/2013 | Sleeman | |
| 8,501,184 | B2 * | 8/2013 | Sleeman | A61K 39/08 424/158.1 |
| 8,748,115 | B2 | 6/2014 | Ni et al. | |
| 8,795,669 | B2 | 8/2014 | Walsh | |
| 8,829,165 | B2 | 9/2014 | Jackson | |
| 8,883,157 | B1 | 11/2014 | Clube | |
| 8,945,560 | B1 | 2/2015 | Clube | |
| 9,034,332 | B1 | 5/2015 | Clube | |
| 9,127,068 | B2 | 9/2015 | Okamoto | |
| 9,193,801 | B2 | 11/2015 | Walsh | |
| 9,358,287 | B2 | 6/2016 | Harp | |
| 9,540,449 | B2 | 1/2017 | Yancopoulos | |
| 9,550,837 | B2 * | 1/2017 | Sleeman | C07K 16/1282 |
| 9,561,155 | B2 | 2/2017 | Hanotin | |
| 9,724,411 | B2 | 8/2017 | Sleeman | |
| 10,023,654 | B2 * | 7/2018 | Sleeman | A61K 39/08 |
| 2003/0092606 | A1 | 5/2003 | L'Italien | |
| 2003/0113316 | A1 | 6/2003 | Kaisheva | |
| 2003/0118592 | A1 | 6/2003 | Ledbetter | |
| 2003/0133939 | A1 | 7/2003 | Ledbetter | |
| 2004/0101920 | A1 | 5/2004 | Radziejewski | |
| 2004/0197324 | A1 | 10/2004 | Liu | |
| 2005/0281831 | A1 | 12/2005 | Davis-Smyth | |
| 2006/0147945 | A1 | 7/2006 | Edmonds | |
| 2007/0082345 | A1 | 4/2007 | Ota | |
| 2007/0224663 | A1 | 9/2007 | Rosen | |
| 2008/0008697 | A1 | 1/2008 | Mintier | |
| 2009/0142352 | A1 | 6/2009 | Jackson | |
| 2009/0232795 | A1 | 9/2009 | Condra | |
| 2009/0246192 | A1 | 10/2009 | Condra | |
| 2009/0269350 | A1 | 10/2009 | Glucksmann | |
| 2009/0318536 | A1 | 12/2009 | Freier | |
| 2009/0326202 | A1 | 12/2009 | Jackson | |
| 2010/0040610 | A1 | 2/2010 | Sitlani | |
| 2010/0040611 | A1 | 2/2010 | Sparrow | |
| 2010/0041102 | A1 | 2/2010 | Sitlani | |
| 2010/0068199 | A1 | 3/2010 | Liang | |
| 2010/0136028 | A1 | 6/2010 | Sparrow | |
| 2010/0150937 | A1 | 6/2010 | Sparrow | |
| 2010/0166768 | A1 | 7/2010 | Sleeman | |
| 2010/0233177 | A1 | 9/2010 | Yowe | |
| 2011/0027287 | A1 | 2/2011 | Jackson | |
| 2011/0033465 | A1 | 2/2011 | Hedrick | |
| 2011/0065902 | A1 | 3/2011 | Sleeman | |
| 2011/0098450 | A1 | 4/2011 | Igawa | |
| 2011/0111406 | A1 | 5/2011 | Igawa | |
| 2011/0142849 | A1 | 6/2011 | Rue | |
| 2011/0171241 | A1 | 7/2011 | Dix | |
| 2011/0229489 | A1 | 9/2011 | Pons | |
| 2011/0256148 | A1 | 10/2011 | Sleeman | |
| 2012/0014951 | A1 | 1/2012 | Liang | |
| 2012/0015435 | A1 | 1/2012 | Liange | |
| 2012/0020975 | A1 | 1/2012 | Jackson | |
| 2012/0027765 | A1 | 2/2012 | Jackson | |
| 2012/0076799 | A1 | 3/2012 | Sparrow | |
| 2012/0077964 | A1 | 3/2012 | Sparrow | |
| 2012/0082679 | A1 | 4/2012 | Sparrow | |
| 2012/0082680 | A1 | 4/2012 | Sitlani | |
| 2012/0093818 | A1 | 4/2012 | Jackson | |
| 2012/0097565 | A1 | 4/2012 | Dix | |
| 2012/0195910 | A1 | 8/2012 | Wu | |
| 2012/0213794 | A1 | 8/2012 | Luo | |
| 2012/0213797 | A1 | 8/2012 | Jackson | |
| 2012/0219558 | A1 | 8/2012 | Ni | |
| 2012/0231005 | A1 | 9/2012 | Luo | |
| 2012/0251544 | A1 | 10/2012 | Jackson | |
| 2013/0011866 | A1 | 1/2013 | Igawa | |
| 2013/0064825 | A1 | 3/2013 | Chan | |
| 2013/0064834 | A1 | 3/2013 | Sleeman | |
| 2013/0085266 | A1 | 4/2013 | Sleeman | |
| 2013/0243784 | A1 | 9/2013 | Swergold | |
| 2014/0004122 | A1 | 1/2014 | Chan | |
| 2014/0099312 | A1 | 4/2014 | Sleeman | |
| 2014/0154262 | A1 | 6/2014 | Hanotin | |
| 2014/0161821 | A1 | 6/2014 | Udata | |
| 2014/0356370 | A1 | 12/2014 | Swergold | |
| 2014/0356371 | A1 | 12/2014 | Swergold | |
| 2015/0140002 | A1 | 5/2015 | Baccara-Dinet | |
| 2015/0152191 | A1 | 6/2015 | Baccara-Dinet | |
| 2015/0231236 | A1 | 8/2015 | Pordy | |
| 2015/0283236 | A1 | 10/2015 | Baccara-Dinet | |
| 2015/0284473 | A1 | 10/2015 | Bessac | |
| 2016/0032015 | A1 | 2/2016 | Walsh | |
| 2016/0152734 | A1 | 2/2016 | Udata | |
| 2017/0049886 | A1 | 2/2017 | Pordy | |
| 2017/0096496 | A1 | 4/2017 | Sleeman | |
| 2017/0296657 | A1 | 10/2017 | Sleeman | |
| 2018/0044436 | A1 | 2/2018 | Walsh | |
| 2018/0296675 | A1 | 10/2018 | Pordy | |
| 2018/0333490 | A1 | 11/2018 | Swergold | |
| 2019/0284301 | A1 | 9/2019 | Walsh | |
| 2019/0330371 | A1 | 10/2019 | Swergold | |

FOREIGN PATENT DOCUMENTS

| | | |
|---|---|---|
| EP | 0521471 | 1/1993 |
| EP | 1067182 | 1/2001 |
| EP | 1514933 | 3/2005 |
| EP | 1317537 | 12/2006 |
| EP | 1618212 | 11/2007 |
| EP | 2703008 | 8/2012 |
| EP | 2703009 | 8/2012 |
| EP | 2706070 | 3/2014 |
| WO | 1993/000807 | 1/1993 |
| WO | 1997/035620 | 10/1997 |
| WO | 1998/22136 | 5/1998 |
| WO | 1999/38495 | 8/1999 |
| WO | 2001/057081 | 8/2001 |
| WO | 2004/055164 | 7/2004 |
| WO | 2004/097047 | 11/2004 |
| WO | 2005/103081 | 11/2005 |
| WO | 2007/143315 | 12/2007 |
| WO | 2007/146511 | 12/2007 |
| WO | 2007/149334 | 12/2007 |
| WO | 2008/057457 | 5/2008 |
| WO | 2008/057458 | 5/2008 |
| WO | 2008/057459 | 5/2008 |
| WO | 2008/063382 | 5/2008 |
| WO | 2008/066776 | 6/2008 |
| WO | 2008/125623 | 10/2008 |
| WO | 2008/133647 | 11/2008 |
| WO | 2008/138536 | 1/2009 |
| WO | 2009/026558 | 2/2009 |
| WO | 2009/042765 | 4/2009 |
| WO | 2009/055783 | 4/2009 |
| WO | 2009/100297 | 8/2009 |
| WO | 2009/100318 | 8/2009 |
| WO | 2010/029513 | 3/2010 |
| WO | 2010/032220 | 3/2010 |
| WO | 2010/077854 | 7/2010 |
| WO | 2010/102241 | 9/2010 |
| WO | 2010/148337 | 12/2010 |
| WO | 2011/028938 | 3/2011 |

(56) References Cited

FOREIGN PATENT DOCUMENTS

| | | |
|---|---|---|
| WO | 2011/039578 | 4/2011 |
| WO | 2011/053759 | 5/2011 |
| WO | 2011/061712 | 5/2011 |
| WO | 2011/072263 | 6/2011 |
| WO | 2011/111007 | 9/2011 |
| WO | 2012/054438 | 4/2012 |
| WO | 2012/064792 | 5/2012 |
| WO | 2012/101251 | 8/2012 |
| WO | 2012/101252 | 8/2012 |
| WO | 2012/101253 | 8/2012 |
| WO | 2012/109530 | 8/2012 |
| WO | 2012/146776 | 11/2012 |
| WO | 2012/154999 | 11/2012 |
| WO | 2013/039958 | 3/2013 |
| WO | 2013/039969 | 3/2013 |
| WO | 2013/158984 | 10/2013 |
| WO | 2013/166448 | 11/2013 |
| WO | 2013/169886 | 11/2013 |
| WO | 2013/177536 | 11/2013 |
| WO | 2014/194111 | 12/2014 |
| WO | 2014/197752 | 12/2014 |
| WO | 2011/117401 | 3/2015 |
| WO | 2015/054619 | 4/2015 |
| WO | 2015/073494 | 5/2015 |
| WO | 2015/123423 | 8/2015 |
| WO | 2015/140079 | 9/2015 |
| WO | 2015/142668 | 9/2015 |
| WO | 2016/011256 | 1/2016 |
| WO | 2016/011260 | 1/2016 |

OTHER PUBLICATIONS

Bambauer, Rolf et al., "LDL—Apheresis: Technical and Clinical Aspects", Review Article, The Scientific World Journal, vol. 2012, Article ID 314283, 19 pages.

Abifadel et al. (2003) Nature Genetics 34(2):154-156 "Mutations in PCSK9 cause autosomal dominant hypercholesterolemia."

Abifadel et al. (2009) Human Mutation 30(4):520-529 "Mutations and polymorphisms in the proprotein convertase subtilisin kexin 9 (PCSK9) gene in cholesterol metabolism and disease."

Abifadel et al. (2012) Atherosclerosis 223(2):394-400 "Identification and characterization of new gain-of-function mutations in the PCSK9 gene responsible for autosomal dominant hypercholesterolemia."

Alborn et al. (2007) Clinical Chemistry 53(10):1814-1819 "Serum proprotein convertase subtilisin Kexin type 9 is correlated directly with serum LDL cholesterol."

Almagro et al. (2008) Frontiers in Bioscience 13:1619-1633 "Humanization of antibodies."

Al-Mashhadi et al. (2013) Science Translation Medicine, American Association for the Advancement of Science 5(166):44-53 "Atherosclerosis: Familial hypercholesterolemia and atherosclerosis in clones minipigs created by DNA transposition of a human PCSK9 gain-of-function mutant."

Altschul et al. (1990) Journal of Molecular Biology 215(3):403-410 "Basic local alignment search tool."

Altschul et al. (1997) Nucleic Acids Research 25(17):3389-3402 "Gapped BLAST and PSI-BLAST: a new generation of protein database search programs."

Amgen (2010) Ascending Multiple Dose Study to Evaluate the Safety, Tolerability, Pharmacokinetics and Pharmacodynamics of AMG 145 in Subjects With Hyperlipidemia on Stable Doses of a Statin; Available website: www.clinicaltrials.gov/ct2/show/nct01133522?term=amg+145&rank=2 ; Last update: Mar. 16, 2012; Accessed on: Aug. 6, 2014.

Angal et al. (1993) Molecular Immunology 30(1):105-108 "A single amino acid substitution abolishes the heterogeneity of chimeric mouse/human (IgG4) antibody."

Annex to Form PCT/ISA/206—Communication Relating to the Results of the Partial International Search for PCT/US2009/068013, dated Mar. 10, 2010.

Anonymous: A Randomized, Double-Blind, Placebo-Controlled, Parallel Group Study to Evaluate the Effect of Alirocumab (SAR236553/REGN727) on the Occurrence of Cardiovascular Events in Patients Who Have Recently Experienced an Acute Coronary Syndrome. Archive from ClinicalTrials.gov for NCT01663402 on Mar. 11, 2014 (3 pages).

Anonymous: Long-term Safety and Tolerability of Alirocumab SAR236553 (REGN727) in High Cardiovascular Risk Patients With Hypercholesterolemia Not Adequately Controlled With Their Lipid Modifying Therapy: A Randomized, Double-Blind, Placebo-Controlled Study. Archive from ClinicalTrials.gov for NCT01507831 on Jun. 27, 2013.

Anthem.com (Sep. 21, 2015) Proprotein Convertase Subtilisin Kexin 9 (PCSK9) Inhibitors; Available Website: www.anthem.com/ca/medicalpolicies/policies/mp_pw_c182635.htm; Last Update: Aug. 4, 2016; Accessed on: Apr. 27, 2016.

Ason (2011) Journal of Lipid Research 52:679-687 "Improved Efficacy for Ezetimibe and Rosuvastatin by Attenuating the Induction of PCSK9."

Ason, Brandon, et al., "Improved efficacy for ezetimibe and rosuvastatin by attenuating the induction of PCSK9," Journal of Lipid Research, vol. 52, 2011, pp. 679-687.

Attie and Seidah (2005) Cell Metabolism 5:290-292 "Dual regulation of the LDL receptor—Some clarity and new questions."

Barbie and Lefranc (1998) Exp. Clin. Immunogenet. 15:171-183 "The Human Immunoglobulin Kappa Variable (IGKV) Genes and Joining (IGKJ) Segments."

Bays et al. (2014) Circulation 130:2105-2126 "Efficacy and safety of combining alirocumab with atorvastatin or rosuvastatin versus statin intensification or adding ezetimibe in high cardiovascular risk patients: ODYSSEY OPTIONS I and II."

Bays et al. (2014) Circulation 130:A16194 "PCSK9 Inhibitor Alirocumab as Add-on to Atorvastatin versus Other Lipid Treatment Strategies in Patients at High CVD Risk: ODYSSEY OPTIONS I."

Bays et al. (2015) J Clin Lipidol. 9(3):471-472 Abstract 183 "Alirocumab treatment effect on non-HDL-C: pooled analyses of ten Phase 3 trials in the ODYSSEY program."

Bee et al. (2009) Journal of Pharmaceutical Sciences 98(9): 3290-3301 "Precipitation of a monoclonal antibody by soluble tungsten."

Benjannet et al. (2006) J. Biological Chemistry 281(41):30561-30572 "The Proprotein Convertase (PC) PCSK9 Is Inactivated by Furin and/or PC5/6A."

Berthold and Berthold (2013) Atherosclerosis Supplements 14:1-5 "Hyperlipoproteinemia(a): Clinical significance and treatment options."

Bird et al. (1988) Science 242(4877):423-426 "Single-chain antigen-binding proteins."

Blom et al. (2014) New England Journal of Medicine 370(19):1809-1819 "A 52-Week Placebo-Controlled Trial of Evolocumab in Hyperlipidemia."

Breen et al. (2001) Pharmaceutical Research 18(9): 1345-1353 "Effect of moisture on the stability of a lyophilized humanized monoclonal antibody formulation."

Brouwers, M.C.G.J., et al. "Plasma proprotein convertase subtilisin kexin type 9 levels are related to markers of cholesterol synthesis in familial combined hyperlipidemia," SciVerse ScienceDirect Nutrition, Metabolism & Cardiovascular Diseases (2013) 23, 1115-1121.

Cannon et al. (2015) Eur Heart J 36(19):1186-1194 "The ODYSSEY COMBO II Investigators. Efficacy and safety of alirocumab in high cardiovascular risk patients with inadequately controlled hypercholesterolaemia on maximally tolerated doses of statins: the ODYSSEY COMBO II randomized controlled trial."

Cannon et al. (Aug. 31, 2014) Presented at ESC Congress "Efficacy and safety of alirocumab in high cardiovascular risk patients with inadequately controlled hypercholesterolaemia on maximally tolerated daily statin: results from the ODYSSEY COMBO II study" abstract not published.

Cariou et al. (May 23-26, 2015) International Symposium on Atherosclerosis. Abstract No. 1039 "Patient and physician perspectives on administration of the PCSK9 monoclonal antibody alirocumab, an injectable medication to lower LDL-C levels."

Carpenter (1997) Pharm. Res. 14(8):969-975 Rational Design of Stable Lyophilized Protein Formulations: Some Practical Advice.

(56) References Cited

OTHER PUBLICATIONS

Catapano and Papadopoulos (2013) Atherosclerosis 228(1):18-28 "The safety of therapeutic monoclonal antibodies: implications for cardiovascular disease and targeting the PCSK9 pathway."
Chan et al. (2009) PNAS 106(24):9820-9825 "A proprotein convertase subtilisin/kexin type 9 neutralizing antibody reduces serum cholesterol in mice and nonhuman primates."
Chaparro-Riggers et al. (2012) J. Biological Chemistry 287(14):11090-11097 "Increasing serum half-life and extending cholesterol lowering in vivo by engineering antibody with pH-sensitive binding to PCSK9."
Chaudhary et al., "PCSK9 Inhibitors: A New Era of Lipid Lowering Therapy", World Journal of Cardiology, Feb. 26, 2017, 9(2):76-91.
Chinese Office Action from CN2012-80015477.6 dated Dec. 2, 2014 with English summary.
Chinese Office Action from CN2012-80015571.1 dated Sep. 3, 2014 with English summary.
clinicaltrials.gov (Dec. 23, 2010) "View of NCT01266876," US National Institutes of Health. [accessible on the internet at: https://clinicaltrials.gov/archive/NCT01266876/2010_12_23].
clinicaltrials.gov (Feb. 1, 2011) "View of NCT01288443," US National Institutes of Health. [accessible on the internet at: https://clinicaltrials.gov/archive/NCT01288443/2011_02_01).
clinicaltrials.gov "View of NCT01288469," US National Institutes of Health. [accessible on the internet at: https://clinicaltrials.gov/ct2/show/NCT01288469?term=NCT01288469&rank=1].
clinicaltrials.gov "View of NCT01507831," US National Institutes of Health. [accessible on the internet at: https://clinicaltrials.gov/ct2/show/NCT01507831?term=NCT01507831&rank=1].
clinicaltrials.gov "View of NCT01644175," US National Institutes of Health. [accessible on the internet at: https://clinicaltrials.gov/ct2/show/NCT01644175?term=NCT01644175&rank=1].
clinicaltrials.gov "View of NCT01644188," US National Institutes of Health. [accessible on the internet at: https://clinicaltrials.gov/ct2/show/NCT01644188?term=NCT01644188&rank=1].
clinicaltrials.gov "View of NCT01644474," US National Institutes of Health. [accessible on the internet at: https://clinicaltrials.gov/ct2/show/NCT01644474?term=NCT01644474&rank=1].
clinicaltrials.gov "View of NCT01161082," US National Institutes of Health. [accessible on the internet at: https://clinicaltrials.gov/ct2/show/NCT01161082?term=NCT01161082&rank=1].
clinicaltrials.gov "View of NCT01617655," US National Institutes of Health. [accessible on the internet at: https://clinicaltrials.gov/ct2/show/NCT01617655?term=NCT01617655&rank=1].
clinicaltrials.gov "View of NCT01709500," US National Institutes of Health. [accessible on the internet at: https://clinicaltrials.gov/ct2/show/NCT01709500?term=NCT01709500&rank=1].
clinicaltrials.gov "View of NCT01663402," US National Institutes of Health. [accessible on the internet at: https://clinicaltrials.gov/ct2/show/NCT01663402].
Colhoun et al. (2014) BMC Cardiovascular Disorders, Biomed Central 14(1):121 "Efficacy and safety of alirocumab, a fully human PCSK0 monoclonal antibody, in high cardiovascular risk patients with poorly controlled hypercholesterolemia on maximally tolerated doses of statins: rationale and design of the ODYSSEY COMBO I and II trials."
Costet (2012) Drugs of the Future 37(5):331-341 "PCSK9 inhibitors as LDL cholesterol-lowering agents: Rationale, concerns and preliminary outcomes."
Daughterty et al. (2006) Advanced Drug Delivery Reviews 58:686-706 "Formulation and delivery issues for monoclonial antibody therapeutics."
Davidson et al. (2011) Journal of Clinical Lipidology 5:338-367 "Clinical utility of inflammatory markers and advanced lipoprotein testing: Advice from an expert panel of lipid specialists."
Defesche et al. (Jun. 2-5, 2013) Abstract of a presentation presented at the 81st European Atherosclerosis Society (EAS) Congress, Lyon, France "Natural history of autosomal dominant hypercholesterolemia caused by gain-of-function mutations in proprotein convertase subtilisin/kexin type 9 (PCSK9) (funded by Regeneron/Sanofi)."
Defesche et al. (Jun. 2-5, 2013) Presentation presented at the 81st European Atherosclerosis Society (EAS) Congress, Lyon, France "Natural history of autosomal dominant hypercholesterolemia caused by gain-of-function mutations in proprotein convertase subtilisin/kexin type 9 (PCSK9) (funded by Regeneron/Sanofi)."
Dube et al. (2012) Current Opinion Lipidol 23(2):133-140 "Lipoprotein(a): more interesting than ever after 50 years."
Duff et al. (2009) Biochem Journal, the Biochemical Society 419(3):577-584 "Antibody-mediated disruption of the interaction between PCSK9 and the low-density lipoprotein receptor."
Dufour et al. (2012) Circulation 126 Abstract A16127 "Effect of REGN727/SAR236553 PCSK9 fully human monoclonal antibody in patients with elevated triglycerides/low high-density lipoprotein cholesterol: data from three phase 2 studies."
Dufour et al. (2014) Can J Cardiol 30(10 suppl):S338 Abstract 546 "One year open-label treatment with alirocumab 150 mg every two weeks in heterozygous familial hypercholesterolemic patients."
European Office Action Article 94(3) EP App No. 12701015.5 dated May 30, 2014.
European Office Action Article 94(3) EP App No. 12701015.5 dated Apr. 24, 2015.
European Office Action Article 94(3) EP App No. 12701742.4 dated Jun. 1, 2015.
European Office Action Article 94(3) EP App No. 12701742.4 dated May 28, 2014.
European Opposition from EP Application No. 09793408.7 dated Oct. 11, 2017.
Fallon et al. (2000) J. Biological Chemistry 275(10):6790-6797 "Increased endosomal sorting of ligand to recycling enhances potency of an intereukin-2 analog."
Farnier (2011) American Journal of Cardiovascular Drugs 11(3):145-152 "The role of proprotein convertase subtilisin/kexin type 9 in hyperlipidemia: Focus on therapeutic implications."
Farnier et al (2014) Atherosclerosis 235(2):e34-e35 [Abstract MP02E] "Relationship between alirocumab, PCSK9 and LDL-C levels: results from the ODYSSEY MONO Phase 3 trial of alirocumab 75 mg every 2 weeks."
Fasano (2009) Atherosclerosis 203:166-171 "Degradation of LDLR Protein Mediated by Gain of Function PCSK9 Mutants in Normal and ARH Cells."
Fasano et al. (2008) NMCD Nutrition Metabolism and Cardiovascular Diseases 18(1):S46 "45-Activity of Gain-of-Function PCSK9 Mutants on LDLR Correlates with Total-Cholesterol Values in ADH patients."
Foody et al. (2013) Circulation 128:A17254 "Attainment of low-density lipoprotein cholesterol goals in patients at high cardiovascular risk: results from a managed care population study."
Foote and Winter (1992) J. Mol. Biol. 224:487-499 "Antibody Framework Residues Affecting the Conformation of the Hypervariable Loops."
Gaudet et al. (2012) Circulation 126:Abstract A14725 "Effect of SAR236553/REGN727 fully human monoclonal anti-proprotein convertase subtilisin/kexin type 9 antibody on plasma lipoprotein(a) concentrations: pooled analysis from three phase 2 studies (NCT:01266876; 01288469; 01288443)."
Gaudet et al. (2013) J Clin Lipidol 7(3):283-284 Abstract 178 "Alirocumab, a fully human monoclonal antibody to PCSK9, reduces high plasma Lp(a) concentration: pooled analysis of 352 patients from phase 2."
Gaudet et al. (2014) Am J Cardiol 114(5):711-715 "Effect of Alirocumab, a Monoclonal Proprotein Convertase Subtilisin/Kexin 9 Antibody, on Lipoprotein(a) Concentrations (a Pooled Analysis of 150 mg Every 2 Weeks Dosing from Phase 2 Trials)."
Gaudet et al. (2017) Am Journal Cardiology 119:40-46 "Effect of Alirocumab on Lipoprotein(a) Over ‡1.5 Years (from the Phase 3 ODYSSEY Program)."
Ginsberg et al. (2014) Circulation 130:2119 "ODYSSEY HIGH FH: Efficacy and Safety of Alirocumab in Patients with Severe Heterozygous Familial Hypercholesterolemia."
Gonnet et al. (1992) Science 256:1443-1445 Exhaustive Matching of the Entire Protein Sequence Database.
Goodson (1984) Medical Applications of Controlled Release 2:115-138 "Chapter 6:Dental Applications."

(56) References Cited

OTHER PUBLICATIONS

Gorcyca et al. (2015) J Clin Lipidol. 9(3):424 Abstract 118 "Prevalence of atherosclerotic cardiovascular disease and diabetes in the United States."
Grozdanov et al. (2006) Biochem. Cell. Biol. 84:80-92 "Expression and localization of PCSK9 in rat hepatic cells."
Gusarova (2013) "PCSK9 inhibition by monoclonal antibody as a promising strategy for LDL-C lowering" Presented as an oral presentation at South East Lipid Research Conference Sep. 25-28, 2013, Georgia, USA.
Gusarova et al. (2012) Abstract of oral presentation at the Keystone Symposia on Molecular and Cellular Biology, Mar. 25-30, 2012 Montana, USA "Fully human antibody that blocks PCSK9 demonstrates reduction in LDL-C preclinically and in early clinical trials."
Gusarova et al. (2012) Clin Lipidol 7(6):737-743 "Reduction of LDL cholesterol by a monoclonal antibody to PCSK9 in rodents and nonhuman primates."
Haddley et al. (2013) Drugs of the Future 38(4):213-219 "ALIROCUMAB:Anti-Proprotein Convertase 9 (PCSK9) MAb Treatment of Hypercholesterolemia."
Heap et al. (2005) Journal of General Virology 86(6):1791-1800 "Analysis of a 17-amino acid residue, virus-neutralizing microantibody."
Hirayama et al. (2014) Circulation Journal 78(5):1073-1082 "Effects of evolocumab (AMG 145), a monoclonal antibody to PCSK9, in hypercholesterolemic, statin-treated Japanese patients at high cardiovascular risk—primary results from the phase 2 YUKAWA study."
Hochleitner et al. (2000) Protein Science 9:487-496 "Characterization of a discontinuous epitope of the human immunodeficiency virus (HIV) core protein p24 by epitope excision and differential chemical modification followed by mass spectrometric peptide mapping analysis."
Hollinger et al. (1993) Proceedings of the National Academy of Sciences 90(14):6444-6448 "'Diabodies': small bivalent and bispecific antibody fragments."
Hopkins et al. (2007) Otolaryngology-Head and Neck Surgery 137(4):555-561 "The Lund-Mackay staging system for chronic rhino sinusitis: How is it used and what does it predict?"
Hopkins et al. (2011) Journal of Clinical Lipidology 5(3):S9-S17 "Familial Hypercholesterolemias: Prevalence, genetics, diagnosis and screening recommendations from the National Lipid Association Expert Panel on Familial Hypercholesterolemia."
Hopkins et al. (2013) Circulation 128:Abstract A17156 "A randomized placebo-phase clinical trial with the monoclonal antibody alirocumab demonstrates reductions in low-density lipoprotein cholesterol in patients with proprotein convertase subtilisin/kexin type 9 gain-of-function mutations."
Hopkins et al. (2015) Circ Cardiovasc Genet. 8(6):823-831 "Characterization of Autosomal Dominant Hypercholesterolemia Caused by PCSK9 Gain of Function Mutations and its Specific Treatment with Alirocumab, a PCSK9 Monoclonal Antibody."
Horton et al. (2007) Trends Biochem Sci. 32(2):71-77 "Molecular biology of PCSK9: its role in LDL metabolism."
Hovingh et al. (2013) Eur Heart Journal 34(13):962-971 Diagnosis and treatment of familial hypercholesterolaemia.
Huang et al. (2015) J Clin Lipidol. 9(3):437-438 Abstract 134 "Clinical characteristics and unmet need among real-world atherosclerotic cardiovascular disease (ASCVD) patients stratified by statin use."
Huston et al. (1988) Proceedings of the National Academy of Sciences 85(16):5879 "Protein engineering of antibody binding sites: Recovery of specific activity in an anti-digoxin single-chain Fv analogue produced in *Escherichia coli*."
Igawa et al. (2010) Nature Biotechnology 28(11):1203-1208 "Antibody recycling by engineered pH-dependent antigen binding improves the duration of antigen neutralization."
Ito et al. (1992) Federation of European Biochemical Societies 309(1):85-88 "The His-probe method: effects of histidine residues introduced into the complementarity-determining regions of antibodies on antigen-antibody interactions at different pH values."
Jones et al. (2015) J Am Coll Cardiol 65(10S):A1363 "Pooled safety and adverse events in nine randomized, placebo-controlled, phase 2 and 3 clinical trials of alirocumab."
Jorgensen et al. (2013) European Heart Journal 34:1826-1833 "Genetically elevated non-fasting triglycerides and calculated remnant cholesterol as casual risk factors for myocardial infarction."
Junghans et al. (1990) Cancer Research 50:1495-1502 "Anti-Tac-H, a Humanized Antibody to the Interleukin 2 Receptor with New Features for Immunotherapy in Malignant and Immune Disorders."
Kastelein et al. (2014) Cardiovascular Drugs and Therapy 28(3):281-289 "Efficacy and Safety of Alirocumab in Patients with Heterozygous Familial Hypercholesterolemia not Adequately Controlled with Current Lipid-Lowering Therapy: Design and Rationale of the ODYSSEY FH Studies" ODYSSEY FH I and FH II studies; presented at ESC Congress Aug. 31, 2014, abstract not published.
Kastelein et al. (2015) Eur Heart J. 36(43):2996-3003 "ODYSSEY FH I and FH II: 78-week results with alirocumab treatment in 735 patients with heterozygous familial hypercholesterolemia."
Katayama et al. (2004) J. Pharm. Sci. 93(10):2609-2623 "Retrospective statistical analysis of lypophilized Protein Formulations of Progenipoietin Using PLS: Determination of the Critical Parameters for Long-Term Storage Stability."
Kostner et al. (2013) European Heart Journal 34:3268-3276 "When should we measure lipoprotein (a)?"
Krauss et al. (2014) Circulation 130:A15525 "Alirocumab, a fully human monoclonal antibody to proprotein convertase subtilisin/kexin type 9, and its effects on lipoprotein subfractions determined by ion mobility."
Kühnast et al. (2014) J Lipid Res. 55(10):2103-2112 "Alirocumab inhibits atherosclerosis, improves the plaque morphology, and enhances the effects of a statin."
Kühnast et al. (2013) Circulation 128:A15823 "PCSK-9 monoclonal antibody alirocumab dose-dependently decreases atherosclerosis development and enhances the effects of atorvastatin in APOE*3Leiden.CETP mice."
Kuiper (2015) Pharmo ISA Poster "Statin use and low density lipoprotein cholesterol goal attainment among a high cardiovascular risk population in the Netherlands."
Lagace et al. (2006) J Clin Invest Am Soc Clin Invest 116(11):2995-3005 "Secreted PCSK9 decreases the number of LDL receptors in hepatocytes and in liver of parabiotic mice."
Lambert et al. (2012) J Lipid Res 53(12):2515-2524 "The PCSK9 decade."
Lambert et al. (2014) J Am Coll Cardiol 64(21):2299-2300 "Normalization of Low-Density Lipoprotein Receptor Expression in Receptor Defective Homozygous Familial Hypercholesterolemia by Inhibition of PCSK9 With Alirocumab."
Lambert, Gilles, et al. "Molecular basis of PCSK9 Function" Atherosclerosis 203 (2009 1-7) (Listed in JP OA as Yamashita, Sizuya, "PCSK9 (proprotein convertase subtilisin/kexin type 9)", *Prevention of Arteriosclerosis*, Feb. 10, 2013, vol. 11, No. 4, p. 101-105).
Lamon-Fava et al. (2011) Journal of Lipid Research 52:1181-1187 "Lipoprotein(a) levels, apo(a) isoform size, and coronary heart disease risk in the Framingham Offspring Study."
Langer et al. (1990) Science 249(4976):1527-1533 "New methods of drug delivery."
Lefranc et al.(2009) Nucleic Acids Research 37:D1006-D1012 "IMGT®, the international ImMunoGeneTics information system®."
Leuenberger et al. (1996) Recueil des Travaux Chimiques des Pays-Bas. 115(7):382 "A Multilingual Glossary of Biotechnological Terms."
Li et al. (2009) Recent Patents on DNA and Gene Sequences 3(3):201-212 "Recent Patents on PCSK9: A New Target for Treating Hypercholesterolemia."
Lippi and Guidi (2000) QJ Med 93:75-84 "Lipoprotein(a): from ancestral benefit to modern pathogen?"
Lopez (2008) Drug News & Perspectives Abstract 21(6):323 "Inhibition of PCSK9 as a Novel Strategy for the Treatment of Hypercholesterolemia."
Lose et al. (2013) Pharmacotherapy: The Journal of Human Pharmacology and Drug Therapy 33(4):447-460 "Evaluation of Proprotein

(56) References Cited

OTHER PUBLICATIONS

Convertase Subtilisin/Kexin Type 9: Focus on Potential Clinical and Therapeutic Implications for Low-Density Lipoprotein Cholesterol Lowering."
Lunven et al. (2014) J Am Coll Cardiol 63(12 Suppl 1):A1377 "A randomized study of the relative bioavailability, pharmacodynamics, and safety of alirocumab, a fully human monoclonal antibody to proprotein convertase subtilison/ kexin type 9, after single subcutaneous administration at three different injection sites in healthy subjects."
Lunven et al. (2014) Cardiovasc Ther. 32(6):297-301 "A randomized study of the relative pharmacokinetics, pharmacodynamics and safety of alirocumab, a fully human monoclonal antibody to PCSK9, after single subcutaneous administration at three different injection sites in healthy subjects."
Maeda et al. (2002) J. Controlled Release 82:71-82 "pH-dependent receptor/ligand dissociation as a determining factor for intracellular sorting of ligands for epidermal growth factor receptors in rat hepatocytes."
Majumdar et al. (2011) Journal of Pharmaceutical Sciences 100(7):2563-2573 "Evaluation of the effect of syringe surfaces on protein formulations."
Marcovina and Koschinsky (1998) The American Journal of Cardiology 82(12A):57U-66U "Lipoprotein(a) as a Risk Factor for Coronary Artery Disease."
Maxwell and Breslow (2004) PNAS 101(18):7100-7105 "Adenoviral-mediated expression of Pcsk9 in mice results in a low-density lipoprotein receptor knockout phenotype."
McKenney et al. (2012) Presented as a late-breaking oral presentation at the American College of Cardiology (ACC) Annual Scientific Session, Mar. 24-27, 2012, Chicago, Illinois, USA "A randomized, double-blind, placebo-controlled trial of the safety and efficacy of a monoclonal antibody to proprotein convertase subtilisin/ kexin type 9 serine protease, REGN727/SAR236553, in patients with primary hypercholesterolemia (NCT: 01288443)."
McKenney et al. (Jun. 2012) Journal of the American College of Cardiology 59(25):2344-2353 "Safety and Efficacy of a Monoclonal Antibody to Proprotein Convertase Subtilisin/Kexin Type 9 Serine Protease, SAR236553/REGN727, in Patients With Primary Hyperchoesterolemia Receiving Ongoing Stable Atorvastatin Therapy."
McKenney et al. (2013) Abstract 81st European Atherosclerosis Society (EAS) Congress, Jun. 2-5, 2013, Lyon, France "Dynamics between the monoclonal antibody SAR236553/REGN727, proprotein convertase subtilisin/kexin type 9 and low-density lipoprotein cholesterol (LDL-C) levels (funding: Regeneron/Sanofi)."
McKenney et al. (2013) Presented as a poster presentation at the 81st European Atherosclerosis Society (EAS) Congress, Jun. 2-5, 2013, Lyon, France "Dynamics between the monoclonal antibody SAR236553/REGN727, proprotein convertase subtilisin/kexin type 9 (PCSK9) and low-density lipoprotein cholesterol (LDL-C) levels (funding: Regeneron/Sanofi)."
McNutt, et al., "So Far, PCSK9 Inhibitors Work for All Heterozygous FH Patients," DOI: 10.1161/CIRCGENETICS.115.001256, Dec. 2015.
McPherson (2013) Journal of the American College of Cardiology 61(4):437-439 "Remnant Cholesterol: Non-(HDL-C + LDL-C) as a Coronary Artery Disease Risk Factor."
Meehan et al. (1996) J. Controlled Release 46:107-116 "A microinfusor device for the delivery of therapeutic levels of peptides and macromolecules."
Miettinen et al. (1971) Circulation 44(5):842-850 "Cholesterol production in obesity."
Missouri DU Report (Oct./Nov. 2003) Drug Use Review Newsletter 8(6):1-9 "Statin Therapy."
Moon (2007) Cardiology 108:282-289 "Lipoprotein(a) and LDL Particle Size are Related to the Severity of Coronary Artery Disease."
Moriarty (2015) 10th International Society for Apheresis Congress XP55317363, Cancun Mexico "PCSK9 Inhibitors and their Effect on Patients who are Statin Intolerant or Receiving Lipoprotein-apheresis."
Moriarty et al. (2013) Eur Heart J. 34(Suppl 1):doi:10.1093/eurheartj/eht307.142 "Homogeneity of treatment effect of REGN727/SAR236553, a fully human monoclonal antibody against PCSK9, in lowering LDL-C: data from three phase 2 studies."
Moriarty et al. (2014) Circulation 130:2108 "ODYSSEY ALTERNATIVE: Efficacy and safety of the proprotein convertase subtilisin/kexin type 9 monoclonal antibody, alirocumab, versus ezetimibe, in patients with statin intolerance as defined by a placebo run-in and statin rechallenge arm."
Moriarty et al. (2014) J Clin Lipidol. 8(6):554-561 "Efficacy and safety of alirocumab, a monoclonal antibody to PCSK9, in statin-intolerant patients: Design and rationale of ODYSSEY ALTERNATIVE, a randomized Phase 3 trial."
Moriarty et al. (2015) J Clin Lipidol. 9(6):758-769 "Efficacy and safety of alirocumab versus ezetimibe in statin-intolerant patients, with a statin-re-challenge arm: The ODYSSEY ALTERNATIVE randomized trial."
Nakasako et al. (1999) J. Mol. Biol. 291:117-134 "The pH-dependent structural variation of complementarity-determining region H3 in the crystal structures of the Fv fragment from an anti-dansyl monoclonal antibody."
Naureckiene et al. (2003) Archives of Biochemistry and Biophysics 420:55-67 "Functional characterization of Narc 1, a novel proteinase related to proteinase K."
Ned, Renee M., et al., "Cascade Screening for Familial Hypercholesterolemia (FH)," PLOS Currents Evidence on Genomic Tests Jul. 1, 2011. Edition 1 doi:10.1371/currents.RRN1238.
Noguchi et al. (2010) Atherosclerosis 210(1):166-172 "The E32K variant of PCSK9 exacerbates the phenotype of familial hypercholesterolemia by increasing PCSK9 function and concentration in the circulation."
Nordestgaard et al. (2010) European Heart Journal 31(23):2844-2853 "Lipoprotein(s) as cardiovascular risk factor: current status."
Padlan et al. (1995) The FASEB Journal 9(1):133-139 "Identification of specificity-determining residues in antibodies."
Parhofer (2011) Current Pharmaceutical Design 17(9):871-876 "Lipoprotein(a): Medical Treatment Options for an Elusive Molecule."
Park et al. (2004) J. Biol. Chem. 279:50630-50638 "Lipids and Lipoproteins: Post-transcriptional Regulation of Low Density Lipoprotein Receptor Protein by Proprotein Convertase Subtilisin/Kexin Type 9a in Mouse Liver."
Partial International Search Report from PCT/US2014/040163 dated Nov. 6, 2014.
PCT IPRP for International Application No. PCT/EP12/051321 dated Jul. 30, 2013.
PCT ISR and WO for corresponding International Application No. PCT/US2014/040695 dated Oct. 6, 2014.
PCT ISR and WO for International Application No. PCT/US2013/023784 mailed Jul. 10, 2013.
PCT ISR and WO for International Application No. PCT/US2014/046170 dated Oct. 2, 2014.
PCT ISR and WO for International Application No. PCT/US2014/060109 mailed Apr. 16, 2015.
PCT ISR and WO from PCT/US2014/040050 dated Oct. 6, 2014.
PCT ISR for International Application No. PCT/EP12/051321 dated Aug. 2, 2012.
PCT ISR for International Application No. PCT/EP2012/051320 Sep. 21, 2012.
PCT ISR for International Application No. PCT/US2012/42338 mailed Aug. 23, 2012.
PCT ISR for International Application No. PCT/US2013/057898 dated Feb. 13, 2014.
PCT ISR for International Patent Application No. PCT/US2013/055747 mailed Feb. 13, 2014.
PCT ISR with WO for International Patent Application No. PCT/EP2012/051321 mailed Apr. 19, 2012.
PCT ISR with WO for International Patent Application No. PCT/EP2015/055369 mailed May 21, 2015.

(56) References Cited

OTHER PUBLICATIONS

PCT ISR with WO for International Patent Application No. PCT/US2014/041204 mailed Oct. 17, 2014.
PCT ISR with WO for International Patent Application No. PCT/US2015/040754 mailed Oct. 14, 2015.
PCT ISR with WO for International Patent Application No. PCT/US2015/040765 mailed Nov. 26, 2015.
Pearson (1994) Methods in Molecular Biology (Computer Analysis of Sequence Data) 24:307-331 "Using the FASTA program to search protein and DNA sequence databases."
Pfizer (Nov. 3, 2012) "Safety and Tolerability of Multiple Doses of PF-04950615 (RN316) in Subjects With Hypercholesterolemia" Available website: www.clinicaltrials.gov/ct2/show/NCT01243151; Last update: Jul. 9, 2012; Accessed on: Feb. 27, 2017.
Pordy et al. (2013) J Clin Lipidol 7(3):279 "Alirocumab, a fully human monoclonal antibody to proprotein convertase subtilisin/kexin type 9: therapeutic dosing in phase 3 studies."
Powell et al. (1998) Journal of Pharmaceutical Science and Technology 52(5): 238-311 "Compendium of Excipients for Parenteral Formulations PDA."
Qui et al. (2007) Nature Biotechnology 25( 8):921-929 "Small antibody mimetics comprising two complementarity-determining regions and a framework region for tumor targeting."
Rader et al. (1995) The Journal of Clinical Investigation, Inc. 95:1403-1408 "The Low Density Lipoprotein Receptor Is Not Required for Normal Catabolism of Lp(a) in Humans."
Rahilly-Tierney, Catherine R., "Low-Density Lipoprotein Reduction and Magnitude of Cardiovascular Risk Reduction," Clinical Study, Preventive Cardiology, Spring 2009, MAVERIC, pp. 80-87.
Ramanathan et al. (2013) Circulation128:A12052 "Role of alirocumab (proprotein convertase subtilisin/kexin type 9 antibody) on CD81 levels and hepatitis C virus entry into hepatocytes."
Rashid et al. (2005) PNAS 102(15):5374-5379 "Decreased plasma cholesterol and hypersensitivity to statins in mice lacking Pcsk9."
Ray (2015) Clin Lipidol. 10(1):9-12 "Alirocumab: an investigational treatment for hypercholesterolemia."
Ray et al. (2013) Value Health 16(7):A513 "Attainment of low-density lipoprotein cholesterol goals in patients at very high cardiovascular risk in the United Kingdom: results from a general practice population study."
Reddy et al. (2000) The Journal of Immunology 164(4):1925-1933 "Elimination of Fc receptor-dependent effector functions of a modified IgG4 monoclonal antibody to human CD4."
Reineke (2004) Antibody Engineering: Methods and Protocols, Humana Press pp. 443-463 "Antibody epitope mapping using arrays of synthetic peptides."
Rey et al. (2014) J Am Coll Cardiol 63(12S1):A1375 "Randomized, partial blind study of the pharmacodynamics, pharmacokinetics and safety of multiple subcutaneous doses of alirocumab, a fully human monoclonal antibody to proprotein convertase subtilisin/kexin type 9, administered every 4 weeks alone or in combination with ezetimibe or fenofibrate in healthy subjects."
Reyes-Soffer et al. (2015) Arterioscler Thromb Vasc Biol 35:A129 "Effects of a proprotein convertase subtilisin/kexin type 9 inhibitor, alirocumab, on lipid and lipoprotein metabolism in normal subjects."
Reyes-Soffer et al. (2017) Circulation 135:352-362 "Effects of PCSK9 Inhibition with Alirocumab on Lipoprotein Metabolism in Healthy Humans."
Rhainds et al. (2012) Clinical Lipidology 7(6):621-640 "PCSK9 inhibition and LDL cholesterol lowering: The biology of an attractive therapeutic target and critical review of the latest clinical trials."
Robinson (2002) PNAS 99(8):5283-5288 "Protein Deamidation."
Robinson et al. "Long-term safety, tolerability and efficacy of alirocumab versus placebo in high cardiovascular risk patients: first results from the ODYSSEY LONG TERM study in 2,341 patients" presented at ESC Congress Aug. 31, 2014, abstract not published.
Robinson et al. (2014) Circulation 130:2120 "Long-term safety, tolerability and efficacy of alirocumab versus placebo in high cardiovascular risk patients: first results from the ODYSSEY LONG TERM study in 2,341 patients."
Robinson et al. (2014) Clinical Cardiology 37(10):597-604 "Efficacy and Safety of Alirocumab as Add-on Therapy in High-Cardiovascular-Risk Patients with Hypercholesterolemia Not Adequately Controlled with Atorvastatin (20 or 40 mg) or Rosuvastatin (10 or 20 mg): Design and Rationale of the ODYSSEY OPTIONS Studies."
Robinson et al. (2015) J Am Coll Cardiol 65(10S):A1350 "Adverse events in patients with low-density lipoprotein cholesterol levels <25 or <15 mg/dL on at least two consecutive visits in fourteen randomized, controlled, clinical trials of alirocumab."
Robinson et al. (2015) N Eng J Med. 372:1489-1499 "Odyssey Long Term Investigators. Efficacy and Safety of Alirocumab in Reducing Lipids and Cardiovascular Events."
Romagnuolo et al. (2015) The Journal of Biological Chemistry 290(18):11649-11662 "Lipoprotein(a) Catabolism is Regulated by Proprotein Convertase Subtilisin/Kexin Type 9 through the Low Density Lipoprotein Receptor."
Roth et al. (2012) J Am Coll Cardiol 59:E1620 "The effects of co-administering a monoclonal antibody to proprotein convertase subtilisin/kexin type 9 serine protease, REGN727/SAR236553, with 10 and 80 mg atorvastatin compared to 80 mg atorvastatin alone in patients with primary hypercholesterolemia (NCT: 01288469)."
Roth et al. (2012) N Engl J Med. 367(20):1891-1900 "Atorvastatin with or without an antibody to PCSK9 in primary hypercholesterolemia."
Roth et al. (2014) Future Cardiology 10(2):183-199 "Alirocumab for hyperlipidemia: physiology of PCSK9 inhibition, pharmacodynamics and Phase I and II clinical trial results of a PCSK9 monoclonal antibody."
Roth et al. (2014) Int J Cardiol 176(1):55-61 "Monotherapy with the PCSK9 inhibitor alirocumab versus ezetimibe in patients with hypercholesterolemia: Results of a 24 week, double-blind, randomized Phase 3 trial."
Roth et al. (2014) J Am Coll Cardiol 63(12 Suppl 1):A1370 "A 24-week study of alirocumab monotherapy versus ezetimibe: The first phase 3 data of a proprotein convertase subtilisin/kexin type 9 inhibitor."
Roth et al. (2015) International Symposium on Atherosclerosis, Abstract No. 254 "Phase 3 Randomized Trial Evaluating Alirocumab Every Four Weeks Dosing as Add-on to Statin or as Monotherapy: ODYSSEY CHOICE I."
Roth et al. (2015) Future Cardiol 11(1):27-37 "ODYSSEY MONO: effect of alirocumab 75 mg subcutaneously every 2 weeks as monotherapy versus ezetimibe over 24 weeks."
Roth et al. (2015) J. Clin. Lipidol. 37(9):1945-1954 "Patient and physician perspectives on administration of the PCSK9 monoclonal antibody alirocumab, an injectable medication to lower LDL-C levels."
Saeedi and Frohlich (2016) Clinical Diabetes and Endocrinology 2:7 "Lipoprotein (a), an independent cardiovascular risk marker."
Sahebkar et al. (2013) Clinical Therapeutics 35(8):1082-1098 "New LDL-Cholesterol Lowering Therapies: Pharmacology, Clinical Trials, and Relevance to Acute Coronary Syndromes."
Sarkar et al. (2002) Nature Biotechnology 20:908-913 "Rational cytokine design for increased lifetime and enhanced potency using pH-activated histidine switching."
Scaviner et al. (1999) Exp. Clin. Immunogenet. 16:234-240 "Protein Displays of the Human Immunoglobulin Heavy, Kappa and Lambda Variable and Joining Regions."
Schäfer et al. (2011) "Cholesterol lowering effect of SAR236553/REGN727, a fully human PCSK9 blocking monoclonal antibody in male Syrian hamster" Presented as a poster at the Drugs Affecting Lipid Metabolism (DALM)—XVII International Symposium, Mar. 14-16, 2011, Doha, Qatar.
Schwartz et al. (Nov. 2014) Am Heart J. 168(5):682-689.e1 "Effect of alirocumab, a monoclonal antibody to pcsk9, on long-term cardiovascular outcomes following acute coronary syndromes: Rationale and design of the odyssey outcomes trial."

(56) References Cited

OTHER PUBLICATIONS

Sefton (1986) Critical Reviews in Biomedical Engineering 14(3):201-240 "Implantable Pumps."
Seidah et al. (2003) PNAS 100(3):928-933 "The secretory proprotein convertase neural apoptosis-regulated convertase 1 (NARC-1): liver regeneration and neuronal differentiation."
Shao (2014) Scientific Symposium "New Therapies for Lowering LDL-C: Targeting PCSK9" Abstract of oral presentation at the Sino-American Pharmaceutical Professionals Association Apr. 26, 2014, New Jersey, USA.
Shields et al. (2002) Journal of Biological Chemistry 277(30):26733-26740 "Lack of fucose on human IgG1 N-linked oligosaccharide improves binding to human FcγRIII and antibody-dependent cellular toxicity."
Shoji et al. (1998) J Am Soc Nephrol 9:1277-1284 "Intermediate-Destiny Lipoprotein as an Independent Risk Factor for Aortic Atherosclerosis in Hemodialysis Patients."
Soutar (2011) Current Opinion in Lipodology 22:192-196 "Unexpected Roles for PCSK9 in Lipid Metabolism."
Stahl (2010) "Early Clinical Development #1 REGN727: anti-PCSK9," Regeneron Pharmaceuticals. Accessible on the Internet at URL: http://files.shareholder.com/downloads/REGN/0x0x387214/534aaeb6-5e66-4e8f-86a9-0f9cac20d72f/REGN%20Investor%20Day%20Early%20Clinical%20Development1.pdf.
Steen et al. (2014) Circulation 130:A19949 Attainment of Lipid Levels in Patients at High Cardiovascular Risk: Results from a U.S. Managed Care Population Study.
Steen et al. (2015) J Am Coll Cardiol 65(10S):A1647 "Cardiovascular Event Rates in a High-Risk Managed Care Population in the United States."
Stein and Swergold (Feb. 2013) Current Atherosclerosis Reports 15(310):1-14 "Potential of proprotein Convertase Subtilisin/Kexin Type 9 Based Therapeutics."
Stein et al. (2012) New England Journal of Medicine 366(12):1108-1118 "Effect of a Monoclonal Antibody to PCSK9 on LDL Cholesterol."
Stein et al. (2012) Obstetrical and Gynecological Survey 67(7):413-414 "Effect of a monoclonal antibody to PCSK9 on LDL cholesterol."
Stein et al. (2012) Presented as an oral presentation at the 80th European Atherosclerosis Society (EAS) Congress, May 25-28, 2012, Milan, Italy. Abstract 1398 "Safety and efficacy of a monoclonal antibody to PCSK9, REGN727/SAR236553, in statin-treated heterozygous familial hypercholesterolemia patients."
Stein et al. (2012) The Lancet 380:29-36 "Effect of a monoclonal antibody to PCSK9, REGN727/SAR236553, to reduce low-density lipoprotein cholesterol in patients with heterozygofamilial hypercholesterolemia on stable statin dose with or without ezetimibe therapy: a phase 2 randomized controlled trial."
Stein et al. (2014) J Am Coll Cardiol 63(12 Suppl 1): A1371 "One year open-label treatment with alirocumab 150 mg every two weeks in heterozygous familial hypercholesterolemic patients."
Steinberg et al. (2009) Proceedings of the National Academy of Sciences USA 106(24):9546-9547 "Inhibition of PCSK9: A powerful weapon for achieving ideal LDL cholesterol levels."
Stone , Neil J. et al., "2013 ACC/AHA Guideline on the Treatment of Blood Cholesterol to Reduce Atherosclerotic Cardiovascular Risk in Adults", A report of the American College of Cardiology/American Heart Association Task Force on Practice Guidelines, (2014) JACC, vol. 63, No. 25, Nov. 12, 2013, :pp. 2889-2934.
Stroes et al. (2014) J. Am. Coll. Cardiol. 63(23):2541-2548 "Anti-PCSK9 Antibody Effectively Lowers Cholesterol in Patients With Statin Intolerance."
Stroes et al. (2015) J Am Coll Cardiol 65(10S):A1370 "Efficacy and safety of different dosing regimens of alirocumab (starting doses of 75 mg every two weeks and 150 mg every four weeks) versus placebo in patients with hypercholesterolemia not treated using statins: the ODYSSEY CHOICE II study."
Sullivan et al. (2012) JAMA 308(23):2497-2506 "Effect of a Monoclonal Antibody to PCSK9 on Low-Density Lipoprotein Cholesterol Levels in Statin-Intolerant Patients."
Swergold et al. (2010) Circulation 122:Abstract A23251 "Safety, lipid, and lipoprotein effects of REGN727/SAR236553, a fully human proprotein convertase subtilisin kexin 9 (PCSK9) neutralizing monoclonal antibody administered intravenously to healthy volunteers."
Swergold et al. (2011) Circulation 124:Abstract A16265 "Inhibition of proprotein convertase subtilisin/kexin type 9 with a monoclonal antibody REGN727/SAR236553, effectively reduces low-density-lipoprotein cholesterol, as mono or add-on therapy in heterozygous familial and non-familial hypercholesterolemia."
Swergold et al. (2011) J Am Coll Cardiol 57(14s1):E2023 "REGN727/SAR236553, a fully human proprotein convertase subtilisin kexin 9 (PCSK9) monoclonal antibody: effects on safety and lipid and lipoprotein profiles when administered subcutaneously."
Swergold et al. (2011) J Clin Lipidol 5(3):219 "REGN727/SAR236553, a fully-human monoclonal antibody to proprotein convertase subtilisin kexin 9 (PCSK9), decreases ApoB and non-HDL-C when administered intravenously to healthy volunteers."
Swergold et al. (2013) Abstract of a poster presentation at the American Society of Human Genetics (ASHG), Oct. 22-26, 2013, Boston, USA "Identification and characterization of patients with autosomal dominant hypercholesterolemia caused by gain-of-function mutations in proprotein convertase subtilisin/kexin type 9 and comparison with patients with Familial Hypercholesterolemia (FH) and Familial Defective apolipoprotein B (FDB)."
Teramoto et al. (2014) Circulation 130:A13651 "Efficacy and safety of alirocumab in Japanese patients with hypercholesterolemia on stable statin therapy: first data with the 75 mg every two weeks dose."
Timms et al. (2004) Human Genetics 114(4):349-353 "A mutation in PCSK9 causing autosomal-dominant hypercholesterolemia in a Utah pedigree."
Tiwari et al. (2011) Journal of Pharmacy and Pharmacology 63(8):983-998 "Statins therapy: a review on conventional and novel formulation approaches."
Todo, Yasuhiro, et al., "Detailed Analysis of Serum Lipids and Lipoproteins from Japanese Type III Hyperlipoproteinemia with Apolipoprotein E2/2 Phenotype," Clinica Chimica Acta 348 (2004) 35-40.
Toth et al. (2013) Circulation 128:A17313 "Alirocumab, a proprotein convertase subtilisin/kexin type 9 monoclonal antibody, reduces cholesterol concentrations of all serum low-density lipoprotein cholesterol fractions."
Toth et al. (2014) Atherosclerosis 235(2):e107-e108 [Abstract 593] "Proprotein convertase subtilisin/kexin 9 monoclonal antibody therapy significantly reduces apoprotein CII and CIII levels in serum."
Toth, et al. (2013) Circulation 128(22):A17492 "Alirocumab, a Proprotein Convertase Substilisin/Kexin Type 9 Monoclonal Antibody, Reduces Cholesterol Concentrations of Serum Remnant Lipoprotein Fractions, Very Low-Density Lipoproteins and Triglycerides."
Tsimikas et al. (2015) The Lancet 386(10002):1472-1483 "Antisense therapy targeting apoliopoprotein(a): a randomised, double-blind, placebo-controlled phase 1 study."
Tutt et al. (1991) The Journal of Immunology 147(1):60-69 "Trispecific F (ab') 3 derivatives that use cooperative signaling via the TCR/CD3 complex and CD2 to activate and redirect resting cytotoxic T cells."
Vajdos et al. (2002) Journal of Molecular Biology 320(2):415-428 "Comprehensive functional maps of the antigen-binding site of an anti-ErbB2 antibody obtained with shotgun scanning mutagenesis."
Van der Hoorn et al. (2014) Atherosclerosis 235(2):e19 [Abstract WS16] "Alirocumab, a monoclonal antibody to PCSK-9, dose-dependently decreases atherosclerosis, improves plaque stability and shows additive effects with atorvastatin in APOE*3Leiden. CETP mice."
Varbo et al. (2013) Journal of the American College of Cardiology 61(4):427-436 "Remnant Cholesterol as a Casual Risk Factor for Ischemic Heart Disease."
Varrett et al. (1999) Am. J. Hum. Genet. 64:1378-1387 "A third major locus for autosomal dominant hyperchloseterolemia Maps to 1p34.1-p32."

(56) References Cited

OTHER PUBLICATIONS

Wang (1999) International J. Pharmaceutics 185(2):129-188 "Instability, stabilization, and formulation of liquid protein pharmaceuticals."
Wang et al. (2007) Journal of Pharmaceutical Sciences 96(1):1-26 "Antibody Structure, Instability, and Formulation."
Wang et al. (2009) Clin. Pharmacology 49(9):1012-1024 "Fixed Dosing Versus Body Sized-Based Dosing of Monoclonal Antibodies in Adult Clinical Trials."
Ward et al. (1989) Nature 341(6242):544-546 "Binding activities of a repertoire of single immunoglobulin variable domains secreted from *Escherichia coli*."
Watanabe et al. (2009) J. Biological Chemistry 284(18):12373-12383 "Optimizing pH response of affinity between protein G and IgG Fc."
Webb et al. (2002) J. Pharm. Sci. 91(2):543-558 "A new mechanism for decreasing aggregation of Recombinant Human Interferon-Y by a Surfactant: Slowed Dissolution of Lyophilized Formulations in a Solution Containing 0.03% Polysorbate 20."
Westerterp et al. (2006) Arterioscler Thromb Vasc Biol 26(11):2552-2559 "Cholesteryl Ester Transfer Protein Decreases High-Density Lipoprotein and Severely Aggravates Atherosclerosis in APOE*3-Leiden Mice."
Winter and Harris (1993) Immunology Today 14(6):243-246 "Humanized Antibodies."
Wong (2014) J Clin Lipidol. 8:323-324 Residual Dyslipidemia According to LDL-C, non-HDL-C and Apolipoprotein B by cardiovascular Risk Category in Statin Treated US Adults. Presented as a poster presentation at the National Lipid Association Scientific Sessions, May 1-4, 2014, Orlando, Florida, USA.
Written Opinion of the International Searching Authority for International Application No. PCT/EP2012/051320, dated Jul. 30, 2013 (16 pages).
Wu et al. (1987) Journal of Biological Chemistry 262(10):4429-4432 "Receptor-mediated in vitro gene transformation by a soluble DNA carrier system."
Zimmerman (2015) Am Health Drug Benefits 8(8):436-442 "How do PCSK9 Inhibitors Stack Up to Statins for Low-Density Lipoprotein Cholesterol Control", American Health & Drug Benefits, Nov. 1, 2015, p. 436.
Yamashita, Sizuya, "PCSK9 (proprotein convertase subtilisin/kexin type 9)", Prevention of Arteriosclerosis, Feb. 10, 2013, vol. 11, No. 4, pp. 101-105 (Lambert, Gilles, et al., "Molecular basis of PCSK9 function," Atherosclerosis 203 (2009) 1-7).
Voet et al., "Fundamentals of Biochemistry", Von Hoffman Press, Inc., 1999, pp. 260-264.
Voet et al., "Fundamentals of Biochemistry", Von Hoffman Press, Inc., 1999, pp. 80-81.
Bendig, Mary M., "Humanization of rodent monoclonal antibodies by CDR grafting", Methods: A Companion to Methods in Enzymology 8, 83-93 (1995).
Jefferis, Roy et al., "Human Immunoglobulin Allotypes", Review mAbs 1:4, 1-7, Jul./Aug. 2009.
QSM, "Essential medicines and health products", WHO Drug Information, vol. 26, No. 2, 2012.
Lalanne, Florent et al., "Wild-type PCSK9 inhibits LDL clearance but does not affect apoB-containing lipoprotein production in mouse and cultured cells", Journal of Lipid Research, vol. 46, 2005, pp. 1312-1319.
"Sanofi and Regeneron Announce Collaboration with American College of Cardiology for PCSK9 Inhibitor Clinical Program", Dec. 19, 2013, PRNewswire, obtained on Dec. 5, 2018 at: https://newsroom.regeneron.com/news-releases/news-release-details/sanofi-and-regeneron-announce-collaboration-american-college, 5 pages.
"Sanofi and Regeneron Report Positive Top-line Results with Alirocumab from First Phase 3 Study of a PCSK9 Inhibitor for LDL Cholesterol Reduction", Oct. 16, 2013, ePressPack, Jay Edelberg M.D., Ph.D, obtained online on Dec. 5, 2018 at: http://www.epresspack.net/mmr/sanofi-pcsk9-1st-phase3-results/, 3 pages.
Australian Public Assessment Report for Alirocumab (rch), AustralianGovernment, Department of Health, 2016, Therapeutic Goods Administration; https://www.tga.gov.au/auspar/auspar-alirocumab-rch, 2 pages.
Ni, Yan G., et al., "A Proprotein Convertase Subtilisin-like/Kexin Type9 (PCSK9) C-terminal Domain Antibody Antigen-binding Fragment Inhibits PCSK9 Internalization and Restores Low Density Lipoprotein Uptake", The Journal of Biological Chemistry 285.17 (2010): 20 pages.
Kwon, Hyock Joo, et al., "Molecular basis for LDL receptor recognition by PCSK9", Proceedings of the National Academy of Sciences, 2008, 105, 1820-1825.
Anonymous: "NCT02326220 on Dec. 28, 2014: ClinicalTrials.gov Archive", Retrieved from the internet: (https://clinicaltrials.gov/archive/NCT02326220/2014_12_28), retrieved on Nov. 7, 2016, 5 pages.
Anonymous: ""NCT02326220 on Mar. 10, 2015: ClinicalTrials.gov Archive"", Retrieved from the Internet: (https://clinicaltrials.gov/archive/NCT02326220/2015_03_10), retrieved on—Nov. 7, 2016, 5 pgs.
Anonymous: ""NCT02326220 on Apr. 7, 2015: ClinicalTrials.gov Archive"", Retrieved from the Internet: (https://clinicaltrials.gov/archive/NCT02326220/2015_04_07), retrieved on—Nov. 7, 2016, 5 pgs.
Kawashiri et al. (2012) Circulation 126(21):13869 "Statin Therapy Improves Fractional Catabolic Rate of LDL without Affecting Impaired VLDL and VLDL Remnant Catabolism in Homozygous FH Patient Due to PCSK9 Gene Mutation: Evidence from Kinetic Study with Stable Isotope."
Kereiakes et al. (2014) Circulation 130(23):2119-2120 "Efficacy and safety of alirocumab in high cardiovascular risk patients with suboptimally controlled hypercholesterolemia on maximally tolerated doses of statins: the ODYSSEY COMBO I study."
Kereiakes et al. (2015) Am Heart J 169(6):906-915 "Efficacy and safety of the proprotein convertase subtilisin/kexin type 9 inhibitor alirocumab among high cardiovascular risk patients on maximally tolerated statin therapy: the ODYSSEY COMBO I study."
Kolata (2015) The New York Times "Praluent Looks Cheap to Those with Extreme Cholesterol" Website [Online] Available Website: www.nytimes.com/2015/07/28/health/praluent-looks-cheap-to-those-with-extreme-cholesterol.html; Last Update: unknown; Accessed on: Nov. 8, 2016.
Konrad et al. (2011) Lipids in Health and Disease 10(1):38 "Effects of currently prescribed LDL-C-lowering drugs on PCSK9 and implications for the next generation of LDL-C-lowering agents."
Koren et al. (2012) Eur Heart J 33(Abstract Supplement)37 Abstract 429 "Efficacy, safety and tolerability of 150 mg Q2W dose of the anti-PCSK9 mAb, REGN727/SAR236553: data from 3 phase 2 studies."
Koren et al. (2013) J Clin Lipidol 7(3):279-280 Abstract 172 "Efficacy, safety and tolerability of alirocumab 150 mg Q2W, a fully human PCSK9 monoclonal antibody: a pooled analysis of 352 patients from phase 2."
Koren et al. (2014) J Am Coll Cardiol 63(12 Suppl 1):A1373 "Effects of alirocumab, a fully human monoclonal antibody to proprotein convertase subtilisin/kexin type 9, on lipoprotein particle concentrations determined by nuclear magnetic resonance: substudy of a randomized double-blind phase II clinical trial."
Koren et al. (2015) Postgrad Med 22:1-8 "Safety and efficacy of alirocumab 150 mg every 2 weeks, a fully human proprotein convertase subtilisin/kexin type 9 monoclonal antibody: a Phase II pooled analysis."
Koschinsky and Boffa (2014) Endocrinology and Metabolism Clinics of North America 43(4):949-962 "Lipoprotein(a): An Important Cardiovascular Risk Factor and a Clinical Conundrum."

* cited by examiner

```
                                   10        20        30        40
H1H316P VH (SEQ ID NO:90)   EVQLVESGGGLVQPGGSLRLSCAAS[GFTFNNYA]MNWVRQAPGKG
H1M300N VH (SEQ ID NO:218)  EMQLVESGGGLVQPGGSLRLSCAAS[GFTFSSHW]MKWVRQAPGKG
                                                       CDR1

                                  50        60        70        80
H1H316P VH (SEQ ID NO:90)   LDWVST[ISGSGGTT]NYADSVKGRFIISRDSSKHTLYLQMNSLRA
H1M300N VH (SEQ ID NO:218)  LEWVAN[INQDGSEK]YYVDSVKGRFTISRDNAKNSLFLQMNSLRA
                                    CDR2

                            90        100       110       120
H1H316P VH (SEQ ID NO:90)   EDTAVYYC[AKDSNWGNFDL---------]WGRGTLVTVSS
H1M300N VH (SEQ ID NO:218)  EDTAVYYC[ARDIVLMVYDMDYYYYGMDV]WGQGTTVTVSS
                                            CDR3

                                   10        20        30        40
H1H316P VK (SEQ ID NO:92)   DIVMTQSPDSLAVSLGERATINCKSS[QSVLYRSNNRNF]LGWYQQ
H1M300N VK (SEQ ID NO:226)  DIVMTQSPLSLPVTPGEPASISCRSS[QSLLHSNGNNY-]LDWYLQ
                                                            CDR1

                                  50        60        70        80
H1H316P VK (SEQ ID NO:92)   KPGQPPNLLIY[WAS]TRESGVPDRFSGSGSGTDFTLTISSLQAED
H1M300N VK (SEQ ID NO:226)  KPGQSPQLLIY[LGS]NRASGVPDRFSGSGSGTDFTLKISRVEAED
                                        CDR2

                            90        100       110
H1H316P VK (SEQ ID NO:92)   VAVYYC[QQYYTTPYT]FGQGTKLEIK
H1M300N VK (SEQ ID NO:226)  VGVYYC[MQTLQTPLT]FGGGTKVEIK
                                   CDR3
```

Fig. 1

ANTI-PCSK9 ANTIBODIES

CROSS-REFERENCE TO RELATED APPLICATIONS

This application is a continuation of U.S. application Ser. No. 15/377,364, filed on 13 Dec. 2016, which is a continuation of U.S. application Ser. No. 14/737,488, filed on 12 Jun. 2015, now. U.S. Pat. No. 9,550,837, Issued 24 Jan. 2017, which is a continuation of U.S. application Ser. No. 13/690,585, filed on 30 Nov. 2012, which is a continuation of U.S. application Ser. No. 12/949,846 filed on 19 Nov. 2010, now U.S. Pat. No. 8,501,184, Issued 6 Aug. 2013, which is a divisional of U.S. application Ser. No. 12/637,942, filed 15 Dec. 2009, now U.S. Pat. No. 8,062,640, Issued 22 Nov. 2011, which claims the benefit under 35 USC § 119(e) of U.S. Provisional 61/261,776 filed 17 Nov. 2009, 61/249,135 filed 6 Oct. 2009, 61/218,136 filed 18 Jun. 2009, 61/168,753 filed 13 Apr. 2009, 61/210,566 filed 18 Mar. 2009 and 61/122,482 filed 15 Dec. 2008, which applications are herein specifically incorporated by reference in their entirety.

FIELD OF THE INVENTION

The present invention is related to human antibodies and antigen-binding fragments of human antibodies that specifically bind human proprotein convertase subtilisin/kexin type 9 (PCSK9), and therapeutic methods of using those antibodies.

STATEMENT OF RELATED ART

Proprotein convertase subtilisin/kexin type 9 (PCSK9) is a proprotein convertase belonging to the proteinase K subfamily of the secretory subtilase family. The encoded protein is synthesized as a soluble zymogen that undergoes autocatalytic intramolecular processing in the endoplasmic reticulum. Evidence suggest that PCSK9 increases plasma LDL cholesterol by promoting degradation of the LDL receptor, which mediates LDL endocytosis in the liver, the major route of LDL clearance from circulation. The structure of PCSK9 protein shows that it has a signal sequence, followed by a prodomain, a catalytic domain that contains a conserved triad of residues (D186, H226 and S386), and a C-terminal domain. It is synthesized as a soluble 74-kDa precursor that undergoes autocatalytic cleavage in the ER, generating a 14-kDa prodomain and 60-kDa catalytic fragment. The autocatalytic activity has been shown to be required for secretion. After cleavage, the prodomain remains tightly associated with the catalytic domain.

Antibodies to PCSK9 are described in, for example, WO 2008/057457, WO 2008/057458, WO 2008/057459, WO 2008/063382, WO 2008/125623, and US 2008/0008697.

BRIEF SUMMARY OF THE INVENTION

In a first aspect, the invention provides fully human monoclonal antibodies (mAbs) and antigen-binding fragments thereof that specifically bind and neutralize human PCSK9 (hPCSK9) activity.

In one embodiment, the invention comprises an antibody or antigen-binding fragment of an antibody that specifically binds hPCSK9 and is characterized by at least one of:

(i) capable of reducing serum total cholesterol at least about 25-35% and sustaining the reduction over at least a 24 day period relative to a predose level, preferably the reduction in serum total cholesterol is at least about 30-40%;

(ii) capable of reducing serum LDL cholesterol at least about 65-80% and sustaining the reduction over at least a 24-day period relative to a predose level;

(iii) capable of reducing serum triglyceride at least about 25-40% relative to predose level;

(iv) does not reduce serum HDL cholesterol or reduces serum HDL cholesterol no more than 5% relative to predose level.

In one embodiment, the invention comprises an antibody or antigen-binding fragment of an antibody that specifically binds hPCSK9 and is characterized by at least one of:

(i) capable of reducing serum LDL cholesterol at least about 40-70% and sustaining the reduction over at least a 60 or 90 day period relative to a predose level;

(ii) capable of reducing serum triglyceride at least about 25-40% relative to predose level;

(iii) does not reduce serum HDL cholesterol or reduces serum HDL cholesterol no more than 5% relative to predose level.

In one embodiment, the antibody or antigen-binding fragment is characterized as binding an epitope comprising amino acid residue 238 of hPCSK9 (SEQ ID NO:755). In a more specific embodiment, the antibody or antigen-binding fragment binds an epitope comprising one or more of amino acid residue 238, 153, 159 and 343 of hPCSK9 (SEQ ID NO:755).). In a more specific embodiment, the antibody or fragment thereof is characterized as binding an epitope that does not comprise an amino acid residue at position 192, 194, 197 and/or 237 of SEQ ID NO:755.

In one embodiment, the antibody or antigen-binding fragment is characterized as binding an epitope comprising amino acid residue 366 of hPCSK9 (SEQ ID NO:755). In a more specific embodiment, the antibody or antigen-binding fragment binds an epitope comprising one or more of amino acid residue at position 147, 366 and 380 of SEQ ID NO:755. In a more specific embodiment, the antibody or antigen-binding fragment of an antibody is characterized as binding an epitope that does not comprise an amino acid residue at position 215 or 238 of SEQ ID NO:755.

In one embodiment, the antibody or antigen-binding fragment is characterized as exhibiting an enhanced binding affinity ($K_D$) for hPCSK9 at pH 5.5 relative to the $K_D$ at pH 7.4, as measured by plasmon surface resonance. In a specific embodiment, the antibody or fragment thereof exhibits at least a 20-fold, at least a 40-fold or at least a 50-fold enhanced affinity for PCSK9 at an acidic pH relative to a neutral pH, as measured by surface plasmon resonance.

In one embodiment, the antibody or antigen-binding fragment is characterized as not exhibiting an enhanced binding affinity for PCSK9 at an acidic pH relative to a neutral pH, as measured by surface plasmon resonance. In a specific embodiment, the antibody or fragment thereof exhibits a decreased binding affinity at an acidic pH.

In another embodiment, the antibody or antigen-binding fragment binds human, human GOF mutation D374Y, cynomolgus monkey, rhesus monkey, mouse, rat and hamster PCSK9.

In one embodiment, the antibody or antigen-binding fragment binds human and monkey PCSK9, but does not bind mouse, rat or hamster PCSK9.

The mAbs can be full-length (e.g., an IgG1 or IgG4 antibody) or may comprise only an antigen-binding portion (e.g., a Fab, $F(ab')_2$ or scFv fragment), and may be modified to affect functionality, e.g., to eliminate residual effector functions (Reddy et al. (2000) J. Immunol. 164:1925-1933).

In one embodiment, the invention comprises an antibody or antigen-binding fragment of an antibody comprising a heavy chain variable region (HCVR) selected from the group consisting of SEQ ID NO:2, 18, 22, 26, 42, 46, 50, 66, 70, 74, 90, 94, 98, 114, 118, 122, 138, 142, 146, 162, 166, 170, 186, 190, 194, 210, 214, 218, 234, 238, 242, 258, 262, 266, 282, 286, 290, 306, 310, 314, 330, 334, 338, 354, 358, 362, 378, 382, 386, 402, 406, 410, 426, 430, 434, 450, 454, 458, 474, 478, 482, 498, 502, 506, 522, 526, 530, 546, 550, 554, 570, 574, 578, 594, 598, 602, 618, 622, 626, 642, 646, 650, 666, 670, 674, 690, 694, 698, 714, 718, 722, 738 and 742, or a substantially similar sequence thereof having at least 90%, at least 95%, at least 98% or at least 99% sequence identity. In one embodiment, the HCVR comprises an amino acid sequence selected from the group consisting of SEQ ID NO:50, 66, 70, 74, 90, 94, 122, 138, 142, 218, 234, 238, 242, 258, 262, 314, 330 and 334. In a more specific embodiment, the HCVR comprises SEQ ID NO:90 or 218.

In one embodiment, the antibody or fragment thereof further comprises a light chain variable region (LCVR) selected from the group consisting of SEQ ID NO:10, 20, 24, 34, 44, 48, 58, 68, 72, 82, 92, 96, 106, 116, 120, 130, 140, 144, 154, 164, 168, 178, 188, 192, 202, 212, 216, 226, 236, 240, 250, 260, 264, 274, 284, 288, 298, 308, 312, 322, 332, 336, 346, 356, 360, 370, 380, 384, 394, 404, 408, 418, 428, 432, 442, 452, 456, 466, 476, 480, 490, 500, 504, 514, 524, 528, 538, 548, 552, 562, 572, 576, 586, 596, 600, 610, 620, 624, 634, 644, 648, 658, 668, 672, 682, 692, 696, 706, 716, 720, 730, 740 and 744, or a substantially similar sequence thereof having at least 90%, at least 95%, at least 98% or at least 99% sequence identity. In one embodiment, the LCVR comprises an amino acid sequence selected from the group consisting of SEQ ID NO: 58, 68, 72, 82, 92, 96, 130, 140, 144, 226, 236, 240, 250, 260, 264, 322, 332 and 336. In a more specific embodiment, the LCVR comprises SEQ ID NO:92 or 226.

In specific embodiments, the antibody or fragment thereof comprises a HCVR and LCVR (HCVR/LCVR) sequence pair selected from the group consisting of SEQ ID NO: 2/10, 18/20, 22/24, 26/34, 42/44, 46/48, 50/58, 66/68, 70/72, 74/82, 90/92, 94/96, 98/106, 114/116, 118/120, 122/130, 138/140, 142/144, 146/154, 162/164, 166/168, 170/178, 186/188, 190/192, 194/202, 210/212, 214/216, 218/226, 234/236, 238/240, 242/250, 258/260, 262/264, 266/274, 282/284, 286/288, 290/298, 306/308, 310/312, 314/322, 330/332, 334/336, 338/346, 354/356, 358/360, 362/370, 378/380, 382/384, 386/394, 402/404, 406/408, 410/418, 426/428, 430/432, 434/442, 450/452, 454/456, 458/466, 474/476, 478/480, 482/490, 498/500, 502/504, 506/514, 522/524, 526/528, 530/538, 546/548, 550/552, 554/562, 570/572, 574/576, 578/586, 594/596, 598/600, 602/610, 618/620, 622/624, 626/634, 642/644, 646/648, 650/658, 666/668, 670/672, 674/682, 690/692, 694/696, 698/706, 714/716, 718/720, 722/730, 738/740 and 742/744. In one embodiment, the HCVR and LCVR sequence pair comprises one of SEQ ID NO: 50/58, 66/68, 70/72, 74/82, 90/92, 94/96, 122/130, 138/140, 142/144, 218/226, 234/236, 238/240, 242/250, 258/260, 262/264, 314/322, 330/332 and 334/336. In a more specific embodiment, the HCVR/LCVR pair comprises SEQ ID NO:90/92 or 218/226.

In a second aspect, the invention features an antibody or antigen-binding fragment of an antibody comprising a heavy chain CDR3 (HCDR3) domain selected from the group consisting of SEQ ID NO:8, 32, 56, 80, 104, 128, 152, 176, 200, 224, 248, 272, 296, 320, 344, 368, 392, 416, 440, 464, 488, 512, 536, 560, 584, 608, 632, 656, 680, 704 and 728, or a substantially similar sequence thereof having at least 90%, at least 95%, at least 98% or at least 99% sequence identity; and a light chain CDR3 (LCDR3) domain selected from the group consisting of SEQ ID NO:16, 40, 64, 88, 112, 136, 160, 184, 208, 232, 256, 280, 304, 328, 352, 376, 400, 424, 448, 472, 496, 520, 544, 568, 592, 616, 640, 664, 688, 712 and 736, or substantially similar sequences thereof having at least 90%, at least 95%, at least 98% or at least 99% sequence identity. In one embodiment, the HCDR3/LCDR3 sequence pair is selected from the group consisting of SEQ ID NO:56/64, 80/88, 128/136, 224/232, 248/256 and 320/328. In a more specific embodiment, the HCDR3/LCDR3 sequence pair comprises SEQ ID NO:80/88 or 224/232.

In a further embodiment, the invention comprising an antibody or fragment thereof further comprising a heavy chain CDR1 (HCDR1) domain selected from the group consisting of SEQ ID NO:4, 28, 52, 76, 100, 124, 148, 172, 196, 220, 244, 268, 292, 316, 340, 364, 388, 412, 436, 460, 484, 508, 532, 556, 580, 604, 628, 652, 676, 700 and 724, or a substantially similar sequence thereof having at least 90%, at least 95%, at least 98% or at least 99% sequence identity; a heavy chain CDR2 (HCDR2) domain selected from the group consisting of SEQ ID NO:6, 30, 54, 78, 102, 126, 150, 174, 198, 222, 246, 270, 294, 318, 342, 366, 390, 414, 438, 462, 486, 510, 534, 558, 582, 606, 630, 654, 678, 702 and 726, or a substantially similar sequence thereof having at least 90%, at least 95%, at least 98% or at least 99% sequence identity; a light chain CDR1 (LCDR1) domain selected from the group consisting of SEQ ID NO:12, 36, 60, 84, 108, 132, 156, 180, 204, 228, 252, 276, 300, 324, 348, 372, 396, 420, 444, 468, 492, 516, 540, 564, 588, 612, 636, 660, 684, 708 and 732, or a substantially similar sequence thereof having at least 90%, at least 95%, at least 98% or at least 99% sequence identity; and a light chain CDR2 (LCDR2) domain selected from the group consisting of SEQ ID NO:14, 38, 62, 86, 110, 134, 158, 182, 206, 230, 254, 278, 302, 326, 350, 374, 398, 422, 446, 470, 494, 518, 542, 566, 590, 614, 638, 662, 686, 710 and 734, or a substantially similar sequence thereof having at least 90%, at least 95%, at least 98% or at least 99% sequence identity. In one embodiment, the heavy and light chain CDR sequences comprise a sequence selected from the group consisting of SEQ ID NO:52, 54, 56, 60, 62, 64; 76, 78, 80, 84, 86, 88; 124, 126, 128, 132, 134, 136; 220, 222, 224, 228, 230, 232; 244, 246, 248, 252, 254, 256; and 316, 318, 320, 324, 326, 328. In more specific embodiments, the CDR sequences comprise SEQ ID NO: 76, 78, 80, 84, 86, 88; or 220, 222, 224, 228, 230, 232.

In a related embodiment, the invention comprises an antibody or antigen-binding fragment of an antibody which specifically binds hPCSK9, wherein the antibody or fragment comprises heavy and light chain CDR domains contained within heavy and light chain sequence pairs selected from the group consisting of SEQ ID NO: 2/10, 18/20, 22/24, 26/34, 42/44, 46/48, 50/58, 66/68, 70/72, 74/82, 90/92, 94/96, 98/106, 114/116, 118/120, 122/130, 138/140, 142/144, 146/154, 162/164, 166/168, 170/178, 186/188, 190/192, 194/202, 210/212, 214/216, 218/226, 234/236, 238/240, 242/250, 258/260, 262/264, 266/274, 282/284, 286/288, 290/298, 306/308, 310/312, 314/322, 330/332, 334/336, 338/346, 354/356, 358/360, 362/370, 378/380, 382/384, 386/394, 402/404, 406/408, 410/418, 426/428, 430/432, 434/442, 450/452, 454/456, 458/466, 474/476, 478/480, 482/490, 498/500, 502/504, 506/514, 522/524, 526/528, 530/538, 546/548, 550/552, 554/562, 570/572, 574/576, 578/586, 594/596, 598/600, 602/610, 618/620, 622/624, 626/634, 642/644, 646/648, 650/658, 666/668, 670/672, 674/682, 690/692, 694/696, 698/706, 714/716, 718/720, 722/730, 738/740 and 742/744. In one embodiment, the CDR sequences are contained within HCVR and LCVR selected from the amino acid sequence pairs of SEQ ID NO: 50/58, 66/68, 70/72, 74/82, 90/92, 94/96, 122/130, 138/140, 142/144, 218/226, 234/236, 238/240, 242/250, 258/260, 262/264, 314/322, 330/332 and 334/336. In more specific embodiments, the CDR sequences are comprised within HCVR/LCVR sequences selected from SEQ ID NO: 90/92 or 218/226.

In one embodiment, the invention provides fully human monoclonal antibody or antigen-binding fragment thereof that specifically bind hPCSK9 and neutralize PCSK9 activity, wherein the antibody or fragment thereof exhibits one or more of the following characteristics: (i) capable of reducing serum total cholesterol at least about 25-35% and sustaining the reduction over at least a 24 day period relative to a predose level, preferably the reduction in serum total cholesterol is at least about 30-40%; (ii) capable of reducing serum LDL cholesterol at least about 65-80% and sustaining the reduction over at least a 24 day period relative to a predose level; (iii) capable of reducing serum triglyceride at least about 25-40% relative to predose level; (iv) does not reduce serum HDL cholesterol or reduces serum HDL cholesterol no more than 5% relative to predose level; (v) binds an epitope comprising amino acid residue 238 of hPCSK9 (SEQ ID NO:755); (vi) exhibits an enhanced binding affinity ($K_D$) for hPCSK9 at pH 5.5 relative to the $K_D$ at pH 7.4, as measured by plasmon surface resonance, wherein the enhanced affinity is at least about a 20- to 50-fold increase in affinity; (vii) binds human, human GOF mutation D374Y, cynomolgus monkey, rhesus monkey, mouse, rat and hamster PCSK9; (viii) comprises heavy and light chain CDR3 sequences comprising SEQ ID NO:80 and 88; and (ix) comprises CDR sequences from SEQ ID NO:90 and 92.

In one embodiment, the invention provides fully human monoclonal antibody or antigen-binding fragment thereof that specifically bind human PCSK9 (hPCSK9) and neutralize PCSK9 activity, wherein the antibody or fragment thereof exhibits one or more of the following characteristics: (i) capable of reducing serum LDL cholesterol at least about 40-70% and sustaining the reduction over at least a 60 or 90 day period relative to a predose level; (ii) capable of reducing serum triglyceride at least about 25-40% relative to predose level; (iii) does not reduce serum HDL cholesterol or reduces serum HDL cholesterol no more than 5% relative to predose level; (iv) binds an epitope comprising amino acid residue 366 of hPCSK9 (SEQ ID NO:755); (v) does not exhibit an enhanced binding affinity for PCSK9 at an acidic pH relative to a neutral pH, as measured by surface plasmon resonance; (vi) binds human and monkey PCSK9, but does not bind mouse, rat or hamster PCSK9; (vii) comprises heavy and light chain CDR3 sequences comprising SEQ ID NO:224 and 232; and (viii) comprises CDR sequences from SEQ ID NO:218 and 226.

In a third aspect, the invention provides nucleic acid molecules encoding anti-PCSK9 antibodies or fragments thereof. Recombinant expression vectors carrying the nucleic acids of the invention, and host cells into which such vectors have been introduced, are also encompassed by the invention, as are methods of producing the antibodies by culturing the host cells under conditions permitting production of the antibodies, and recovering the antibodies produced.

In one embodiment, the invention provides an antibody or fragment thereof comprising a HCVR encoded by a nucleic acid sequence selected from the group consisting of SEQ ID NO: 1, 17, 21, 25, 41, 45, 49, 65, 69, 73, 89, 93, 97, 113, 117, 121, 137, 141, 145, 161, 165, 169, 185, 189, 193, 209, 213, 217, 233, 237, 241, 257, 261, 265, 281, 285, 289, 305, 309, 313, 329, 333, 337, 353, 357, 361, 377, 381, 385, 401, 405, 409, 425, 429, 433, 449, 453, 457, 473, 477, 481, 497, 501, 505, 521, 525, 529, 545, 549, 553, 569, 573, 577, 593, 597, 601, 617, 621, 625, 641, 645, 649, 665, 669, 673, 689, 693, 697, 713, 717, 721, 737 and 741, or a substantially identical sequence having at least 90%, at least 95%, at least 98%, or at least 99% homology thereof. In one embodiment, the HCVR is encoded by a nucleic acid sequence selected from the group consisting of SEQ ID NO: 49, 65, 69, 73, 89, 93, 121, 137, 141, 217, 233, 237, 241, 257, 261, 313, 329 and 333. In more specific embodiments, the HCVR is encoded by a nucleic acid sequence selected from the group consisting of SEQ ID NO: 89 and 217.

In one embodiment, the antibody or fragment thereof further comprises a LCVR encoded by a nucleic acid sequence selected from the group consisting of SEQ ID NO: 9, 19, 23, 33, 43, 47, 57, 67, 71, 81, 91, 95, 105, 115, 119, 129, 139, 143, 153, 163, 167, 177, 187, 191, 201, 211, 215, 225, 235, 239, 249, 259, 263, 273, 283, 287, 297, 307, 311, 321, 331, 335, 345, 355, 359, 369, 379, 383, 393, 403, 407, 417, 427, 431, 441, 451, 455, 465, 475, 479, 489, 499, 503, 513, 523, 527, 537, 547, 551, 561, 571, 575, 585, 595, 599, 609, 619, 623, 633, 643, 647, 657, 667, 671, 681, 691, 695, 705, 715, 719, 729, 739 and 743, or a substantially identical sequence having at least 90%, at least 95%, at least 98%, or at least 99% homology thereof. In one embodiment, the LCVR is encoded by a nucleic acid sequence selected from the group consisting of SEQ ID NO: 57, 67, 71, 81, 91, 95, 129, 139, 143, 225, 235, 239, 249, 259, 263, 321, 331 and 335. In more specific embodiments, the LCVR is encoded by a nucleic acid sequence selected from the group consisting of SEQ ID NO: 91 and 225.

In one embodiment, the invention features an antibody or antigen-binding fragment of an antibody comprising a HCDR3 domain encoded by a nucleotide sequence selected from the group consisting of SEQ ID NO:7, 31, 55, 79, 103, 127, 151, 175, 199, 223, 247, 271, 295, 319, 343, 367, 391, 415, 439, 463, 487, 511, 535, 559, 583, 607, 631, 655, 679, 703 and 727, or a substantially identical sequence having at least 90%, at least 95%, at least 98%, or at least 99% homology thereof; and a LCDR3 domain encoded by a nucleotide sequence selected from the group consisting of SEQ ID NO: 15, 39, 63, 87, 111, 135, 159, 183, 207, 231, 255, 279, 303, 327, 351, 375, 399, 423, 447, 471, 495, 519, 543, 567, 591, 615, 639, 663, 687, 711 and 735, or a substantially identical sequence having at least 90%, at least 95%, at least 98%, or at least 99% homology thereof. In one embodiment, the HCDR3 and LCDR3 comprise a sequence pair encoded by the nucleic acid sequence of SEQ ID NO: 55/63, 79/87, 127/135, 223/231, 247/255 and 319/327, respectively. In more specific embodiments, the HCDR3 and LCDR3 comprise a sequence pair encoded by the nucleic acid sequence of SEQ ID NO: 79/87 and 223/231.

In a further embodiment, the antibody or fragment thereof further comprises, a HCDR1 domain encoded by a nucleotide sequence selected from the group consisting of SEQ ID NO: 3, 27, 51, 75, 99, 123, 147, 171, 195, 219, 243, 267, 291, 315, 339, 363, 387, 411, 435, 459, 483, 507, 531, 555, 579, 603, 627, 651, 675, 699 and 723, or a substantially identical sequence having at least 90%, at least 95%, at least 98%, or at least 99% homology thereof; a HCDR2 domain encoded by a nucleotide sequence selected from the group consisting of SEQ ID NO:5, 29, 53, 77, 101, 125, 149, 173, 197, 221, 245, 269, 293, 317, 341, 365, 389, 413, 437, 461, 485, 509, 533, 557, 581, 605, 629, 653, 677, 701 and 725, or a substantially identical sequence having at least 90%, at least 95%, at least 98%, or at least 99% homology thereof; a LCDR1 domain encoded by a nucleotide sequence selected from the group consisting of SEQ ID NO: 11, 35, 59, 83, 107, 131, 155, 179, 203, 227, 251, 275, 299, 323, 347, 371, 395, 419, 443, 467, 491, 515, 539, 563, 587, 611, 635, 659, 683, 707 and 731, or a substantially identical sequence having at least 90%, at least 95%, at least 98%, or at least 99% homology thereof; and a LCDR2 domain encoded by a nucleotide sequence selected from the group consisting of SEQ ID NO: 13, 37, 61, 85, 109, 133, 157, 181, 205, 229, 253, 277, 301, 325, 349, 373, 397, 421, 445, 469, 493, 517, 541, 565, 589, 613, 637, 661, 685, 709 and 733, or a substantially identical sequence having at least 90%, at least 95%, at least 98%, or at least 99% homology thereof. In one embodiment, the heavy and light chain CDR sequences are encoded by the nucleic acid sequences of SEQ ID NO: 51, 53, 55, 59, 61, 63; 75, 77, 79, 83, 85, 87; 123, 125, 127, 131, 133, 135; 219, 221, 223, 227, 229, 231; 243, 245, 247, 251, 253, 255; and 315, 317, 319, 323, 325, 327. In more specific embodiments, the heavy and light chain CDR sequences are encoded by the nucleic acid sequences of SEQ ID NO: 75, 77, 79, 83, 85, 87; and 219, 221, 223, 227, 229, 231.

In a fourth aspect, the invention features an isolated antibody or antigen-binding fragment thereof that specifically binds hPCSK9, comprising a HCDR3 and a LCDR3, wherein HCDR3 comprises an amino acid sequence of the formula $X^1$-$X^2$-$X^3$-$X^4$-$X^5$-$X^6$-$X^7$-$X^8$-$X^9$-$X^{10}$-$X^{11}$-$X^{12}$-$X^{13}$-$X^{14}$-$X^{15}$-$X^{16}$-$X^{17}$-$X^{18}$-$X^{19}$-$X^{20}$ (SEQ ID NO:747), wherein $X^1$ is Ala, $X^2$ is Arg or Lys, $X^3$ is Asp, $X^4$ is Ser or Ile, $X^5$ is Asn or Val, $X^6$ is Leu or Trp, $X^7$ is Gly or Met, $X^8$ is Asn or Val, $X^9$ is Phe or Tyr, $X^{10}$ is Asp, $X^{11}$ is Leu or Met, $X^{12}$ is Asp or absent, $X^{13}$ is Tyr or absent, $X^{14}$ is Tyr or absent, $X^{15}$ is Tyr or absent, $X^{16}$ is Tyr or absent, $X^{17}$ is Gly or absent, $X^{18}$ is Met or absent, $X^{19}$ is Asp or absent, and $X^{20}$ is Val or absent; and LCDR3 comprises an amino acid sequence of the formula $X^1$-$X^2$-$X^3$-$X^4$-$X^5$-$X^6$-$X^7$-$X^8$-$X^9$ (SEQ ID NO:750), wherein $X^1$ is Gin or Met, $X^2$ is Gin, $X^3$ is Tyr or Thr, $X^4$ is Tyr or Leu, $X^5$ is Thr or Gin, $X^6$ is Thr, $X^7$ is Pro, $X^8$ is Tyr or Leu, and $X^9$ is Thr.

In a further embodiment, the antibody or fragment thereof further comprise a HCDR1 sequence of the formula $X^1$-$X^2$-$X^3$-$X^4$-$X^5$-$X^6$-$X^7$-$X^8$ (SEQ ID NO:745), wherein $X^1$ is Gly, $X^2$ is Phe, $X^3$ is Thr, $X^4$ is Phe, $X^5$ is Ser or Asn, $X^6$ is Ser or Asn, $X^7$ is Tyr or His, and $X^8$ is Ala or Trp; a HCDR2 sequence of the formula $X^1$-$X^2$-$X^3$-$X^4$-$X^5$-$X^6$-$X^7$-$X^8$ (SEQ ID NO:746), wherein $X^1$ is Ile, $X^2$ is Ser or Asn, $X^3$ is Gly or Gin, $X^4$ is Asp or Ser, $X^5$ is Gly, $X^6$ is Ser or Gly, $X^7$ is Thr or Glu, and $X^8$ is Thr or Lys; a LCDR1 sequence of the formula $X^1$-$X^2$-$X^3$-$X^4$-$X^5$-$X^6$-$X^7$-$X^8$-$X^9$-$X^{10}$-$X^{11}$-$X^{12}$ (SEQ ID NO:748) wherein $X^1$ is Gln, $X^2$ is Ser, $X^3$ is Val or Leu, $X^4$ is Leu, $X^5$ is His or Tyr, $X^6$ is Arg or Ser, $X^7$ is Ser or Asn, $X^8$ is Asn or Gly, $X^9$ is Asn, $X^{10}$ is Arg or Asn, $X^{11}$ is Asn or Tyr, and $X^{12}$ is Phe or absent; a LCDR2 sequence of the formula $X^1$-$X^2$-$X^3$ (SEQ ID NO:749) wherein $X^1$ is Trp or Leu, $X^2$ is Ala or Gly, and $X^3$ is Ser. FIG. 1 shows the sequence alignment of heavy and light chain variable regions for 316P and 300N mAbs.

In a fifth aspect, the invention features a human anti-PCSK9 antibody or antigen-binding fragment of an antibody comprising a heavy chain variable region (HCVR) encoded by nucleotide sequence segments derived from $V_H$, $D_H$ and $J_H$ germline sequences, and a light chain variable region (LCVR) encoded by nucleotide sequence segments derived from $V_K$ and $J_K$ germline sequences, wherein the germline sequences are (a) $V_H$ gene segment 3-23, $D_H$ gene segment 7-27, $J_H$ gene segment 2, $V_K$ gene segment 4-1 and $J_K$ gene segment 2; or (b) $V_H$ gene segment 3-7, $D_H$ gene segment 2-8, $J_H$ gene segment 6, $V_K$ gene segment 2-28 and $J_K$ gene segment 4.

In a sixth aspect, the invention features an antibody or antigen-binding fragment thereof that binds to a PCSK9 protein of SEQ ID NO:755, wherein the binding of the antibody or fragment thereof to a variant PCSK9 protein is less than 50% of the binding between the antibody or fragment thereof and the PCSK9 protein of SEQ ID NO:755. In specific embodiment, the antibody or fragment thereof binds to the variant PCSK9 protein with a binding affinity ($K_D$) which is less than about 50%, less than about 60%, less than about 70%, less than about 80%, less than about 90% or less than about 95% compared to the binding to PCSK9 (SEQ ID NO:755).

In one embodiment, the variant PCSK9 protein comprises at least one mutation at position 238 of SEQ ID NO:755. In a more specific embodiment, the mutation is D238R. In one embodiment, the antibody or antibody fragment binding affinity for the variant PCSK9 protein is at least 90% less relative to the wildtype protein of SEQ ID NO:755, wherein the variant protein comprises a mutation at residue 238. In one embodiment, the antibody or antibody fragment binding affinity for the variant PCSK9 protein is at least 80% less relative to the wildtype protein of SEQ ID NO:755, wherein the variant protein comprises a mutation at one or more of residue 153, 159, 238 and 343. In a more specific embodiment, the mutation is one of S153R, E159R, D238R and D343R.

In one embodiment, the variant PCSK9 protein comprises at least one mutation at position 366 of SEQ ID NO:755. In a more specific embodiment, the mutation is E366K. In one embodiment, the antibody or antibody fragment binding affinity for the variant PCSK9 protein is at least 95% less relative to the wildtype protein of SEQ ID NO:755, wherein the variant protein comprises a mutation at residue 366. In one embodiment, the antibody or antibody fragment binding affinity for the variant PCSK9 protein is at least 90% less relative to the wildtype protein of SEQ ID NO:755, wherein the variant protein comprises a mutation at one or more of residue 147, 366 and 380. In a more specific embodiment, the mutation is one of S147F, E366K and V380M. In one embodiment, the antibody or antibody fragment binding affinity for the variant PCSK9 protein is at least 80% less relative to the wildtype protein of SEQ ID NO:755, wherein the variant protein comprises a mutation at one or more of residue 147, 366 and 380. In a more specific embodiment, the mutation is one of S147F, E366K and V380M.

The invention encompasses anti-PCSK9 antibodies having a modified glycosylation pattern. In some applications, modification to remove undesirable glycosylation sites may be useful, or e.g., removal of a fucose moiety to increase antibody dependent cellular cytotoxicity (ADCC) function (see Shield et al. (2002) JBC 277:26733). In other applications, modification of galactosylation can be made in order to modify complement dependent cytotoxicity (CDC).

In a seventh aspect, the invention features a pharmaceutical composition comprising a recombinant human antibody or fragment thereof that specifically binds hPCSK9 and a pharmaceutically acceptable carrier. In one embodiment, the invention features a composition that is a combination of an antibody or antigen-binding fragment of an antibody of the invention, and a second therapeutic agent. The second therapeutic agent may be any agent that is advantageously combined with the antibody or fragment thereof of the invention, for example, an agent capable of inducing a cellular depletion of cholesterol synthesis by inhibiting 3-hydroxy-3-methylglutaryl (HMG)-coenzyme A (CoA) reductase, such as, for example, cerovastatin, atorvastatin, simvastatin, pitavastin, rosuvastatin, fluvastatin, lovastatin, pravastatin, etc.; capable of inhibiting cholesterol uptake and or bile acid re-absorption; capable of increasing lipoprotein catabolism (such as niacin); and/or activators of the LXR transcription factor that plays a role in cholesterol elimination such as 22-hydroxycholesterol.

In an eighth aspect, the invention features methods for inhibiting hPCSK9 activity using the anti-PCSK9 antibody or antigen-binding portion of the antibody of the invention, wherein the therapeutic methods comprise administering a therapeutically effective amount of a pharmaceutical composition comprising an antibody or antigen-binding fragment of an antibody of the invention. The disorder treated is any disease or condition that is improved, ameliorated, inhibited or prevented by removal, inhibition or reduction of PCSK9 activity. Specific populations treatable by the therapeutic methods of the invention include subjects indicated for LDL apheresis, subjects with PCSK9-activating mutations (gain of function mutations, "GOF"), subjects with heterozygous Familial Hypercholesterolemia (heFH); subjects with primary hypercholesterolemia who are statin intolerant or statin uncontrolled; and subjects at risk for developing hypercholesterolemia who may be preventably treated. Other indications include dyslipidemia associated with secondary causes such as Type 2 diabetes mellitus, cholestatic liver diseases (primary biliary cirrhosis), nephrotic syndrome, hypothyroidism, obesity; and the prevention and treatment of atherosclerosis and cardiovascular diseases.

In specific embodiments of the method of the invention, the anti-hPCSK9 antibody or antibody fragment of the invention is useful to reduce elevated total cholesterol, non-HDL cholesterol, LDL cholesterol, and/or apolipoprotein B (apolipoprotein B100).

The antibody or antigen-binding fragment of the invention may be used alone or in combination with a second agent, for example, an HMG-CoA reductase inhibitor and/or other lipid lowering drugs.

Other embodiments will become apparent from a review of the ensuing detailed description.

BRIEF DESCRIPTION OF THE FIGURES

FIG. 1. Sequence comparison tables of heavy chain (A) and light chain (B) variable regions and CDRs of antibodies H1H316P and H1M300N.

DETAILED DESCRIPTION

Figure 2:
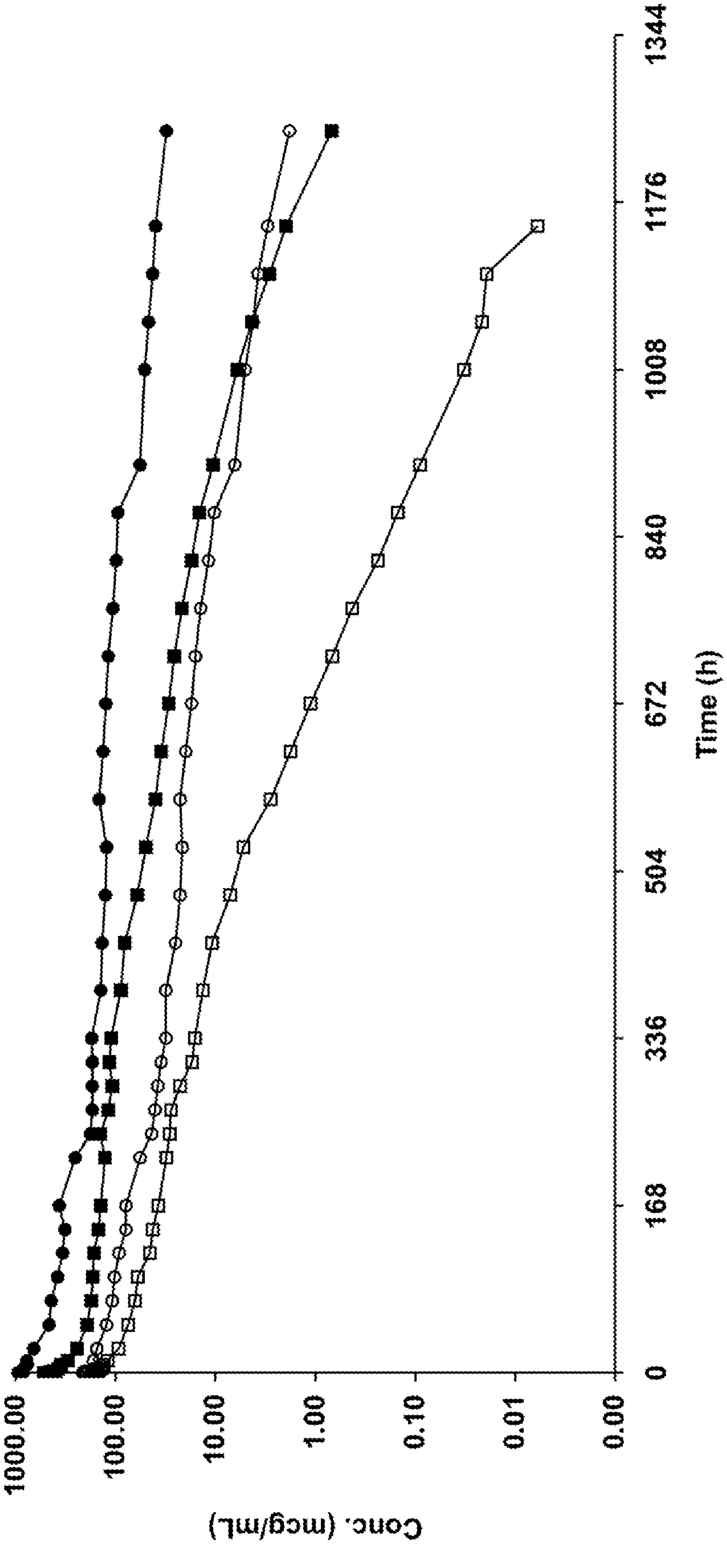
FIG. 2. Antibody concentrations in serum over time. 316P 5 mg/kg (□); 300N 5 mg/kg (○); 316P 15 mg/kg (■); 300N 15 mg/kg (●).
Figure 3:
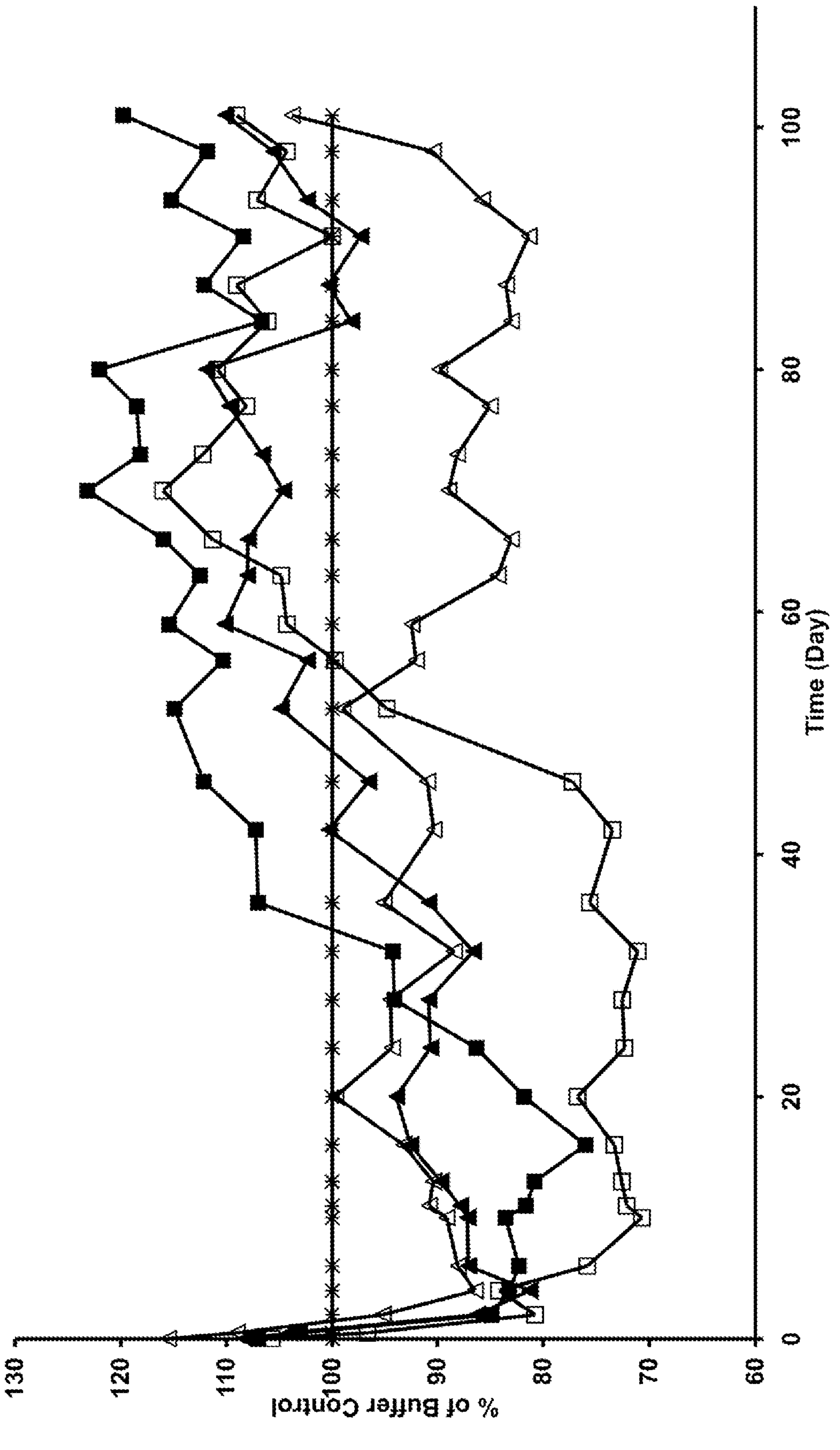
FIG. 3. Serum total cholesterol level as a percentage of change over buffer control. Buffer control (*) 316P 5 mg/kg (■); 300N 5 mg/kg (▲); 316P 15 mg/kg (□); 300N 15 mg/kg (Δ).
Figure 4:
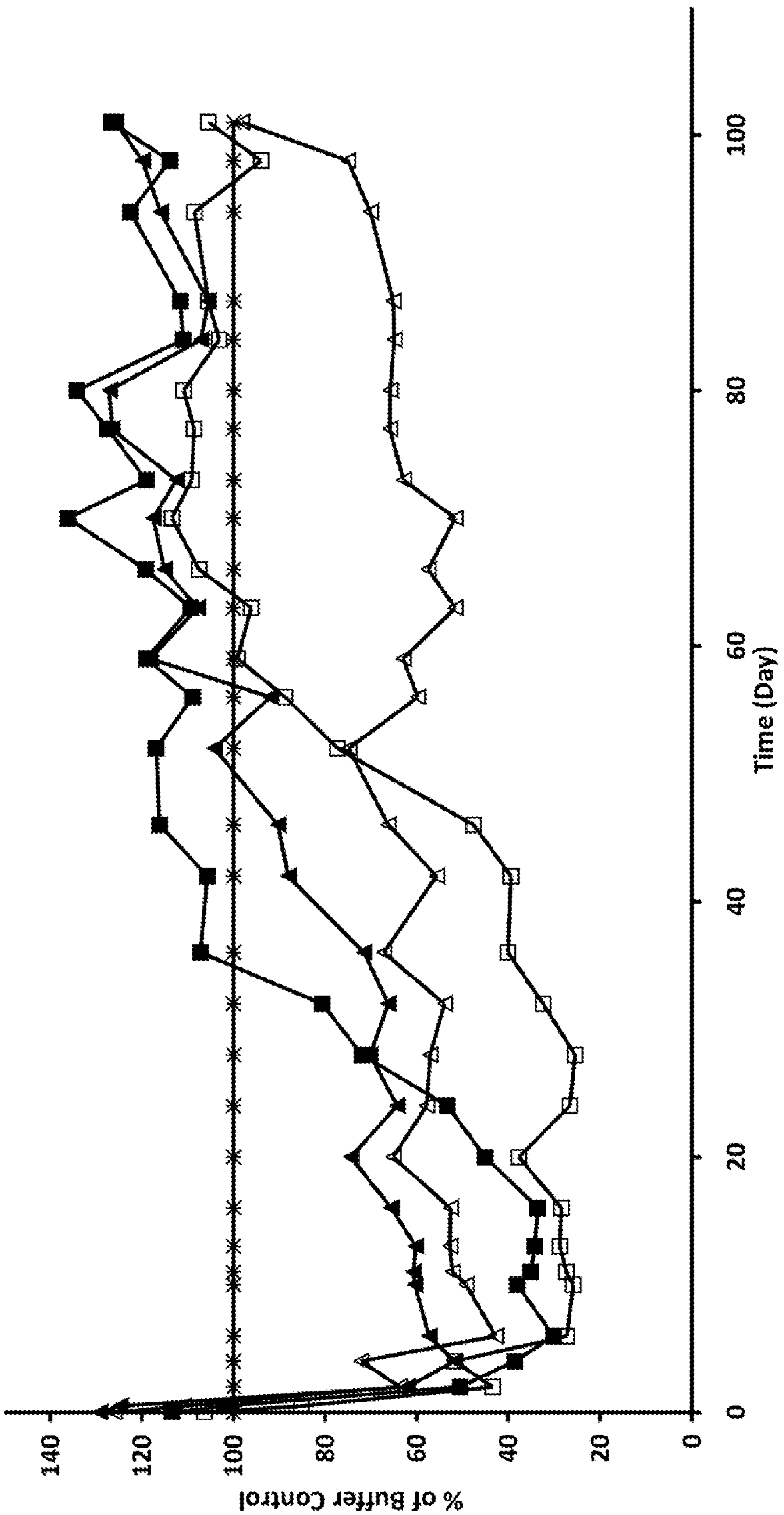
FIG. 4. Serum LDL cholesterol level as a percentage of change over buffer control: Buffer Control (*); 316P 5 mg/kg (■); 300N 5 mg/kg (▲); 316P 15 mg/kg (□); 300N 15 mg/kg (Δ).
Figure 5:
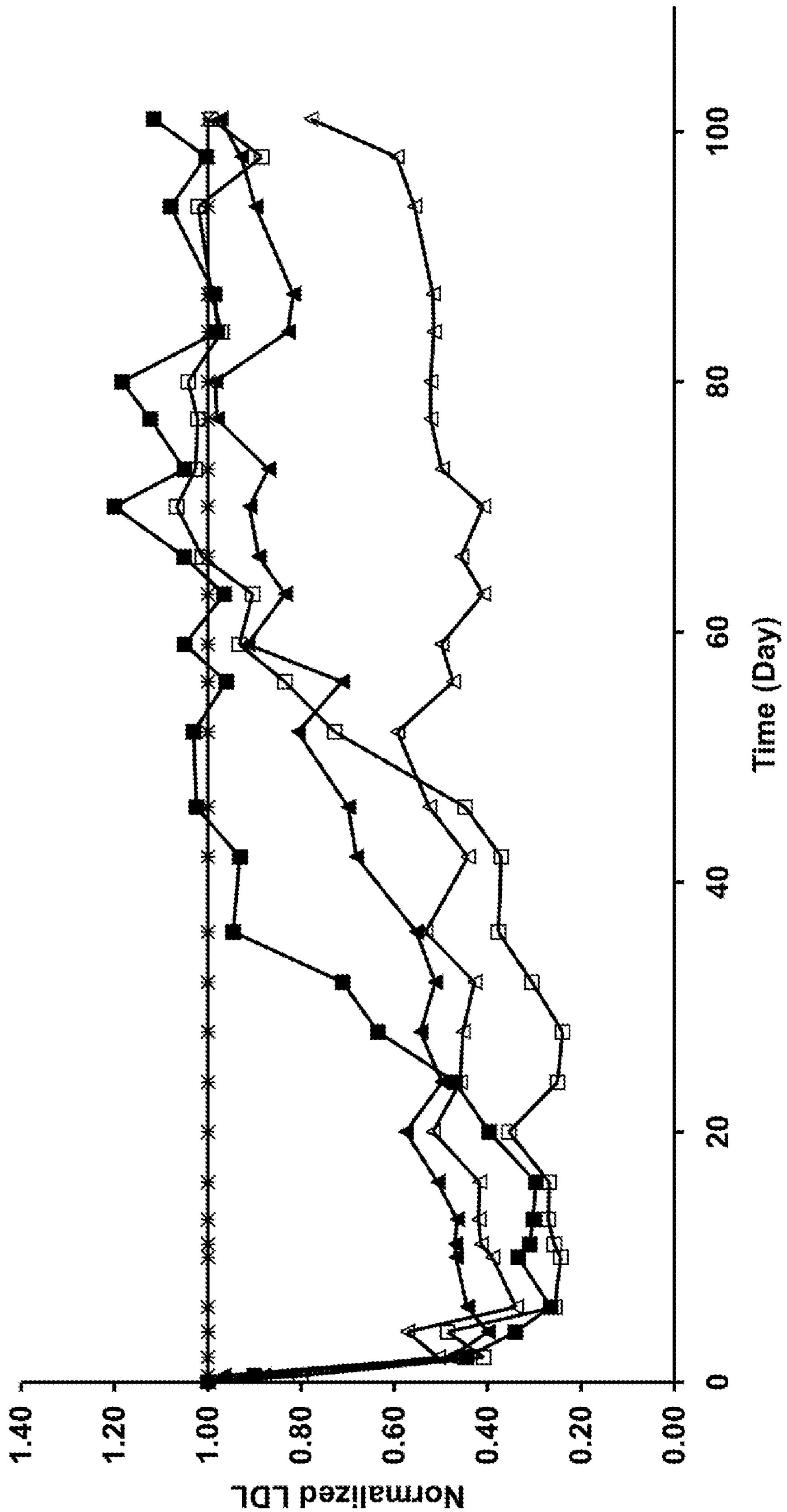
FIG. 5. Serum LDL cholesterol level normalized to buffer control. Buffer control (*); 316P 5 mg/kg (■); 300N 5 mg/kg (Δ); 316P 15 mg/kg (□); 300N 15 mg/kg (Δ).

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, preferred methods and materials are now described. All publications mentioned herein are incorporated herein by reference in their entirety.

Definitions

The term "human proprotein convertase subtilisin/kexin type 9" or "hPCSK9", as used herein, refers to hPCSK9 having the nucleic acid sequence shown in SEQ ID NO:754 and the amino acid sequence of SEQ ID NO:755, or a biologically active fragment thereof.

The term "antibody", as used herein, is intended to refer to immunoglobulin molecules comprised of four polypeptide chains, two heavy (H) chains and two light (L) chains inter-connected by disulfide bonds. Each heavy chain is comprised of a heavy chain variable region ("HCVR" or "VH") and a heavy chain constant region (comprised of domains CH1, CH2 and CH3). Each light chain is comprised of a light chain variable region ("LCVR or "VL") and a light chain constant region (CL). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The term "human antibody", as used herein, is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences.

The term "specifically binds," or the like, means that an antibody or antigen-binding fragment thereof forms a complex with an antigen that is relatively stable under physiologic conditions. Specific binding can be characterized by an equilibrium dissociation constant of at least about $1\times10^{-6}$ M or less (e.g., a smaller $K_D$ denotes a tighter binding). Methods for determining whether two molecules specifically bind are well known in the art and include, for example, equilibrium dialysis, surface plasmon resonance, and the like. An isolated antibody that specifically binds hPCSK9 may, however, exhibit cross-reactivity to other antigens such as PCSK9 molecules from other species. Moreover, multi-specific antibodies (e.g., bispecifics) that bind to hPCSK9 and one or more additional antigens are nonetheless considered antibodies that "specifically bind" hPCSK9, as used herein.

The term "high affinity" antibody refers to those mAbs having a binding affinity to hPCSK9 of at least $10^{-10}$ M; preferably $10^{-11}$ M; even more preferably $10^{-12}$ M, as measured by surface plasmon resonance, e.g., BIACORE™ or solution-affinity ELISA.

By the term "slow off rate", "Koff" or "kd" is meant an antibody that dissociates from hPCSK9 with a rate constant of $1\times10^{-3}$ $s^{-1}$ or less, preferably $1\times10^{-4}$ $s^{-1}$ or less, as determined by surface plasmon resonance, e.g., BIACORE™.

The term "antigen-binding portion" of an antibody (or simply "antibody fragment"), as used herein, refers to one or more fragments of an antibody that retain the ability to specifically bind to hPCSK9. An antibody fragment may include a Fab fragment, a $F(ab')_2$ fragment, a Fv fragment, a dAb fragment, a fragment containing a CDR, or an isolated CDR.

The specific embodiments, antibody or antibody fragments of the invention may be conjugated to a therapeutic moiety ("immunoconjugate"), such as a cytotoxin, a chemotherapeutic drug, an immunosuppressant or a radioisotope.

An "isolated antibody", as used herein, is intended to refer to an antibody that is substantially free of other mAbs having different antigenic specificities (e.g., an isolated antibody that specifically binds hPCSK9 is substantially free of mAbs that specifically bind antigens other than hPCSK9). An isolated antibody that specifically binds hPCSK9 may, however, have cross-reactivity to other antigens, such as PCSK9 molecules from other species.

A "neutralizing antibody", as used herein (or an "antibody that neutralizes PCSK9 activity"), is intended to refer to an antibody whose binding to hPCSK9 results in inhibition of at least one biological activity of PCSK9. This inhibition of the biological activity of PCSK9 can be assessed by measuring one or more indicators of PCSK9 biological activity by one or more of several standard in vitro or in vivo assays known in the art (see examples below).

The term "surface plasmon resonance", as used herein, refers to an optical phenomenon that allows for the analysis of real-time biospecific interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope" is a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% A of the nucleotide bases, as measured by any well-known algorithm of sequence identity, such as FASTA, BLAST or GAP, as discussed below.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions that are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT, which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215: 403 410 and (1997) Nucleic Acids Res. 25:3389 402, each of which is herein incorporated by reference.

In specific embodiments, the antibody or antibody fragment for use in the method of the invention may be monospecific, bispecific, or multispecific. Multispecific antibodies may be specific for different epitopes of one target polypeptide or may contain antigen-binding domains specific for epitopes of more than one target polypeptide. An exemplary bi-specific antibody format that can be used in the context of the present invention involves the use of a first immunoglobulin (Ig) CH3 domain and a second Ig CH3 domain, wherein the first and second Ig CH3 domains differ from one another by at least one amino acid, and wherein at least one amino acid difference reduces binding of the bispecific antibody to Protein A as compared to a bi-specific antibody lacking the amino acid difference. In one embodiment, the first Ig CH3 domain binds Protein A and the second Ig CH3 domain contains a mutation that reduces or abolishes Protein A binding such as an H95R modification (by IMGT exon numbering; H435R by EU numbering). The second CH3 may further comprise an Y96F modification (by IMGT; Y436F by EU). Further modifications that may be found within the second CH3 include: D16E, L18M, N44S, K52N, V57M, and V82I (by IMGT; D356E, L358M, N384S, K392N, V397M, and V422I by EU) in the case of IgG1 mAbs; N44S, K52N, and V82I (IMGT; N384S, K392N, and V422I by EU) in the case of IgG2 mAbs; and Q15R, N44S, K52N, V57M, R69K, E79Q, and V82I (by IMGT; Q355R, N384S, K392N, V397M, R409K, E419Q, and V422I by EU) in the case of IgG4 mAbs. Variations on the bi-specific antibody format described above are contemplated within the scope of the present invention.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

Preparation of Human Antibodies

Methods for generating human antibodies in transgenic mice are known (see for example, U.S. Pat. No. 6,596,541, Regeneron Pharmaceuticals, VELOCIMMUNE™). The VELOCIMMUNE™ technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody. In specific embodiment, the cell is a CHO cell.

Antibodies may be therapeutically useful in blocking a ligand-receptor interaction or inhibiting receptor component interaction, rather than by killing cells through fixation of complement and participation in complement-dependent cytotoxicity (CDC), or killing cells through antibody-dependent cell-mediated cytotoxicity (ADCC). The constant region of an antibody is thus important in the ability of an antibody to fix complement and mediate cell-dependent cytotoxicity. Thus, the isotype of an antibody may be selected on the basis of whether it is desirable for the antibody to mediate cytotoxicity.

Human antibodies can exist in two forms that are associated with hinge heterogeneity. In one form, an antibody molecule comprises a stable four-chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, CH2, or CH3 region, which may be desirable, for example, in production, to improve the yield of the desired antibody form.

Generally, a VELOCIMMUNE™ mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. As described below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4 (for example, SEQ ID NO:751, 752, 753). While the constant region selected may vary according to specific use, high affinity antigen binding and target specificity characteristics reside in the variable region.

Epitope Mapping and Related Technologies

To screen for antibodies that bind to a particular epitope (e.g., those which block binding of IgE to its high affinity receptor), a routine cross-blocking assay such as that described *Antibodies*, Harlow and Lane (Cold Spring Harbor Press, Cold Spring Harb., N.Y.) can be performed. Other methods include alanine scanning mutants, peptide blots (Reineke (2004) Methods Mol Biol 248:443-63) (herein specifically incorporated by reference in its entirety), or peptide cleavage analysis. In addition, methods such as epitope excision, epitope extraction and chemical modification of antigens can be employed (Tomer (2000) Protein Science 9: 487-496) (herein specifically incorporated by reference in its entirety).

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (US 2004/0101920, herein specifically incorporated by reference in its entirety). Each category may reflect a unique epitope either distinctly different from or partially overlapping with epitope represented by another category. This technology allows rapid filtering of genetically identical mAbs, such that characterization can be focused on genetically distinct mAbs. When applied to hybridoma screening, MAP may facilitate identification of rare hybridoma clones that produce mAbs having the desired characteristics. MAP may be used to sort the anti-PCSK9 mAbs of the invention into groups of mAbs binding different epitopes.

In various embodiments, the anti-hPCSK9 antibody or antigen-binding fragment of an antibody binds an epitope within the catalytic domain, which is about 153 to 425 of SEQ ID NO:755); more specifically, an epitope from about 153 to about 250 or from about 250 to about 425; more specifically, the antibody or antibody fragment of the invention binds an epitope within the fragment from about 153 to about 208, from about 200 to about 260, from about 250 to about 300, from about 275 to about 325, from about 300 to about 360, from about 350 to about 400, and/or from about 375 to about 425.

In various embodiments, the anti-hPCSK9 antibody or antigen-binding fragment of an antibody binds an epitope within the propeptide domain (residues 31 to 152 of SEQ ID NO:755); more specifically, an epitope from about residue 31 to about residue 90 or from about residue 90 to about residue 152; more specifically, the antibody or antibody fragment of the invention binds an epitope within the fragment from about residue 31 to about residue 60, from about residue 60 to about residue 90, from about residue 85 to about residue 110, from about residue 100 to about residue 130, from about residue 125 to about residue 150, from about residue 135 to about residue 152, and/or from about residue 140 to about residue 152.

In some embodiments, the anti-hPCSK9 antibody or antigen-binding fragment of an antibody binds an epitope within the C-terminal domain, (residues 426 to 692 of SEQ ID NO:755); more specifically, an epitope from about residue 426 to about residue 570 or from about residue 570 to about residue 692; more specifically, the antibody or antibody fragment of the invention binds an epitope within the fragment from about residue 450 to about residue 500, from about residue 500 to about residue 550, from about residue 550 to about residue 600, and/or from about residue 600 to about residue 692.

In some embodiments, the antibody or antibody fragment binds an epitope which includes more than one of the enumerated epitopes within the catalytic, propeptide or C-terminal domain, and/or within two or three different domains (for example, epitopes within the catalytic and C-terminal domains, or within the propeptide and catalytic domains, or within the propeptide, catalytic and C-terminal domains.

In some embodiments, the antibody or antigen-binding fragment binds an epitope on hPCSK9 comprising amino acid residue 238 of hPCSK9 (SEQ ID NO:755). Experimental results (Table 27) show that when D238 was mutated, the $K_D$ of mAb 316P exhibited >400-fold reduction in binding affinity (~$1\times10^{-9}$ M to ~$410\times10^{-9}$ M) and $T_{1/2}$ decreased >30-fold (from ~37 to ~1 min). In a specific embodiment, the mutation was D238R. In specific embodiments, the antibody or antigen-binding fragment of the invention binds an epitope of hPCSK9 comprising two or more of amino acid residues at positions 153, 159, 238 and 343.

As shown below, a mutation in amino acid residue 153, 159 or 343 resulted in about a 5- to 10-fold decrease in affinity or similar shortening in $T_{1/2}$. In specific embodiments, the mutation was S153R, E159R and/or D343R.

In some embodiments, the antibody or antigen-binding fragment binds an epitope on hPCSK9 comprising amino acid residue 366 of hPCSK9 (SEQ ID NO:755). Experimental results (Table 27) show that when E366 was mutated, the affinity of mAb 300N exhibited about 50-fold decrease (~$0.7\times10^{-9}$M to ~$36\times10^{-9}$M) and a similar shortening in $T_{1/2}$ (from ~120 to ~2 min). In a specific embodiment, the mutation is E366K.

The present invention includes anti-PCSK9 antibodies that bind to the same epitope as any of the specific exemplary antibodies described herein. Likewise, the present invention also includes anti-PCSK9 antibodies that compete for binding to PCSK9 or a PCSK9 fragment with any of the specific exemplary antibodies described herein.

One can easily determine whether an antibody binds to the same epitope as, or competes for binding with, a reference anti-PCSK9 antibody by using routine methods known in the art. For example, to determine if a test antibody binds to the same epitope as a reference anti-PCSK9 antibody of the invention, the reference antibody is allowed to bind to a PCSK9 protein or peptide under saturating conditions. Next, the ability of a test antibody to bind to the PCSK9 molecule is assessed. If the test antibody is able to bind to PCSK9 following saturation binding with the reference anti-PCSK9 antibody, it can be concluded that the test antibody binds to a different epitope than the reference anti-PCSK9 antibody. On the other hand, if the test antibody is not able to bind to the PCSK9 molecule following saturation binding with the reference anti-PCSK9 antibody, then the test antibody may bind to the same epitope as the epitope bound by the reference anti-PCSK9 antibody of the invention.

To determine if an antibody competes for binding with a reference anti-PCSK9 antibody, the above-described binding methodology is performed in two orientations: In a first orientation, the reference antibody is allowed to bind to a PCSK9 molecule under saturating conditions followed by assessment of binding of the test antibody to the PCSK9 molecule. In a second orientation, the test antibody is allowed to bind to a PCSK9 molecule under saturating conditions followed by assessment of binding of the reference antibody to the PCSK9 molecule. If, in both orientations, only the first (saturating) antibody is capable of binding to the PCSK9 molecule, then it is concluded that the test antibody and the reference antibody compete for binding to PCSK9. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

In a specific embodiment, the invention comprises an anti-PCSK9 antibody or antigen binding fragment of an antibody that binds an PCSK9 protein of SEQ ID NO:755, wherein the binding between the antibody or fragment thereof to PCSK9 and a variant PCSK9 protein is less than 50% of the binding between the antibody or fragment and the PCSK9 protein of SEQ ID NO:755. In one specific embodiment, the variant PCSK9 protein comprises at least one mutation of a residue at a position selected from the group consisting of 153, 159, 238 and 343. In a more specific embodiment, the at least one mutation is S153R, E159R, D238R, and/or D343R. In another specific embodiment, the variant PCSK9 protein comprises at least one mutation of a residue at a position selected from the group consisting of 366. In one specific embodiment, the variant PCSK9 protein comprises at least one mutation of a residue at a position selected from the group consisting of 147, 366 and 380. In a more specific embodiment, the mutation is S147F, E366K and V380M.

Immunoconjugates

The invention encompasses a human anti-PCSK9 monoclonal antibody conjugated to a therapeutic moiety ("immunoconjugate"), such as a cytotoxin, a chemotherapeutic drug, an immunosuppressant or a radioisotope. Cytotoxin agents include any agent that is detrimental to cells. Examples of suitable cytotoxin agents and chemotherapeutic agents for forming immunoconjugates are known in the art, see for example, WO 05/103081.

Bispecifics

The antibodies of the present invention may be monospecific, bispecific, or multispecific. Multispecific mAbs may be specific for different epitopes of one target polypeptide or may contain antigen-binding domains specific for more than one target polypeptide. See, e.g., Tutt et al. (1991) J. Immunol. 147:60-69. The human anti-PCSK9 mAbs can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment, to produce a bispecific or a multispecific antibody with a second binding specificity.

An exemplary bi-specific antibody format that can be used in the context of the present invention involves the use of a first immunoglobulin (Ig) CH3 domain and a second Ig CH3 domain, wherein the first and second Ig CH3 domains differ from one another by at least one amino acid, and wherein at least one amino acid difference reduces binding of the bispecific antibody to Protein A as compared to a bi-specific antibody lacking the amino acid difference. In one embodiment, the first Ig CH3 domain binds Protein A and the second Ig CH3 domain contains a mutation that reduces or abolishes Protein A binding such as an H95R modification (by IMGT exon numbering; H435R by EU numbering). The second CH3 may further comprise a Y96F modification (by IMGT; Y436F by EU). Further modifications that may be found within the second CH3 include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Bioequivalents

The anti-PCSK9 antibodies and antibody fragments of the present invention encompass proteins having amino acid sequences that vary from those of the described mAbs, but that retain the ability to bind human PCSK9. Such variant mAbs and antibody fragments comprise one or more additions, deletions, or substitutions of amino acids when compared to parent sequence, but exhibit biological activity that is essentially equivalent to that of the described mAbs. Likewise, the anti-PCSK9 antibody-encoding DNA sequences of the present invention encompass sequences that comprise one or more additions, deletions, or substitutions of nucleotides when compared to the disclosed sequence, but that encode an anti-PCSK9 antibody or antibody fragment that is essentially bioequivalent to an anti-PCSK9 antibody or antibody fragment of the invention. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied. In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-PCSK9 antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation.

Treatment Population

The invention provides therapeutic methods for treating a human patient in need of a composition of the invention. While modifications in lifestyle and conventional drug treatment are often successful in reducing cholesterol levels, not all patients are able to achieve the recommended target cholesterol levels with such approaches. Various conditions, such as familial hypercholesterolemia (FH), appear to be resistant to lowering of LDL-C levels in spite of aggressive use of conventional therapy. Homozygous and heterozygous familial hypercholesterolemia (hoFH, heFH) is a condition associated with premature atherosclerotic vascular disease. However, patients diagnosed with hoFH are largely unresponsive to conventional drug therapy and have limited treatment options. Specifically, treatment with statins, which reduce LDL-C by inhibiting cholesterol synthesis and upregulating the hepatic LDL receptor, may have little effect in patients whose LDL receptors are non-existent or defective. A mean LDL-C reduction of only less than about 20% has been recently reported in patients with genotype-confirmed hoFH treated with the maximal dose of statins. The addition of ezetimibe 10 mg/day to this regimen resulted in a total reduction of LDL-C levels of 27%, which is still far from optimal. Likewise, many patients are statin non-responsive, poorly controlled with statin therapy, or cannot tolerate statin therapy; in general, these patients are unable to achieve cholesterol control with alternative treatments. There is a large unmet medical need for new treatments that can address the shortcomings of current treatment options.

Specific populations treatable by the therapeutic methods of the invention include patients indicated for LDL apheresis, subjects with PCSK9-activating (GOF) mutations, heterozygous Familial Hypercholesterolemia (heFH); subjects with primary hypercholesterolemia who are statin intolerant or statin uncontrolled; and subjects at risk for developing hypercholesterolemia who may be preventably treated.

Therapeutic Administration and Formulations

The invention provides therapeutic compositions comprising the anti-PCSK9 antibodies or antigen-binding fragments thereof of the present invention. The administration of therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose may vary depending upon the age and the size of a subject to be administered, target disease, conditions, route of administration, and the like. When the antibody of the present invention is used for treating various conditions and diseases associated with PCSK9, including hypercholesterolemia, disorders associated with LDL and apolipoprotein B, and lipid metabolism disorders, and the like, in an adult patient, it is advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The pharmaceutical composition can be also delivered in a vesicle, in particular a liposome (see Langer (1990) Science 249:1527-1533; Treat et al. (1989) in Liposomes in the Therapy of Infectious Disease and Cancer, Lopez Berestein and Fidler (eds.), Liss, New York, pp. 353-365; Lopez-Berestein, ibid., pp. 317-327; see generally ibid.).

In certain situations, the pharmaceutical composition can be delivered in a controlled release system. In one embodiment, a pump may be used (see Langer, supra; Sefton (1987) CRC Crit. Ref. Biomed. Eng. 14:201). In another embodiment, polymeric materials can be used; see, Medical Applications of Controlled Release, Langer and Wise (eds.), CRC Pres., Boca Raton, Fla. (1974). In yet another embodiment, a controlled release system can be placed in proximity of the composition's target, thus requiring only a fraction of the systemic dose (see, e.g., Goodson, in Medical Applications of Controlled Release, supra, vol. 2, pp. 115-138, 1984).

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule. A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but certainly are not limited to the SOLOSTAR™ pen (sanofi-aventis), the FLEXPEN™ (Novo Nordisk), and the KWIKPEN™ (Eli Lilly).

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

The invention provides therapeutic methods in which the antibody or antibody fragment of the invention is useful to treat hypercholesterolemia associated with a variety of conditions involving hPCSK9. The anti-PCSK9 antibodies or antibody fragments of the invention are particularly useful for the treatment of hypercholesterolemia and the like. Combination therapies may include the anti-PCSK9 antibody of the invention with, for example, one or more of any agent that (1) induces a cellular depletion of cholesterol synthesis by inhibiting 3-hydroxy-3-methylglutaryl (HMG)-coenzyme A (CoA) reductase, such as cerivastatin, atorvastatin, simvastatin, pitavastatin, rosuvastatin, fluvastatin, lovastatin, pravastatin; (2) inhibits cholesterol uptake and or bile acid re-absorption; (3) increase lipoprotein catabolism (such as niacin); and activators of the LXR transcription factor that plays a role in cholesterol elimination such as 22-hydroxycholesterol or fixed combinations such as ezetimibe plus simvastatin; a statin with a bile resin (e.g., cholestyramine, colestipol, colesevelam), a fixed combination of niacin plus a statin (e.g., niacin with lovastatin); or with other lipid lowering agents such as omega-3-fatty acid ethyl esters (for example, omacor).

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used but some experimental errors and deviations should be accounted for. Unless indicated otherwise, molecular weight is average molecular weight, temperature is in degrees Centigrade, and pressure is at or near atmospheric.

Example 1: Generation of Human Antibodies to Human PCSK9

VELOCIMMUNE™ mice were immunized with human PCSK9, and the antibody immune response monitored by antigen-specific immunoassay using serum obtained from these mice. Anti-hPCSK9 expressing B cells were harvested from the spleens of immunized mice shown to have elevated anti-hPCSK9 antibody titers were fused with mouse myeloma cells to form hybridomas. The hybridomas were screened and selected to identify cell lines expressing hPCSK9-specific antibodies using assays as described below. The assays identified several cell lines that produced chimeric anti-hPCSK9 antibodies designated as H1M300, H1M504, H1M505, H1M500, H1M497, H1M498, H1M494, H1M309, H1M312, H1M499, H1M493, H1M496, H1M503, H1M502, H1M508, H1M495 and H1M492.

Human PCSK9-specific antibodies were also isolated directly from antigen-immunized B cells without fusion to myeloma cells, as described in U.S. 2007/0280945A1, hereby incorporated by reference in its entirety. Heavy and light chain variable regions were cloned to generate fully human anti-hPCSK9 antibodies designated as H1H313, H1H314, H1H315, H1H316, H1H317, H1H318, H1H320, H1H321 and H1H334. Stable recombinant antibody-expressing CHO cell lines expressing these antibodies were established.

Example 2. Gene Utilization Analysis

To analyze the structure of the mAbs produced, the nucleic acids encoding antibody variable regions were cloned and sequenced. The predicted amino acid sequences of the variable regions were confirmed by N-terminal amino acid sequencing. From the nucleic acid sequence and predicted amino acid sequence of the mAbs, gene usage was identified for each antibody chain.

TABLE 1

| | Heavy Chain Variable Region | | | Light Chain Variable Region | |
|---|---|---|---|---|---|
| Antibody | VH | D | JH | VK | JK |
| H1H313 | 3-13 | 1-26 | 4 | 3-15 | 3 |
| H1H314 | 3-33 | 3-3 | 4 | 1-5 | 2 |
| H1H315 | 3-33 | 3-3 | 4 | 4-1 | 1 |
| H1H316 | 3-23 | 7-27 | 2 | 4-1 | 2 |
| H1H317 | 3-13 | 1-26 | 4 | 1-6 | 1 |
| H1H318 | 4-59 | 3-10 | 6 | 1-9 | 1 |
| H1H320 | 1-18 | 2-2 | 6 | 2-30 | 1 |
| H1H321 | 2-5 | 1-7 | 6 | 2-28 | 4 |
| H1H334 | 2-5 | 6-6 | 6 | 2-28 | 4 |

TABLE 1-continued

| | Heavy Chain Variable Region | | | Light Chain Variable Region | |
|---|---|---|---|---|---|
| Antibody | VH | D | JH | VK | JK |
| H1M300 | 3-7 | 2-8 | 6 | 2-28 | 4 |
| H1M504 | 3-30 | 2-8 | 6 | 2-28 | 4 |
| H1M505 | 3-30 | 2-8 | 6 | 2-28 | 4 |
| H1M500 | 2-5 | 5-5 | 6 | 2-28 | 4 |
| H1M497 | 1-18 | 2-2 | 6 | 2-30 | 2 |
| H1M498 | 3-21 | 2-2 | 4 | 1-5 | 2 |
| H1M494 | 3-11 | 5-12 | 6 | 3-20 | 4 |
| H1M309 | 3-21 | 6-13 | 4 | 1-5 | 1 |
| H1M312 | 3-21 | 6-13 | 4 | 1-5 | 1 |
| H1M499 | 3-21 | 6-13 | 4 | 1-5 | 1 |
| H1M493 | 3-21 | 6-13 | 4 | 1-5 | 1 |
| H1M496 | 3-13 | 6-19 | 4 | 3-15 | 3 |
| H1M503 | 1-18 | 2-2 | 6 | 2-28 | 1 |
| H1M502 | 3-13 | 6-13 | 4 | 3-15 | 3 |
| H1M508 | 3-13 | 6-13 | 4 | 3-15 | 3 |
| H1M495 | 3-9 | 4-17 | 6 | 1-9 | 3 |
| H1M492 | 3-23 | 3-3 | 2 | 3-20 | 4 |

Example 3. Antigen Binding Affinity Determination

Equilibrium dissociation constants ($K_D$) for hPCSK9 binding to mAbs generated by hybridoma cell lines described above were determined by surface kinetics in a real-time biosensor surface plasmon resonance assay (BIACORE™ T100). Each antibody was captured at a flow rate of 4 μl/min for 90 sec on a goat anti-mouse IgG polyclonal antibody surface created through direct chemical coupling to a BIACORE™ chip to form a captured antibody surface. Human PCSK9-myc-myc-his (hPCSK9-mmh) at a concentration of 50 nM or 12.5 nM was injected over the captured antibody surfaces at a flowrate of 50 μl/min for 300 sec, and antigen-antibody dissociation was monitored for 15 min at either 25° C. or 37° C. ($K_D$=pM; $T_{1/2}$=min).

TABLE 2

| | 25° C. | | 37° C. | |
|---|---|---|---|---|
| Antibody | $K_D$ | $T_{1/2}$ | $K_D$ | $T_{1/2}$ |
| H1M300 | 399 | 170 | 1510 | 32 |
| H1M309 | 29.9 | 7461 | 537 | 326 |
| H1M312 | 0.225 | 15568 | 432 | 392 |
| H1M493 | 46.5 | 4921 | 522 | 341 |
| H1M494 | 870 | 114 | 2350 | 30 |
| H1M495 | 440 | 222 | 7500 | 19 |
| H1M496 | 254 | 257 | 421 | 118 |
| H1M497 | 20.1 | 5801 | 480 | 290 |
| H1M498 | 6400 | 30 | 7500 | 14 |
| H1M499 | 106 | 2253 | 582 | 316 |
| H1M500 | 1400 | 91 | 6010 | 15 |
| H1M502 | 78.3 | 958 | 411 | 151 |
| H1M503 | 510 | 118 | 1880 | 30 |
| H1M504 | 3470 | 35 | 11200 | 6 |
| H1M505 | 2740 | 42 | 9200 | 6 |
| H1M508 | 138 | 572 | 442 | 139 |
| H1M510 | 1070 | 68 | 3960 | 10 |

Equilibrium dissociation constants ($K_D$) for hPCSK9 binding to mAbs generated via direct isolation of splenocytes were determined by surface kinetics in a real-time biosensor surface plasmon resonance assay (BIACORE™ T100). Each selected antibody was captured at a flowrate of 2 μl/min for 6 min on a goat anti-human IgG polyclonal antibody surface created through direct chemical coupling to a BIACORE™ chip to form a captured antibody surface. Human PCSK9-mmh at a concentration of 50 nM or 12.5 nM was injected over the captured antibody surface at a flowrate of 70 μl/min for 5 min, and antigen-antibody dissociation was monitored for 15 min at either 25° C. or 37° C. ($K_D$=pM; $T_{1/2}$=min).

TABLE 3

| | 25° C. | | 37° C. | |
|---|---|---|---|---|
| Antibody | $K_D$ | $T_{1/2}$ | $K_D$ | $T_{1/2}$ |
| H1H313P | 244 | 230 | 780 | 60 |
| H1H314P | 3990 | 65 | 3560 | 43 |
| H1H315P | 129 | 151 | 413 | 35 |
| H1H316P | 377 | 42 | 1080 | 11 |
| H1H317P | 30400 | 137 | 18600 | 70 |
| H1H318P | 972 | 59 | 1690 | 28 |
| H1H320P | 771 | 28 | 1930 | 8 |
| H1H321P | 865 | 106 | 3360 | 23 |
| H1H334P | 3750 | 46 | 15900 | 8 |

Dissociation rate (kd) of selected mAbs for tagged rhesus monkey (*Macaca mulata*) PCSK9 (mmPCSK9; SEQ ID NO:756) (mmPCSK9-mmh) at 25° C. was determined as described above.

TABLE 4

| Antibody | kd (1/s) | $T_{1/2}$ (min) |
|---|---|---|
| H1H313P | $2.92 \times 10^{-5}$ | 396 |
| H1H318P | $3.69 \times 10^{-3}$ | 3 |
| H1H334P | $8.06 \times 10^{-3}$ | 1 |
| H1H315P | $2.29 \times 10^{-4}$ | 51 |
| H1H316P | $2.29 \times 10^{-4}$ | 51 |
| H1H320P | $3.17 \times 10^{-4}$ | 36 |
| H1M300 | $1.52 \times 10^{-4}$ | 76 |
| H1M504 | $5.04 \times 10^{-4}$ | 23 |
| H1M497 | $6.60 \times 10^{-5}$ | 175 |
| H1M503 | $8.73 \times 10^{-5}$ | 132 |
| H1M496 | $4.45 \times 10^{-5}$ | 260 |

Example 4. Effect of pH on Antigen Binding Affinity

The effects of pH on antigen binding affinity for CHO cell-produced fully human anti-hPCSK9 mAbs was assessed as described above. The mAbs tested are fully human versions of H1H316P ("316P") (HCVR/LCVR SEQ ID NO: 90/92; CDR sequences SEQ ID NO: 76/78/80 and 84/86/88) and H1M300N ("300N") (HCVR/LCVR SEQ ID NO: 218/226; CDR sequences SEQ ID NO:220/222/224 and 228/230/232). Human PCSK9-myc-myc-his (hPCSK9-mmh) was captured on an anti-myc mAb surface either at a high density (about 35 to 45 resonance units) (RU) or at a low density (about 5 to 14 RU). Each antibody, at 50 nM in HBST (pH 7.4 or pH 5.5) was injected over the captured hPCSK9 surface at a flow rate of 100 μl/ml for 1.5 min at 25° C. and antigen-antibody dissociation was monitored for 10 min. Control I: anti-hPCSK9 mAb SEQ ID NO:79/101 (WO 2008/063382) ($K_D$=pM; $T_{1/2}$=min).

TABLE 5

| | High hPCSK9 Density Surface | | | | Low hPCSK9 Density Surface | | | |
|---|---|---|---|---|---|---|---|---|
| Anti- | pH 7.4 | | pH 5.5 | | pH 7.4 | | pH 5.5 | |
| body | $K_D$ | $T_{1/2}$ | $K_D$ | $T_{1/2}$ | $K_D$ | $T_{1/2}$ | $K_D$ | $T_{1/2}$ |
| 316P | 191 | 74 | 144 | 83 | 339 | 45 | 188 | 58 |
| 300N | 65 | 507 | 1180 | 26 | 310 | 119 | 1380 | 13 |
| Control I | 20000 | 29 | ND | ND | ND | ND | ND | ND |

The antigen binding properties of 316P and 300N at pH 7.4 or pH 5.5 were determined by a modified BIACORE™ assay as described above. Briefly, mAbs were immobilized onto BIACORE™ CM5 sensor chips via amine coupling. Varying concentrations of myc-myc-his tagged hPCSK9, mouse PCSK9 (mPCSK9, SEQ ID NO:757), hPCSK9 with a gain of function (GOF) point mutation of D374Y (hPCSK9 (D374Y), cynomolgus monkey (*Macaca fascicularis*) PCSK9 (mfPCSK9, SEQ ID NO:761) (mfPCSK9), rat (*Rattus norvegicus*) PCSK9 (rPCSK9, SEQ ID NO:763), and his-tagged Syrian golden hamster (*Mesocricetus auratus*) PCSK9 (maPCSK9, SEQ ID NO:762) (maPCSK9), ranging from 11 to 100 nM, were injected over the antibody surface at the flow rate of 100 μl/ml for 1.5 min and antigen-antibody dissociation was monitored in real time for 5 min at either 25° C. (Table 6) or 37° C. (Table 7). Control II: anti-hPCSK9 mAbs SEQ ID NO:67/12 (WO 2009/026558) (NB: no binding was observed under the experimental condition) ($K_D$=pM; $T_{1/2}$=min).

TABLE 6

| pH Effect at 25° C. | | | | |
|---|---|---|---|---|
| | pH 7.4 | | pH 5.5 | |
| Antigen | $K_D$ | $T_{1/2}$ | $K_D$ | $T_{1/2}$ |
| 316P | | | | |
| hPCSK9-mmh | 1260 | 36 | 22 | 39 |
| mPCSK9-mmh | 4460 | 10 | 63 | 11 |
| hPCSK9(D347Y)-mmh | 2490 | 15 | 166 | 13 |
| mfPCSK9-mmh | 1420 | 42 | 8 | 23 |
| maPCSK9-h | 8350 | 8 | 87 | 8 |
| rPCSK9-mmh | 24100 | 2 | 349 | 5 |
| 300N | | | | |
| hPCSK9-mmh | 1100 | 76 | 3100 | 5 |
| mPCSK9-mmh | NB | NB | NB | NB |
| hPCSK9(D347Y)-mmh | 1310 | 46 | 9030 | 3 |
| mfPCSK9-mmh | 2170 | 31 | 38500 | 0.4 |
| maPCSK9-h | NB | NB | NB | NB |
| rPCSK9-mmh | NB | NB | NB | NB |
| Control I | | | | |
| hPCSK9-mmh | 33100 | 14 | 1740 | 31 |
| mPCSK9-mmh | NB | NB | NB | NB |
| hPCSK9(D347Y)-mmh | 71000 | 11 | 7320 | 30 |
| mfPCSK9-mmh | 362000 | 0.2 | 67200 | 3 |
| maPCSK9-h | NB | NB | NB | NB |
| rPCSK9-mmh | NB | NB | NB | NB |
| Control II | | | | |
| hPCSK9-mmh | 143 | 266 | 2 | 212 |
| mPCSK9-mmh | 3500 | 11 | 33 | 12 |
| hPCSK9(D347Y)-mmh | 191 | 155 | 49 | 56 |
| mfPCSK9-mmh | 102 | 262 | 12 | 63 |
| maPCSK9-h | 6500 | 3 | ND | ND |
| rPCSK9-mmh | 22400 | 2 | 106 | 5 |

TABLE 7

| pH Effect at 37° C. | | | | |
|---|---|---|---|---|
| | pH 7.4 | | pH 5.5 | |
| Antigen | $K_D$ | $T_{1/2}$ | $K_D$ | $T_{1/2}$ |
| 316P | | | | |
| hPCSK9-mmh | 4000 | 9 | 142 | 11 |
| mPCSK9-mmh | 12200 | 3 | 13600 | 3 |
| hPCSK9(D347Y)-mmh | 6660 | 4 | 1560 | 5 |
| mfPCSK9-mmh | 3770 | 11 | 44 | 5 |
| maPCSK9-h | 21700 | 2 | ND | ND |
| rPCSK9-mmh | 55100 | 2 | 399 | 1 |
| 300N | | | | |
| hPCSK9-mmh | 2470 | 20 | 11900 | 1 |
| mPCSK9-mmh | NB | NB | NB | NB |
| hPCSK9(D347Y)-mmh | 2610 | 14 | 28000 | 1 |
| mfPCSK9-mmh | 4810 | 8 | 65200 | 0.1 |
| maPCSK9-h | NB | NB | NB | NB |
| rPCSK9-mmh | NB | NB | NB | NB |
| Control I | | | | |
| hPCSK9-mmh | 45900 | 0.1 | 11300 | 3 |
| mPCSK9-mmh | NB | NB | NB | NB |
| hPCSK9(D347Y)-mmh | 169000 | 0.4 | 27000 | 3 |
| mfPCSK9-mmh | 500000 | 0.6 | 5360 | 0.3 |
| maPCSK9-h | NB | NB | NB | NB |
| rPCSK9 | NB | NB | NB | NB |
| Control II | | | | |
| hPCSK9-mmh | 284 | 87 | 20 | 44 |
| mPCSK9-mmh | 8680 | 3 | 89 | 3 |
| hPCSK9(D347Y)-mmh | 251 | 57 | 483 | 26 |
| mfPCSK9-mmh | 180 | 127 | 214 | 65 |
| maPCSK9-h | 8830 | 0.5 | ND | ND |
| rPCSK9p-mmh | 30200 | 1 | 233 | 1 |

Example 5. Anti-hPCSK9 mAbs Binding to hPCSK9 with Point Mutation D374Y

The binding affinity of selected anti-hPCSK9 mAbs to hPCSK9 with a gain of function (GOF) point mutation of D374Y (hPCSK9(D374Y)-mmh) was determined as described above. Each antibody was captured at a flowrate of 40 µl/min for 8-30 sec on a goat anti-human IgG polyclonal antibody surface created through direct chemical coupling to a BIACORE™ chip to form a captured antibody surface. hPCSK9(D374Y)-mmh at varying concentrations of 1.78 nM to 100 nM was injected over the captured antibody surface at a flowrate of 50 µl/min for 5 min, and the dissociation of hPCSK9(D374Y)-mmh and antibody was monitored for 15 min at 25° C. Control III: anti-hPCSK9 mAbs SEQ ID NO:49/23 (WO 2009/026558) ($K_D$=pM; $T_{1/2}$=min).

TABLE 8

| Antibody | $K_D$ | $T_{1/2}$ |
|---|---|---|
| 316P | 1780 | 14 |
| 300N | 1060 | 49 |
| Control I | 23600 | 25 |
| Control II | 66 | 216 |
| Control III | 1020 | 126 |

Example 6. Binding Specificity of Anti-hPCSK9 mAbs 316P, 300N, and Control I anti-hPCSK9 mAbs were captured on an amine-coupled anti-hFc CM5 chip on BIACORE™2000. Tagged (myc-myc-his) human PCSK9, human PCSK1 (hPCSK1) (SEQ ID NO:759), human PCSK7 (hPCSK7) (SEQ ID NO:760), or mouse PCSK9 were injected (100 nM) over the captured mAb surface and allowed to bind at 25° C. for 5 min. Changes in RU were recorded. Results: 300N and Control I bound only to hPCSK9, and 316P bound both hPCSK9 and mPCSK9.

The binding specificities of anti-hPCSK9 mAbs were determined by ELISA. Briefly, anti-hPCSK9 antibody was coated on a 96-well plate. Human PCSK9-mmh, mPCSK9-mmh, maPCSK9-h, hPCSK1-mmh, or hPCSK7-mmh, at 1.2 nM, were added to antibody-coated plates and incubated at RT for 1 hr. Plate-bound PCSK protein was then detected by HRP-conjugated anti-His antibody. Results show that 316P binds human, mouse, and hamster PCSK9, whereas 300N and Control I only bound hPCSK9. None of the anti-hPCSK9 mAbs exhibited significant binding to hPCSK1 or hPCSK7.

Example 7. Cross-Reactivity of Anti-h PCSK9 mAbs

Cross-reactivity of anti-hPCSK9 mAbs with mmPCSK9, mfPCSK9, mPCSK9, maPCSK9, or rPCSK9 was determined using BIACORE™3000. Briefly, anti-hPCSK9 mAbs were captured on an anti-hFc surface created through direct chemical coupling to a BIACORE™ chip. Purified tagged hPCSK9, hPCSK9(D374Y), mmPCSK9, mfPCSK9, mPCSK9, maPCSK9, or rPCSK9, each at 1.56 nM to 50 nM, was injected over the antibody surface at either 25° C. or 37° C. Binding between 316P, 300N, Control I, Control II, or Control III and the PCSK9 proteins was determined ($K_D$=pM; $T_{1/2}$=min) (ND=not determined).

TABLE 9

| 316P mAb | | | | |
|---|---|---|---|---|
| | 37° C. | | 25° C. | |
| Antigen | $K_D$ | $T_{1/2}$ | $K_D$ | $T_{1/2}$ |
| hPCSK9-mmh | 1800 | 9 | 580 | 36 |
| hPCSK9(D374Y)-mmh | 4200 | 4 | 1690 | 15 |
| mmPCSK9-mmh | 1800 | 21 | 550 | 92 |
| mfPCSK9-mmh | 1800 | 11 | 520 | 60 |
| mPCSK9-mmh | 4700 | 3 | 2300 | 11 |
| maPCSK9-h | 19000 | 1 | 6810 | 5 |
| rPCSK9-mmh | 37500 | 1 | 14500 | 2 |

TABLE 10

| 300N mAb | | | | |
|---|---|---|---|---|
| | 37° C. | | 25° C. | |
| Antigen | $K_D$ | $T_{1/2}$ | $K_D$ | $T_{1/2}$ |
| hPCSK9-mmh | 2400 | 22 | 740 | 110 |
| hPCSK9(D374Y)-mmh | 2200 | 14 | 900 | 65 |
| mmPCSK9-mmh | 1600 | 26 | 610 | 79 |
| mfPCSK9-mmh | 3800 | 11 | 1500 | 45 |
| mPCSK9-mmh | NB | NB | NB | NB |
| maPCSK9-h | NB | NB | NB | NB |
| rPCSK9-mmh | NB | NB | NB | NB |

TABLE 11

| Control I mAb | | | | |
|---|---|---|---|---|
| | 37° C. | | 25° C. | |
| Antigen | $K_D$ | $T_{1/2}$ | $K_D$ | $T_{1/2}$ |
| hPCSK9-mmh | 226000 | 2 | 27500 | 16 |
| hPCSK9(D374Y)-mmh | ND | ND | 23600 | 25 |
| mmPCSK9-mmh | 420000 | 3 | 291000 | 2 |
| mfPCSK9-mmh | 14300 | 10 | 24900 | 14 |
| mPCSK9-mmh | NB | NB | NB | NB |
| maPCSK9-h | NB | NB | NB | NB |
| rPCSK9-mmh | NB | NB | NB | NB |

TABLE 12

| Control II mAb | | | | |
|---|---|---|---|---|
| | 37° C. | | 25° C. | |
| Antigen | $K_D$ | $T_{1/2}$ | $K_D$ | $T_{1/2}$ |
| hPCSK9-mmh | 91 | 162 | 61 | 372 |
| hPCSK9(D374Y)-mmh | 93 | 90 | 66 | 216 |
| mfPCSK9-mmh | 33 | 252 | 26 | 546 |
| mPCSK9-mmh | 4700 | 3 | 2300 | 11 |
| maPCSK9-h | 60800 | 0.4 | 25000 | 2 |
| rPCSK9-mmh | 14100 | 1 | 6900 | 3 |

TABLE 13

| Control III mAb | | | | |
|---|---|---|---|---|
| | 37° C. | | 25° C. | |
| Antigen | $K_D$ | $T_{1/2}$ | $K_D$ | $T_{1/2}$ |
| hPCSK9-mmh | 380 | 378 | 490 | 450 |
| hPCSK9(D374Y)-mmh | 130 | 660 | 1000 | 126 |
| mfPCSK9-mmh | 110 | 750 | 340 | 396 |
| mPCSK9-mmh | 33500 | 1 | 10900 | 4 |
| maPCSK9-h | 780 | 107 | 2100 | 67 |
| rPCSK9-mmh | NB | NB | 33200 | 2 |

Example 8. Inhibition of Binding Between hPCSK9 and hLDLR Domains

The ability of selected anti-hPCSK9 mAbs to block hPCSK9 binding to human LDLR full-length extracellular domain (hLDLR-ecto SEQ ID NO:758), hLDLR EGF-A domain (amino acids 313-355 of SED ID NO:758), or hLDLR EGF-AB domains (amino acids of 314-393 of SEQ ID NO:758) (LDLR Genbank number NM_000527) was evaluated using BIACORE™ 3000. Briefly, hLDLR-ecto, EGF-A-hFc, or EGF-AB-hFc protein was amine-coupled on a CM5 chip to create a receptor or receptor fragment surface. Selected anti-hPCSK9 mAbs, at 62.5 nM (2.5 fold excess over antigen), were premixed with 25 nM of hPCSK9-mmh, followed by 40 min incubation at 25° C. to allow antibody-antigen binding to reach equilibrium to form equilibrated solutions. The equilibrated solutions were injected over the receptor or receptor fragment surfaces at 2 μl/min for 40 min at 25° C. Changes in RU due to the binding of the anti-hPCSK9 mAbs to hLDLR-ecto, EGF-A-hFc, or EGF-AB-hFc were determined. Results show that H1H316P and H1M300N blocked the binding of hPCSK9-mmh to hLDLR-ecto, hLDLR EGF-A domain, and hLDLR EGF-AB domains; H1H320P blocked the binding of hPCSK9-mmh to hLDLR-ecto and hLDLR EGF-A domain; and H1H321P blocked the binding of hPCSK9-mmh to hLDLR EGF-A domain.

The ability of the mAbs to block hPCSK9 binding to hLDLR-ecto, hLDLR EGF-A domain, or hLDLR EGF-AB domains was also evaluated with an ELISA-based immunoassay. Briefly, hLDLR-ecto, hLDLR EGF-A-hFc or hLDLR EGF-AB-hFc, each at 2 μg/ml, was coated on a 96-well plate in PBS buffer overnight at 4° C., and nonspecific binding sites blocked with BSA. This plate was used to measure free hPCSK9-mmh in a PCSK9-mmh solution pre-equilibrated with varying concentrations of anti-hPCSK9 mAbs. A constant amount of hPCSK9-mmh (500 pM) was pre-mixed with varied amounts of antibody, ranging from 0 to ~50 nM in serial dilutions, followed by 1 hr incubation at room temperature (RT) to allow antibody-antigen binding to reach equilibrium. The equilibrated sample solutions were transferred to receptor or receptor fragment coated plates. After 1 hour of binding, the plates were washed and bound hPCSK9-mmh detected using HRP conjugated anti-myc antibody. $IC_{50}$ values (in pM) were determined as the amount of antibody required to achieve 50% reduction of hPCSK9-mmh bound to the plate-coated receptor or receptor fragment. The results show that specific mAbs functionally block PCSK9 from binding the three receptors at both neutral pH (7.2) and acidic pH (5.5).

TABLE 14

| | pH 7.2 | | | pH 5.5 | | |
|---|---|---|---|---|---|---|
| | Plate Coating Surface | | | | | |
| Ab | hLDLR-ecto | EGF-A | EGF-AB | hLDLR-ecto | EGF-A | EGF-AB |
| 316P | <125 | <125 | <125 | <125 | <125 | <125 |
| 300N | 144 | 146 | <125 | 1492 | 538 | 447 |
| Control I | — | >100,000 | >100,000 | — | >100,000 | >100,000 |
| Control II | 288 | 510 | 274 | 411 | 528 | 508 |
| Control III | 303 | 635 | 391 | 742 | 787 | 1073 |

The ability of the mAbs to block hPCSK9 GOF mutant hPCSK9(D374Y)-mmh binding to hLDLR EGF-A domain or hLDLR EGF-AB domain ($IC_{50}$ values in pM) was also evaluated with the ELISA-based immunoassay described above using a constant amount of 0.05 nM hPCSK9 (D374Y)-mmh.

TABLE 15

| | Plate Coating Surface | | | |
|---|---|---|---|---|
| | pH 7.2 | | pH 5.5 | |
| | EGF-A | EGF-AB | EGF-A | EGF-AB |
| 316P | 203 | 139 | 1123 | 1139 |
| 300N | 135 | 142 | 3463 | 3935 |
| Control I | >100,000 | >100,000 | >100,000 | >100,000 |
| Control II | 72 | 57 | 129 | 118 |
| Control III | 537 | 427 | 803 | 692 |

The ability of the mAbs to block either mmPCSK9 or mPCSK9 binding to hLDLR-ecto domain, hLDLR EGF-A domain, or hLDLR EGF-AB domain ($IC_{50}$ values in pM) was evaluated at neutral pH (7.2) with the ELISA-based immunoassay describe above using a constant amount of 1 nM of mmh-tagged mmPCSK9 or 1 nM of mPCSK9.

TABLE 16

| | 1 nM mmPCSK9-mmh | | | 1 nM mPCSK9-mmh | |
|---|---|---|---|---|---|
| | hLDLR-ecto | EGF-A | EGF-AB | EGF-A | EGF-AB |
| 316P | <250 | <250 | <250 | <250 | <250 |
| 300N | 255 | 256 | 290 | >33000 | >33000 |

The ability of the mAbs to block hPCSK9, mmPCSK9, rPCSK9, maPCSK9, mfPCSK9, or mPCSK9 binding to hLDLR EGF-A domain ($IC_{50}$ values in pM) was evaluated at neutral pH (7.2) (Table 17) acidic pH (5.5, Table 18) with the ELISA-based immunoassay described above using a constant amount of 0.5 nM of hPCSK9-mmh, 1 nM of mmPCSK9-mmh, 1 nM of rPCSK9-mmh, 1 nM of maPCSK9-h, 0.3 nM of mfPCSK9-mmh, or 1 nM of mPCSK9-mmh.

TABLE 17

| | hPCSK9 | mmPCSK9 | rPCSK9 | maPCSK9 | mfPCSK9 | mPCSK9 |
|---|---|---|---|---|---|---|
| 316P | <125 | <250 | 2662 | 349 | 75 | 305 |
| 300N | 182 | 460 | >100000 | >100000 | 473 | >100000 |
| Control I | — | >100000 | >100000 | >100000 | >100000 | >100000 |
| Control II | 146 | 83 | 2572 | 2038 | 361 | 855 |
| Control III | 249 | 293 | >100000 | 245 | 572 | >100000 |

TABLE 18

| | hPCSK9 | mmPCSK9 | rPCSK9 | maPCSK9 | mPCSK9 |
|---|---|---|---|---|---|
| 316P | <125 | <250 | 42880 | 1299 | 991 |
| 300N | 223 | 3704 | >100000 | >100000 | >100000 |
| Control I | >10000 | >100000 | >100000 | >100000 | >100000 |
| Control II | 154 | <250 | 11640 | 8339 | 2826 |
| Control III | 390 | 376 | >100000 | 414 | >100000 |

The ability of 316P and Control I to block hPCSK9 binding to hLDLR was also determined. Briefly, either recombinant hLDLR or hLDLR-EGFA-mFc was immobilized onto BIACORE™ CM5 chips via amine coupling. An antigen-antibody mixture of 100 nM hPCSK9-mmh and 316P, Control I mAb, or a non-hPCSK9 specific mAb (each at 250 nM) was incubated at RT for 1 hr, and then injected over the hLDLR or hLDLR-EGFA surface at the flow rate of 10 μl/ml for 15 min at 25° C. Changes in RU due to the binding between the free hPCSK9-mmh in the mixture to either hLDLR or hLDLR-EGFA were recorded. The binding of hPCSK9 to either hLDLR or hLDLR-EGFA was completely blocked by 316P and 300N but not by Control I mAb.

Example 9. Epitope Mapping

In order to determine epitope-binding specificity, three chimeric PCSK9-mmh proteins were generated in which specific human PCSK9 domains were substituted with mouse PCSK9 domains. Chimeric protein #1 consists of a mouse PCSK9 pro-domain (amino acid residues 1-155 of SEQ ID NO:757) followed by a human PCSK9 catalytic domain (residues 153-425 of SEQ ID NO:755) and a mouse PCSK9 C-terminal domain (residues 429-694 SEQ ID NO:757) (mPro-hCat-mC-term-mmh). Chimeric protein #2 consists of a human PCSK9 pro-domain (residues 1-152 of SEQ ID NO:755) followed by a mouse PCSK9 catalytic domain (residues 156-428 of SEQ ID NO:757) and a mouse PCSK9 C-terminal (hPro-mCat-mC-term-mmh). Chimeric protein #3 consists of mouse PCSK9 pro-domain and a mouse PCSK9 catalytic domain followed by a human PCSK9 C-terminal domain (residues 426-692 of SEQ ID NO:755) (mPro-mCat-hC-term-mmh). In addition, hPCSK9 with a point mutation of D374Y (hPCSK9 (D374Y)-mmh) was generated.

Binding specificity of mAbs to test proteins hPCSK9-mmh, mouse PCSK9-mmh, chimeric proteins #1, #2, and #3, and hPCSK9 (D374Y)-mmh were tested as follows: the mAbs were coated on a 96-well plate overnight at 4° C., then each test protein (1.2 nM) was added to the plate. After 1 hr binding at RT, the plate was washed and bound test protein detected using HRP-conjugated anti-myc polyclonal antibody (++=OD>1.0; +=OD 0.4-1.0; −=OD<0.4).

TABLE 19

| | | | Chimeric Protein | | | |
|---|---|---|---|---|---|---|
| Antibody | hPCSK9 | mPCSK9 | #1 | #2 | #3 | hPCSK9(D374Y) |
| H1M300 | ++ | − | ++ | + | − | ++ |
| H1M309 | ++ | − | − | − | ++ | ++ |
| H1M312 | ++ | − | − | − | ++ | ++ |
| H1M492 | ++ | − | − | − | − | + |
| H1M493 | ++ | − | − | − | ++ | ++ |
| H1M494 | ++ | − | − | + | ++ | ++ |
| H1M495 | ++ | − | − | − | ++ | ++ |
| H1M496 | ++ | − | − | − | ++ | ++ |
| H1M497 | ++ | − | − | ++ | + | ++ |
| H1M498 | ++ | − | − | − | + | ++ |
| H1M499 | ++ | − | − | − | ++ | ++ |
| H1M500 | ++ | − | ++ | − | − | ++ |
| H1M502 | ++ | − | − | − | ++ | ++ |
| H1M503 | ++ | − | − | ++ | − | ++ |
| H1M504 | ++ | − | − | − | − | + |
| H1M505 | ++ | − | ++ | + | − | ++ |
| H1M508 | ++ | − | − | − | ++ | ++ |

TABLE 19-continued

| Antibody | hPCSK9 | mPCSK9 | Chimeric Protein #1 | #2 | #3 | hPCSK9(D374Y) |
|---|---|---|---|---|---|---|
| H1H318P | ++ | − | ++ | − | − | ++ |
| H1H334P | ++ | − | ++ | − | − | ++ |
| H1H316P | ++ | ++ | ++ | ++ | ++ | ++ |
| H1H320P | ++ | − | − | ++ | − | ++ |
| Control I | ++ | − | − | − | ++ | ++ |

Binding specificity of 316P, 300N and control anti-hPCSK9 mAbs to hPCSK9-mmh, mPCSK9-mmh, mmPCSK9-mmh, mfPCSK9-mmh, rPCSK9-mmh, chimeric proteins #1, #2, and #3, and hPCSK9 (D374Y)-mmh were tested as described above except that the protein concentration is 1.7 nM (−=OD<0.7; +=OD 0.7-1.5; ++=OD>1.5).

TABLE 20

| | 316P | 300N | Control I | Control II | Control III |
|---|---|---|---|---|---|
| hPCSK9-mmh | ++ | ++ | ++ | ++ | ++ |
| mPCSK9-mmh | ++ | − | − | ++ | ++ |
| mmPCSK9-mmh | ++ | ++ | ++ | ++ | ++ |
| mfPCSK9-mmh | ++ | ++ | ++ | ++ | ++ |
| rPCSK9-mmh | ++ | − | − | ++ | + |
| Chimeric Protein #1 | ++ | ++ | − | ++ | ++ |
| Chimeric Protein #2 | ++ | ++ | − | ++ | ++ |
| Chimeric Protein #3 | ++ | + | ++ | ++ | ++ |
| hPCSK9 (D374Y) | ++ | ++ | ++ | ++ | ++ |

Similar results for selected mAbs were obtained by BIACORE™ binding assay. Briefly, 316P, 300N, or Control I mAb was captured on an amine-coupled anti-hFc CM5 chip and 100 nM of each protein injected over the mAb-captured surface. Changes in RU due to the binding of each protein to the mAb surface was determined.

TABLE 21

| Antibody | hPCSK9 | mPCSK9 | Chimeric Protein #1 | #2 | #3 |
|---|---|---|---|---|---|
| 316P | 500 | 505 | 529 | 451 | 467 |
| 300N | 320 | 13 | 243 | 76 | 10 |
| Control I | 65 | 7 | 4 | 3 | 69 |

To further assess the binding specificity of 316P, which cross-reacts with mPCSK9-mmh, a cross-competition ELISA assay was developed to determine binding domain specificity. Briefly, mAbs specific for chimeric protein #1, #2, or #3, were first coated on a 96-well plate overnight at 1 μg/ml. Human PCSK9-mmh (2 μg/ml) was then added to each well followed by 1 hr incubation at RT. 316P (1 μg/ml) was added and incubated for another hour at RT. Plate-bound 316P was detected using HRP-conjugated anti-hFc polyclonal antibody. Although 316P binding to hPCSK9-mmh was not affected by the presence of mAbs specific for either chimeric protein #2 or chimeric protein #3, 316P binding to hPCSK9-mmh was greatly reduced by the presence of antibody specific for chimeric protein #1.

Example 10. BIACORE™-Based Antigen Binding Profile Assessment

Antibody binding profiles were also established for 316P, 300N, Control I, II, and III mAbs using BIACORE™1000.

Briefly, hPCSK9-mmh was captured on an anti-myc surface. A first anti-hPCSK9 mAb (50 μg/ml) was injected over the PCSK9-bound surface for 10 min, at a flow rate of 10 μl/min at 25° C. A second anti-hPCSK9 mAb (50 μg/ml) was then injected over the first mAb-bound surface for 10 min, at a flow rate of 10 μl/min at 25° C. Ability of the first mAb to block binding of the second mAb was measured and is expressed as percent inhibition.

TABLE 22

| First mAb | Second mAb 316P | 300N | Control I | Control II | Control III |
|---|---|---|---|---|---|
| 316P | 100 | 101 | 27 | 99 | 101 |
| 300N | 77 | 100 | 12 | 82 | −2 |
| Control I | 6 | 12 | 100 | 6 | 9 |
| Control II | 91 | 102 | −6 | 100 | 3 |
| Control III | 73 | 10 | −12 | 1 | 100 |

Example 11. Increase of LDL Uptake by Anti-hPCSK9 Antibodies

The ability of anti-hPCSK9 mAbs to increase LDL uptake in vitro was determined using a human hepatocellular liver carcinoma cell line (HepG2). HepG2 cells were seeded onto 96-well plates at $9\times10^4$ cells/well in DMEM complete media and incubated at 37° C., 5% $CO_2$, for 6 hr to form HepG2 monolayers. Human PCSK9-mmh, at 50 nM in lipoprotein deficient medium (LPDS), and a test mAb was added in various concentrations from 500 nM to 0.98 nM in LPDS medium. Data are expressed as $IC_{50}$ values for each experiment ($IC_{50}$=antibody concentration at which increases LDL uptake by 50%). In addition, the experiment also showed that both 316P and 300N were able to completely reverse the inhibitory effect of hPCSK9 on LDL uptake, while Control I mAb or H1M508 anti-hPCSK9 mAb reversed the inhibitory effect by about 50%.

TABLE 23

| Antibody | $IC_{50}$ (nM) |
|---|---|
| 316P | 21.30 |
| 300N | 22.12 |
| Control I | >250 |
| H1M508 | >250 |

The ability of anti-hPCSK9 mAbs to reverse the inhibitory effect on LDL uptake by PCSK9 protein from different mammalian species was also tested in a HepG2 cell line as described above. Briefly, HepG2 cells were incubated overnight with serial dilutions of antibody in LPDS medium (beginning with 500 nM) and 50 nM of hPCSK9-mmh, mfPCSK9-mmh, mPCSK9-mmh, rPCSK9-mmh, or maPCSK9-h. HepG2 cells were also incubated overnight with serial dilutions of antibody in LPDS (beginning with 50 nM) and 1 nM hPCSK9(D374Y). As shown in Table 24, while 316P was able to completely reverse the inhibitory effect on LDL by all PCSK9 proteins tested, 300N was only able to reverse the inhibitory effect on LDL uptake by hPCSK9, hPCSK9 (D374Y), and mfPCSK9. Values are expressed as nM $IC_{50}$.

TABLE 24

| | 316P | 300N | Control I | Control II | Control III |
|---|---|---|---|---|---|
| hPCSK9-mmh | 14.1 | 12.6 | >500 | 13.4 | 12.4 |
| hPCSK9(D374Y)-mmh | 2.1 | 1.1 | >50 | 0.7 | 0.6 |
| mfPCSK9-mmh | 14.7 | 13.4 | >500 | 14.2 | 13.6 |
| mPCSK9-mmh | 21.2 | >500 | >500 | 19 | >500 |
| rPCSK9-mmh | 27.7 | >500 | >500 | 21.9 | >500 |
| maPCSK9-h | 14.4 | >500 | >500 | 29.5 | 12.7 |

Example 12. Neutralization of Biological Effect of hPCSK9 In Vivo

To assess the biological effect of neutralizing PCSK9, hPCSK9 was over-expressed in C57BL/6 mice by hydrodynamic delivery (HDD) of DNA constructs encoding full-length hPCSK9-mmh. 4 mice (C57BL/6) were injected with empty vector/saline (control), and 16 mice were injected with a 50 μg hPCSK9-mmh-DNA/saline mixture in the tail vein equal to 10% of their body weight. At day 7 after HDD, delivery of hPCSK9 resulted in a 1.6-fold elevation of total cholesterol, 3.4-fold elevation in LDL-cholesterol (LDL-C) and a 1.9-fold elevation in non-HDL cholesterol (relative to control). Serum hPCSK9 levels on day 7 were all greater than 1 μg/ml, as assessed by quantitative ELISA.

Administration of H1M300N on day 6 after HDD to 3 experimental groups (1, 5 or 10 mg/kg) (n=4 per group) via intraperitoneal (i.p.) injection resulted in a significant attenuation of serum cholesterol levels. At 18 hours after administration, total cholesterol was reduced by 9.8%, 26.3% and 26.8%, LDL-C was reduced by 5.1%, 52.3% and 56.7%, and non-HDL cholesterol was reduced by 7.4%, 33.8% and 28.6% in the 1, 5 or 10 mg/kg H1M300N treated groups, respectively.

Example 13. Pharmacokinetic and Serum Chemistry Study in Monkeys

A pharmacokinetic (PK) study was conducted in naïve male cynomolgus monkeys (*Macaca fascicularis*) with a body weight range between 5-7 kg and aged between 3-5 years.

Group Assignments.

The monkeys were assigned into 5 treatment groups: Treatment Group 1 (n=3) received control buffer (10 mM sodium phosphate, pH 6, 1 ml/kg); Treatment Group 2 (n=3) received 1 ml/kg of 316P (5 mg/ml); Treatment Group 3 (n=3) received 1 ml/kg 300N (5 mg/ml); Treatment Group 4 (n=3) received 1 ml/kg 316P (15 mg/ml); and Treatment Group 5 (n=3) received 1 ml/kg 300N (15 mg/ml). All treatments were administered by IV bolus followed by a 1 ml saline flush. Total dose volume (ml) was calculated on the most recent body weight (each animal was weighed twice during acclimation and once weekly throughout the study). A single dose of test mAb or buffer control was administered on Day 1.

Animal Care.

Animals were housed in a temperature- and humidity-monitored environment. The targeted range of temperature and relative humidity was between 18-29° C. and 30-70%, respectively. An automatic lighting system provided a 12-hour diurnal cycle. The dark cycle could be interrupted for study- or facility-related activities. The animals were individually housed in cages that comply with the Animal Welfare Act and recommendations set forth in The Guide for the Care and Use of Laboratory Animals (National Research Council 1996).

Diet and Feeding.

Animals were fed twice per day according to SNBL USA SOPs. Animals were fasted when required by specific procedures (e.g., prior to blood draws for serum chemistry, urine collection, or when procedures involving sedation are performed). The diet was routinely analyzed for contaminants and found to be within manufacturer's specifications. No contaminants were expected to be present at levels that would interfere with the outcome of the study.

Experimental Design.

An appropriate number of animals were selected from SNBL USA stock. Animals were examined for health by veterinary staff, and had undergone serum chemistry, hematology, and coagulation screening. Sixteen males, confirmed healthy, were assigned to the study. Fifteen males were assigned to specific study groups and the remaining animal was available as a spare. A stratified randomization scheme incorporating serum cholesterol level (based on the average of two draws in acclimation) was used to assign animals to study groups.

Acclimation Period.

Previously quarantined animals were acclimated to the study room for a minimum of 14 days prior to initiation of dosing. Acclimation phase data was collected from all animals, including the spare. All animals were assessed for behavioral abnormalities that could affect performance on study. The spare animal was returned to stock after day 1.

Blood Collection.

Blood was collected by venipuncture from a peripheral vein from restrained, conscious animals. Whenever possible, blood was collected via a single draw and then divided appropriately.

PK Study.

Blood samples (1.5 ml) were collected at pre-dose, 2 min, 15, min, 30 min, 1 hr, 2 hr, 4 hr, 8 hr, 12 hr, 24 hr, and subsequently once every 24 hr in serum separator tubes (SST). Specimen storage serum is transferred to 2 vials and stored at −60° C. or below.

Serum samples were analyzed using an optimized ELISA (enzyme-linked immunosorbant assay) procedure. Briefly, a microtiter plate was first coated with hPCSK9-mmh. Test mAb 316P or 300N was then captured on the hPCSK9-mmh plate. The captured 316P or 300N was detected using a biotinylated mouse anti-hIgG4 followed by binding to NeutrAvidin-HRP. Varying concentrations of 316P or 300N, ranging from 100 to 1.56 ng/ml, were used as standards. One percent monkey serum (assay matrix) in the absence of 316P or 300N was used as the zero (0 ng/ml) standard. The results, shown in FIG. 2, indicate a dose-dependent increase in serum 316P and 300N levels. PK parameters were analyzed using WinNonlin software (Noncompartmental analysis, Model 201-IV bolus administration).

TABLE 25

| PK | 316P | | 300N | |
|---|---|---|---|---|
| Parameter | 5 mg/kg | 15 mg/kg | 5 mg/kg | 15 mg/kg |
| $T_{max}$ (h) | 0.428 | 0.105 | 4.02 | 0.428 |
| $C_{max}$ (μg/ml) | 184 | 527 | 226 | 1223 |
| $T_{1/2}$ (h) | 83 | 184 | 215 | 366 |

Serum Chemistry.

Blood samples were collected at pre-dose, 12 hr, 48 hr, and subsequently once every 48 hr, for clinical chemistry analysis, in particular lipid profiles (i.e. cholesterol, LDL-C, HDL-C, triglycerides). With the exception of the 12 hr post-dose sample, all animals were subject to an overnight fast prior to sample collection. The sample volume was approximately 1 ml. Chemistry parameters were determined using an Olympus automated analyzer. Parameters measured (Xybion code): Albumin (ALB); Alkaline Phosphatase (ALP); Alanine Aminotransferase (ALT); Aspartate Transaminase (AST); Total Bilirubin (TBIL); Calcium (Ca); Total Cholesterol (TCho); Creatine Kinase (CK); Creatinine (CRN); Gamma Glutamyltransaminase (GGT); Glucose (GLU); Inorganic Phosphorus (IP); Total Protein (TP); Triglyceride (TRIG); Blood Urea Nitrogen (BUN); Globulin (GLOB); Albumin/Globulin Ratio (A/G); Chloride (CI); Potassium (K); Sodium (Na); LDL and HDL cholesterol. Residual serum was stored at −20° C. or below and disposed of no sooner than one week after analysis.

Figure 6:
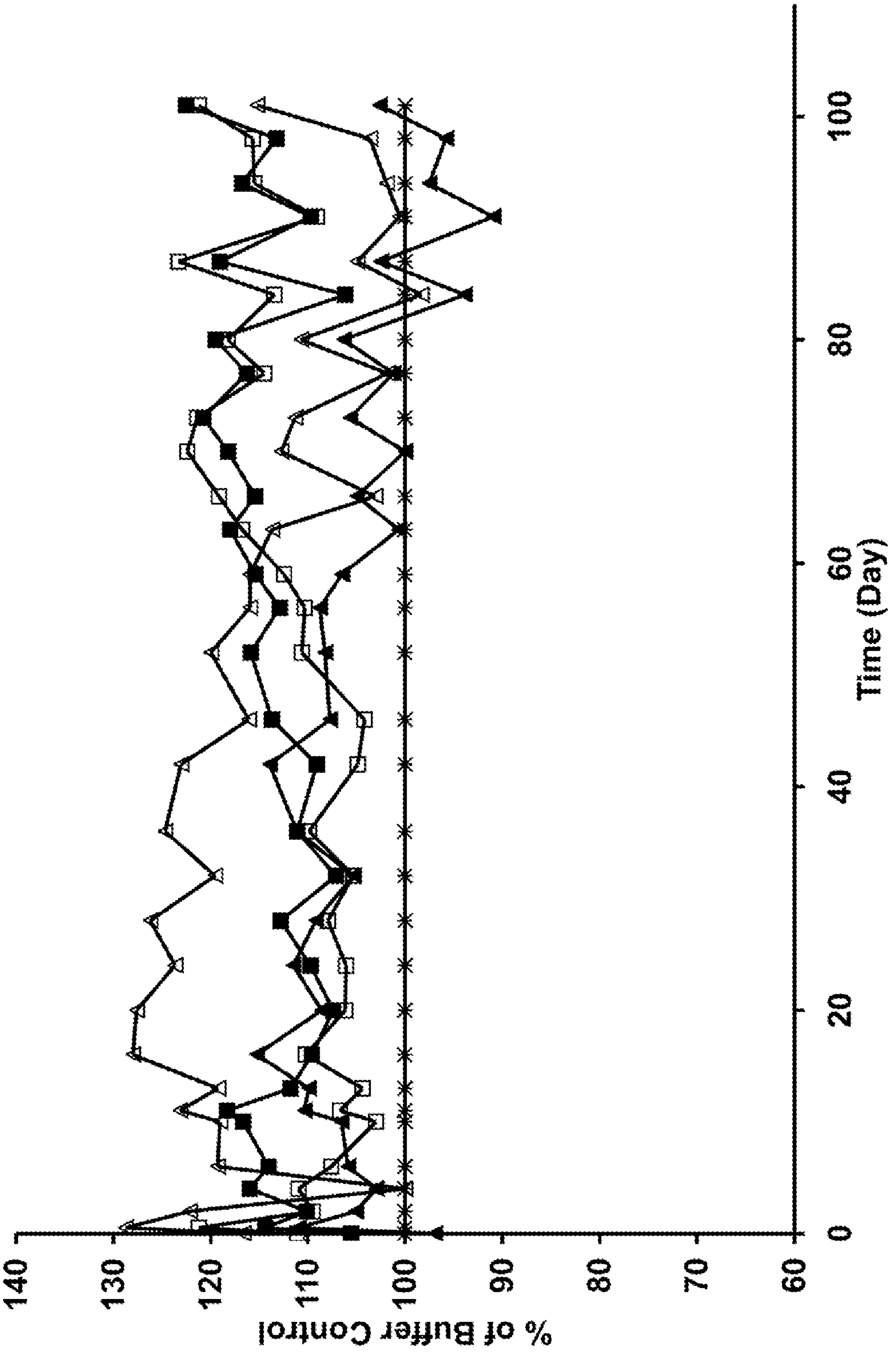
FIG. 6. Serum HDL cholesterol level as a percentage of change over buffer control. Buffer control (*); 316P 5 mg/kg (■); 300N 5 mg/kg (Δ); 316P 15 mg/kg (□); 300N 15 mg/kg (Δ).
Figure 7:
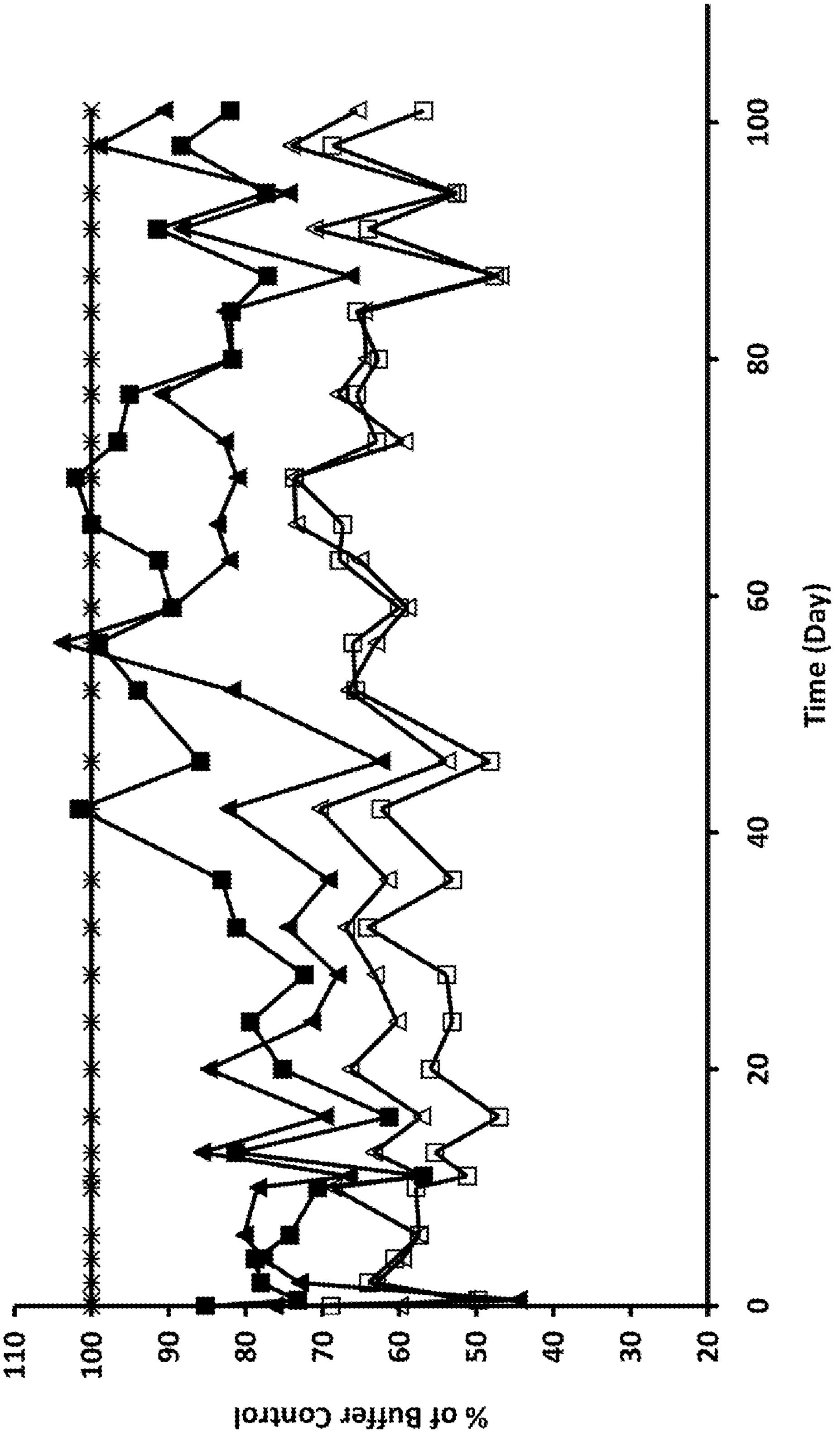
FIG. 7. Serum triglyceride level expressed as a percentage of change over buffer control. Buffer control (*); 316P 5 mg/kg (■); 300N 5 mg/kg (▲); 316P 15 mg/kg (□); 300N 15 mg/kg (Δ).

Results from samples through Day 105 post-dose time point are shown in FIGS. 3-7. There was a reduction in total cholesterol and LDL-C in animals receiving 316P and 300N, regardless of dose, within 24 hours of the first dose. Serum total cholesterol reduced rapidly and robustly (~35%, FIG. 3). A robust decrease of ~80% was seen in LDL-C (FIGS. 4-5) by day 6. In animals that received a 15 mg/kg dose of 300N, the reduction in both total cholesterol (~10-15% reduction) and LDL-C (~40% reduction) continued to at least day 80 of the study. In addition, HDL-C was elevated in animals that received 316P at 15 mg/kg (FIG. 6). Animals that received a higher dose (15 mg/kg) of either 316P or 300N also showed a reduction in triglycerides during the course of study (FIG. 7). 316P exhibited maximal suppression of LDL-C levels of up to 80% relative to baseline. The length of this suppression was dose-dependent with at least 60% suppression (relative to baseline LDL-C levels) lasting approximately 18 days (5 mg/kg dose) and approximately 45 days (15 mg/kg dose). 300N exhibits a distinct pharmacodynamic profile from 316P. LDL-C suppression by 300N was sustained for a much longer period of time at comparable doses (50% LDL-C suppression for 28 days following a 5 mg/kg dose and 50% LDL-C suppression for approximately 90 days following a 15 mg/kg dose). There was little or no measurable change in liver function as determined by ALT and AST measurements. All animals receiving an anti-PCSK9 antibody in the study exhibited a rapid suppression If LDL-C and total cholesterol.

Figure 8:
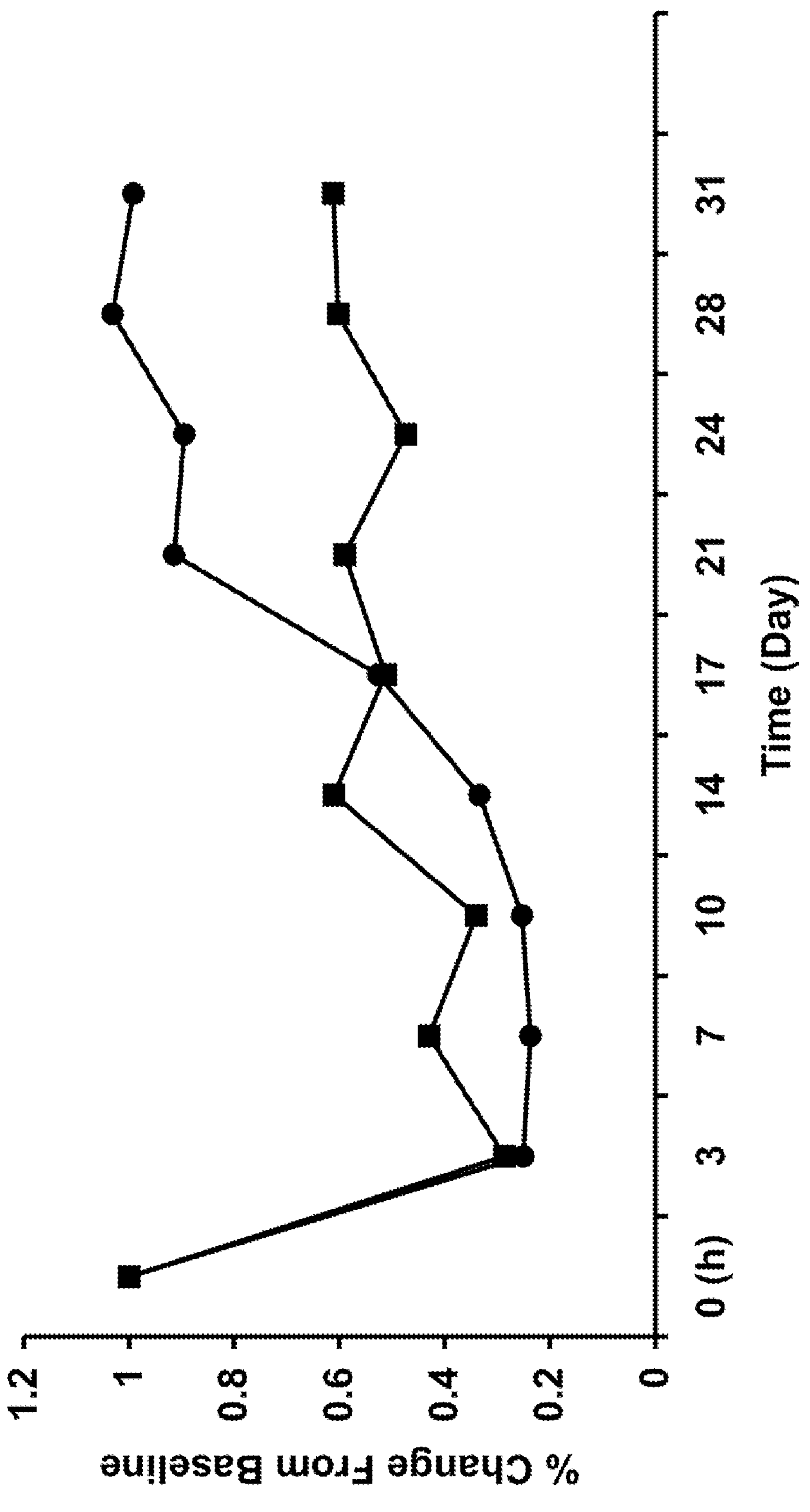
FIG. 8. Serum LDL cholesterol level expressed as a percentage of change over baseline following a single dose subcutaneous administration. 316P 5 mg/kg (■); 300N 5 mg/kg (●).
Figure 9:
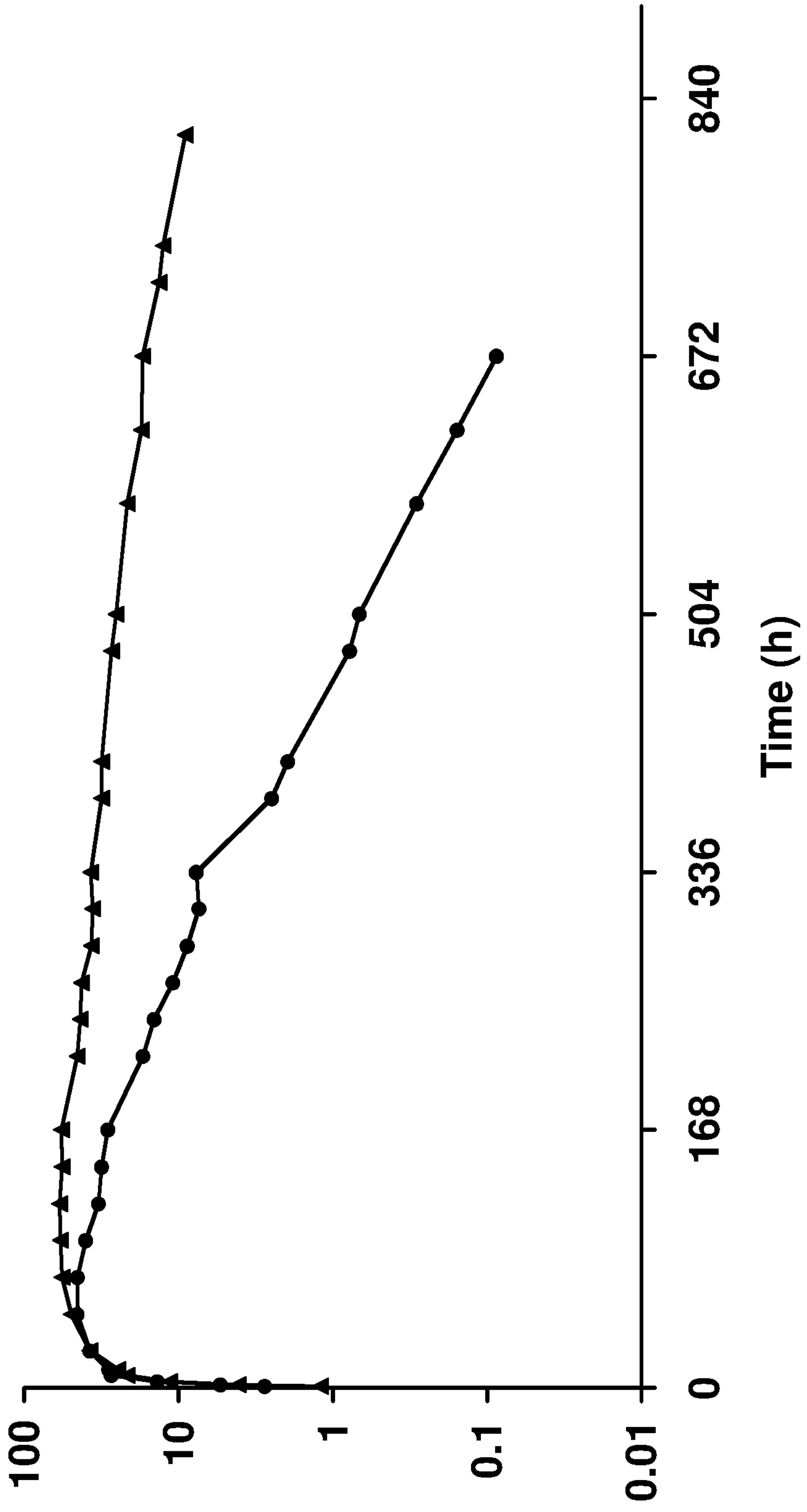
FIG. 9. Antibody concentrations in serum over time following a single dose subcutaneous administration. 316P 5 mg/kg (●); 300N 5 mg/kg (▲).

A similar LDL-C lowering effect of 316P and 300N was also observed in cynomolgous monkeys that received a single subcutaneous (SC) administration of either 5 mg/kg 316P or 5 mg/kg 300N (FIG. 8). Both 316P and 300N dramatically suppressed LDL-C levels and maintained an LDL-C lowering effect for approximately 15 and 30 days, respectively (FIG. 8). The pharmacodynamic effect (approximately 40% LDL-C suppression) approximately correlates with functional antibody levels in monkey serum (FIG. 9). As antibody levels decrease below 10 μg/ml, LDL-C suppression appeared to diminish as well. In addition, 300N demonstrated a substantially longer circulating half-life than 316P and hence a longer observed LDL-C suppression.

TABLE 26

| PK Parameter | 316P | 300N |
|---|---|---|
| $T_{max}$ (h) | 60 | 84 |
| $C_{max}$ (μg/ml) | 46 | 63 |
| $T_{1/2}$ (h) | 64 | 286 |

Example 14. Attenuation of LDL Receptor Degradation by Anti-h PCSK9 Antibodies

To assess the biological effect of PCSK9 on hepatic LDL receptor levels and subsequent effects on serum LDL-C levels, hPCSK9 was administered to mice expressing hPCSK9 but not mPCSK9 ($PCSK9^{hu/hu}$ mice) by intravenous injection. Specifically, $PCSK9^{hu/hu}$ mice were injected with PBS (control), or 1.2 mg/kg hPCSK9-mmh via the tail vein. Six hours after delivery of hPCSK9, a 1.4-fold elevation (relative to baseline level) in total cholesterol and a 2.3-fold elevation in LDL-C) in serum were observed. Analysis of hepatic LDL receptor levels in a separate cohort (n=3) of animals 4 hours after hPCSK9 administration revealed a significant reduction in detectable LDL receptor in liver homogenates.

Figure 10:
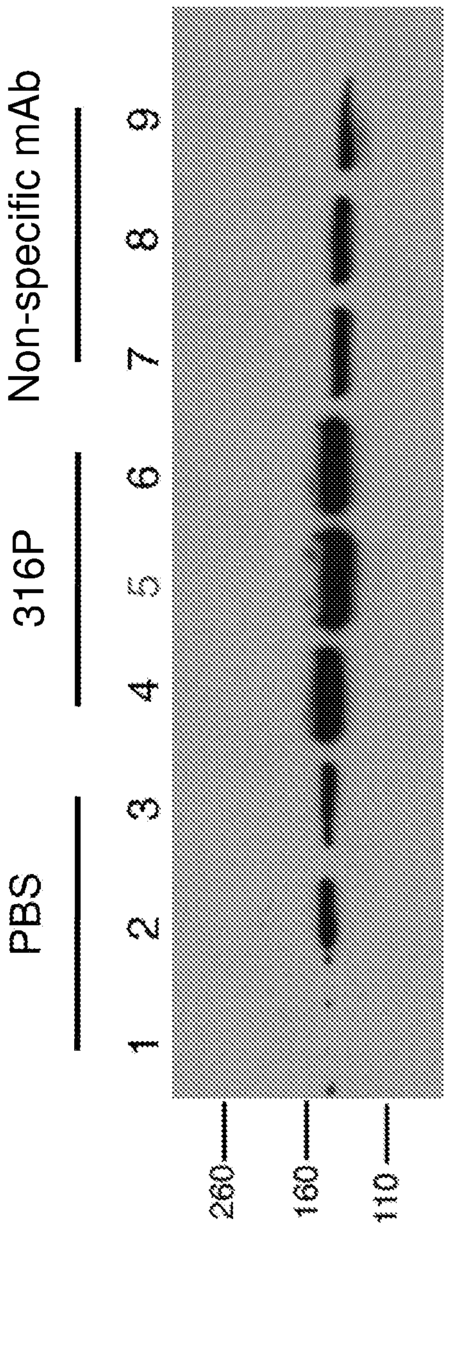
FIG. 10. Western blot for mouse LDL receptor of total liver homogenates. Samples were taken 24 hours after PBS (lanes 1-3), 5 mg/kg 316P (lanes 4-6), or 5 mg/kg of non-hPCSK9 specific mAb (lanes 7-8) administration and 4 hours after 1.2 mg/kg hPCSK9-mmh (all lanes).

To assess the biological effect of anti-hPCSK9 on hepatic LDL receptor levels and subsequent effects on serum LDL-C levels, 316P and a non-hPCSK9 specific mAb were administered to $PCSK9^{hu/hu}$ mice at equivalent dose (5 mg/kg i.p.) 20 hours prior to the hPCSK9-mmh protein injection described above. Four hours after the hPCSK9 administration, mice were sacrificed, a total of eight tissues (liver, brain, lung, kidney, heart, ileum, adrenal, and pancreas) were collected, and levels of LDL receptor were determined by Western blot. Changes in LDL receptor levels were only observed in liver. In comparison to PBS control dosing, administration of 316P significantly blocked the PCSK9-mediated increases in total cholesterol and LDL cholesterol (LDL-C=2.49 mg/dl at baseline and 3.1 mg/dl 6 hours after PCSK9; a 25% increase compared to 135% with vehicle). Prior administration of the non-hPCSK9 specific mAb blocked LDL-C increases by approximately 27% from PBS alone (LDL-C=4.1 mg/dl compared to PBS 5.6 mg/dl). Analysis of LDL receptor levels in a separate cohort of mice (n=3 per treatment group) revealed a significant reduction in LDL receptor levels with PCSK9 administration, which was blocked by 316P but not by the non-hPCSK9 specific mAb (FIG. 10).

Figure 11:
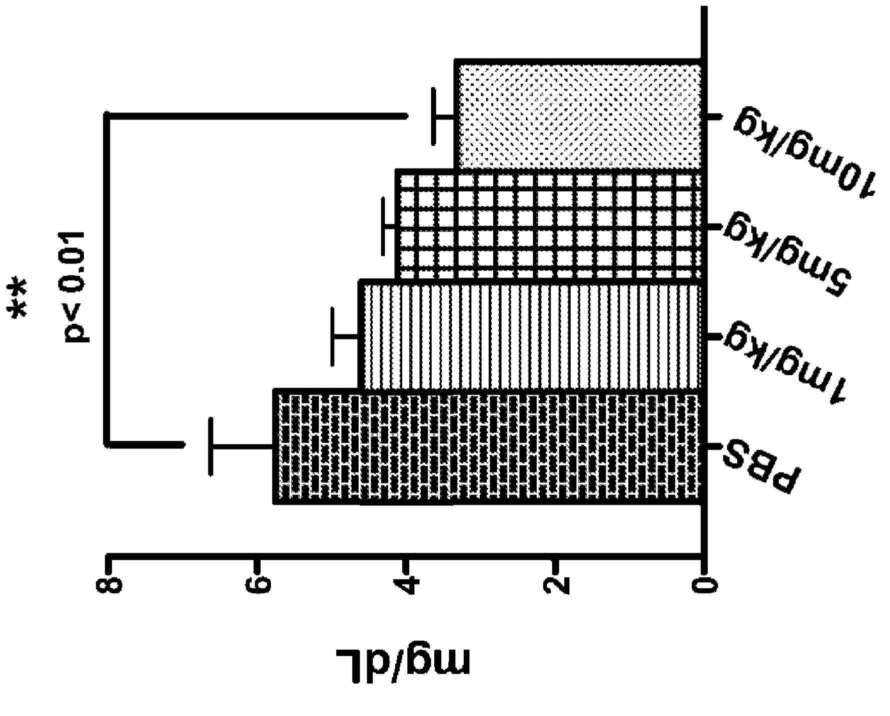
FIG. 11. Effects of 316P on serum LDL cholesterol level in PCSK9$^{hu/hu}$ mice. Buffer ⊞ control 316P 1 mg/kg (⊟); 316P 5 mg/kg (▦); 316P 10 mg/kg (░).

Effect of different doses of 316P was also evaluated in $PCSK9^{hu/hu}$ mice with both elevated LDL-C and elevated hPCSK9 levels. $PCSK9^{hu/hu}$ mice were first placed on a high carbohydrate diet for 8 weeks, resulting in a ~2-fold elevation in both LDL-C and hPCSK9 levels. Either 316P or a non-hPCSK9 specific mAb, each at 1 mg/kg, 5 mg/kg, or 10 mg/kg, were administered to the mice. Sera were collected 24 hours later and LDL-C levels were analyzed. 316P was effective in decreasing LDL-C levels in a dose-dependent manner (FIG. 11). In addition, 316P administered at a dose of 10 mg/kg, rapidly reduced LDL-C levels back to original (pre-diet) values within 24 hours.

Example 15. Mouse PK Studies

Figure 12:
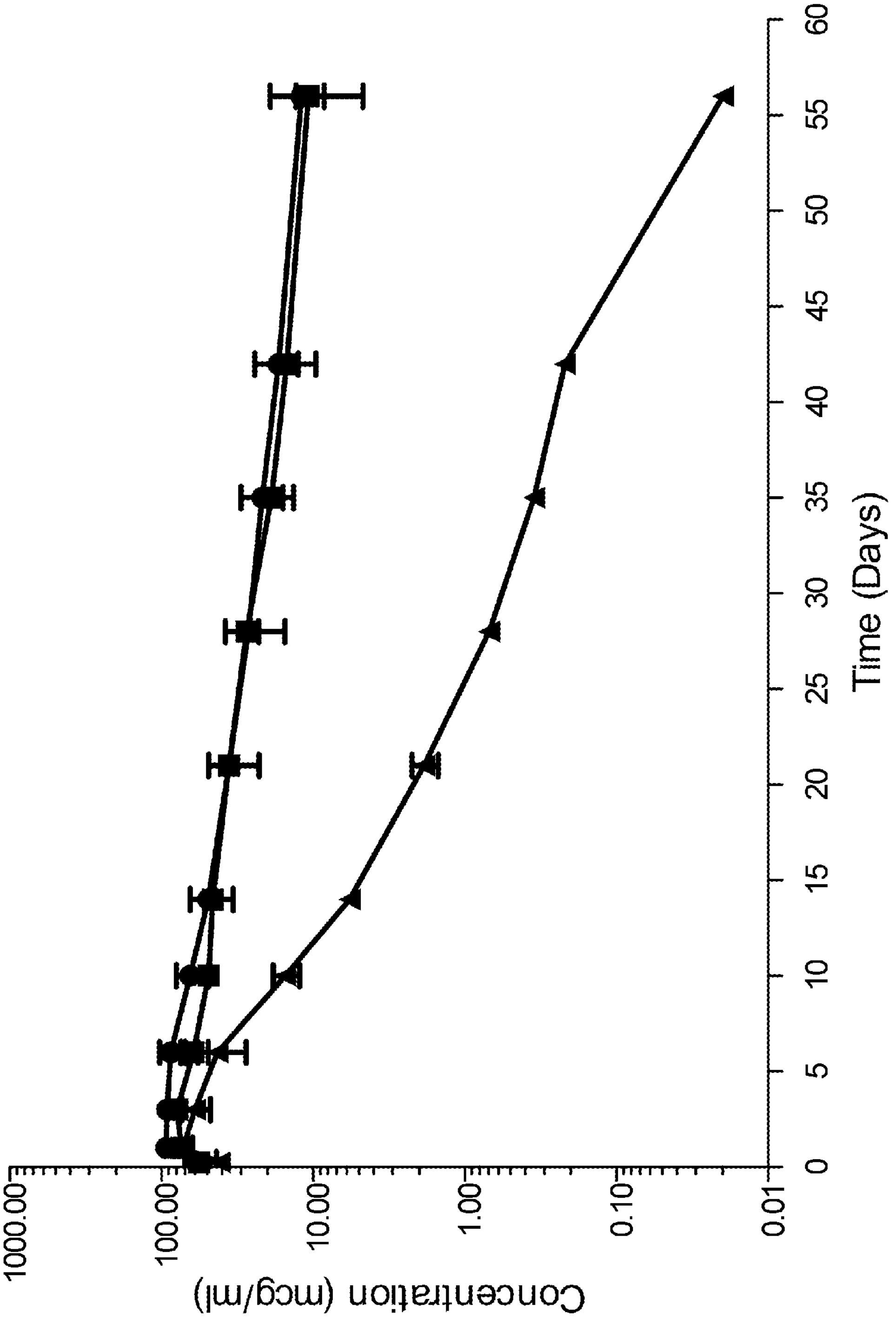
FIG. 12. Anti-hPCSK9 mAb serum pharmacokinetic profile in C57BL/6 mice. Single dose of Control I mAb (●) at 10 mg/kg; 316P (▲) at 10 mg/kg and 300N (■) at 10 mg/kg.
Figure 13:
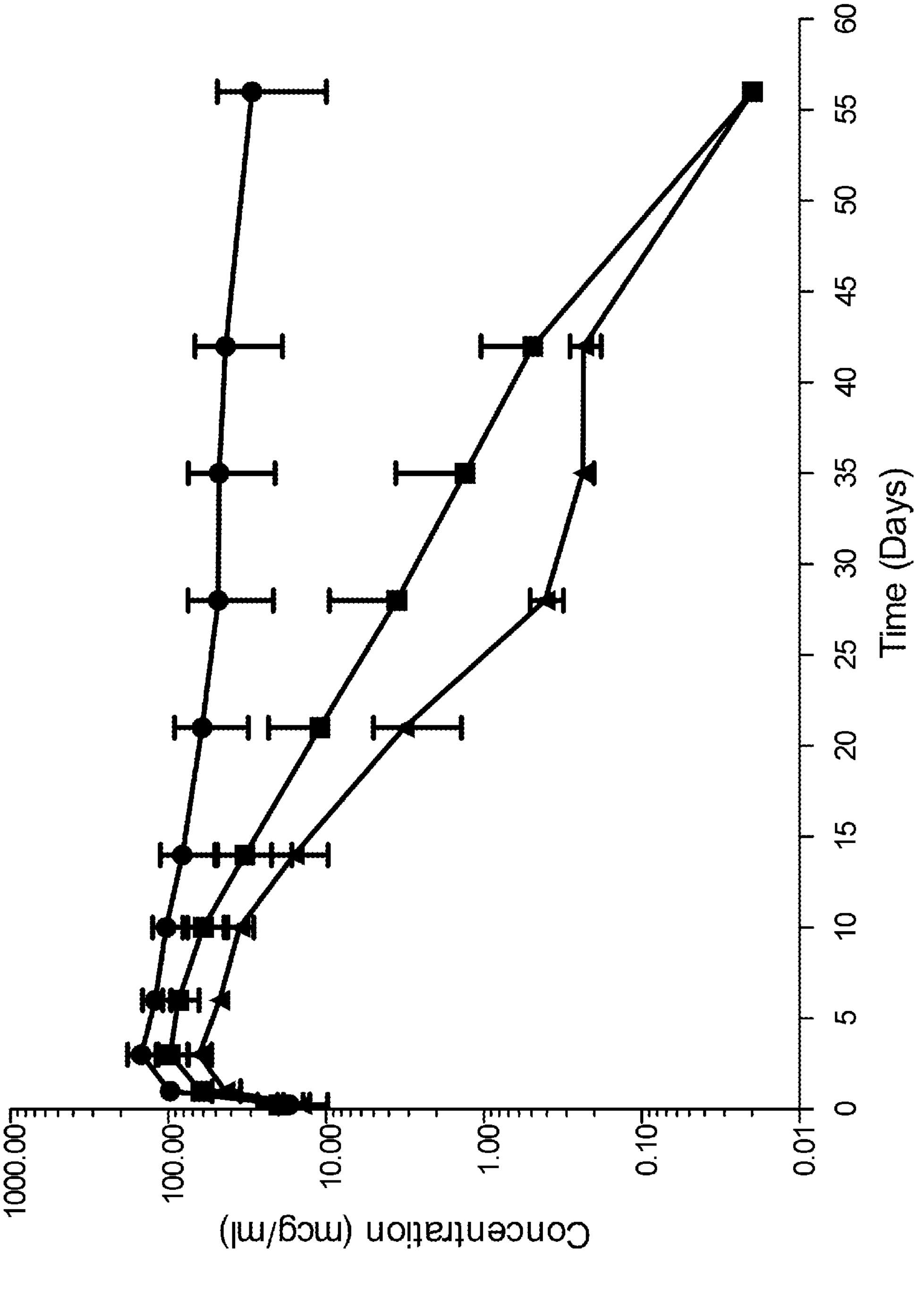
FIG. 13. Anti-hPCSK9 mAb serum pharmacokinetic profile in hPCSK9 heterozygous mice. Single dose of Control I mAb (●) at 10 mg/kg; 316P (▲) at 10 mg/kg and 300N (■) at 10 mg/kg.

A PK study was conducted in 6-week-old C57BL/6 mice and 11-15 week old hPCSK9 heterozygous mice. A single injection of Control I, 316P, or 300N, each at 10 mg/kg, was administered SC. Serum bleeds were measured for hIgG levels at 0 hr (pre-bleed), 6 hr, day 1, 3, 6, 10, 14, 21, 28, 35, 42 and 56, for a total of 12 time points, using an anti-hFc capture and anti-hFc detection sandwich ELISA (FIGS. 12 and 13). All mAbs achieved their $T_{max}$ at approximately 3 days with corresponding $C_{max}$ levels of approximately 47-115 μg/ml for C57BL/6 mice and 55-196 μg/ml for hPCSK9 heterozygous mice. At Day 56, Control I mAb levels were about 12 μg/ml and 300N levels were about 11 μg/ml whereas 316P levels were about less than 0.02 μg/ml in C57BL/6 mice. At Day 56 in hPCSK9 heterozygous mice, Control I mAb levels were about 29 μg/ml, while both 300N and 316P levels were below the quantifiable limit (BQL) of 0.02 μg/ml.

Example 16. Anti-hPCSK9 Antibody Binding to Mutant/Variant hPCSK9

To further assess binding between hPCSK9 and anti-hPCSK9 mAbs, 21 variant hPCSK9 proteins in which each variant contained a single point mutation and two variant hPCSK9 proteins each contained a double mutation were generated. Each selected antibody was captured on a $F(ab')_2$ anti-hIgG surface created through direct chemical coupling to a BIACORE™ chip to form a captured antibody surface. Each mmh-tagged variant hPCSK9 at varying concentrations from 100 nM to 25 nM was then injected over the captured antibody surface at a flowrate of 60 μl/min for 240 sec, and the dissociation of variant hPCSK9 and antibody was monitored in real time for 20 min at 25° C. nb: no binding was observed under these experimental conditions ($K_D$=M×$10^{-9}$; $T_{1/2}$=min; WT=wildtype).

TABLE 27

| | 316P | | 300N | | Control I | | Control II | | Control III | |
|---|---|---|---|---|---|---|---|---|---|---|
| | $K_D$ | $T_{1/2}$ | $K_D$ | $T_{1/2}$ | $K_D$ | $T_{1/2}$ | $K_D$ | $T_{1/2}$ | $K_D$ | $T_{1/2}$ |
| WT | 1.00 | 37 | 0.69 | 120 | 30.6 | 16 | 0.10 | 333 | 0.60 | 481 |
| P70A | 1.42 | 32 | 1.68 | 80 | 19.0 | 16 | 0.24 | 168 | 0.90 | 325 |
| S127R | 2.40 | 36 | 1.87 | 110 | 25.0 | 18 | 0.26 | 288 | 0.55 | 550 |
| D129G | 1.27 | 36 | 1.40 | 88 | 22.9 | 18 | 0.19 | 257 | 0.75 | 445 |
| S147F | 1.29 | 32 | 9.07 | 24 | 21.1 | 15 | 0.22 | 178 | 0.23 | 1468 |
| S153R | 5.64 | 4 | 0.56 | 141 | 36.6 | 17 | 0.09 | 322 | 3.33 | 60 |
| E159R | 6.96 | 5 | 0.82 | 94 | 31.7 | 16 | 0.08 | 350 | 2.97 | 68 |
| T162R | 0.98 | 43 | 0.58 | 140 | 29.0 | 17 | 0.09 | 322 | 0.48 | 362 |
| D192R | 1.35 | 28 | 0.75 | 119 | 30.2 | 15 | 0.09 | 326 | nb | nb |
| R194E | 0.38 | 71 | 0.65 | 129 | 31.4 | 16 | 0.07 | 389 | nb | nb |
| E197R | 1.42 | 27 | 0.67 | 115 | 30.2 | 17 | 0.09 | 339 | nb | nb |
| R215H | 0.86 | 41 | 1.03 | 98 | 37.8 | 17 | 0.65 | 49 | 0.74 | 272 |
| R215E | 0.90 | 43 | 1.81 | 77 | 44.0 | 16 | 4.48 | 12 | 0.78 | 276 |
| F216L | 1.83 | 32 | 0.99 | 121 | 21.2 | 15 | 1.35 | 39 | 0.33 | 880 |
| R237E | 2.48 | 15 | 1.03 | 109 | 29.6 | 15 | 0.07 | 481 | 5.89 | 43 |
| D238R | 410 | 1 | 0.78 | 123 | 25.9 | 19 | 0.24 | 144 | 0.14 | 1273 |
| A341R | 1.54 | 21 | 0.34 | 190 | 28.7 | 18 | 0.08 | 340 | 0.88 | 200 |
| D343R | 7.88 | 6 | 1.18 | 89 | 27.0 | 16 | 0.08 | 402 | 4.13 | 66 |
| R357H | 6.26 | 30 | 6.53 | 66 | 26.4 | 13 | 0.63 | 165 | 1.91 | 896 |
| E366K | 2.92 | 13 | 36.0 | 2 | 28.8 | 18 | 0.46 | 69 | 0.38 | 808 |
| D374Y | 2.04 | 15 | 0.66 | 83 | 25.0 | 17 | 0.08 | 285 | 1.02 | 161 |
| V380M | 0.48 | 63 | 2.82 | 28 | 25.9 | 17 | 0.15 | 177 | 0.35 | 711 |
| P70A, S147F | 1.18 | 34 | 7.87 | 24 | 23.5 | 18 | 0.23 | 164 | 0.79 | 348 |
| E366K, V380M | 3.33 | 12 | 78.3 | 1 | 25.5 | 18 | 0.59 | 60 | 0.52 | 551 |

The results show that when residue D238 was mutated, the binding affinity of 316P for hPCSK9 was reduced >400-fold, from a $K_D$ of $1\times10^{-9}$ M to $410\times10^{-9}$ M; and $T_{1/2}$ shortened about 30-fold, from 37 to 1 min, indicating that 316P binds an epitope on hPCSK9 comprising D238 of hPCSK9 (SEQ ID NO:755). Additionally, BIACORE™ assays show that 316P binding affinity and $T_{1/2}$ were reduced about 5- to 10-fold when a residue at 153, 159 or 343 was mutated. Specifically, $K_D$ was reduced from about $1\times10^{-9}$ M to between about 5-$8\times10^{-9}$ M when any one of S153, E159 or D343 were mutated; while $T_{1/2}$ was decreased from about 37 min to between about 4-6 min.

300N binding to hPCSK9 was reduced about 50-fold when the residue at position 366 was mutated, resulting in a decreased $K_D$ of from about $0.7\times10^{-9}$ M to about $36\times10^{-9}$ M and a shorter $T_{1/2}$ from about 120 to 2 min. These results indicate that 300N binds an epitope on hPCSK9 comprising E366 of hPCSK9 (SEQ ID NO:755). Additionally, the BIACORE™ assays show that 300N binding affinity and $T_{1/2}$ were reduced between 2- to >10-fold when a residue at 147 or 380 was mutated. Specifically, $K_D$ was reduced from about $0.69\times10^{-9}$ M to between about 2-$9\times10^{-9}$ M when any of S147 or V380 were mutated; while $T_{1/2}$ was shortened from about 120 min to between about 24-66 min. Compared to 316P, 300N binding to hPCSK9 was not reduced by a mutation at residue 238.

In contrast, Control I antibody did not exhibit an altered binding affinity or $T_{1/2}$ in response to any of the positional mutations tested; Control II antibody exhibited a 40-fold decreased affinity when residue 215 was mutated (R215E) (from ~$0.1\times10^{-9}$ to ~$4.5\times10^{-9}$), and $T_{1/2}$ was about 27-fold shorter (from ~333 to 12 min); while Control III antibody exhibited a decreased affinity when residue 237 was mutated ($K_D$ decreased from ~$0.6\times10^{-9}$ to ~$5.9\times10^{-9}$, and $T_{1/2}$ decreased from ~481 to ~43 min).

Binding specificity of 316P, 300N, and control anti-hPCSK9 mAbs to hPCSK9 variants was tested using an ELISA-based immunoassay. Anti-PCSK9 mAbs were coated on a 96-well plate overnight at 4° C. Each mmh-tagged variant hPCSK9 in CHO-k1 transient transfection lysate supernatants was added to the antibody-coated plate at various concentrations ranging from 0 to 5 nM. After 1 hr binding at RT, the plate was washed and bound variant hPCSK9 was detected using HRP-conjugated anti-myc polyclonal antibody (−=OD<0.7; +=OD 0.7-1.5; ++=OD>1.5).

TABLE 28

| hPCSK9 or Variant | 316P | 300N | Control I | Control II | Control III |
|---|---|---|---|---|---|
| hPCSK9(WT) | ++ | ++ | ++ | ++ | ++ |
| hPCSK9(S127R) | ++ | ++ | ++ | ++ | ++ |
| hPCSK9(D129G) | ++ | ++ | ++ | ++ | ++ |
| hPCSK9(S153R) | ++ | ++ | ++ | ++ | ++ |
| hPCSK9(R215H) | ++ | ++ | ++ | ++ | ++ |
| hPCSK9(F216L) | ++ | ++ | ++ | ++ | ++ |
| hPCSK9(R237E) | ++ | ++ | ++ | ++ | ++ |
| hPCSK9(D238R) | − | ++ | ++ | ++ | ++ |
| hPCSK9(A341R) | ++ | ++ | ++ | ++ | ++ |
| hPCSK9(D343R) | ++ | ++ | ++ | ++ | ++ |
| hPCSK9(R357H) | ++ | ++ | ++ | ++ | ++ |
| hPCSK9(E159R) | ++ | ++ | ++ | ++ | ++ |
| hPCSK9(T162R) | ++ | ++ | ++ | ++ | ++ |
| HPCSK9(D192R) | ++ | ++ | ++ | ++ | − |
| hPCSK9(R194E) | ++ | ++ | ++ | ++ | − |
| hPCSK9(E197R) | ++ | ++ | ++ | ++ | − |
| hPCSK9(R215E) | ++ | ++ | ++ | ++ | ++ |
| hPCSK9(P70A) | ++ | ++ | ++ | ++ | ++ |
| hPCSK9(S147F) | ++ | ++ | ++ | ++ | ++ |
| hPCSK9(E366K) | ++ | + | ++ | ++ | ++ |
| hPCSK9(V380M) | ++ | ++ | ++ | ++ | ++ |
| hPCSK9(P70A, S147F) | ++ | ++ | ++ | ++ | ++ |
| hPCSK9(E366K, V380M) | ++ | + | ++ | ++ | ++ |

Example 17. Effect of 316P on Normolipemic and Hyperlipemic Hamster

Figure 14:
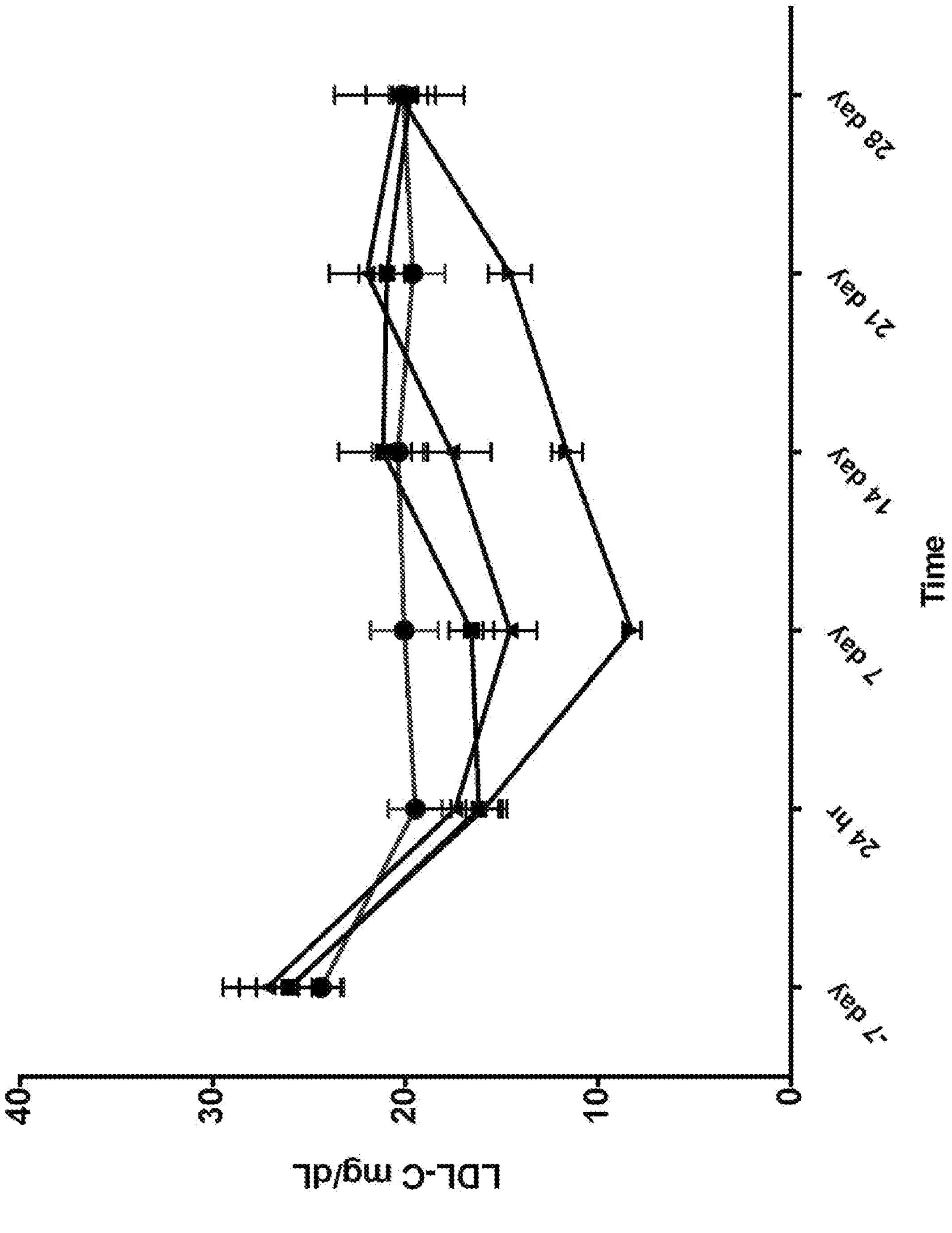
FIG. 14. Effect of 316P on serum LDL cholesterol levels in Syrian Hamster fed a normal diet. Buffer control (●); 316P 1 mg/kg (■); 316P 3 mg/kg (▲); 316P 5 mg/kg (▼).

The ability of anti-PCSK9 mAb 316P to reduce serum LDL-C was tested in normolipemic or hyperlipemic Gold Syrian hamsters (*Mesocricetus auratus*). Male Syrian Hamsters, age 6-8 weeks, weighing between 80-100 grams, were allowed to acclimate for a period of 7 days before entry into the study. All animals were placed on either a standard chow diet or a hyperlipemic diet of chow supplemented with 0.1% cholesterol and 10% coconut oil. The 316P mAb was delivered to hamsters by a single subcutaneous injection at doses of 1, 3, or 10 mg/kg for normolipemic hamsters and at doses of 3, 10, or 30 mg/kg for hyperlipemic hamsters. Serum samples were taken from all groups at 24 hr and 7, 14, and 22 days post injection, at which time serum lipid levels were assessed and compared to baseline levels taken 7 days prior to the administration of the mAbs. Circulating total cholesterol and LDL-C in normolipemic hamsters was significantly reduced in a dose-dependent manner compared to vehicle injection. As shown in FIG. 14, administration of 316P effectively reduced LDL-C levels by up to 60% seven days post injection at the highest dose (10 mg/kg) tested. Similar cholesterol reducing effect of 316P was not observed in hyperlipemic hamsters.

We claim:

1. A nucleic acid molecule comprising:

a first nucleotide sequence encoding a heavy chain variable region (HCVR) of an antibody that binds human proprotein convertase subtilisin/kexin type 9 (PCSK9), wherein the HCVR comprises a heavy chain complementarity determining region (HCDR)1 comprising SEQ ID NO:76, an HCDR2 comprising SEQ ID NO:78, and an HCDR3 comprising SEQ ID NO:80; and a second nucleotide sequence encoding a light chain variable region (LCVR) of an antibody that binds human PCSK9, wherein the LCVR comprises a light chain complementarity determining region (LCDR)1 comprising SEQ ID NO:84, an LCDR2 comprising SEQ ID NO:86, and an LCDR3 comprising SEQ ID NO:88.

2. The A-nucleic acid molecule of claim 1, wherein the first nucleotide sequence encodes an HCVR comprising SEQ ID NO:90 and the second nucleotide sequence encodes an LCVR comprising SEQ ID NO:92.

3. The nucleic acid molecule of claim 1, wherein the first nucleotide sequence has at least 95% sequence identity to SEQ ID:89 and the second nucleotide sequence has at least 95% sequence identity to SEQ ID NO:91.

4. The nucleic acid molecule of claim 1, wherein the first nucleotide sequence comprises SEQ ID NO:89 and the second nucleotide sequence comprises SEQ ID NO:91.

5. A recombinant expression vector comprising the nucleic acid molecule of claim 1.

6. A host cell containing the recombinant expression vector of claim 5.

7. The host cell of claim 6, wherein the host cell is a Chinese Hamster Ovary (CHO) cell.

8. A method of producing an antibody that binds human PCSK9, the method comprising growing the host cell of claim 6 under conditions in which the antibody is produced, and recovering the antibody so produced.

* * * * *

SEQUENCE LISTING

<160> NUMBER OF SEQ ID NOS: 763

<210> SEQ ID NO 1
<211> LENGTH: 351
<212> TYPE: DNA
<213> ORGANISM: Artificial Sequence
<220> FEATURE:
<223> OTHER INFORMATION: Synthetic

<400> SEQUENCE: 1
caggtccagc tggtgcagtc tgggggaggc ttggtacagc ctggggggtc cctgagactc 60
tcctgtgcag cctctggatt tactctaagt agttacgaca tgcactgggt ccgccaatct 120
acaggaaaag gtctggagtg ggtctcagct attggttcta ccggtgacac atactatcca 180
ggctccgtga agggccgatt caccatcacc agagaaaaag ccaagaactc cgtgtatctt 240
caaatgaaca gcctgagagc cggggacacg gctgtgtatt actgtgtaag agaggggtgg 300
gaggtaccct ttgactactg gggccaggga accctggtca ctgtctcctc a 351

<210> SEQ ID NO 2
<211> LENGTH: 117
<212> TYPE: PRT
<213> ORGANISM: Artificial Sequence
<220> FEATURE:
<223> OTHER INFORMATION: Synthetic

<400> SEQUENCE: 2

Gln Val Gln Leu Val Gln Ser Gly Gly Gly Leu Val Gln Pro Gly Gly
1 5 10 15

Ser Leu Arg Leu Ser Cys Ala Ala Ser Gly Phe Thr Leu Ser Ser Tyr
20 25 30

Asp Met His Trp Val Arg Gln Ser Thr Gly Lys Gly Leu Glu Trp Val
35 40 45

Ser Ala Ile Gly Ser Thr Gly Asp Thr Tyr Tyr Pro Gly Ser Val Lys
50 55 60

Gly Arg Phe Thr Ile Thr Arg Glu Lys Ala Lys Asn Ser Val Tyr Leu

```
65                  70                  75                  80

Gln Met Asn Ser Leu Arg Ala Gly Asp Thr Ala Val Tyr Tyr Cys Val
                85                  90                  95

Arg Glu Gly Trp Glu Val Pro Phe Asp Tyr Trp Gly Gln Gly Thr Leu
            100                 105                 110

Val Thr Val Ser Ser
        115


<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3

ggatttactc taagtagtta cgac                                            24


<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly Phe Thr Leu Ser Ser Tyr Asp
1               5


<210> SEQ ID NO 5
<211> LENGTH: 21
<212> TYPE: DNA
<213> ORGANISM: Artificial Sequence
<220> FEATURE:
<223> OTHER INFORMATION: Synthetic

<400> SEQUENCE: 5

attggttcta ccggtgacac a                                               21


<210> SEQ ID NO 6
<211> LENGTH: 7
<212> TYPE: PRT
<213> ORGANISM: Artificial Sequence
<220> FEATURE:
<223> OTHER INFORMATION: Synthetic

<400> SEQUENCE: 6

Ile Gly Ser Thr Gly Asp Thr
1               5


<210> SEQ ID NO 7
<211> LENGTH: 33
<212> TYPE: DNA
<213> ORGANISM: Artificial Sequence
<220> FEATURE:
<223> OTHER INFORMATION: Synthetic

<400> SEQUENCE: 7

gtaagagagg ggtgggaggt accctttgac tac                                  33


<210> SEQ ID NO 8
<211> LENGTH: 11
<212> TYPE: PRT
<213> ORGANISM: Artificial Sequence
<220> FEATURE:
```

-continued

<223> OTHER INFORMATION: Synthetic

<400> SEQUENCE: 8

```
Val Arg Glu Gly Trp Glu Val Pro Phe Asp Tyr
1               5                   10
```

<210> SEQ ID NO 9
<211> LENGTH: 327
<212> TYPE: DNA
<213> ORGANISM: Artificial Sequence
<220> FEATURE:
<223> OTHER INFORMATION: Synthetic

<400> SEQUENCE: 9

```
gacatccaga tgacccagtc tccagccacc ctgtctgtgt ctccagggga aagagccgcc     60

ctctcctgca gggccagtca gagtgttagc agcaacttag cctggtacca ccagaaacct    120

ggccaggctc ccaggctcct catctatggt gcatccacca gggccactgg tatcccagcc    180

aggttcagtg gcattgggtc tgggacagag ttcactctca ttatcagcag cctgcagtct    240

gaagattttg cattttattt ctgtcagcag tataataact ggcctccatt cactttcggc    300

cctgggacca aggtggagat caaacga                                        327
```

<210> SEQ ID NO 10
<211> LENGTH: 109
<212> TYPE: PRT
<213> ORGANISM: Artificial Sequence
<220> FEATURE:
<223> OTHER INFORMATION: Synthetic

<400> SEQUENCE: 10

```
Asp Ile Gln Met Thr Gln Ser Pro Ala Thr Leu Ser Val Ser Pro Gly
1               5                   10                  15

Glu Arg Ala Ala Leu Ser Cys Arg Ala Ser Gln Ser Val Ser Ser Asn
            20                  25                  30

Leu Ala Trp Tyr His Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ile Gly Ser Gly Thr Glu Phe Thr Leu Ile Ile Ser Ser Leu Gln Ser
65                  70                  75                  80

Glu Asp Phe Ala Phe Tyr Phe Cys Gln Gln Tyr Asn Asn Trp Pro Pro
                85                  90                  95

Phe Thr Phe Gly Pro Gly Thr Lys Val Glu Ile Lys Arg
            100                 105
```

<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11

```
cagagtgtta gcagcaac                                                   18
```

<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12

Gln Ser Val Ser Ser Asn
1 5

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 ggtgcatcc 9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

Gly Ala Ser
1

<210> SEQ ID NO 15
<211> LENGTH: 30
<212> TYPE: DNA
<213> ORGANISM: Artificial Sequence
<220> FEATURE:
<223> OTHER INFORMATION: Synthetic

<400> SEQUENCE: 15
cagcagtata ataactggcc tccattcact 30

<210> SEQ ID NO 16
<211> LENGTH: 10
<212> TYPE: PRT
<213> ORGANISM: Artificial Sequence
<220> FEATURE:
<223> OTHER INFORMATION: Synthetic

<400> SEQUENCE: 16

Gln Gln Tyr Asn Asn Trp Pro Pro Phe Thr
1 5 10

<210> SEQ ID NO 17
<211> LENGTH: 351
<212> TYPE: DNA
<213> ORGANISM: Artificial Sequence
<220> FEATURE:
<223> OTHER INFORMATION: Synthetic

<400> SEQUENCE: 17
gaggtgcagc tggtggagtc tgggggaggc ttggtacagc ctggggggtc cctgagactc 60
tcctgtgcag cctctggatt tactctaagt agttacgaca tgcactgggt ccgccaatct 120
acaggaaaag gtctggagtg ggtctcagct attggttcta ccggtgacac atactatcca 180
ggctccgtga agggccgatt caccatcacc agagaaaaag ccaagaactc cgtgtatctt 240
caaatgaaca gcctgagagc cggggacacg gctgtgtatt actgtgtaag agaggggtgg 300
gaggtaccct ttgactactg gggccaggga accctggtca ccgtctcctc a 351

<210> SEQ ID NO 18
<211> LENGTH: 117
<212> TYPE: PRT
<213> ORGANISM: Artificial Sequence
<220> FEATURE:
<223> OTHER INFORMATION: Synthetic

<400> SEQUENCE: 18

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Leu Ser Ser Tyr
20 25 30

Asp Met His Trp Val Arg Gln Ser Thr Gly Lys Gly Leu Glu Trp Val
35 40 45

Ser Ala Ile Gly Ser Thr Gly Asp Thr Tyr Tyr Pro Gly Ser Val Lys
50 55 60

Gly Arg Phe Thr Ile Thr Arg Glu Lys Ala Lys Asn Ser Val Tyr Leu
65 70 75 80

Gln Met Asn Ser Leu Arg Ala Gly Asp Thr Ala Val Tyr Tyr Cys Val
85 90 95

Arg Glu Gly Trp Glu Val Pro Phe Asp Tyr Trp Gly Gln Gly Thr Leu
100 105 110

Val Thr Val Ser Ser
115

<210> SEQ ID NO 19
<211> LENGTH: 324
<212> TYPE: DNA
<213> ORGANISM: Artificial Sequence
<220> FEATURE:
<223> OTHER INFORMATION: Synthetic

<400> SEQUENCE: 19
gaaatagtga tgacgcagtc tccagccacc ctgtctgtgt ctccagggga aagagccgcc 60
ctctcctgca gggccagtca gagtgttagc agcaacttag cctggtacca ccagaaacct 120
ggccaggctc ccaggctcct catctatggt gcatccacca gggccactgg tatcccagcc 180
aggttcagtg gcattgggtc tgggacagag ttcactctca ttatcagcag cctgcagtct 240
gaagattttg cattttattt ctgtcagcag tataataact ggcctccatt cactttcggc 300
cctgggacca aagtggatat caaa 324

<210> SEQ ID NO 20
<211> LENGTH: 108
<212> TYPE: PRT
<213> ORGANISM: Artificial Sequence
<220> FEATURE:
<223> OTHER INFORMATION: Synthetic

<400> SEQUENCE: 20

Glu Ile Val Met Thr Gln Ser Pro Ala Thr Leu Ser Val Ser Pro Gly
1 5 10 15

Glu Arg Ala Ala Leu Ser Cys Arg Ala Ser Gln Ser Val Ser Ser Asn
20 25 30

Leu Ala Trp Tyr His Gln Lys Pro Gly Gln Ala Pro Arg Leu Leu Ile
35 40 45

Tyr Gly Ala Ser Thr Arg Ala Thr Gly Ile Pro Ala Arg Phe Ser Gly
50 55 60

Ile Gly Ser Gly Thr Glu Phe Thr Leu Ile Ile Ser Ser Leu Gln Ser
65 70 75 80

```
Glu Asp Phe Ala Phe Tyr Phe Cys Gln Gln Tyr Asn Asn Trp Pro Pro
                85                  90                  95

Phe Thr Phe Gly Pro Gly Thr Lys Val Asp Ile Lys
            100                 105


<210> SEQ ID NO 21
<211> LENGTH: 351
<212> TYPE: DNA
<213> ORGANISM: Artificial Sequence
<220> FEATURE:
<223> OTHER INFORMATION: Synthetic

<400> SEQUENCE: 21

gaggtgcagc tggtggagtc tgggggaggc ttggtacagc ctgggggtc cctgagactc      60

tcctgtgcag cctctggatt tactctaagt agttacgaca tgcactgggt ccgccaagct     120

acaggaaaag gtctggagtg ggtctcagct attggttcta ccggtgacac atactatcca     180

ggctccgtga agggccgatt caccatctcc agagaaaatg ccaagaactc cttgtatctt     240

caaatgaaca gcctgagagc cggggacacg gctgtgtatt actgtgtaag agaggggtgg     300

gaggtaccct ttgactactg gggccaggga accctggtca ccgtctcctc a              351


<210> SEQ ID NO 22
<211> LENGTH: 117
<212> TYPE: PRT
<213> ORGANISM: Artificial Sequence
<220> FEATURE:
<223> OTHER INFORMATION: Synthetic

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Asp Met His Trp Val Arg Gln Ala Thr Gly Lys Gly Leu Glu Trp Val
        35                  40                  45

Ser Ala Ile Gly Ser Thr Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Val
                85                  90                  95

Arg Glu Gly Trp Glu Val Pro Phe Asp Tyr Trp Gly Gln Gly Thr Leu
            100                 105                 110

Val Thr Val Ser Ser
        115


<210> SEQ ID NO 23
<211> LENGTH: 324
<212> TYPE: DNA
<213> ORGANISM: Artificial Sequence
<220> FEATURE:
<223> OTHER INFORMATION: Synthetic

<400> SEQUENCE: 23

gaaatagtga tgacgcagtc tccagccacc ctgtctgtgt ctccagggga aagagccacc      60

ctctcctgca gggccagtca gagtgttagc agcaacttag cctggtacca gcagaaacct     120

ggccaggctc ccaggctcct catctatggt gcatccacca gggccactgg tatcccagcc     180
```

```
aggttcagtg gcagtgggtc tgggacagag ttcactctca ccatcagcag cctgcagtct    240

gaagattttg cagtttatta ctgtcagcag tataataact ggcctccatt cactttcggc    300

cctgggacca aagtggatat caaa                                           324
```

<210> SEQ ID NO 24
<211> LENGTH: 108
<212> TYPE: PRT
<213> ORGANISM: Artificial Sequence
<220> FEATURE:
<223> OTHER INFORMATION: Synthetic

<400> SEQUENCE: 24

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Phe Thr Phe Gly Pro Gly Thr Lys Val Asp Ile Lys
            100                 105
```

<210> SEQ ID NO 25
<211> LENGTH: 342
<212> TYPE: DNA
<213> ORGANISM: Artificial Sequence
<220> FEATURE:
<223> OTHER INFORMATION: Synthetic

<400> SEQUENCE: 25

```
caggtgcagc tggtgcagtc tgggggaggc gtggtccagc ctgggaggtc cctgagactc     60

tcctgtgcag cgtctggatt caccttcagt agctatggca tgcactgggt ccgccaggct    120

ccaggcaagg ggctggagtg ggtggcgttt ataggatttg atggaagtaa tatacattat    180

ggagactccg tgaggggccg aatcatcata tccagagaca attccgagaa cacgttgtat    240

ctggaaatga acagcctgag agccgaggac acggcaatgt actattgtgc gagagagaag    300

ggtttagact ggggccaggg aaccacggtc accgtctcct ca                       342
```

<210> SEQ ID NO 26
<211> LENGTH: 114
<212> TYPE: PRT
<213> ORGANISM: Artificial Sequence
<220> FEATURE:
<223> OTHER INFORMATION: Synthetic

<400> SEQUENCE: 26

```
Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Gly Phe Asp Gly Ser Asn Ile His Tyr Gly Asp Ser Val
```

```
    50                  55                  60

Arg Gly Arg Ile Ile Ile Ser Arg Asp Asn Ser Glu Asn Thr Leu Tyr
65                  70                  75                  80

Leu Glu Met Asn Ser Leu Arg Ala Glu Asp Thr Ala Met Tyr Tyr Cys
                85                  90                  95

Ala Arg Glu Lys Gly Leu Asp Trp Gly Gln Gly Thr Thr Val Thr Val
            100                 105                 110

Ser Ser


<210> SEQ ID NO 27
<211> LENGTH: 24
<212> TYPE: DNA
<213> ORGANISM: Artificial Sequence
<220> FEATURE:
<223> OTHER INFORMATION: Synthetic

<400> SEQUENCE: 27

ggattcacct tcagtagcta tggc                                            24


<210> SEQ ID NO 28
<211> LENGTH: 8
<212> TYPE: PRT
<213> ORGANISM: Artificial Sequence
<220> FEATURE:
<223> OTHER INFORMATION: Synthetic

<400> SEQUENCE: 28

Gly Phe Thr Phe Ser Ser Tyr Gly
1               5


<210> SEQ ID NO 29
<211> LENGTH: 24
<212> TYPE: DNA
<213> ORGANISM: Artificial Sequence
<220> FEATURE:
<223> OTHER INFORMATION: Synthetic

<400> SEQUENCE: 29

ataggatttg atggaagtaa tata                                            24


<210> SEQ ID NO 30
<211> LENGTH: 8
<212> TYPE: PRT
<213> ORGANISM: Artificial Sequence
<220> FEATURE:
<223> OTHER INFORMATION: Synthetic

<400> SEQUENCE: 30

Ile Gly Phe Asp Gly Ser Asn Ile
1               5


<210> SEQ ID NO 31
<211> LENGTH: 21
<212> TYPE: DNA
<213> ORGANISM: Artificial Sequence
<220> FEATURE:
<223> OTHER INFORMATION: Synthetic

<400> SEQUENCE: 31

gcgagagaga agggtttaga c                                               21


<210> SEQ ID NO 32
<211> LENGTH: 7
<212> TYPE: PRT
```

<213> ORGANISM: Artificial Sequence
<220> FEATURE:
<223> OTHER INFORMATION: Synthetic

<400> SEQUENCE: 32

Ala Arg Glu Lys Gly Leu Asp
1 5

<210> SEQ ID NO 33
<211> LENGTH: 321
<212> TYPE: DNA
<213> ORGANISM: Artificial Sequence
<220> FEATURE:
<223> OTHER INFORMATION: Synthetic

<400> SEQUENCE: 33
gccatccaga tgacccagtc tccttccacc ctgtctgcat ctgtaggaga cagagtcacc 60
atcacttgcc gggccagtca gagtattagt agctggttgg cctggtatca gcagaaacca 120
gggaaagccc ctaagctcct gatctataag gcgtctagtt tagaaagtgg ggtcccatca 180
aggttcagcg gcagtggatc tgggacagaa ttcactctca ccatcagcag cctgcagcct 240
gatgattttg caacttatta ctgccaacag tataatagtt attacacttt tggccagggg 300
accaaggtgg aaatcaaacg a 321

<210> SEQ ID NO 34
<211> LENGTH: 107
<212> TYPE: PRT
<213> ORGANISM: Artificial Sequence
<220> FEATURE:
<223> OTHER INFORMATION: Synthetic

<400> SEQUENCE: 34

Ala Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Ser Ser Trp
20 25 30

Leu Ala Trp Tyr Gln Gln Lys Pro Gly Lys Ala Pro Lys Leu Leu Ile
35 40 45

Tyr Lys Ala Ser Ser Leu Glu Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Tyr Asn Ser Tyr Tyr Thr
85 90 95

Phe Gly Gln Gly Thr Lys Val Glu Ile Lys Arg
100 105

<210> SEQ ID NO 35
<211> LENGTH: 18
<212> TYPE: DNA
<213> ORGANISM: Artificial Sequence
<220> FEATURE:
<223> OTHER INFORMATION: Synthetic

<400> SEQUENCE: 35
cagagtatta gtagctgg 18

<210> SEQ ID NO 36
<211> LENGTH: 6
<212> TYPE: PRT
<213> ORGANISM: Artificial Sequence
<220> FEATURE:
<223> OTHER INFORMATION: Synthetic

<400> SEQUENCE: 36

Gln Ser Ile Ser Ser Trp
1               5

<210> SEQ ID NO 37
<211> LENGTH: 9
<212> TYPE: DNA
<213> ORGANISM: Artificial Sequence
<220> FEATURE:
<223> OTHER INFORMATION: Synthetic

<400> SEQUENCE: 37 aaggcgtct 9

<210> SEQ ID NO 38
<211> LENGTH: 3
<212> TYPE: PRT
<213> ORGANISM: Artificial Sequence
<220> FEATURE:
<223> OTHER INFORMATION: Synthetic

<400> SEQUENCE: 38

Lys Ala Ser
1

<210> SEQ ID NO 39
<211> LENGTH: 24
<212> TYPE: DNA
<213> ORGANISM: Artificial Sequence
<220> FEATURE:
<223> OTHER INFORMATION: Synthetic

<400> SEQUENCE: 39
caacagtata atagttatta cact 24

<210> SEQ ID NO 40
<211> LENGTH: 8
<212> TYPE: PRT
<213> ORGANISM: Artificial Sequence
<220> FEATURE:
<223> OTHER INFORMATION: Synthetic

<400> SEQUENCE: 40

Gln Gln Tyr Asn Ser Tyr Tyr Thr
1               5

<210> SEQ ID NO 41
<211> LENGTH: 342
<212> TYPE: DNA
<213> ORGANISM: Artificial Sequence
<220> FEATURE:
<223> OTHER INFORMATION: Synthetic

<400> SEQUENCE: 41
caggtgcagc tggtggagtc tgggggaggc gtggtccagc ctgggaggtc cctgagactc 60
tcctgtgcag cgtctggatt caccttcagt agctatggca tgcactgggt ccgccaggct 120
ccaggcaagg ggctggagtg ggtggcgttt ataggatttg atggaagtaa tatacattat 180
ggagactccg tgaggggccg aatcatcata tccagagaca attccgagaa cacgttgtat 240
ctggaaatga acagcctgag agccgaggac acggcaatgt actattgtgc gagagagaag 300
ggtttagact ggggccaggg aaccctggtc accgtctcct ca 342

<210> SEQ ID NO 42
<211> LENGTH: 114
<212> TYPE: PRT
<213> ORGANISM: Artificial Sequence
<220> FEATURE:
<223> OTHER INFORMATION: Synthetic

<400> SEQUENCE: 42

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Gly Phe Asp Gly Ser Asn Ile His Tyr Gly Asp Ser Val
    50                  55                  60

Arg Gly Arg Ile Ile Ile Ser Arg Asp Asn Ser Glu Asn Thr Leu Tyr
65                  70                  75                  80

Leu Glu Met Asn Ser Leu Arg Ala Glu Asp Thr Ala Met Tyr Tyr Cys
                85                  90                  95

Ala Arg Glu Lys Gly Leu Asp Trp Gly Gln Gly Thr Leu Val Thr Val
            100                 105                 110

Ser Ser
```

<210> SEQ ID NO 43
<211> LENGTH: 318
<212> TYPE: DNA
<213> ORGANISM: Artificial Sequence
<220> FEATURE:
<223> OTHER INFORMATION: Synthetic

<400> SEQUENCE: 43

```
gacatccaga tgacccagtc tccttccacc ctgtctgcat ctgtaggaga cagagtcacc      60

atcacttgcc gggccagtca gagtattagt agctggttgg cctggtatca gcagaaacca     120

gggaaagccc ctaagctcct gatctataag gcgtctagtt tagaaagtgg ggtcccatca     180

aggttcagcg gcagtggatc tgggacagaa ttcactctca ccatcagcag cctgcagcct     240

gatgattttg caacttatta ctgccaacag tataatagtt attacacttt tggccagggg     300

accaagctgg agatcaaa                                                   318
```

<210> SEQ ID NO 44
<211> LENGTH: 106
<212> TYPE: PRT
<213> ORGANISM: Artificial Sequence
<220> FEATURE:
<223> OTHER INFORMATION: Synthetic

<400> SEQUENCE: 44

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
```

-continued

```
65                  70                  75                  80

Asp Asp Phe Ala Thr Tyr Tyr Cys Gln Gln Tyr Asn Ser Tyr Tyr Thr
                85                  90                  95

Phe Gly Gln Gly Thr Lys Leu Glu Ile Lys
            100                 105


<210> SEQ ID NO 45
<211> LENGTH: 342
<212> TYPE: DNA
<213> ORGANISM: Artificial Sequence
<220> FEATURE:
<223> OTHER INFORMATION: Synthetic

<400> SEQUENCE: 45

caggtgcagc tggtggagtc tgggggaggc gtggtccagc ctgggaggtc cctgagactc      60

tcctgtgcag cctctggatt caccttcagt agctatggca tgcactgggt ccgccaggct     120

ccaggcaagg ggctggagtg ggtggcagtt ataggatttg atggaagtaa tatatactat     180

gcagactccg tgaagggccg attcaccatc tccagagaca attccaagaa cacgctgtat     240

ctgcaaatga acagcctgag agctgaggac acggctgtgt attactgtgc gagagagaag     300

ggtttagact ggggccaggg aaccctggtc accgtctcct ca                       342


<210> SEQ ID NO 46
<211> LENGTH: 114
<212> TYPE: PRT
<213> ORGANISM: Artificial Sequence
<220> FEATURE:
<223> OTHER INFORMATION: Synthetic

<400> SEQUENCE: 46

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Gly Phe Asp Gly Ser Asn Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Lys Gly Leu Asp Trp Gly Gln Gly Thr Leu Val Thr Val
            100                 105                 110

Ser Ser


<210> SEQ ID NO 47
<211> LENGTH: 319
<212> TYPE: DNA
<213> ORGANISM: Artificial Sequence
<220> FEATURE:
<223> OTHER INFORMATION: Synthetic

<400> SEQUENCE: 47

gacatccaga tgacccagtc tccttccacc ctgtctgcat ctgtaggaga cagagtcacc      60

atcacttgcc gggccagtca gagtattagt agctggttgg cctggtatca gcagaaacca     120

gggaaagccc ctaagctcct gatctataag gcgtctagtt tagaaagtgg ggtcccatca     180
```

-continued

```
aggttcagcg gcagtggatc tgggacagaa ttcactctca ccatcagcag cctgcagcct    240

gatgattttg caacttatta ctgccaacag tataatagtt attacacttt tggccagggg    300

accaagctgg agatcaaac                                                 319


<210> SEQ ID NO 48
<211> LENGTH: 106
<212> TYPE: PRT
<213> ORGANISM: Artificial Sequence
<220> FEATURE:
<223> OTHER INFORMATION: Synthetic

<400> SEQUENCE: 48

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Tyr Thr
                85                  90                  95

Phe Gly Gln Gly Thr Lys Leu Glu Ile Lys
            100                 105


<210> SEQ ID NO 49
<211> LENGTH: 342
<212> TYPE: DNA
<213> ORGANISM: Artificial Sequence
<220> FEATURE:
<223> OTHER INFORMATION: Synthetic

<400> SEQUENCE: 49

caggtgcagc tgcaggagtc tgggggaggc gtggtccagc ctgggaggtc cctgagactc     60

tcctgtgcag cgtctggatt caccttcagt agctatggca tgcactgggt ccgccaggct    120

ccaggcaagg ggctggagtg ggtggcgttt ataggatttg atggaagtaa tatatattat    180

ggagactccg tgaggggccg aatcatcata tccagagaca attccgagaa cacgttgtat    240

ctggaaatga acagcctgag agccgaggac acggcagtgt attattgtgc gagagagaag    300

ggtttagact ggggccaggg aaccctggtc actgtctcct ca                       342


<210> SEQ ID NO 50
<211> LENGTH: 114
<212> TYPE: PRT
<213> ORGANISM: Artificial Sequence
<220> FEATURE:
<223> OTHER INFORMATION: Synthetic

<400> SEQUENCE: 50

Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Gly Phe Asp Gly Ser Asn Ile Tyr Tyr Gly Asp Ser Val
```

```
    50                  55                  60

Arg Gly Arg Ile Ile Ile Ser Arg Asp Asn Ser Glu Asn Thr Leu Tyr
65                  70                  75                  80

Leu Glu Met Asn Ser Leu Arg Ala Glu Asp Thr Ala Val Tyr Tyr Cys
                85                  90                  95

Ala Arg Glu Lys Gly Leu Asp Trp Gly Gln Gly Thr Leu Val Thr Val
            100                 105                 110

Ser Ser


<210> SEQ ID NO 51
<211> LENGTH: 24
<212> TYPE: DNA
<213> ORGANISM: Artificial Sequence
<220> FEATURE:
<223> OTHER INFORMATION: Synthetic

<400> SEQUENCE: 51

ggattcacct tcagtagcta tggc                                            24


<210> SEQ ID NO 52
<211> LENGTH: 8
<212> TYPE: PRT
<213> ORGANISM: Artificial Sequence
<220> FEATURE:
<223> OTHER INFORMATION: Synthetic

<400> SEQUENCE: 52

Gly Phe Thr Phe Ser Ser Tyr Gly
1               5


<210> SEQ ID NO 53
<211> LENGTH: 24
<212> TYPE: DNA
<213> ORGANISM: Artificial Sequence
<220> FEATURE:
<223> OTHER INFORMATION: Synthetic

<400> SEQUENCE: 53

ataggatttg atggaagtaa tata                                            24


<210> SEQ ID NO 54
<211> LENGTH: 8
<212> TYPE: PRT
<213> ORGANISM: Artificial Sequence
<220> FEATURE:
<223> OTHER INFORMATION: Synthetic

<400> SEQUENCE: 54

Ile Gly Phe Asp Gly Ser Asn Ile
1               5


<210> SEQ ID NO 55
<211> LENGTH: 21
<212> TYPE: DNA
<213> ORGANISM: Artificial Sequence
<220> FEATURE:
<223> OTHER INFORMATION: Synthetic

<400> SEQUENCE: 55

gcgagagaga agggtttaga c                                               21


<210> SEQ ID NO 56
<211> LENGTH: 7
<212> TYPE: PRT
```

<213> ORGANISM: Artificial Sequence
<220> FEATURE:
<223> OTHER INFORMATION: Synthetic

<400> SEQUENCE: 56

Ala Arg Glu Lys Gly Leu Asp
1 5

<210> SEQ ID NO 57
<211> LENGTH: 342
<212> TYPE: DNA
<213> ORGANISM: Artificial Sequence
<220> FEATURE:
<223> OTHER INFORMATION: Synthetic

<400> SEQUENCE: 57
gccatccaga tgacccagtc tccagactcc ctggctgtgt ctctgggcga gagggccacc 60
atcaactgca agtccagcca gagtgttttt cacacctcca acaataagaa ctacttagtt 120
tggtatcagc agaaaccagg acagcctcct aagttgctcc tttactgggc ctctacccgg 180
gaatccgggg tccctgaccg attcagtggc agcgggtctg ggacagattt cactctcacc 240
atcagcagcc tgcaggctga agatgtggca aattattact gtcaccaata ttacagtatt 300
ccgtggacgt tcggccaagg gaccaaggtg gagatcaaac ga 342

<210> SEQ ID NO 58
<211> LENGTH: 114
<212> TYPE: PRT
<213> ORGANISM: Artificial Sequence
<220> FEATURE:
<223> OTHER INFORMATION: Synthetic

<400> SEQUENCE: 58

Ala Ile Gln Met Thr Gln Ser Pro Asp Ser Leu Ala Val Ser Leu Gly
1 5 10 15

Glu Arg Ala Thr Ile Asn Cys Lys Ser Ser Gln Ser Val Phe His Thr
20 25 30

Ser Asn Asn Lys Asn Tyr Leu Val Trp Tyr Gln Gln Lys Pro Gly Gln
35 40 45

Pro Pro Lys Leu Leu Leu Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Asn Tyr Tyr Cys His Gln
85 90 95

Tyr Tyr Ser Ile Pro Trp Thr Phe Gly Gln Gly Thr Lys Val Glu Ile
100 105 110

Lys Arg

<210> SEQ ID NO 59
<211> LENGTH: 36
<212> TYPE: DNA
<213> ORGANISM: Artificial Sequence
<220> FEATURE:
<223> OTHER INFORMATION: Synthetic

<400> SEQUENCE: 59
cagagtgttt ttcacacctc caacaataag aactac 36

<210> SEQ ID NO 60
<211> LENGTH: 12

<212> TYPE: PRT
<213> ORGANISM: Artificial Sequence
<220> FEATURE:
<223> OTHER INFORMATION: Synthetic

<400> SEQUENCE: 60

Gln Ser Val Phe His Thr Ser Asn Asn Lys Asn Tyr
1               5                   10

<210> SEQ ID NO 61
<211> LENGTH: 9
<212> TYPE: DNA
<213> ORGANISM: Artificial Sequence
<220> FEATURE:
<223> OTHER INFORMATION: Synthetic

<400> SEQUENCE: 61 tgggcctct 9

<210> SEQ ID NO 62
<211> LENGTH: 3
<212> TYPE: PRT
<213> ORGANISM: Artificial Sequence
<220> FEATURE:
<223> OTHER INFORMATION: Synthetic

<400> SEQUENCE: 62

Trp Ala Ser
1

<210> SEQ ID NO 63
<211> LENGTH: 27
<212> TYPE: DNA
<213> ORGANISM: Artificial Sequence
<220> FEATURE:
<223> OTHER INFORMATION: Synthetic

<400> SEQUENCE: 63
caccaatatt acagtattcc gtggacg 27

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

His Gln Tyr Tyr Ser Ile Pro Trp Thr
1               5

<210> SEQ ID NO 65
<211> LENGTH: 342
<212> TYPE: DNA
<213> ORGANISM: Artificial Sequence
<220> FEATURE:
<223> OTHER INFORMATION: Synthetic

<400> SEQUENCE: 65
caggtgcagc tggtggagtc tgggggaggc gtggtccagc ctgggaggtc cctgagactc 60
tcctgtgcag cgtctggatt caccttcagt agctatggca tgcactgggt ccgccaggct 120
ccaggcaagg ggctggagtg ggtggcgttt ataggatttg atggaagtaa tatatattat 180
ggagactccg tgaggggccg aatcatcata tccagagaca attccgagaa cacgttgtat 240
ctggaaatga acagcctgag agccgaggac acggcagtgt attattgtgc gagagagaag 300
ggtttagact ggggccaggg aaccctggtc accgtctcct ca 342

<210> SEQ ID NO 66
<211> LENGTH: 114
<212> TYPE: PRT
<213> ORGANISM: Artificial Sequence
<220> FEATURE:
<223> OTHER INFORMATION: Synthetic

<400> SEQUENCE: 66

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Phe Ile Gly Phe Asp Gly Ser Asn Ile Tyr Tyr Gly Asp Ser Val
50 55 60

Arg Gly Arg Ile Ile Ile Ser Arg Asp Asn Ser Glu Asn Thr Leu Tyr
65 70 75 80

Leu Glu Met Asn Ser Leu Arg Ala Glu Asp Thr Ala Val Tyr Tyr Cys
85 90 95

Ala Arg Glu Lys Gly Leu Asp Trp Gly Gln Gly Thr Leu Val Thr Val
100 105 110

Ser Ser

<210> SEQ ID NO 67
<211> LENGTH: 339
<212> TYPE: DNA
<213> ORGANISM: Artificial Sequence
<220> FEATURE:
<223> OTHER INFORMATION: Synthetic

<400> SEQUENCE: 67
gacatcgtga tgacccagtc tccagactcc ctggctgtgt ctctgggcga gagggccacc 60
atcaactgca agtccagcca gagtgttttt cacacctcca acaataagaa ctacttagtt 120
tggtatcagc agaaaccagg acagcctcct aagttgctcc tttactgggc ctctacccgg 180
gaatccgggg tccctgaccg attcagtggc agcgggtctg ggacagattt cactctcacc 240
atcagcagcc tgcaggctga agatgtggca aattattact gtcaccaata ttacagtatt 300
ccgtggacgt tcggccaagg gaccaaggtg gaaatcaaa 339

<210> SEQ ID NO 68
<211> LENGTH: 113
<212> TYPE: PRT
<213> ORGANISM: Artificial Sequence
<220> FEATURE:
<223> OTHER INFORMATION: Synthetic

<400> SEQUENCE: 68

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Val Phe His Thr
20 25 30

Ser Asn Asn Lys Asn Tyr Leu Val Trp Tyr Gln Gln Lys Pro Gly Gln
35 40 45

Pro Pro Lys Leu Leu Leu Tyr Trp Ala Ser Thr Arg Glu Ser Gly Val
50 55 60

```
Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Asn Tyr Tyr Cys His Gln
                85                  90                  95

Tyr Tyr Ser Ile Pro Trp Thr Phe Gly Gln Gly Thr Lys Val Glu Ile
            100                 105                 110

Lys


<210> SEQ ID NO 69
<211> LENGTH: 342
<212> TYPE: DNA
<213> ORGANISM: Artificial Sequence
<220> FEATURE:
<223> OTHER INFORMATION: Synthetic

<400> SEQUENCE: 69

caggtgcagc tggtggagtc tgggggaggc gtggtccagc ctgggaggtc cctgagactc      60

tcctgtgcag cctctggatt caccttcagt agctatggca tgcactgggt ccgccaggct     120

ccaggcaagg ggctggagtg ggtggcagtt ataggatttg atggaagtaa tatatactat     180

gcagactccg tgaagggccg attcaccatc tccagagaca attccaagaa cacgctgtat     240

ctgcaaatga acagcctgag agctgaggac acggctgtgt attactgtgc gagagagaag     300

ggtttagact ggggccaggg aaccctggtc accgtctcct ca                        342


<210> SEQ ID NO 70
<211> LENGTH: 114
<212> TYPE: PRT
<213> ORGANISM: Artificial Sequence
<220> FEATURE:
<223> OTHER INFORMATION: Synthetic

<400> SEQUENCE: 70

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Gly Phe Asp Gly Ser Asn Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Lys Gly Leu Asp Trp Gly Gln Gly Thr Leu Val Thr Val
            100                 105                 110

Ser Ser


<210> SEQ ID NO 71
<211> LENGTH: 339
<212> TYPE: DNA
<213> ORGANISM: Artificial Sequence
<220> FEATURE:
<223> OTHER INFORMATION: Synthetic

<400> SEQUENCE: 71

gacatcgtga tgacccagtc tccagactcc ctggctgtgt ctctgggcga gagggccacc      60
```

```
atcaactgca agtccagcca gagtgttttt cacacctcca acaataagaa ctacttagct    120

tggtaccagc agaaaccagg acagcctcct aagctgctca tttactgggc ctctacccgg    180

gaatccgggg tccctgaccg attcagtggc agcgggtctg ggacagattt cactctcacc    240

atcagcagcc tgcaggctga agatgtggca gtttattact gtcaccaata ttacagtatt    300

ccgtggacgt tcggccaagg gaccaaggtg gaaatcaaa                           339
```

<210> SEQ ID NO 72
<211> LENGTH: 113
<212> TYPE: PRT
<213> ORGANISM: Artificial Sequence
<220> FEATURE:
<223> OTHER INFORMATION: Synthetic

<400> SEQUENCE: 72

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Phe His Thr
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Tyr Ser Ile Pro Trp Thr Phe Gly Gln Gly Thr Lys Val Glu Ile
            100                 105                 110

Lys
```

<210> SEQ ID NO 73
<211> LENGTH: 354
<212> TYPE: DNA
<213> ORGANISM: Artificial Sequence
<220> FEATURE:
<223> OTHER INFORMATION: Synthetic

<400> SEQUENCE: 73

```
gaagtgcagc tggtgcagtc tgggggaggc ttggtacagc ctggggggtc cctgagactc     60

tcctgtgcag cctctggatt cacctttaac aactatgcca tgaactgggt ccgccaggct    120

ccaggaaagg gactggactg ggtctcaact attagtggta gcggtggtac tacaaactac    180

gcagactccg tgaagggccg tttcattatt tcccgagaca gttccaaaca cacgctgtat    240

ctgcaaatga acagcctgag agccgaggac acggccgtat attactgtgc gaaagattct    300

aactggggaa atttcgatct ctggggccgt ggcaccacgg tcactgtctc ctca          354
```

<210> SEQ ID NO 74
<211> LENGTH: 118
<212> TYPE: PRT
<213> ORGANISM: Artificial Sequence
<220> FEATURE:
<223> OTHER INFORMATION: Synthetic

<400> SEQUENCE: 74

```
Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
```

```
            20                  25                  30

Ala Met Asn Trp Val Arg Gln Ala Pro Gly Lys Gly Leu Asp Trp Val
        35                  40                  45

Ser Thr Ile Ser Gly Ser Gly Gly Thr Thr Asn Tyr Ala Asp Ser Val
    50                  55                  60

Lys Gly Arg Phe Ile Ile Ser Arg Asp Ser Ser Lys His Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Asn Trp Gly Asn Phe Asp Leu Trp Gly Arg Gly Thr
            100                 105                 110

Thr Val Thr Val Ser Ser
        115


<210> SEQ ID NO 75
<211> LENGTH: 24
<212> TYPE: DNA
<213> ORGANISM: Artificial Sequence
<220> FEATURE:
<223> OTHER INFORMATION: Synthetic

<400> SEQUENCE: 75

ggattcacct ttaacaacta tgcc                                            24


<210> SEQ ID NO 76
<211> LENGTH: 8
<212> TYPE: PRT
<213> ORGANISM: Artificial Sequence
<220> FEATURE:
<223> OTHER INFORMATION: Synthetic

<400> SEQUENCE: 76

Gly Phe Thr Phe Asn Asn Tyr Ala
1               5


<210> SEQ ID NO 77
<211> LENGTH: 24
<212> TYPE: DNA
<213> ORGANISM: Artificial Sequence
<220> FEATURE:
<223> OTHER INFORMATION: Synthetic

<400> SEQUENCE: 77

attagtggta gcggtggtac taca                                            24


<210> SEQ ID NO 78
<211> LENGTH: 8
<212> TYPE: PRT
<213> ORGANISM: Artificial Sequence
<220> FEATURE:
<223> OTHER INFORMATION: Synthetic

<400> SEQUENCE: 78

Ile Ser Gly Ser Gly Gly Thr Thr
1               5


<210> SEQ ID NO 79
<211> LENGTH: 33
<212> TYPE: DNA
<213> ORGANISM: Artificial Sequence
<220> FEATURE:
<223> OTHER INFORMATION: Synthetic

<400> SEQUENCE: 79
```

```
gcgaaagatt ctaactgggg aaatttcgat ctc                                33


<210> SEQ ID NO 80
<211> LENGTH: 11
<212> TYPE: PRT
<213> ORGANISM: Artificial Sequence
<220> FEATURE:
<223> OTHER INFORMATION: Synthetic

<400> SEQUENCE: 80

Ala Lys Asp Ser Asn Trp Gly Asn Phe Asp Leu
1               5                   10


<210> SEQ ID NO 81
<211> LENGTH: 342
<212> TYPE: DNA
<213> ORGANISM: Artificial Sequence
<220> FEATURE:
<223> OTHER INFORMATION: Synthetic

<400> SEQUENCE: 81

gacatccaga tgacccagtc tccagactcc ctggctgtgt ctctgggcga gagggccacc     60

atcaactgca agtccagcca gagtgtttta tacaggtcca acaataggaa cttcttaggt    120

tggtaccagc agaaaccagg gcagcctcct aatctactca tttactgggc atctacccgg    180

gaatccgggg tccctgaccg attcagtggc agcgggtctg ggacagattt cactctcacc    240

atcagcagcc tgcaggctga agatgtggca gtttattact gtcaacaata ttatactact    300

ccgtacactt ttggccaggg gaccaaggtg gaaatcaaac ga                       342


<210> SEQ ID NO 82
<211> LENGTH: 114
<212> TYPE: PRT
<213> ORGANISM: Artificial Sequence
<220> FEATURE:
<223> OTHER INFORMATION: Synthetic

<400> SEQUENCE: 82

Asp Ile Gln Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Arg
            20                  25                  30

Ser Asn Asn Arg Asn Phe Leu Gly Trp Tyr Gln Gln Lys Pro Gly Gln
        35                  40                  45

Pro Pro Asn Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Thr Pro Tyr Thr Phe Gly Gln Gly Thr Lys Val Glu Ile
            100                 105                 110

Lys Arg


<210> SEQ ID NO 83
<211> LENGTH: 36
<212> TYPE: DNA
<213> ORGANISM: Artificial Sequence
<220> FEATURE:
<223> OTHER INFORMATION: Synthetic
```

<400> SEQUENCE: 83
cagagtgttt tatacaggtc caacaatagg aacttc 36

<210> SEQ ID NO 84
<211> LENGTH: 12
<212> TYPE: PRT
<213> ORGANISM: Artificial Sequence
<220> FEATURE:
<223> OTHER INFORMATION: Synthetic

<400> SEQUENCE: 84

Gln Ser Val Leu Tyr Arg Ser Asn Asn Arg Asn Phe
1 5 10

<210> SEQ ID NO 85
<211> LENGTH: 9
<212> TYPE: DNA
<213> ORGANISM: Artificial Sequence
<220> FEATURE:
<223> OTHER INFORMATION: Synthetic

<400> SEQUENCE: 85 tgggcatct 9

<210> SEQ ID NO 86
<211> LENGTH: 3
<212> TYPE: PRT
<213> ORGANISM: Artificial Sequence
<220> FEATURE:
<223> OTHER INFORMATION: Synthetic

<400> SEQUENCE: 86

Trp Ala Ser
1

<210> SEQ ID NO 87
<211> LENGTH: 27
<212> TYPE: DNA
<213> ORGANISM: Artificial Sequence
<220> FEATURE:
<223> OTHER INFORMATION: Synthetic

<400> SEQUENCE: 87
caacaatatt atactactcc gtacact 27

<210> SEQ ID NO 88
<211> LENGTH: 9
<212> TYPE: PRT
<213> ORGANISM: Artificial Sequence
<220> FEATURE:
<223> OTHER INFORMATION: Synthetic

<400> SEQUENCE: 88

Gln Gln Tyr Tyr Thr Thr Pro Tyr Thr
1 5

<210> SEQ ID NO 89
<211> LENGTH: 354
<212> TYPE: DNA
<213> ORGANISM: Artificial Sequence
<220> FEATURE:
<223> OTHER INFORMATION: Synthetic

<400> SEQUENCE: 89
gaggtgcagc tggtggagtc tgggggaggc ttggtacagc ctggggggtc cctgagactc 60

-continued

```
tcctgtgcag cctctggatt cacctttaac aactatgcca tgaactgggt ccgccaggct    120

ccaggaaagg gactggactg ggtctcaact attagtggta gcggtggtac tacaaactac    180

gcagactccg tgaagggccg tttcattatt tcccgagaca gttccaaaca cacgctgtat    240

ctgcaaatga acagcctgag agccgaggac acggccgtat attactgtgc gaaagattct    300

aactggggaa atttcgatct ctggggccgt ggcaccctgg tcactgtctc ctca          354


<210> SEQ ID NO 90
<211> LENGTH: 118
<212> TYPE: PRT
<213> ORGANISM: Artificial Sequence
<220> FEATURE:
<223> OTHER INFORMATION: Synthetic

<400> SEQUENCE: 90

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Ala Met Asn Trp Val Arg Gln Ala Pro Gly Lys Gly Leu Asp Trp Val
        35                  40                  45

Ser Thr Ile Ser Gly Ser Gly Gly Thr Thr Asn Tyr Ala Asp Ser Val
    50                  55                  60

Lys Gly Arg Phe Ile Ile Ser Arg Asp Ser Ser Lys His Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Asn Trp Gly Asn Phe Asp Leu Trp Gly Arg Gly Thr
            100                 105                 110

Leu Val Thr Val Ser Ser
        115


<210> SEQ ID NO 91
<211> LENGTH: 339
<212> TYPE: DNA
<213> ORGANISM: Artificial Sequence
<220> FEATURE:
<223> OTHER INFORMATION: Synthetic

<400> SEQUENCE: 91

gacatcgtga tgacccagtc tccagactcc ctggctgtgt ctctgggcga gagggccacc     60

atcaactgca agtccagcca gagtgtttta tacaggtcca acaataggaa cttcttaggt    120

tggtaccagc agaaaccagg gcagcctcct aatctactca tttactgggc atctacccgg    180

gaatccgggg tccctgaccg attcagtggc agcgggtctg ggacagattt cactctcacc    240

atcagcagcc tgcaggctga agatgtggca gtttattact gtcaacaata ttatactact    300

ccgtacactt ttggccaggg gaccaagctg gagatcaaa                           339


<210> SEQ ID NO 92
<211> LENGTH: 113
<212> TYPE: PRT
<213> ORGANISM: Artificial Sequence
<220> FEATURE:
<223> OTHER INFORMATION: Synthetic

<400> SEQUENCE: 92

Asp Ile Val Met Thr Gln Ser Pro Asp Ser Leu Ala Val Ser Leu Gly
1               5                   10                  15
```

```
Glu Arg Ala Thr Ile Asn Cys Lys Ser Ser Gln Ser Val Leu Tyr Arg
            20                  25                  30

Ser Asn Asn Arg Asn Phe Leu Gly Trp Tyr Gln Gln Lys Pro Gly Gln
        35                  40                  45

Pro Pro Asn Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Thr Pro Tyr Thr Phe Gly Gln Gly Thr Lys Leu Glu Ile
            100                 105                 110

Lys


<210> SEQ ID NO 93
<211> LENGTH: 354
<212> TYPE: DNA
<213> ORGANISM: Artificial Sequence
<220> FEATURE:
<223> OTHER INFORMATION: Synthetic

<400> SEQUENCE: 93

gaggtgcagc tggtggagtc tgggggaggc ttggtacagc ctggggggtc cctgagactc      60

tcctgtgcag cctctggatt cacctttaac aactatgcca tgagctgggt ccgccaggct     120

ccagggaagg ggctggagtg ggtctcagct attagtggta gcggtggtac tacatactac     180

gcagactccg tgaagggccg gttcaccatc tccagagaca attccaagaa cacgctgtat     240

ctgcaaatga acagcctgag agccgaggac acggccgtat attactgtgc gaaagattct     300

aactggggaa atttcgatct ctggggccgt ggcaccctgg tcactgtctc ctca           354


<210> SEQ ID NO 94
<211> LENGTH: 118
<212> TYPE: PRT
<213> ORGANISM: Artificial Sequence
<220> FEATURE:
<223> OTHER INFORMATION: Synthetic

<400> SEQUENCE: 94

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Asn Trp Gly Asn Phe Asp Leu Trp Gly Arg Gly Thr
            100                 105                 110

Leu Val Thr Val Ser Ser
        115


<210> SEQ ID NO 95
<211> LENGTH: 339
```

<212> TYPE: DNA
<213> ORGANISM: Artificial Sequence
<220> FEATURE:
<223> OTHER INFORMATION: Synthetic

<400> SEQUENCE: 95
gacatcgtga tgacccagtc tccagactcc ctggctgtgt ctctgggcga gagggccacc 60
atcaactgca agtccagcca gagtgtttta tacaggtcca acaataggaa cttcttagct 120
tggtaccagc agaaaccagg acagcctcct aagctgctca tttactgggc atctacccgg 180
gaatccgggg tccctgaccg attcagtggc agcgggtctg ggacagattt cactctcacc 240
atcagcagcc tgcaggctga agatgtggca gtttattact gtcaacaata ttatactact 300
ccgtacactt ttggccaggg gaccaagctg gagatcaaa 339

<210> SEQ ID NO 96
<211> LENGTH: 113
<212> TYPE: PRT
<213> ORGANISM: Artificial Sequence
<220> FEATURE:
<223> OTHER INFORMATION: Synthetic

<400> SEQUENCE: 96

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Val Leu Tyr Arg
20 25 30

Ser Asn Asn Arg Asn Phe Leu Ala Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Gln
85 90 95

Tyr Tyr Thr Thr Pro Tyr Thr Phe Gly Gln Gly Thr Lys Leu Glu Ile
100 105 110

Lys

<210> SEQ ID NO 97
<211> LENGTH: 351
<212> TYPE: DNA
<213> ORGANISM: Artificial Sequence
<220> FEATURE:
<223> OTHER INFORMATION: Synthetic

<400> SEQUENCE: 97
caggtgcagc tggtgcagtc tgggggaggc ttggtacagc ctgggggggtc cctgagactc 60 tcctgtgcag tctctggatt caccctcagt agctacgata tgcactgggt ccgccaacct 120
acaggaaaag gtctggagtg ggtctcagct attggttcta ctggtgacac atactatcca 180
ggctccgtga agggccgatt caccatctcc agagaaaatg ccaagaactc cttgtatctt 240
caaatgaaca gcctgagagc cggggacacg gctgtgtatt actgtgcaag agagggatgg 300
gacgtaccct ttgacttctg gggccaggga accctggtca ccgtctcctc a 351

<210> SEQ ID NO 98
<211> LENGTH: 117
<212> TYPE: PRT
<213> ORGANISM: Artificial Sequence
<220> FEATURE:
<223> OTHER INFORMATION: Synthetic

<400> SEQUENCE: 98

Gln Val Gln Leu Val Gln Ser Gly Gly Gly Leu Val Gln Pro Gly Gly
1 5 10 15

Ser Leu Arg Leu Ser Cys Ala Val Ser Gly Phe Thr Leu Ser Ser Tyr
20 25 30

Asp Met His Trp Val Arg Gln Pro Thr Gly Lys Gly Leu Glu Trp Val
35 40 45

Ser Ala Ile Gly Ser Thr Gly Asp Thr Tyr Tyr Pro Gly Ser Val Lys
50 55 60

Gly Arg Phe Thr Ile Ser Arg Glu Asn Ala Lys Asn Ser Leu Tyr Leu
65 70 75 80

Gln Met Asn Ser Leu Arg Ala Gly Asp Thr Ala Val Tyr Tyr Cys Ala
85 90 95

Arg Glu Gly Trp Asp Val Pro Phe Asp Phe Trp Gly Gln Gly Thr Leu
100 105 110

Val Thr Val Ser Ser
115

<210> SEQ ID NO 99
<211> LENGTH: 24
<212> TYPE: DNA
<213> ORGANISM: Artificial Sequence
<220> FEATURE:
<223> OTHER INFORMATION: Synthetic

<400> SEQUENCE: 99
ggattcaccc tcagtagcta cgat 24

<210> SEQ ID NO 100
<211> LENGTH: 8
<212> TYPE: PRT
<213> ORGANISM: Artificial Sequence
<220> FEATURE:
<223> OTHER INFORMATION: Synthetic

<400> SEQUENCE: 100

Gly Phe Thr Leu Ser Ser Tyr Asp
1 5

<210> SEQ ID NO 101
<211> LENGTH: 21
<212> TYPE: DNA
<213> ORGANISM: Artificial Sequence
<220> FEATURE:
<223> OTHER INFORMATION: Synthetic

<400> SEQUENCE: 101
attggttcta ctggtgacac a 21

<210> SEQ ID NO 102
<211> LENGTH: 7
<212> TYPE: PRT
<213> ORGANISM: Artificial Sequence
<220> FEATURE:
<223> OTHER INFORMATION: Synthetic

<400> SEQUENCE: 102

Ile Gly Ser Thr Gly Asp Thr
1 5

<210> SEQ ID NO 103
<211> LENGTH: 33
<212> TYPE: DNA
<213> ORGANISM: Artificial Sequence
<220> FEATURE:
<223> OTHER INFORMATION: Synthetic

<400> SEQUENCE: 103
gcaagagagg gatgggacgt accctttgac ttc 33

<210> SEQ ID NO 104
<211> LENGTH: 11
<212> TYPE: PRT
<213> ORGANISM: Artificial Sequence
<220> FEATURE:
<223> OTHER INFORMATION: Synthetic

<400> SEQUENCE: 104

Ala Arg Glu Gly Trp Asp Val Pro Phe Asp Phe
1 5 10

<210> SEQ ID NO 105
<211> LENGTH: 324
<212> TYPE: DNA
<213> ORGANISM: Artificial Sequence
<220> FEATURE:
<223> OTHER INFORMATION: Synthetic

<400> SEQUENCE: 105
gccatccagt tgacccagtc tccatcctcc ctgtctgcat ctgtaggaga cagagtcacc 60
atcacttgcc gggcaagtca ggacattaga aatgatttag gctggtatca gcagaaacca 120
gggaaagccc ctaagctcct gatctatgct gcatccagtt tacaaagtgg ggtcccatca 180
cggttcagcg gcagtggatc tggcacagat ttcactctca ccatcagcag cctgcagcct 240
gaagattttg caacttatta ctgtctacaa gattacaatt acccgtggac gttcggccaa 300
gggaccaagg tggagatcaa acga 324

<210> SEQ ID NO 106
<211> LENGTH: 108
<212> TYPE: PRT
<213> ORGANISM: Artificial Sequence
<220> FEATURE:
<223> OTHER INFORMATION: Synthetic

<400> SEQUENCE: 106

Ala Ile Gln Leu Thr Gln Ser Pro Ser Ser Leu Ser Ala Ser Val Gly
1 5 10 15

Asp Arg Val Thr Ile Thr Cys Arg Ala Ser Gln Asp Ile Arg Asn Asp
20 25 30

Leu Gly Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Asp Tyr Asn Tyr Pro Trp
85 90 95

Thr Phe Gly Gln Gly Thr Lys Val Glu Ile Lys Arg
100 105

<210> SEQ ID NO 107
<211> LENGTH: 18
<212> TYPE: DNA
<213> ORGANISM: Artificial Sequence
<220> FEATURE:
<223> OTHER INFORMATION: Synthetic

<400> SEQUENCE: 107
caggacatta gaaatgat 18

<210> SEQ ID NO 108
<211> LENGTH: 6
<212> TYPE: PRT
<213> ORGANISM: Artificial Sequence
<220> FEATURE:
<223> OTHER INFORMATION: Synthetic

<400> SEQUENCE: 108

Gln Asp Ile Arg Asn Asp
1 5

<210> SEQ ID NO 109
<211> LENGTH: 9
<212> TYPE: DNA
<213> ORGANISM: Artificial Sequence
<220> FEATURE:
<223> OTHER INFORMATION: Synthetic

<400> SEQUENCE: 109 gctgcatcc 9

<210> SEQ ID NO 110
<211> LENGTH: 3
<212> TYPE: PRT
<213> ORGANISM: Artificial Sequence
<220> FEATURE:
<223> OTHER INFORMATION: Synthetic

<400> SEQUENCE: 110

Ala Ala Ser
1

<210> SEQ ID NO 111
<211> LENGTH: 27
<212> TYPE: DNA
<213> ORGANISM: Artificial Sequence
<220> FEATURE:
<223> OTHER INFORMATION: Synthetic

<400> SEQUENCE: 111
ctacaagatt acaattaccc gtggacg 27

<210> SEQ ID NO 112
<211> LENGTH: 9
<212> TYPE: PRT
<213> ORGANISM: Artificial Sequence
<220> FEATURE:
<223> OTHER INFORMATION: Synthetic

<400> SEQUENCE: 112

Leu Gln Asp Tyr Asn Tyr Pro Trp Thr
1 5

<210> SEQ ID NO 113
<211> LENGTH: 351
<212> TYPE: DNA
<213> ORGANISM: Artificial Sequence
<220> FEATURE:
<223> OTHER INFORMATION: Synthetic

<400> SEQUENCE: 113
gaggtgcagc tggtggagtc tgggggaggc ttggtacagc ctggggggtc cctgagactc 60
tcctgtgcag tctctggatt caccctcagt agctacgata tgcactgggt ccgccaacct 120
acaggaaaag gtctggagtg ggtctcagct attggttcta ctggtgacac atactatcca 180
ggctccgtga agggccgatt caccatctcc agagaaaatg ccaagaactc cttgtatctt 240
caaatgaaca gcctgagagc cggggacacg gctgtgtatt actgtgcaag agagggatgg 300
gacgtaccct ttgacttctg gggccaggga accctggtca ccgtctcctc a 351

<210> SEQ ID NO 114
<211> LENGTH: 117
<212> TYPE: PRT
<213> ORGANISM: Artificial Sequence
<220> FEATURE:
<223> OTHER INFORMATION: Synthetic

<400> SEQUENCE: 114

Glu Val Gln Leu Val Glu Ser Gly Gly Gly Leu Val Gln Pro Gly Gly
1 5 10 15

Ser Leu Arg Leu Ser Cys Ala Val Ser Gly Phe Thr Leu Ser Ser Tyr
20 25 30

Asp Met His Trp Val Arg Gln Pro Thr Gly Lys Gly Leu Glu Trp Val
35 40 45

Ser Ala Ile Gly Ser Thr Gly Asp Thr Tyr Tyr Pro Gly Ser Val Lys
50 55 60

Gly Arg Phe Thr Ile Ser Arg Glu Asn Ala Lys Asn Ser Leu Tyr Leu
65 70 75 80

Gln Met Asn Ser Leu Arg Ala Gly Asp Thr Ala Val Tyr Tyr Cys Ala
85 90 95

Arg Glu Gly Trp Asp Val Pro Phe Asp Phe Trp Gly Gln Gly Thr Leu
100 105 110

Val Thr Val Ser Ser
115

<210> SEQ ID NO 115
<211> LENGTH: 321
<212> TYPE: DNA
<213> ORGANISM: Artificial Sequence
<220> FEATURE:
<223> OTHER INFORMATION: Synthetic

<400> SEQUENCE: 115
gccatccaga tgacccagtc tccatcctcc ctgtctgcat ctgtaggaga cagagtcacc 60
atcacttgcc gggcaagtca ggacattaga aatgatttag gctggtatca gcagaaacca 120
gggaaagccc ctaagctcct gatctatgct gcatccagtt tacaaagtgg ggtcccatca 180
cggttcagcg gcagtggatc tggcacagat ttcactctca ccatcagcag cctgcagcct 240
gaagattttg caacttatta ctgtctacaa gattacaatt acccgtggac gttcggccaa 300
gggaccaagg tggaaatcaa a 321

<210> SEQ ID NO 116
<211> LENGTH: 107
<212> TYPE: PRT
<213> ORGANISM: Artificial Sequence
<220> FEATURE:

<223> OTHER INFORMATION: Synthetic

<400> SEQUENCE: 116

Ala Ile Gln Met Thr Gln Ser Pro Ser Ser Leu Ser Ala Ser Val Gly
1 5 10 15

Asp Arg Val Thr Ile Thr Cys Arg Ala Ser Gln Asp Ile Arg Asn Asp
20 25 30

Leu Gly Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Asp Tyr Asn Tyr Pro Trp
85 90 95

Thr Phe Gly Gln Gly Thr Lys Val Glu Ile Lys
100 105

<210> SEQ ID NO 117
<211> LENGTH: 351
<212> TYPE: DNA
<213> ORGANISM: Artificial Sequence
<220> FEATURE:
<223> OTHER INFORMATION: Synthetic

<400> SEQUENCE: 117
gaggtgcagc tggtggagtc tgggggaggc ttggtacagc ctggggggtc cctgagactc 60
tcctgtgcag cctctggatt caccctcagt agctacgata tgcactgggt ccgccaagct 120
acaggaaaag gtctggagtg ggtctcagct attggttcta ctggtgacac atactatcca 180
ggctccgtga agggccgatt caccatctcc agagaaaatg ccaagaactc cttgtatctt 240
caaatgaaca gcctgagagc cggggacacg gctgtgtatt actgtgcaag agagggatgg 300
gacgtaccct ttgacttctg gggccaggga accctggtca ccgtctcctc a 351

<210> SEQ ID NO 118
<211> LENGTH: 117
<212> TYPE: PRT
<213> ORGANISM: Artificial Sequence
<220> FEATURE:
<223> OTHER INFORMATION: Synthetic

<400> SEQUENCE: 118

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Leu Ser Ser Tyr
20 25 30

Asp Met His Trp Val Arg Gln Ala Thr Gly Lys Gly Leu Glu Trp Val
35 40 45

Ser Ala Ile Gly Ser Thr Gly Asp Thr Tyr Tyr Pro Gly Ser Val Lys
50 55 60

Gly Arg Phe Thr Ile Ser Arg Glu Asn Ala Lys Asn Ser Leu Tyr Leu
65 70 75 80

Gln Met Asn Ser Leu Arg Ala Gly Asp Thr Ala Val Tyr Tyr Cys Ala
85 90 95

Arg Glu Gly Trp Asp Val Pro Phe Asp Phe Trp Gly Gln Gly Thr Leu
100 105 110

Val Thr Val Ser Ser

115

<210> SEQ ID NO 119
<211> LENGTH: 321
<212> TYPE: DNA
<213> ORGANISM: Artificial Sequence
<220> FEATURE:
<223> OTHER INFORMATION: Synthetic

<400> SEQUENCE: 119
gccatccaga tgacccagtc tccatcctcc ctgtctgcat ctgtaggaga cagagtcacc 60
atcacttgcc gggcaagtca ggacattaga aatgatttag gctggtatca gcagaaacca 120
gggaaagccc ctaagctcct gatctatgct gcatccagtt tacaaagtgg ggtcccatca 180
aggttcagcg gcagtggatc tggcacagat ttcactctca ccatcagcag cctgcagcct 240
gaagattttg caacttatta ctgtctacaa gattacaatt acccgtggac gttcggccaa 300
gggaccaagg tggaaatcaa a 321

<210> SEQ ID NO 120
<211> LENGTH: 107
<212> TYPE: PRT
<213> ORGANISM: Artificial Sequence
<220> FEATURE:
<223> OTHER INFORMATION: Synthetic

<400> SEQUENCE: 120

Ala Ile Gln Met Thr Gln Ser Pro Ser Ser Leu Ser Ala Ser Val Gly
1 5 10 15

Asp Arg Val Thr Ile Thr Cys Arg Ala Ser Gln Asp Ile Arg Asn Asp
20 25 30

Leu Gly Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Asp Tyr Asn Tyr Pro Trp
85 90 95

Thr Phe Gly Gln Gly Thr Lys Val Glu Ile Lys
100 105

<210> SEQ ID NO 121
<211> LENGTH: 384
<212> TYPE: DNA
<213> ORGANISM: Artificial Sequence
<220> FEATURE:
<223> OTHER INFORMATION: Synthetic

<400> SEQUENCE: 121
caggtgcagc tgcaggagtc ggggccagga ctggtgaagc cttcggagac cctgtccctc 60
acctgcactg tctctgggga ctccatcaat acttactact ggagctggtt ccggcagccc 120
ccagggaagg gactggagtg gattgggtat atctattata gtggaaccac caactacaac 180
ccctccctca agagtcgagt caccatatca atagacacgc ccaggaacca gttctccctg 240
aagctgatct ctgtgaccgc agcggacacg gccgtgtatt actgtgcgag agagaggatt 300
actatgattc ggggagttac cctctactat tactcctacg gtatggacgt ctggggccaa 360
gggaccacgg tcaccgtctc ctca 384

<210> SEQ ID NO 122
<211> LENGTH: 128
<212> TYPE: PRT
<213> ORGANISM: Artificial Sequence
<220> FEATURE:
<223> OTHER INFORMATION: Synthetic

<400> SEQUENCE: 122

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Asn Thr Tyr
            20                  25                  30

Tyr Trp Ser Trp Phe Arg Gln Pro Pro Gly Lys Gly Leu Glu Trp Ile
        35                  40                  45

Gly Tyr Ile Tyr Tyr Ser Gly Thr Thr Asn Tyr Asn Pro Ser Leu Lys
    50                  55                  60

Ser Arg Val Thr Ile Ser Ile Asp Thr Pro Arg Asn Gln Phe Ser Leu
65                  70                  75                  80

Lys Leu Ile Ser Val Thr Ala Ala Asp Thr Ala Val Tyr Tyr Cys Ala
                85                  90                  95

Arg Glu Arg Ile Thr Met Ile Arg Gly Val Thr Leu Tyr Tyr Tyr Ser
            100                 105                 110

Tyr Gly Met Asp Val Trp Gly Gln Gly Thr Thr Val Thr Val Ser Ser
        115                 120                 125

<210> SEQ ID NO 123
<211> LENGTH: 24
<212> TYPE: DNA
<213> ORGANISM: Artificial Sequence
<220> FEATURE:
<223> OTHER INFORMATION: Synthetic

<400> SEQUENCE: 123
ggggactcca tcaatactta ctac 24

<210> SEQ ID NO 124
<211> LENGTH: 8
<212> TYPE: PRT
<213> ORGANISM: Artificial Sequence
<220> FEATURE:
<223> OTHER INFORMATION: Synthetic

<400> SEQUENCE: 124

Gly Asp Ser Ile Asn Thr Tyr Tyr
1               5

<210> SEQ ID NO 125
<211> LENGTH: 21
<212> TYPE: DNA
<213> ORGANISM: Artificial Sequence
<220> FEATURE:
<223> OTHER INFORMATION: Synthetic

<400> SEQUENCE: 125
atctattata gtggaaccac c 21

<210> SEQ ID NO 126
<211> LENGTH: 7
<212> TYPE: PRT
<213> ORGANISM: Artificial Sequence
<220> FEATURE:
<223> OTHER INFORMATION: Synthetic

<400> SEQUENCE: 126

Ile Tyr Tyr Ser Gly Thr Thr
1               5

<210> SEQ ID NO 127
<211> LENGTH: 66
<212> TYPE: DNA
<213> ORGANISM: Artificial Sequence
<220> FEATURE:
<223> OTHER INFORMATION: Synthetic

<400> SEQUENCE: 127
gcgagagaga ggattactat gattcgggga gttaccctct actattactc ctacggtatg 60
gacgtc 66

<210> SEQ ID NO 128
<211> LENGTH: 22
<212> TYPE: PRT
<213> ORGANISM: Artificial Sequence
<220> FEATURE:
<223> OTHER INFORMATION: Synthetic

<400> SEQUENCE: 128

Ala Arg Glu Arg Ile Thr Met Ile Arg Gly Val Thr Leu Tyr Tyr Tyr
1               5                   10                  15

Ser Tyr Gly Met Asp Val
            20

<210> SEQ ID NO 129
<211> LENGTH: 324
<212> TYPE: DNA
<213> ORGANISM: Artificial Sequence
<220> FEATURE:
<223> OTHER INFORMATION: Synthetic

<400> SEQUENCE: 129
gacatccaga tgacccagtc tccatccttc ctgtctgcat ctgtaggaga cagagtcacc 60
atcacttgct gggccagtca ggacattagc agttatttag cctggtatca gcaaaaacca 120
gggatagccc ctaagctcct gatctatgct gcatccactt tgcaaagtgg ggtcccatca 180
aggttcggcg gcagtggatc tgggacagaa ttcactctca caatcagcag cctgcagcct 240
gaagattttg caacttatta ctgtcaacag cttaatagtt accctcggac gttcggccaa 300
gggaccaagg tggaaatcaa acga 324

<210> SEQ ID NO 130
<211> LENGTH: 108
<212> TYPE: PRT
<213> ORGANISM: Artificial Sequence
<220> FEATURE:
<223> OTHER INFORMATION: Synthetic

<400> SEQUENCE: 130

Asp Ile Gln Met Thr Gln Ser Pro Ser Phe Leu Ser Ala Ser Val Gly
1               5                   10                  15

Asp Arg Val Thr Ile Thr Cys Trp Ala Ser Gln Asp Ile Ser Ser Tyr
            20                  25                  30

Leu Ala Trp Tyr Gln Gln Lys Pro Gly Ile Ala Pro Lys Leu Leu Ile
        35                  40                  45

Tyr Ala Ala Ser Thr Leu Gln Ser Gly Val Pro Ser Arg Phe Gly Gly
    50                  55                  60

```
Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Arg
                85                  90                  95

Thr Phe Gly Gln Gly Thr Lys Val Glu Ile Lys Arg
            100                 105


<210> SEQ ID NO 131
<211> LENGTH: 18
<212> TYPE: DNA
<213> ORGANISM: Artificial Sequence
<220> FEATURE:
<223> OTHER INFORMATION: Synthetic

<400> SEQUENCE: 131

caggacatta gcagttat                                                      18


<210> SEQ ID NO 132
<211> LENGTH: 6
<212> TYPE: PRT
<213> ORGANISM: Artificial Sequence
<220> FEATURE:
<223> OTHER INFORMATION: Synthetic

<400> SEQUENCE: 132

Gln Asp Ile Ser Ser Tyr
1               5


<210> SEQ ID NO 133
<211> LENGTH: 9
<212> TYPE: DNA
<213> ORGANISM: Artificial Sequence
<220> FEATURE:
<223> OTHER INFORMATION: Synthetic

<400> SEQUENCE: 133

gctgcatcc                                                                 9


<210> SEQ ID NO 134
<211> LENGTH: 3
<212> TYPE: PRT
<213> ORGANISM: Artificial Sequence
<220> FEATURE:
<223> OTHER INFORMATION: Synthetic

<400> SEQUENCE: 134

Ala Ala Ser
1


<210> SEQ ID NO 135
<211> LENGTH: 27
<212> TYPE: DNA
<213> ORGANISM: Artificial Sequence
<220> FEATURE:
<223> OTHER INFORMATION: Synthetic

<400> SEQUENCE: 135

caacagctta atagttaccc tcggacg                                            27


<210> SEQ ID NO 136
<211> LENGTH: 9
<212> TYPE: PRT
<213> ORGANISM: Artificial Sequence
<220> FEATURE:
<223> OTHER INFORMATION: Synthetic
```

<400> SEQUENCE: 136

Gln Gln Leu Asn Ser Tyr Pro Arg Thr
1 5

<210> SEQ ID NO 137
<211> LENGTH: 384
<212> TYPE: DNA
<213> ORGANISM: Artificial Sequence
<220> FEATURE:
<223> OTHER INFORMATION: Synthetic

<400> SEQUENCE: 137
caggtgcagc tgcaggagtc ggggccagga ctggtgaagc cttcggagac cctgtccctc 60
acctgcactg tctctgggga ctccatcaat acttactact ggagctggtt ccggcagccc 120
ccagggaagg gactggagtg gattgggtat atctattata gtggaaccac caactacaac 180
ccctccctca agagtcgagt caccatatca atagacacgc ccaggaacca gttctccctg 240
aagctgatct ctgtgaccgc agcggacacg gccgtgtatt actgtgcgag agagaggatt 300
actatgattc ggggagttac cctctactat tactcctacg gtatggacgt ctggggccaa 360
gggaccacgg tcaccgtctc ctca 384

<210> SEQ ID NO 138
<211> LENGTH: 128
<212> TYPE: PRT
<213> ORGANISM: Artificial Sequence
<220> FEATURE:
<223> OTHER INFORMATION: Synthetic

<400> SEQUENCE: 138

Gln Val Gln Leu Gln Glu Ser Gly Pro Gly Leu Val Lys Pro Ser Glu
1 5 10 15

Thr Leu Ser Leu Thr Cys Thr Val Ser Gly Asp Ser Ile Asn Thr Tyr
20 25 30

Tyr Trp Ser Trp Phe Arg Gln Pro Pro Gly Lys Gly Leu Glu Trp Ile
35 40 45

Gly Tyr Ile Tyr Tyr Ser Gly Thr Thr Asn Tyr Asn Pro Ser Leu Lys
50 55 60

Ser Arg Val Thr Ile Ser Ile Asp Thr Pro Arg Asn Gln Phe Ser Leu
65 70 75 80

Lys Leu Ile Ser Val Thr Ala Ala Asp Thr Ala Val Tyr Tyr Cys Ala
85 90 95

Arg Glu Arg Ile Thr Met Ile Arg Gly Val Thr Leu Tyr Tyr Tyr Ser
100 105 110

Tyr Gly Met Asp Val Trp Gly Gln Gly Thr Thr Val Thr Val Ser Ser
115 120 125

<210> SEQ ID NO 139
<211> LENGTH: 321
<212> TYPE: DNA
<213> ORGANISM: Artificial Sequence
<220> FEATURE:
<223> OTHER INFORMATION: Synthetic

<400> SEQUENCE: 139
gacatccaga tgacccagtc tccatccttc ctgtctgcat ctgtaggaga cagagtcacc 60
atcacttgct gggccagtca ggacattagc agttatttag cctggtatca gcaaaaacca 120
gggatagccc ctaagctcct gatctatgct gcatccactt tgcaaagtgg ggtcccatca 180

-continued

```
aggttcggcg gcagtggatc tgggacagaa ttcactctca caatcagcag cctgcagcct    240

gaagattttg caacttatta ctgtcaacag cttaatagtt accctcggac gttcggccaa    300

gggaccaagg tggaaatcaa a                                              321
```

```
<210> SEQ ID NO 140
<211> LENGTH: 107
<212> TYPE: PRT
<213> ORGANISM: Artificial Sequence
<220> FEATURE:
<223> OTHER INFORMATION: Synthetic

<400> SEQUENCE: 140

Asp Ile Gln Met Thr Gln Ser Pro Ser Phe Leu Ser Ala Ser Val Gly
1               5                   10                  15

Asp Arg Val Thr Ile Thr Cys Trp Ala Ser Gln Asp Ile Ser Ser Tyr
            20                  25                  30

Leu Ala Trp Tyr Gln Gln Lys Pro Gly Ile Ala Pro Lys Leu Leu Ile
        35                  40                  45

Tyr Ala Ala Ser Thr Leu Gln Ser Gly Val Pro Ser Arg Phe Gly Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Arg
                85                  90                  95

Thr Phe Gly Gln Gly Thr Lys Val Glu Ile Lys
            100                 105
```

```
<210> SEQ ID NO 141
<211> LENGTH: 384
<212> TYPE: DNA
<213> ORGANISM: Artificial Sequence
<220> FEATURE:
<223> OTHER INFORMATION: Synthetic

<400> SEQUENCE: 141

caggtgcagc tgcaggagtc gggcccagga ctggtgaagc cttcggagac cctgtccctc     60

acctgcactg tctctgggga ctccatcaat acttactact ggagctggat ccggcagccc    120

ccagggaagg gactggagtg gattgggtat atctattata gtggaaccac caactacaac    180

ccctccctca agagtcgagt caccatatca gtagacacgt ccaagaacca gttctccctg    240

aagctgagct ctgtgaccgc tgcggacacg gccgtgtatt actgtgcgag agagaggatt    300

actatgattc ggggagttac cctctactat tactcctacg gtatggacgt ctggggccaa    360

gggaccacgg tcaccgtctc ctca                                           384
```

```
<210> SEQ ID NO 142
<211> LENGTH: 128
<212> TYPE: PRT
<213> ORGANISM: Artificial Sequence
<220> FEATURE:
<223> OTHER INFORMATION: Synthetic

<400> SEQUENCE: 142

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Asn Thr Tyr
            20                  25                  30

Tyr Trp Ser Trp Ile Arg Gln Pro Pro Gly Lys Gly Leu Glu Trp Ile
        35                  40                  45
```

```
Gly Tyr Ile Tyr Tyr Ser Gly Thr Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Arg Ile Thr Met Ile Arg Gly Val Thr Leu Tyr Tyr Tyr Ser
            100                 105                 110

Tyr Gly Met Asp Val Trp Gly Gln Gly Thr Thr Val Thr Val Ser Ser
        115                 120                 125


<210> SEQ ID NO 143
<211> LENGTH: 321
<212> TYPE: DNA
<213> ORGANISM: Artificial Sequence
<220> FEATURE:
<223> OTHER INFORMATION: Synthetic

<400> SEQUENCE: 143

gacatccaga tgacccagtc tccatcctcc ctgtctgcat ctgtaggaga cagagtcacc      60

atcacttgcc gggcaagtca ggacattagc agttatttag gctggtatca gcagaaacca     120

gggaaagccc ctaagcgcct gatctatgct gcatccagtt tgcaaagtgg ggtcccatca     180

aggttcagcg gcagtggatc tgggacagaa ttcactctca caatcagcag cctgcagcct     240

gaagattttg caacttatta ctgtcaacag cttaatagtt accctcggac gttcggccaa     300

gggaccaagg tggaaatcaa a                                               321


<210> SEQ ID NO 144
<211> LENGTH: 107
<212> TYPE: PRT
<213> ORGANISM: Artificial Sequence
<220> FEATURE:
<223> OTHER INFORMATION: Synthetic

<400> SEQUENCE: 144

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Arg
                85                  90                  95

Thr Phe Gly Gln Gly Thr Lys Val Glu Ile Lys
            100                 105


<210> SEQ ID NO 145
<211> LENGTH: 378
<212> TYPE: DNA
<213> ORGANISM: Artificial Sequence
<220> FEATURE:
<223> OTHER INFORMATION: Synthetic

<400> SEQUENCE: 145
```

```
caggtgcagc tggtgcagtc tggagctgag gtgaagaagc ctggggcctc agtgaaggtc     60

tcctgcaagg cttctggtta cacctttacc aactatggta tcagctgggt gcgacaggcc    120

cctggacaag gacttgagtt aatgggatgg attagtggtt acaatggtaa cacaaactat    180

gcacaagaac tccaggccag agtcaccatg accacagaca catccacgag cacagcctac    240

atggagctga ggaacctgag atctgacgac acggccgtat attactgtgc gagagataga    300

gtcgttgtag cagctgctaa ttactacttt tattctatgg acgtctgggg ccaagggacc    360

acggtcaccg tctcctca                                                   378
```

```
<210> SEQ ID NO 146
<211> LENGTH: 126
<212> TYPE: PRT
<213> ORGANISM: Artificial Sequence
<220> FEATURE:
<223> OTHER INFORMATION: Synthetic

<400> SEQUENCE: 146

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Leu Met
        35                  40                  45

Gly Trp Ile Ser Gly Tyr Asn Gly Asn Thr Asn Tyr Ala Gln Glu Leu
    50                  55                  60

Gln Ala Arg Val Thr Met Thr Thr Asp Thr Ser Thr Ser Thr Ala Tyr
65                  70                  75                  80

Met Glu Leu Arg Asn Leu Arg Ser Asp Asp Thr Ala Val Tyr Tyr Cys
                85                  90                  95

Ala Arg Asp Arg Val Val Val Ala Ala Ala Asn Tyr Tyr Phe Tyr Ser
            100                 105                 110

Met Asp Val Trp Gly Gln Gly Thr Thr Val Thr Val Ser Ser
        115                 120                 125


<210> SEQ ID NO 147
<211> LENGTH: 24
<212> TYPE: DNA
<213> ORGANISM: Artificial Sequence
<220> FEATURE:
<223> OTHER INFORMATION: Synthetic

<400> SEQUENCE: 147

ggttacacct ttaccaacta tggt                                            24


<210> SEQ ID NO 148
<211> LENGTH: 8
<212> TYPE: PRT
<213> ORGANISM: Artificial Sequence
<220> FEATURE:
<223> OTHER INFORMATION: Synthetic

<400> SEQUENCE: 148

Gly Tyr Thr Phe Thr Asn Tyr Gly
1               5


<210> SEQ ID NO 149
<211> LENGTH: 24
<212> TYPE: DNA
<213> ORGANISM: Artificial Sequence
<220> FEATURE:
```

<223> OTHER INFORMATION: Synthetic

<400> SEQUENCE: 149
attagtggtt acaatggtaa caca 24

<210> SEQ ID NO 150
<211> LENGTH: 8
<212> TYPE: PRT
<213> ORGANISM: Artificial Sequence
<220> FEATURE:
<223> OTHER INFORMATION: Synthetic

<400> SEQUENCE: 150

Ile Ser Gly Tyr Asn Gly Asn Thr
1 5

<210> SEQ ID NO 151
<211> LENGTH: 57
<212> TYPE: DNA
<213> ORGANISM: Artificial Sequence
<220> FEATURE:
<223> OTHER INFORMATION: Synthetic

<400> SEQUENCE: 151
gcgagagata gagtcgttgt agcagctgct aattactact tttattctat ggacgtc 57

<210> SEQ ID NO 152
<211> LENGTH: 19
<212> TYPE: PRT
<213> ORGANISM: Artificial Sequence
<220> FEATURE:
<223> OTHER INFORMATION: Synthetic

<400> SEQUENCE: 152

Ala Arg Asp Arg Val Val Val Ala Ala Ala Asn Tyr Tyr Phe Tyr Ser
1 5 10 15

Met Asp Val

<210> SEQ ID NO 153
<211> LENGTH: 339
<212> TYPE: DNA
<213> ORGANISM: Artificial Sequence
<220> FEATURE:
<223> OTHER INFORMATION: Synthetic

<400> SEQUENCE: 153
gccatccaga tgacccagtc tccactctcc ctgtccgtca cccttggaca gccggcctcc 60
atctcctgca ggtctagtca aagcctcgta tacagtgatg gagacaccta cttgaattgg 120
tttcagcaga ggccaggcca atctccaagg cgcctaattt ataaggtttc taaccgggac 180
tctggggtcc cagacagatt cagcggcagt gggtcaggca ctgctttcac actgaaaatc 240
agcggggtgg aggccgagga tgttggggtt tactactgca tgcaagctac acactggcct 300
cggacgttcg gccaagggac caaggtggaa atcaaacga 339

<210> SEQ ID NO 154
<211> LENGTH: 113
<212> TYPE: PRT
<213> ORGANISM: Artificial Sequence
<220> FEATURE:
<223> OTHER INFORMATION: Synthetic

<400> SEQUENCE: 154

Ala Ile Gln Met Thr Gln Ser Pro Leu Ser Leu Ser Val Thr Leu Gly

```
1               5                   10                  15

Gln Pro Ala Ser Ile Ser Cys Arg Ser Ser Gln Ser Leu Val Tyr Ser
            20                  25                  30

Asp Gly Asp Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Ala Phe Thr Leu Lys Ile
65                  70                  75                  80

Ser Gly Val Glu Ala Glu Asp Val Gly Val Tyr Tyr Cys Met Gln Ala
                85                  90                  95

Thr His Trp Pro Arg Thr Phe Gly Gln Gly Thr Lys Val Glu Ile Lys
            100                 105                 110

Arg


<210> SEQ ID NO 155
<211> LENGTH: 33
<212> TYPE: DNA
<213> ORGANISM: Artificial Sequence
<220> FEATURE:
<223> OTHER INFORMATION: Synthetic

<400> SEQUENCE: 155

caaagcctcg tatacagtga tggagacacc tac                              33


<210> SEQ ID NO 156
<211> LENGTH: 11
<212> TYPE: PRT
<213> ORGANISM: Artificial Sequence
<220> FEATURE:
<223> OTHER INFORMATION: Synthetic

<400> SEQUENCE: 156

Gln Ser Leu Val Tyr Ser Asp Gly Asp Thr Tyr
1               5                   10


<210> SEQ ID NO 157
<211> LENGTH: 9
<212> TYPE: DNA
<213> ORGANISM: Artificial Sequence
<220> FEATURE:
<223> OTHER INFORMATION: Synthetic

<400> SEQUENCE: 157

aaggtttct                                                          9


<210> SEQ ID NO 158
<211> LENGTH: 3
<212> TYPE: PRT
<213> ORGANISM: Artificial Sequence
<220> FEATURE:
<223> OTHER INFORMATION: Synthetic

<400> SEQUENCE: 158

Lys Val Ser
1


<210> SEQ ID NO 159
<211> LENGTH: 27
<212> TYPE: DNA
<213> ORGANISM: Artificial Sequence
<220> FEATURE:
<223> OTHER INFORMATION: Synthetic
```

<400> SEQUENCE: 159
atgcaagcta cacactggcc tcggacg 27

<210> SEQ ID NO 160
<211> LENGTH: 9
<212> TYPE: PRT
<213> ORGANISM: Artificial Sequence
<220> FEATURE:
<223> OTHER INFORMATION: Synthetic

<400> SEQUENCE: 160

Met Gln Ala Thr His Trp Pro Arg Thr
1 5

<210> SEQ ID NO 161
<211> LENGTH: 378
<212> TYPE: DNA
<213> ORGANISM: Artificial Sequence
<220> FEATURE:
<223> OTHER INFORMATION: Synthetic

<400> SEQUENCE: 161
caggttcagc tggtgcagtc tggagctgag gtgaagaagc ctggggcctc agtgaaggtc 60
tcctgcaagg cttctggtta cacctttacc aactatggta tcagctgggt gcgacaggcc 120
cctggacaag gacttgagtt aatgggatgg attagtggtt acaatggtaa cacaaactat 180
gcacaagaac tccaggccag agtcaccatg accacagaca catccacgag cacagcctac 240
atggagctga ggaacctgag atctgacgac acggccgtat attactgtgc gagagataga 300
gtcgttgtag cagctgctaa ttactacttt tattctatgg acgtctgggg ccaagggacc 360
acggtcaccg tctcctca 378

<210> SEQ ID NO 162
<211> LENGTH: 126
<212> TYPE: PRT
<213> ORGANISM: Artificial Sequence
<220> FEATURE:
<223> OTHER INFORMATION: Synthetic

<400> SEQUENCE: 162

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asn Tyr
20 25 30

Gly Ile Ser Trp Val Arg Gln Ala Pro Gly Gln Gly Leu Glu Leu Met
35 40 45

Gly Trp Ile Ser Gly Tyr Asn Gly Asn Thr Asn Tyr Ala Gln Glu Leu
50 55 60

Gln Ala Arg Val Thr Met Thr Thr Asp Thr Ser Thr Ser Thr Ala Tyr
65 70 75 80

Met Glu Leu Arg Asn Leu Arg Ser Asp Asp Thr Ala Val Tyr Tyr Cys
85 90 95

Ala Arg Asp Arg Val Val Val Ala Ala Ala Asn Tyr Tyr Phe Tyr Ser
100 105 110

Met Asp Val Trp Gly Gln Gly Thr Thr Val Thr Val Ser Ser
115 120 125

<210> SEQ ID NO 163
<211> LENGTH: 336

<212> TYPE: DNA
<213> ORGANISM: Artificial Sequence
<220> FEATURE:
<223> OTHER INFORMATION: Synthetic

<400> SEQUENCE: 163
gatgttgtga tgactcagtc tccactctcc ctgtccgtca cccttggaca gccggcctcc 60
atctcctgca ggtctagtca aagcctcgta tacagtgatg gagacaccta cttgaattgg 120
tttcagcaga ggccaggcca atctccaagg cgcctaattt ataaggtttc taaccgggac 180
tctggggtcc cagacagatt cagcggcagt gggtcaggca ctgctttcac actgaaaatc 240
agcggggtgg aggccgagga tgttggggtt tactactgca tgcaagctac acactggcct 300
cggacgttcg gccaagggac caaggtggaa atcaaa 336

<210> SEQ ID NO 164
<211> LENGTH: 112
<212> TYPE: PRT
<213> ORGANISM: Artificial Sequence
<220> FEATURE:
<223> OTHER INFORMATION: Synthetic

<400> SEQUENCE: 164

Asp Val Val Met Thr Gln Ser Pro Leu Ser Leu Ser Val Thr Leu Gly
1 5 10 15

Gln Pro Ala Ser Ile Ser Cys Arg Ser Ser Gln Ser Leu Val Tyr Ser
20 25 30

Asp Gly Asp Thr Tyr Leu Asn Trp Phe Gln Gln Arg Pro Gly Gln Ser
35 40 45

Pro Arg Arg Leu Ile Tyr Lys Val Ser Asn Arg Asp Ser Gly Val Pro
50 55 60

Asp Arg Phe Ser Gly Ser Gly Ser Gly Thr Ala Phe Thr Leu Lys Ile
65 70 75 80

Ser Gly Val Glu Ala Glu Asp Val Gly Val Tyr Tyr Cys Met Gln Ala
85 90 95

Thr His Trp Pro Arg Thr Phe Gly Gln Gly Thr Lys Val Glu Ile Lys
100 105 110

<210> SEQ ID NO 165
<211> LENGTH: 378
<212> TYPE: DNA
<213> ORGANISM: Artificial Sequence
<220> FEATURE:
<223> OTHER INFORMATION: Synthetic

<400> SEQUENCE: 165
caggttcagc tggtgcagtc tggagctgag gtgaagaagc ctggggcctc agtgaaggtc 60
tcctgcaagg cttctggtta cacctttacc aactatggta tcagctgggt gcgacaggcc 120
cctggacaag ggcttgagtg gatgggatgg attagtggtt acaatggtaa cacaaactat 180
gcacagaagc tccagggcag agtcaccatg accacagaca catccacgag cacagcctac 240
atggagctga ggagcctgag atctgacgac acggccgtgt attactgtgc gagagataga 300
gtcgttgtag cagctgctaa ttactacttt tattctatgg acgtctgggg ccaagggacc 360
acggtcaccg tctcctca 378

<210> SEQ ID NO 166
<211> LENGTH: 126
<212> TYPE: PRT
<213> ORGANISM: Artificial Sequence -continued
<220> FEATURE:
<223> OTHER INFORMATION: Synthetic

<400> SEQUENCE: 166

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Trp Met
        35                  40                  45

Gly Trp Ile Ser Gly Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Arg Val Val Val Ala Ala Ala Asn Tyr Tyr Phe Tyr Ser
            100                 105                 110

Met Asp Val Trp Gly Gln Gly Thr Thr Val Thr Val Ser Ser
        115                 120                 125
```

<210> SEQ ID NO 167
<211> LENGTH: 336
<212> TYPE: DNA
<213> ORGANISM: Artificial Sequence
<220> FEATURE:
<223> OTHER INFORMATION: Synthetic

<400> SEQUENCE: 167

```
gatgttgtga tgactcagtc tccactctcc ctgcccgtca cccttggaca gccggcctcc     60

atctcctgca ggtctagtca aagcctcgta tacagtgatg gagacaccta cttgaattgg    120

tttcagcaga ggccaggcca atctccaagg cgcctaattt ataaggtttc taaccgggac    180

tctggggtcc cagacagatt cagcggcagt gggtcaggca ctgatttcac actgaaaatc    240

agcagggtgg aggctgagga tgttggggtt tattactgca tgcaagctac acactggcct    300

cggacgttcg gccaagggac caaggtggaa atcaaa                              336
```

<210> SEQ ID NO 168
<211> LENGTH: 112
<212> TYPE: PRT
<213> ORGANISM: Artificial Sequence
<220> FEATURE:
<223> OTHER INFORMATION: Synthetic

<400> SEQUENCE: 168

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asp Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95
```

```
Thr His Trp Pro Arg Thr Phe Gly Gln Gly Thr Lys Val Glu Ile Lys
            100                 105                 110


<210> SEQ ID NO 169
<211> LENGTH: 375
<212> TYPE: DNA
<213> ORGANISM: Artificial Sequence
<220> FEATURE:
<223> OTHER INFORMATION: Synthetic

<400> SEQUENCE: 169

caggtccact tgaaggagtc tggtcctacg ctggtgaaac ccacacagac cctcacgctg      60

acctgcacct tctctggatt ctcactcatc actagtggag tgggtgtggg ctggattcgt     120

cagcccccg gaaaggccct ggagtggctt gcactcattt attggaatgg tgataagcgc     180

tacagcccat ctctgaagag caggctcacc atcaccaagg acacctccaa aaaccaggtg     240

gtccttacaa tgaccaacat ggaccctgtg gacacagcca catattactg tgcacacagg     300

ataactgaaa ctagttacta cttctactac ggtatggacg tctggggcca agggaccacg     360

gtcaccgtct cctca                                                      375


<210> SEQ ID NO 170
<211> LENGTH: 125
<212> TYPE: PRT
<213> ORGANISM: Artificial Sequence
<220> FEATURE:
<223> OTHER INFORMATION: Synthetic

<400> SEQUENCE: 170

Gln Val His Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ile Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Gly Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg Ile Thr Glu Thr Ser Tyr Tyr Phe Tyr Tyr Gly Met
            100                 105                 110

Asp Val Trp Gly Gln Gly Thr Thr Val Thr Val Ser Ser
        115                 120                 125


<210> SEQ ID NO 171
<211> LENGTH: 30
<212> TYPE: DNA
<213> ORGANISM: Artificial Sequence
<220> FEATURE:
<223> OTHER INFORMATION: Synthetic

<400> SEQUENCE: 171

ggattctcac tcatcactag tggagtgggt                                       30


<210> SEQ ID NO 172
<211> LENGTH: 10
<212> TYPE: PRT
<213> ORGANISM: Artificial Sequence
<220> FEATURE:
```

<223> OTHER INFORMATION: Synthetic

<400> SEQUENCE: 172

Gly Phe Ser Leu Ile Thr Ser Gly Val Gly
1 5 10

<210> SEQ ID NO 173
<211> LENGTH: 21
<212> TYPE: DNA
<213> ORGANISM: Artificial Sequence
<220> FEATURE:
<223> OTHER INFORMATION: Synthetic

<400> SEQUENCE: 173
atttattgga atggtgataa g 21

<210> SEQ ID NO 174
<211> LENGTH: 7
<212> TYPE: PRT
<213> ORGANISM: Artificial Sequence
<220> FEATURE:
<223> OTHER INFORMATION: Synthetic

<400> SEQUENCE: 174

Ile Tyr Trp Asn Gly Asp Lys
1 5

<210> SEQ ID NO 175
<211> LENGTH: 51
<212> TYPE: DNA
<213> ORGANISM: Artificial Sequence
<220> FEATURE:
<223> OTHER INFORMATION: Synthetic

<400> SEQUENCE: 175
gcacacagga taactgaaac tagttactac ttctactacg gtatggacgt c 51

<210> SEQ ID NO 176
<211> LENGTH: 17
<212> TYPE: PRT
<213> ORGANISM: Artificial Sequence
<220> FEATURE:
<223> OTHER INFORMATION: Synthetic

<400> SEQUENCE: 176

Ala His Arg Ile Thr Glu Thr Ser Tyr Tyr Phe Tyr Tyr Gly Met Asp
1 5 10 15

Val

<210> SEQ ID NO 177
<211> LENGTH: 339
<212> TYPE: DNA
<213> ORGANISM: Artificial Sequence
<220> FEATURE:
<223> OTHER INFORMATION: Synthetic

<400> SEQUENCE: 177
gacatccaga tgacccagtc tccactctcc ctgcccgtca cccctggaga gccggcctcc 60
atctcctgca ggtctagtca gagcctcctg catagtcatg gatacgacta tttggattgg 120
tacctgcaga agccagggca gtctccacag ctcctgatct atttgggttc taatcgggcc 180
tccggggtcc ctgacaggtt cagtggcagt ggatcaggca cagattttac actgaaaatc 240
agcagagtgg aggctgagga tgttggggtt tattactgca tgcaagctct acaaactccg 300
ctcactttcg gcggagggac caaggtggaa atcaaacga 339

<210> SEQ ID NO 178
<211> LENGTH: 113
<212> TYPE: PRT
<213> ORGANISM: Artificial Sequence
<220> FEATURE:
<223> OTHER INFORMATION: Synthetic

<400> SEQUENCE: 178

Asp Ile Gln Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

His Gly Tyr Asp Tyr Leu Asp Trp Tyr Leu Gln Lys Pro Gly Gln Ser
35 40 45

Pro Gln Leu Leu Ile Tyr Leu Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Ala
85 90 95

Leu Gln Thr Pro Leu Thr Phe Gly Gly Gly Thr Lys Val Glu Ile Lys
100 105 110

Arg

<210> SEQ ID NO 179
<211> LENGTH: 33
<212> TYPE: DNA
<213> ORGANISM: Artificial Sequence
<220> FEATURE:
<223> OTHER INFORMATION: Synthetic

<400> SEQUENCE: 179
cagagcctcc tgcatagtca tggatacgac tat 33

<210> SEQ ID NO 180
<211> LENGTH: 11
<212> TYPE: PRT
<213> ORGANISM: Artificial Sequence
<220> FEATURE:
<223> OTHER INFORMATION: Synthetic

<400> SEQUENCE: 180

Gln Ser Leu Leu His Ser His Gly Tyr Asp Tyr
1 5 10

<210> SEQ ID NO 181
<211> LENGTH: 9
<212> TYPE: DNA
<213> ORGANISM: Artificial Sequence
<220> FEATURE:
<223> OTHER INFORMATION: Synthetic

<400> SEQUENCE: 181 ttgggttct 9

<210> SEQ ID NO 182
<211> LENGTH: 3
<212> TYPE: PRT
<213> ORGANISM: Artificial Sequence
<220> FEATURE:
<223> OTHER INFORMATION: Synthetic

<400> SEQUENCE: 182

Leu Gly Ser
1

<210> SEQ ID NO 183
<211> LENGTH: 27
<212> TYPE: DNA
<213> ORGANISM: Artificial Sequence
<220> FEATURE:
<223> OTHER INFORMATION: Synthetic

<400> SEQUENCE: 183
atgcaagctc tacaaactcc gctcact 27

<210> SEQ ID NO 184
<211> LENGTH: 9
<212> TYPE: PRT
<213> ORGANISM: Artificial Sequence
<220> FEATURE:
<223> OTHER INFORMATION: Synthetic

<400> SEQUENCE: 184

Met Gln Ala Leu Gln Thr Pro Leu Thr
1 5

<210> SEQ ID NO 185
<211> LENGTH: 375
<212> TYPE: DNA
<213> ORGANISM: Artificial Sequence
<220> FEATURE:
<223> OTHER INFORMATION: Synthetic

<400> SEQUENCE: 185
cagatcacct tgaaggagtc tggtcctacg ctggtgaaac ccacacagac cctcacgctg 60
acctgcacct tctctggatt ctcactcatc actagtggag tgggtgtggg ctggattcgt 120
cagccccccg gaaaggccct ggagtggctt gcactcattt attggaatgg tgataagcgc 180
tacagcccat ctctgaagag caggctcacc atcaccaagg acacctccaa aaaccaggtg 240
gtccttacaa tgaccaacat ggaccctgtg gacacagcca catattactg tgcacacagg 300
ataactgaaa ctagttacta cttctactac ggtatggacg tctggggcca agggaccacg 360
gtcaccgtct cctca 375

<210> SEQ ID NO 186
<211> LENGTH: 125
<212> TYPE: PRT
<213> ORGANISM: Artificial Sequence
<220> FEATURE:
<223> OTHER INFORMATION: Synthetic

<400> SEQUENCE: 186

Gln Ile Thr Leu Lys Glu Ser Gly Pro Thr Leu Val Lys Pro Thr Gln
1 5 10 15

Thr Leu Thr Leu Thr Cys Thr Phe Ser Gly Phe Ser Leu Ile Thr Ser
20 25 30

Gly Val Gly Val Gly Trp Ile Arg Gln Pro Pro Gly Lys Ala Leu Glu
35 40 45

Trp Leu Ala Leu Ile Tyr Trp Asn Gly Asp Lys Arg Tyr Ser Pro Ser
50 55 60

Leu Lys Ser Arg Leu Thr Ile Thr Lys Asp Thr Ser Lys Asn Gln Val
65 70 75 80

Val Leu Thr Met Thr Asn Met Asp Pro Val Asp Thr Ala Thr Tyr Tyr
85 90 95

Cys Ala His Arg Ile Thr Glu Thr Ser Tyr Tyr Phe Tyr Tyr Gly Met
100 105 110

Asp Val Trp Gly Gln Gly Thr Thr Val Thr Val Ser Ser
115 120 125

<210> SEQ ID NO 187
<211> LENGTH: 336
<212> TYPE: DNA
<213> ORGANISM: Artificial Sequence
<220> FEATURE:
<223> OTHER INFORMATION: Synthetic

<400> SEQUENCE: 187
gatattgtga tgactcagtc tccactctcc ctgcccgtca cccctggaga gccggcctcc 60
atctcctgca ggtctagtca gagcctcctg catagtcatg gatacgacta tttggattgg 120
tacctgcaga agccagggca gtctccacag ctcctgatct atttgggttc taatcgggcc 180
tccggggtcc ctgacaggtt cagtggcagt ggatcaggca cagattttac actgaaaatc 240
agcagagtgg aggctgagga tgttggggtt tattactgca tgcaagctct acaaactccg 300
ctcactttcg gcggagggac caaggtggag atcaaa 336

<210> SEQ ID NO 188
<211> LENGTH: 112
<212> TYPE: PRT
<213> ORGANISM: Artificial Sequence
<220> FEATURE:
<223> OTHER INFORMATION: Synthetic

<400> SEQUENCE: 188

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

His Gly Tyr Asp Tyr Leu Asp Trp Tyr Leu Gln Lys Pro Gly Gln Ser
35 40 45

Pro Gln Leu Leu Ile Tyr Leu Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Ala
85 90 95

Leu Gln Thr Pro Leu Thr Phe Gly Gly Gly Thr Lys Val Glu Ile Lys
100 105 110

<210> SEQ ID NO 189
<211> LENGTH: 375
<212> TYPE: DNA
<213> ORGANISM: Artificial Sequence
<220> FEATURE:
<223> OTHER INFORMATION: Synthetic

<400> SEQUENCE: 189
cagatcacct tgaaggagtc tggtcctacg ctggtgaaac ccacacagac cctcacgctg 60
acctgcacct tctctggatt ctcactcatc actagtggag tgggtgtggg ctggatccgt 120
cagcccccag gaaaggccct ggagtggctt gcactcattt attggaatgg tgataagcgc 180
tacagcccat ctctgaagag caggctcacc atcaccaagg acacctccaa aaaccaggtg 240
gtccttacaa tgaccaacat ggaccctgtg gacacagcca catattactg tgcacacagg 300
ataactgaaa ctagttacta cttctactac ggtatggacg tctggggcca agggaccacg 360
gtcaccgtct cctca 375

<210> SEQ ID NO 190
<211> LENGTH: 125
<212> TYPE: PRT
<213> ORGANISM: Artificial Sequence
<220> FEATURE:
<223> OTHER INFORMATION: Synthetic

<400> SEQUENCE: 190

Gln Ile Thr Leu Lys Glu Ser Gly Pro Thr Leu Val Lys Pro Thr Gln
1 5 10 15

Thr Leu Thr Leu Thr Cys Thr Phe Ser Gly Phe Ser Leu Ile Thr Ser
20 25 30

Gly Val Gly Val Gly Trp Ile Arg Gln Pro Pro Gly Lys Ala Leu Glu
35 40 45

Trp Leu Ala Leu Ile Tyr Trp Asn Gly Asp Lys Arg Tyr Ser Pro Ser
50 55 60

Leu Lys Ser Arg Leu Thr Ile Thr Lys Asp Thr Ser Lys Asn Gln Val
65 70 75 80

Val Leu Thr Met Thr Asn Met Asp Pro Val Asp Thr Ala Thr Tyr Tyr
85 90 95

Cys Ala His Arg Ile Thr Glu Thr Ser Tyr Tyr Phe Tyr Tyr Gly Met
100 105 110

Asp Val Trp Gly Gln Gly Thr Thr Val Thr Val Ser Ser
115 120 125

<210> SEQ ID NO 191
<211> LENGTH: 336
<212> TYPE: DNA
<213> ORGANISM: Artificial Sequence
<220> FEATURE:
<223> OTHER INFORMATION: Synthetic

<400> SEQUENCE: 191
gatattgtga tgactcagtc tccactctcc ctgcccgtca cccctggaga gccggcctcc 60
atctcctgca ggtctagtca gagcctcctg catagtcatg gatacgacta tttggattgg 120
tacctgcaga agccagggca gtctccacag ctcctgatct atttgggttc taatcgggcc 180
tccggggtcc ctgacaggtt cagtggcagt ggatcaggca cagattttac actgaaaatc 240
agcagagtgg aggctgagga tgttggggtt tattactgca tgcaagctct acaaactccg 300
ctcactttcg gcggagggac caaggtggag atcaaa 336

<210> SEQ ID NO 192
<211> LENGTH: 112
<212> TYPE: PRT
<213> ORGANISM: Artificial Sequence
<220> FEATURE:
<223> OTHER INFORMATION: Synthetic

<400> SEQUENCE: 192

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

```
His Gly Tyr Asp Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110
```

<210> SEQ ID NO 193
<211> LENGTH: 375
<212> TYPE: DNA
<213> ORGANISM: Artificial Sequence
<220> FEATURE:
<223> OTHER INFORMATION: Synthetic

<400> SEQUENCE: 193

```
cagatcacct tgaaggagtc tggtcctact ctggtgaaac cctcacagac cctcacgctg     60

acctgcacct tctctgggtt ctcactcagc actagtggag tgggtgtggg ctggatccgt    120

cagcccccag gaaaggccct ggagtggctt gcactcattt attggaattc tgataagcgc    180

tacagcccat ctctgaagag caggctcacc atcaccaagg acacctccaa aaaccaggta    240

gtccttacaa tgaccaacat ggaccctgtg gacacagcca catattactg tgcacacaga    300

catgacagct cgtcctacta cttctactac ggtatggacg tctggggcca agggatcacg    360

gtcaccgtct cctca                                                     375
```

<210> SEQ ID NO 194
<211> LENGTH: 125
<212> TYPE: PRT
<213> ORGANISM: Artificial Sequence
<220> FEATURE:
<223> OTHER INFORMATION: Synthetic

<400> SEQUENCE: 194

```
Gln Ile Thr Leu Lys Glu Ser Gly Pro Thr Leu Val Lys Pro Ser Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Ser Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg His Asp Ser Ser Ser Tyr Tyr Phe Tyr Tyr Gly Met
            100                 105                 110

Asp Val Trp Gly Gln Gly Ile Thr Val Thr Val Ser Ser
        115                 120                 125
```

<210> SEQ ID NO 195
<211> LENGTH: 30
<212> TYPE: DNA
<213> ORGANISM: Artificial Sequence
<220> FEATURE:
<223> OTHER INFORMATION: Synthetic

<400> SEQUENCE: 195
gggttctcac tcagcactag tggagtgggt 30

<210> SEQ ID NO 196
<211> LENGTH: 10
<212> TYPE: PRT
<213> ORGANISM: Artificial Sequence
<220> FEATURE:
<223> OTHER INFORMATION: Synthetic

<400> SEQUENCE: 196

Gly Phe Ser Leu Ser Thr Ser Gly Val Gly
1 5 10

<210> SEQ ID NO 197
<211> LENGTH: 21
<212> TYPE: DNA
<213> ORGANISM: Artificial Sequence
<220> FEATURE:
<223> OTHER INFORMATION: Synthetic

<400> SEQUENCE: 197
atttattgga attctgataa g 21

<210> SEQ ID NO 198
<211> LENGTH: 7
<212> TYPE: PRT
<213> ORGANISM: Artificial Sequence
<220> FEATURE:
<223> OTHER INFORMATION: Synthetic

<400> SEQUENCE: 198

Ile Tyr Trp Asn Ser Asp Lys
1 5

<210> SEQ ID NO 199
<211> LENGTH: 51
<212> TYPE: DNA
<213> ORGANISM: Artificial Sequence
<220> FEATURE:
<223> OTHER INFORMATION: Synthetic

<400> SEQUENCE: 199
gcacacagac atgacagctc gtcctactac ttctactacg gtatggacgt c 51

<210> SEQ ID NO 200
<211> LENGTH: 17
<212> TYPE: PRT
<213> ORGANISM: Artificial Sequence
<220> FEATURE:
<223> OTHER INFORMATION: Synthetic

<400> SEQUENCE: 200

Ala His Arg His Asp Ser Ser Ser Tyr Tyr Phe Tyr Tyr Gly Met Asp
1 5 10 15

Val

<210> SEQ ID NO 201
<211> LENGTH: 339
<212> TYPE: DNA
<213> ORGANISM: Artificial Sequence
<220> FEATURE:
<223> OTHER INFORMATION: Synthetic

<400> SEQUENCE: 201
gacatccaga tgacccagtc tccgctctcc ctgcccgtca cccctggaga gccggcctcc 60
atctcctgca ggtctagtca gagcctcctc catagtcatg gatacaacta tttggattgg 120
tacctgcaga agccagggca gtctccacaa ctcctgatct atttgggttc taatcgggcc 180
tccggggtcc ctgacaggtt cagtggcggt ggatcaggca cagattttac actgaaaatc 240
agcagagtgg aggctgagga tgttgggatt tattactgca tgcaagctct acagactcct 300
ctcactttcg gcggagggac caaggtggag atcaaacga 339

<210> SEQ ID NO 202
<211> LENGTH: 113
<212> TYPE: PRT
<213> ORGANISM: Artificial Sequence
<220> FEATURE:
<223> OTHER INFORMATION: Synthetic

<400> SEQUENCE: 202

Asp Ile Gln Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

His Gly Tyr Asn Tyr Leu Asp Trp Tyr Leu Gln Lys Pro Gly Gln Ser
35 40 45

Pro Gln Leu Leu Ile Tyr Leu Gly Ser Asn Arg Ala Ser Gly Val Pro
50 55 60

Asp Arg Phe Ser Gly Gly Gly Ser Gly Thr Asp Phe Thr Leu Lys Ile
65 70 75 80

Ser Arg Val Glu Ala Glu Asp Val Gly Ile Tyr Tyr Cys Met Gln Ala
85 90 95

Leu Gln Thr Pro Leu Thr Phe Gly Gly Gly Thr Lys Val Glu Ile Lys
100 105 110

Arg

<210> SEQ ID NO 203
<211> LENGTH: 33
<212> TYPE: DNA
<213> ORGANISM: Artificial Sequence
<220> FEATURE:
<223> OTHER INFORMATION: Synthetic

<400> SEQUENCE: 203
cagagcctcc tccatagtca tggatacaac tat 33

<210> SEQ ID NO 204
<211> LENGTH: 11
<212> TYPE: PRT
<213> ORGANISM: Artificial Sequence
<220> FEATURE:
<223> OTHER INFORMATION: Synthetic

<400> SEQUENCE: 204

Gln Ser Leu Leu His Ser His Gly Tyr Asn Tyr
1 5 10

<210> SEQ ID NO 205
<211> LENGTH: 9
<212> TYPE: DNA
<213> ORGANISM: Artificial Sequence
<220> FEATURE:

<223> OTHER INFORMATION: Synthetic

<400> SEQUENCE: 205 ttgggttct 9

<210> SEQ ID NO 206
<211> LENGTH: 3
<212> TYPE: PRT
<213> ORGANISM: Artificial Sequence
<220> FEATURE:
<223> OTHER INFORMATION: Synthetic

<400> SEQUENCE: 206

Leu Gly Ser
1

<210> SEQ ID NO 207
<211> LENGTH: 27
<212> TYPE: DNA
<213> ORGANISM: Artificial Sequence
<220> FEATURE:
<223> OTHER INFORMATION: Synthetic

<400> SEQUENCE: 207
atgcaagctc tacagactcc tctcact 27

<210> SEQ ID NO 208
<211> LENGTH: 9
<212> TYPE: PRT
<213> ORGANISM: Artificial Sequence
<220> FEATURE:
<223> OTHER INFORMATION: Synthetic

<400> SEQUENCE: 208

Met Gln Ala Leu Gln Thr Pro Leu Thr
1 5

<210> SEQ ID NO 209
<211> LENGTH: 375
<212> TYPE: DNA
<213> ORGANISM: Artificial Sequence
<220> FEATURE:
<223> OTHER INFORMATION: Synthetic

<400> SEQUENCE: 209
cagatcacct tgaaggagtc tggtcctact ctggtgaaac cctcacagac cctcacgctg 60
acctgcacct tctctgggtt ctcactcagc actagtggag tgggtgtggg ctggatccgt 120
cagcccccag gaaaggccct ggagtggctt gcactcattt attggaattc tgataagcgc 180
tacagcccat ctctgaagag caggctcacc atcaccaagg acacctccaa aaaccaggta 240
gtccttacaa tgaccaacat ggaccctgtg gacacagcca catattactg tgcacacaga 300
catgacagct cgtcctacta cttctactac ggtatggacg tctggggcca agggaccacg 360
gtcaccgtct cctca 375

<210> SEQ ID NO 210
<211> LENGTH: 125
<212> TYPE: PRT
<213> ORGANISM: Artificial Sequence
<220> FEATURE:
<223> OTHER INFORMATION: Synthetic

<400> SEQUENCE: 210

Gln Ile Thr Leu Lys Glu Ser Gly Pro Thr Leu Val Lys Pro Ser Gln 1 5 10 15

Thr Leu Thr Leu Thr Cys Thr Phe Ser Gly Phe Ser Leu Ser Thr Ser
20 25 30

Gly Val Gly Val Gly Trp Ile Arg Gln Pro Pro Gly Lys Ala Leu Glu
35 40 45

Trp Leu Ala Leu Ile Tyr Trp Asn Ser Asp Lys Arg Tyr Ser Pro Ser
50 55 60

Leu Lys Ser Arg Leu Thr Ile Thr Lys Asp Thr Ser Lys Asn Gln Val
65 70 75 80

Val Leu Thr Met Thr Asn Met Asp Pro Val Asp Thr Ala Thr Tyr Tyr
85 90 95

Cys Ala His Arg His Asp Ser Ser Ser Tyr Tyr Phe Tyr Tyr Gly Met
100 105 110

Asp Val Trp Gly Gln Gly Thr Thr Val Thr Val Ser Ser
115 120 125

<210> SEQ ID NO 211
<211> LENGTH: 336
<212> TYPE: DNA
<213> ORGANISM: Artificial Sequence
<220> FEATURE:
<223> OTHER INFORMATION: Synthetic

<400> SEQUENCE: 211
gatattgtga tgactcagtc tccgctctcc ctgcccgtca cccctggaga gccggcctcc 60
atctcctgca ggtctagtca gagcctcctc catagtcatg gatacaacta tttggattgg 120
tacctgcaga agccagggca gtctccacaa ctcctgatct atttgggttc taatcgggcc 180
tccggggtcc ctgacaggtt cagtggcggt ggatcaggca cagattttac actgaaaatc 240
agcagagtgg aggctgagga tgttgggatt tattactgca tgcaagctct acagactcct 300
ctcactttcg gcggagggac caaggtggag atcaaa 336

<210> SEQ ID NO 212
<211> LENGTH: 112
<212> TYPE: PRT
<213> ORGANISM: Artificial Sequence
<220> FEATURE:
<223> OTHER INFORMATION: Synthetic

<400> SEQUENCE: 212

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

His Gly Tyr Asn Tyr Leu Asp Trp Tyr Leu Gln Lys Pro Gly Gln Ser
35 40 45

Pro Gln Leu Leu Ile Tyr Leu Gly Ser Asn Arg Ala Ser Gly Val Pro
50 55 60

Asp Arg Phe Ser Gly Gly Gly Ser Gly Thr Asp Phe Thr Leu Lys Ile
65 70 75 80

Ser Arg Val Glu Ala Glu Asp Val Gly Ile Tyr Tyr Cys Met Gln Ala
85 90 95

Leu Gln Thr Pro Leu Thr Phe Gly Gly Gly Thr Lys Val Glu Ile Lys
100 105 110

<210> SEQ ID NO 213
<211> LENGTH: 375

<212> TYPE: DNA
<213> ORGANISM: Artificial Sequence
<220> FEATURE:
<223> OTHER INFORMATION: Synthetic

<400> SEQUENCE: 213
cagatcacct tgaaggagtc tggtcctacg ctggtgaaac ccacacagac cctcacgctg 60
acctgcacct tctctgggtt ctcactcagc actagtggag tgggtgtggg ctggatccgt 120
cagcccccag gaaaggccct ggagtggctt gcactcattt attggaattc tgataagcgc 180
tacagcccat ctctgaagag caggctcacc atcaccaagg acacctccaa aaaccaggtg 240
gtccttacaa tgaccaacat ggaccctgtg gacacagcca catattactg tgcacacaga 300
catgacagct cgtcctacta cttctactac ggtatggacg tctggggcca agggaccacg 360
gtcaccgtct cctca 375

<210> SEQ ID NO 214
<211> LENGTH: 125
<212> TYPE: PRT
<213> ORGANISM: Artificial Sequence
<220> FEATURE:
<223> OTHER INFORMATION: Synthetic

<400> SEQUENCE: 214

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Ser Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg His Asp Ser Ser Ser Tyr Tyr Phe Tyr Tyr Gly Met
            100                 105                 110

Asp Val Trp Gly Gln Gly Thr Thr Val Thr Val Ser Ser
        115                 120                 125

<210> SEQ ID NO 215
<211> LENGTH: 336
<212> TYPE: DNA
<213> ORGANISM: Artificial Sequence
<220> FEATURE:
<223> OTHER INFORMATION: Synthetic

<400> SEQUENCE: 215
gatattgtga tgactcagtc tccactctcc ctgcccgtca cccctggaga gccggcctcc 60
atctcctgca ggtctagtca gagcctcctc catagtcatg gatacaacta tttggattgg 120
tacctgcaga agccagggca gtctccacag ctcctgatct atttgggttc taatcgggcc 180
tccggggtcc ctgacaggtt cagtggcagt ggatcaggca cagattttac actgaaaatc 240
agcagagtgg aggctgagga tgttggggtt tattactgca tgcaagctct acagactcct 300
ctcactttcg gcggagggac caaggtggag atcaaa 336

<210> SEQ ID NO 216

<211> LENGTH: 112
<212> TYPE: PRT
<213> ORGANISM: Artificial Sequence
<220> FEATURE:
<223> OTHER INFORMATION: Synthetic

<400> SEQUENCE: 216

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

His Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 217
<211> LENGTH: 381
<212> TYPE: DNA
<213> ORGANISM: Artificial Sequence
<220> FEATURE:
<223> OTHER INFORMATION: Synthetic

<400> SEQUENCE: 217
gagatgcaac tggtggagtc tgggggaggc ttggtccagc ctggggggtc cctgagactc 60
tcctgtgcag cctctggatt cacctttagt agtcactgga tgaagtgggt ccgccaggct 120
ccagggaagg ggctggagtg ggtggccaac ataaaccaag atggaagtga gaaatactat 180
gtggactctg tgaagggccg attcaccatc tccagagaca acgccaagaa ctcactgttt 240
ctgcaaatga acagcctgag agccgaggac acggctgtgt attactgtgc gagagatatt 300
gtactaatgg tctatgatat ggactactac tactacggta tggacgtctg gggccaaggg 360
accacggtca ccgtctcctc a 381

<210> SEQ ID NO 218
<211> LENGTH: 127
<212> TYPE: PRT
<213> ORGANISM: Artificial Sequence
<220> FEATURE:
<223> OTHER INFORMATION: Synthetic

<400> SEQUENCE: 218

Glu Met Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Trp Met Lys Trp Val Arg Gln Ala Pro Gly Lys Gly Leu Glu Trp Val
        35                  40                  45

Ala Asn Ile Asn Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys

-continued

```
                85                  90                  95

Ala Arg Asp Ile Val Leu Met Val Tyr Asp Met Asp Tyr Tyr Tyr Tyr
            100                 105                 110

Gly Met Asp Val Trp Gly Gln Gly Thr Thr Val Thr Val Ser Ser
        115                 120                 125


<210> SEQ ID NO 219
<211> LENGTH: 24
<212> TYPE: DNA
<213> ORGANISM: Artificial Sequence
<220> FEATURE:
<223> OTHER INFORMATION: Synthetic

<400> SEQUENCE: 219

ggattcacct ttagtagtca ctgg                                            24


<210> SEQ ID NO 220
<211> LENGTH: 8
<212> TYPE: PRT
<213> ORGANISM: Artificial Sequence
<220> FEATURE:
<223> OTHER INFORMATION: Synthetic

<400> SEQUENCE: 220

Gly Phe Thr Phe Ser Ser His Trp
1               5


<210> SEQ ID NO 221
<211> LENGTH: 24
<212> TYPE: DNA
<213> ORGANISM: Artificial Sequence
<220> FEATURE:
<223> OTHER INFORMATION: Synthetic

<400> SEQUENCE: 221

ataaaccaag atggaagtga gaaa                                            24


<210> SEQ ID NO 222
<211> LENGTH: 8
<212> TYPE: PRT
<213> ORGANISM: Artificial Sequence
<220> FEATURE:
<223> OTHER INFORMATION: Synthetic

<400> SEQUENCE: 222

Ile Asn Gln Asp Gly Ser Glu Lys
1               5


<210> SEQ ID NO 223
<211> LENGTH: 60
<212> TYPE: DNA
<213> ORGANISM: Artificial Sequence
<220> FEATURE:
<223> OTHER INFORMATION: Synthetic

<400> SEQUENCE: 223

gcgagagata ttgtactaat ggtctatgat atggactact actactacgg tatggacgtc     60


<210> SEQ ID NO 224
<211> LENGTH: 20
<212> TYPE: PRT
<213> ORGANISM: Artificial Sequence
<220> FEATURE:
<223> OTHER INFORMATION: Synthetic

<400> SEQUENCE: 224
```

```
Ala Arg Asp Ile Val Leu Met Val Tyr Asp Met Asp Tyr Tyr Tyr Tyr
1               5                   10                  15

Gly Met Asp Val
            20


<210> SEQ ID NO 225
<211> LENGTH: 336
<212> TYPE: DNA
<213> ORGANISM: Artificial Sequence
<220> FEATURE:
<223> OTHER INFORMATION: Synthetic

<400> SEQUENCE: 225

gatattgtga tgactcagtc tccactctcc ctgcccgtca cccctggaga gccggcctcc     60

atctcctgca ggtctagtca gagcctcctg catagtaatg gaaacaacta tttggattgg    120

tacctgcaga agccagggca gtctccacag ctcctgatct atttgggttc taatcgggcc    180

tccggggtcc ctgacaggtt cagtggcagt ggatcaggca cagattttac actgaaaatc    240

agcagagtgg aggctgagga tgttggggtt tattactgca tgcaaactct acaaactccg    300

ctcactttcg gcggagggac caaggtggag atcaaa                              336


<210> SEQ ID NO 226
<211> LENGTH: 112
<212> TYPE: PRT
<213> ORGANISM: Artificial Sequence
<220> FEATURE:
<223> OTHER INFORMATION: Synthetic

<400> SEQUENCE: 226

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Leu Gln Thr Pro Leu Thr Phe Gly Gly Gly Thr Lys Val Glu Ile Lys
            100                 105                 110


<210> SEQ ID NO 227
<211> LENGTH: 33
<212> TYPE: DNA
<213> ORGANISM: Artificial Sequence
<220> FEATURE:
<223> OTHER INFORMATION: Synthetic

<400> SEQUENCE: 227

cagagcctcc tgcatagtaa tggaaacaac tat                                  33


<210> SEQ ID NO 228
<211> LENGTH: 11
<212> TYPE: PRT
<213> ORGANISM: Artificial Sequence
<220> FEATURE:
<223> OTHER INFORMATION: Synthetic
```

<400> SEQUENCE: 228

Gln Ser Leu Leu His Ser Asn Gly Asn Asn Tyr
1 5 10

<210> SEQ ID NO 229
<211> LENGTH: 9
<212> TYPE: DNA
<213> ORGANISM: Artificial Sequence
<220> FEATURE:
<223> OTHER INFORMATION: Synthetic

<400> SEQUENCE: 229 ttgggttct 9

<210> SEQ ID NO 230
<211> LENGTH: 3
<212> TYPE: PRT
<213> ORGANISM: Artificial Sequence
<220> FEATURE:
<223> OTHER INFORMATION: Synthetic

<400> SEQUENCE: 230

Leu Gly Ser
1

<210> SEQ ID NO 231
<211> LENGTH: 27
<212> TYPE: DNA
<213> ORGANISM: Artificial Sequence
<220> FEATURE:
<223> OTHER INFORMATION: Synthetic

<400> SEQUENCE: 231
atgcaaactc tacaaactcc gctcact 27

<210> SEQ ID NO 232
<211> LENGTH: 9
<212> TYPE: PRT
<213> ORGANISM: Artificial Sequence
<220> FEATURE:
<223> OTHER INFORMATION: Synthetic

<400> SEQUENCE: 232

Met Gln Thr Leu Gln Thr Pro Leu Thr
1 5

<210> SEQ ID NO 233
<211> LENGTH: 381
<212> TYPE: DNA
<213> ORGANISM: Artificial Sequence
<220> FEATURE:
<223> OTHER INFORMATION: Synthetic

<400> SEQUENCE: 233
gaggtgcagc tggtggagtc tgggggaggc ttggtccagc ctggggggtc cctgagactc 60
tcctgtgcag cctctggatt cacctttagt agtcactgga tgaagtgggt ccgccaggct 120
ccagggaagg ggctggagtg ggtggccaac ataaaccaag atggaagtga gaaatactat 180
gtggactctg tgaagggccg attcaccatc tccagagaca acgccaagaa ctcactgttt 240
ctgcaaatga acagcctgag agccgaggac acggctgtgt attactgtgc gagagatatt 300
gtactaatgg tctatgatat ggactactac tactacggta tggacgtctg gggccaaggg 360
accacggtca ccgtctcctc a 381

<210> SEQ ID NO 234
<211> LENGTH: 127
<212> TYPE: PRT
<213> ORGANISM: Artificial Sequence
<220> FEATURE:
<223> OTHER INFORMATION: Synthetic

<400> SEQUENCE: 234

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser His
20 25 30

Trp Met Lys Trp Val Arg Gln Ala Pro Gly Lys Gly Leu Glu Trp Val
35 40 45

Ala Asn Ile Asn Gln Asp Gly Ser Glu Lys Tyr Tyr Val Asp Ser Val
50 55 60

Lys Gly Arg Phe Thr Ile Ser Arg Asp Asn Ala Lys Asn Ser Leu Phe
65 70 75 80

Leu Gln Met Asn Ser Leu Arg Ala Glu Asp Thr Ala Val Tyr Tyr Cys
85 90 95

Ala Arg Asp Ile Val Leu Met Val Tyr Asp Met Asp Tyr Tyr Tyr Tyr
100 105 110

Gly Met Asp Val Trp Gly Gln Gly Thr Thr Val Thr Val Ser Ser
115 120 125

<210> SEQ ID NO 235
<211> LENGTH: 336
<212> TYPE: DNA
<213> ORGANISM: Artificial Sequence
<220> FEATURE:
<223> OTHER INFORMATION: Synthetic

<400> SEQUENCE: 235
gatattgtga tgactcagtc tccactctcc ctgcccgtca cccctggaga gccggcctcc 60
atctcctgca ggtctagtca gagcctcctg catagtaatg gaaacaacta tttggattgg 120
tacctgcaga agccagggca gtctccacag ctcctgatct atttgggttc taatcgggcc 180
tccggggtcc ctgacaggtt cagtggcagt ggatcaggca cagattttac actgaaaatc 240
agcagagtgg aggctgagga tgttggggtt tattactgca tgcaaactct acaaactccg 300
ctcactttcg gcggagggac caaggtggag atcaaa 336

<210> SEQ ID NO 236
<211> LENGTH: 112
<212> TYPE: PRT
<213> ORGANISM: Artificial Sequence
<220> FEATURE:
<223> OTHER INFORMATION: Synthetic

<400> SEQUENCE: 236

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

Asn Gly Asn Asn Tyr Leu Asp Trp Tyr Leu Gln Lys Pro Gly Gln Ser
35 40 45

Pro Gln Leu Leu Ile Tyr Leu Gly Ser Asn Arg Ala Ser Gly Val Pro
50 55 60

```
Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Leu Gln Thr Pro Leu Thr Phe Gly Gly Gly Thr Lys Val Glu Ile Lys
            100                 105                 110


<210> SEQ ID NO 237
<211> LENGTH: 381
<212> TYPE: DNA
<213> ORGANISM: Artificial Sequence
<220> FEATURE:
<223> OTHER INFORMATION: Synthetic

<400> SEQUENCE: 237

gaggtgcagc tggtggagtc tgggggaggc ttggtccagc ctggggggtc cctgagactc     60

tcctgtgcag cctctggatt cacctttagt agtcactgga tgagctgggt ccgccaggct    120

ccagggaagg ggctggagtg ggtggccaac ataaaccaag atggaagtga gaaatactat    180

gtggactctg tgaagggccg attcaccatc tccagagaca acgccaagaa ctcactgtat    240

ctgcaaatga acagcctgag agccgaggac acggctgtgt attactgtgc gagagatatt    300

gtactaatgg tctatgatat ggactactac tactacggta tggacgtctg gggcaaggg    360

accacggtca ccgtctcctc a                                              381


<210> SEQ ID NO 238
<211> LENGTH: 127
<212> TYPE: PRT
<213> ORGANISM: Artificial Sequence
<220> FEATURE:
<223> OTHER INFORMATION: Synthetic

<400> SEQUENCE: 238

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ile Val Leu Met Val Tyr Asp Met Asp Tyr Tyr Tyr Tyr
            100                 105                 110

Gly Met Asp Val Trp Gly Gln Gly Thr Thr Val Thr Val Ser Ser
        115                 120                 125


<210> SEQ ID NO 239
<211> LENGTH: 336
<212> TYPE: DNA
<213> ORGANISM: Artificial Sequence
<220> FEATURE:
<223> OTHER INFORMATION: Synthetic

<400> SEQUENCE: 239

gatattgtga tgactcagtc tccactctcc ctgcccgtca cccctggaga gccggcctcc     60
```

```
atctcctgca ggtctagtca gagcctcctg catagtaatg gaaacaacta tttggattgg    120

tacctgcaga agccagggca gtctccacag ctcctgatct atttgggttc taatcgggcc    180

tccggggtcc ctgacaggtt cagtggcagt ggatcaggca cagattttac actgaaaatc    240

agcagagtgg aggctgagga tgttggggtt tattactgca tgcaaactct acaaactccg    300

ctcactttcg gcggagggac caaggtggag atcaaa                              336


<210> SEQ ID NO 240
<211> LENGTH: 112
<212> TYPE: PRT
<213> ORGANISM: Artificial Sequence
<220> FEATURE:
<223> OTHER INFORMATION: Synthetic

<400> SEQUENCE: 240

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Leu Gln Thr Pro Leu Thr Phe Gly Gly Gly Thr Lys Val Glu Ile Lys
            100                 105                 110


<210> SEQ ID NO 241
<211> LENGTH: 381
<212> TYPE: DNA
<213> ORGANISM: Artificial Sequence
<220> FEATURE:
<223> OTHER INFORMATION: Synthetic

<400> SEQUENCE: 241

caggtgcagc tggtggagtc tgggggaggc gtggtccagc ctgggaggtc cctgagactc     60

tcctgtgcag tctctggatt caccttcagt agctatggca tgcactgggt ccgccaggct    120

ccaggcaagg ggctggagtg ggtggcagct atatcatatg atggaagtaa taaatactat    180

gtagactccg tgaagggccg attcaccatc tccagagaca attccaagaa aacgctgtat    240

ctgcaaatga acagcctgag agctgaggac acggctgtgt ataattgtgc gaaaaatatt    300

gtactagtga tgtatgatat agactatcac tactatggga tggacgtctg gggccaaggg    360

accacggtca ccgtctcctc a                                              381


<210> SEQ ID NO 242
<211> LENGTH: 127
<212> TYPE: PRT
<213> ORGANISM: Artificial Sequence
<220> FEATURE:
<223> OTHER INFORMATION: Synthetic

<400> SEQUENCE: 242

Gln Val Gln Leu Val Glu Ser Gly Gly Gly Val Val Gln Pro Gly Arg
1               5                   10                  15

Ser Leu Arg Leu Ser Cys Ala Val Ser Gly Phe Thr Phe Ser Ser Tyr
```

```
            20                  25                  30

Gly Met His Trp Val Arg Gln Ala Pro Gly Lys Gly Leu Glu Trp Val
        35                  40                  45

Ala Ala Ile Ser Tyr Asp Gly Ser Asn Lys Tyr Tyr Val Asp Ser Val
    50                  55                  60

Lys Gly Arg Phe Thr Ile Ser Arg Asp Asn Ser Lys Lys Thr Leu Tyr
65                  70                  75                  80

Leu Gln Met Asn Ser Leu Arg Ala Glu Asp Thr Ala Val Tyr Asn Cys
                85                  90                  95

Ala Lys Asn Ile Val Leu Val Met Tyr Asp Ile Asp Tyr His Tyr Tyr
            100                 105                 110

Gly Met Asp Val Trp Gly Gln Gly Thr Thr Val Thr Val Ser Ser
        115                 120                 125
```

<210> SEQ ID NO 243
<211> LENGTH: 24
<212> TYPE: DNA
<213> ORGANISM: Artificial Sequence
<220> FEATURE:
<223> OTHER INFORMATION: Synthetic

<400> SEQUENCE: 243
ggattcacct tcagtagcta tggc 24

<210> SEQ ID NO 244
<211> LENGTH: 8
<212> TYPE: PRT
<213> ORGANISM: Artificial Sequence
<220> FEATURE:
<223> OTHER INFORMATION: Synthetic

<400> SEQUENCE: 244

```
Gly Phe Thr Phe Ser Ser Tyr Gly
1               5
```

<210> SEQ ID NO 245
<211> LENGTH: 24
<212> TYPE: DNA
<213> ORGANISM: Artificial Sequence
<220> FEATURE:
<223> OTHER INFORMATION: Synthetic

<400> SEQUENCE: 245
atatcatatg atggaagtaa taaa 24

<210> SEQ ID NO 246
<211> LENGTH: 8
<212> TYPE: PRT
<213> ORGANISM: Artificial Sequence
<220> FEATURE:
<223> OTHER INFORMATION: Synthetic

<400> SEQUENCE: 246

```
Ile Ser Tyr Asp Gly Ser Asn Lys
1               5
```

<210> SEQ ID NO 247
<211> LENGTH: 60
<212> TYPE: DNA
<213> ORGANISM: Artificial Sequence
<220> FEATURE:
<223> OTHER INFORMATION: Synthetic

<400> SEQUENCE: 247

-continued gcgaaaaata ttgtactagt gatgtatgat atagactatc actactatgg gatggacgtc 60

<210> SEQ ID NO 248
<211> LENGTH: 20
<212> TYPE: PRT
<213> ORGANISM: Artificial Sequence
<220> FEATURE:
<223> OTHER INFORMATION: Synthetic

<400> SEQUENCE: 248

Ala Lys Asn Ile Val Leu Val Met Tyr Asp Ile Asp Tyr His Tyr Tyr
1 5 10 15

Gly Met Asp Val
20

<210> SEQ ID NO 249
<211> LENGTH: 336
<212> TYPE: DNA
<213> ORGANISM: Artificial Sequence
<220> FEATURE:
<223> OTHER INFORMATION: Synthetic

<400> SEQUENCE: 249
gatattgtga tgactcagtc tccactctcc ctgcccgtca cccctggaga gccggcctcc 60
atctcctgca ggtctagtca gagcctcctg catagtaatg gatacaacta tttggattgg 120
tacctgcaga agccagggca gtctccacaa ctcctgatct atttgggttt taatcgggcc 180
tccggggtcc ctgacaggtt cagtggcagt ggatcaggca cagattttac actgaaaatc 240
agcagagtgg aggctgagga tgttggggtt tattactgca tgcaagctct acaaactcct 300
ctcactttcg gcggagggac caaggtggag atcaga 336

<210> SEQ ID NO 250
<211> LENGTH: 112
<212> TYPE: PRT
<213> ORGANISM: Artificial Sequence
<220> FEATURE:
<223> OTHER INFORMATION: Synthetic

<400> SEQUENCE: 250

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

Asn Gly Tyr Asn Tyr Leu Asp Trp Tyr Leu Gln Lys Pro Gly Gln Ser
35 40 45

Pro Gln Leu Leu Ile Tyr Leu Gly Phe Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Ala
85 90 95

Leu Gln Thr Pro Leu Thr Phe Gly Gly Gly Thr Lys Val Glu Ile Arg
100 105 110

<210> SEQ ID NO 251
<211> LENGTH: 33
<212> TYPE: DNA
<213> ORGANISM: Artificial Sequence
<220> FEATURE:
<223> OTHER INFORMATION: Synthetic

<400> SEQUENCE: 251
cagagcctcc tgcatagtaa tggatacaac tat 33

<210> SEQ ID NO 252
<211> LENGTH: 11
<212> TYPE: PRT
<213> ORGANISM: Artificial Sequence
<220> FEATURE:
<223> OTHER INFORMATION: Synthetic

<400> SEQUENCE: 252

Gln Ser Leu Leu His Ser Asn Gly Tyr Asn Tyr
1 5 10

<210> SEQ ID NO 253
<211> LENGTH: 9
<212> TYPE: DNA
<213> ORGANISM: Artificial Sequence
<220> FEATURE:
<223> OTHER INFORMATION: Synthetic

<400> SEQUENCE: 253 ttgggtttt 9

<210> SEQ ID NO 254
<211> LENGTH: 3
<212> TYPE: PRT
<213> ORGANISM: Artificial Sequence
<220> FEATURE:
<223> OTHER INFORMATION: Synthetic

<400> SEQUENCE: 254

Leu Gly Phe
1

<210> SEQ ID NO 255
<211> LENGTH: 27
<212> TYPE: DNA
<213> ORGANISM: Artificial Sequence
<220> FEATURE:
<223> OTHER INFORMATION: Synthetic

<400> SEQUENCE: 255
atgcaagctc tacaaactcc tctcact 27

<210> SEQ ID NO 256
<211> LENGTH: 9
<212> TYPE: PRT
<213> ORGANISM: Artificial Sequence
<220> FEATURE:
<223> OTHER INFORMATION: Synthetic

<400> SEQUENCE: 256

Met Gln Ala Leu Gln Thr Pro Leu Thr
1 5

<210> SEQ ID NO 257
<211> LENGTH: 381
<212> TYPE: DNA
<213> ORGANISM: Artificial Sequence
<220> FEATURE:
<223> OTHER INFORMATION: Synthetic

<400> SEQUENCE: 257
caggtgcagc tggtggagtc tgggggaggc gtggtccagc ctgggaggtc cctgagactc 60
tcctgtgcag tctctggatt caccttcagt agctatggca tgcactgggt ccgccaggct 120
ccaggcaagg ggctggagtg ggtggcagct atatcatatg atggaagtaa taaatactat 180
gtagactccg tgaagggccg attcaccatc tccagagaca attccaagaa aacgctgtat 240
ctgcaaatga acagcctgag agctgaggac acggctgtgt ataattgtgc gaaaaatatt 300
gtactagtga tgtatgatat agactatcac tactatggga tggacgtctg ggccaaggg 360 accacggtca ccgtctcctc a 381

<210> SEQ ID NO 258
<211> LENGTH: 127
<212> TYPE: PRT
<213> ORGANISM: Artificial Sequence
<220> FEATURE:
<223> OTHER INFORMATION: Synthetic

<400> SEQUENCE: 258

Gln Val Gln Leu Val Glu Ser Gly Gly Gly Val Val Gln Pro Gly Arg
1 5 10 15

Ser Leu Arg Leu Ser Cys Ala Val Ser Gly Phe Thr Phe Ser Ser Tyr
20 25 30

Gly Met His Trp Val Arg Gln Ala Pro Gly Lys Gly Leu Glu Trp Val
35 40 45

Ala Ala Ile Ser Tyr Asp Gly Ser Asn Lys Tyr Tyr Val Asp Ser Val
50 55 60

Lys Gly Arg Phe Thr Ile Ser Arg Asp Asn Ser Lys Lys Thr Leu Tyr
65 70 75 80

Leu Gln Met Asn Ser Leu Arg Ala Glu Asp Thr Ala Val Tyr Asn Cys
85 90 95

Ala Lys Asn Ile Val Leu Val Met Tyr Asp Ile Asp Tyr His Tyr Tyr
100 105 110

Gly Met Asp Val Trp Gly Gln Gly Thr Thr Val Thr Val Ser Ser
115 120 125

<210> SEQ ID NO 259
<211> LENGTH: 336
<212> TYPE: DNA
<213> ORGANISM: Artificial Sequence
<220> FEATURE:
<223> OTHER INFORMATION: Synthetic

<400> SEQUENCE: 259
gatattgtga tgactcagtc tccactctcc ctgcccgtca cccctggaga gccggcctcc 60
atctcctgca ggtctagtca gagcctcctg catagtaatg gatacaacta tttggattgg 120
tacctgcaga agccagggca gtctccacaa ctcctgatct atttgggttt taatcgggcc 180
tccggggtcc ctgacaggtt cagtggcagt ggatcaggca cagattttac actgaaaatc 240
agcagagtgg aggctgagga tgttggggtt tattactgca tgcaagctct acaaactcct 300
ctcactttcg gcggagggac caaggtggag atcaaa 336

<210> SEQ ID NO 260
<211> LENGTH: 112
<212> TYPE: PRT
<213> ORGANISM: Artificial Sequence
<220> FEATURE:
<223> OTHER INFORMATION: Synthetic

<400> SEQUENCE: 260

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Phe Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 261
<211> LENGTH: 381
<212> TYPE: DNA
<213> ORGANISM: Artificial Sequence
<220> FEATURE:
<223> OTHER INFORMATION: Synthetic

<400> SEQUENCE: 261
caggtgcagc tggtggagtc tgggggaggc gtggtccagc ctgggaggtc cctgagactc     60
tcctgtgcag cctctggatt caccttcagt agctatggca tgcactgggt ccgccaggct    120
ccaggcaagg ggctggagtg ggtggcagtt atatcatatg atggaagtaa taaatactat    180
gcagactccg tgaagggccg attcaccatc tccagagaca attccaagaa cacgctgtat    240
ctgcaaatga acagcctgag agctgaggac acggctgtgt attactgtgc gaaaaatatt    300
gtactagtga tgtatgatat agactatcac tactatggga tggacgtctg ggggcaaggg    360
accacggtca ccgtctcctc a                                              381

<210> SEQ ID NO 262
<211> LENGTH: 127
<212> TYPE: PRT
<213> ORGANISM: Artificial Sequence
<220> FEATURE:
<223> OTHER INFORMATION: Synthetic

<400> SEQUENCE: 262

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Ile Val Leu Val Met Tyr Asp Ile Asp Tyr His Tyr Tyr
            100                 105                 110

Gly Met Asp Val Trp Gly Gln Gly Thr Thr Val Thr Val Ser Ser
        115                 120                 125

<210> SEQ ID NO 263
<211> LENGTH: 336
<212> TYPE: DNA
<213> ORGANISM: Artificial Sequence
<220> FEATURE:
<223> OTHER INFORMATION: Synthetic

<400> SEQUENCE: 263

```
gatattgtga tgactcagtc tccactctcc ctgcccgtca cccctggaga gccggcctcc     60

atctcctgca ggtctagtca gagcctcctg catagtaatg gatacaacta tttggattgg    120

tacctgcaga agccagggca gtctccacag ctcctgatct atttgggttt taatcgggcc    180

tccggggtcc ctgacaggtt cagtggcagt ggatcaggca cagattttac actgaaaatc    240

agcagagtgg aggctgagga tgttggggtt tattactgca tgcaagctct acaaactcct    300

ctcactttcg gcggagggac caaggtggag atcaaa                              336
```

<210> SEQ ID NO 264
<211> LENGTH: 112
<212> TYPE: PRT
<213> ORGANISM: Artificial Sequence
<220> FEATURE:
<223> OTHER INFORMATION: Synthetic

<400> SEQUENCE: 264

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Phe Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110
```

<210> SEQ ID NO 265
<211> LENGTH: 381
<212> TYPE: DNA
<213> ORGANISM: Artificial Sequence
<220> FEATURE:
<223> OTHER INFORMATION: Synthetic

<400> SEQUENCE: 265

```
caggtgcagc tggtggagtc tgggggaggc gtggtccagc ctgggaggtc cctgagactc     60

tcctgtgcag tctctggatt caccttcagt agctatggca tgcactgggt ccgccaggct    120

ccaggcaagg ggctggagtg ggtggcagct atatcatatg atggaagtaa taaatactat    180

gtagactccg tgaagggccg attcaccatc tccagagaca attccaagaa aacgctgtat    240

ctgcaaatga acagcctgag agctgaggac acggctgtgt ataattgtgc gaaaaatatt    300

gtactagtga tgtatgatat agactatcac tactatggga tggacgtctg gggccaaggg    360

accacggtca ccgtctcctc a                                              381
```

<210> SEQ ID NO 266

<211> LENGTH: 127
<212> TYPE: PRT
<213> ORGANISM: Artificial Sequence
<220> FEATURE:
<223> OTHER INFORMATION: Synthetic

<400> SEQUENCE: 266

```
Gln Val Gln Leu Val Glu Ser Gly Gly Gly Val Val Gln Pro Gly Arg
1               5                   10                  15

Ser Leu Arg Leu Ser Cys Ala Val Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Ser Tyr Asp Gly Ser Asn Lys Tyr Tyr Val Asp Ser Val
    50                  55                  60

Lys Gly Arg Phe Thr Ile Ser Arg Asp Asn Ser Lys Lys Thr Leu Tyr
65                  70                  75                  80

Leu Gln Met Asn Ser Leu Arg Ala Glu Asp Thr Ala Val Tyr Asn Cys
                85                  90                  95

Ala Lys Asn Ile Val Leu Val Met Tyr Asp Ile Asp Tyr His Tyr Tyr
            100                 105                 110

Gly Met Asp Val Trp Gly Gln Gly Thr Thr Val Thr Val Ser Ser
        115                 120                 125
```

<210> SEQ ID NO 267
<211> LENGTH: 24
<212> TYPE: DNA
<213> ORGANISM: Artificial Sequence
<220> FEATURE:
<223> OTHER INFORMATION: Synthetic

<400> SEQUENCE: 267
ggattcacct tcagtagcta tggc 24

<210> SEQ ID NO 268
<211> LENGTH: 8
<212> TYPE: PRT
<213> ORGANISM: Artificial Sequence
<220> FEATURE:
<223> OTHER INFORMATION: Synthetic

<400> SEQUENCE: 268

```
Gly Phe Thr Phe Ser Ser Tyr Gly
1               5
```

<210> SEQ ID NO 269
<211> LENGTH: 24
<212> TYPE: DNA
<213> ORGANISM: Artificial Sequence
<220> FEATURE:
<223> OTHER INFORMATION: Synthetic

<400> SEQUENCE: 269
atatcatatg atggaagtaa taaa 24

<210> SEQ ID NO 270
<211> LENGTH: 8
<212> TYPE: PRT
<213> ORGANISM: Artificial Sequence
<220> FEATURE:
<223> OTHER INFORMATION: Synthetic

<400> SEQUENCE: 270

Ile Ser Tyr Asp Gly Ser Asn Lys
1               5

<210> SEQ ID NO 271
<211> LENGTH: 60
<212> TYPE: DNA
<213> ORGANISM: Artificial Sequence
<220> FEATURE:
<223> OTHER INFORMATION: Synthetic

<400> SEQUENCE: 271
gcgaaaaata ttgtactagt gatgtatgat atagactatc actactatgg gatggacgtc 60

<210> SEQ ID NO 272
<211> LENGTH: 20
<212> TYPE: PRT
<213> ORGANISM: Artificial Sequence
<220> FEATURE:
<223> OTHER INFORMATION: Synthetic

<400> SEQUENCE: 272

Ala Lys Asn Ile Val Leu Val Met Tyr Asp Ile Asp Tyr His Tyr Tyr
1               5                   10                  15

Gly Met Asp Val
            20

<210> SEQ ID NO 273
<211> LENGTH: 336
<212> TYPE: DNA
<213> ORGANISM: Artificial Sequence
<220> FEATURE:
<223> OTHER INFORMATION: Synthetic

<400> SEQUENCE: 273
gatattgtga tgactcagtc tccactctcc ctgcccgtca cccctggaga gccggcctcc 60
atctcctgca ggtctagtca gagcctcctg catagtaatg gatacaacta tttggattgg 120
tacctgcaga agccagggca gtctccacaa ctcctgatct atttgggttt taatcgggcc 180
tccggggtcc ctgacaggtt cagtggcagt ggatcaggca cagattttac actgaaaatc 240
agcagagtgg aggctgagga tgttggggtt tattactgca tgcaagctct acaaactcct 300
ctcactttcg gcggagggac caaggtggag atcaga 336

<210> SEQ ID NO 274
<211> LENGTH: 112
<212> TYPE: PRT
<213> ORGANISM: Artificial Sequence
<220> FEATURE:
<223> OTHER INFORMATION: Synthetic

<400> SEQUENCE: 274

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Phe Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala

```
                85                  90                  95

Leu Gln Thr Pro Leu Thr Phe Gly Gly Gly Thr Lys Val Glu Ile Arg
            100                 105                 110


<210> SEQ ID NO 275
<211> LENGTH: 33
<212> TYPE: DNA
<213> ORGANISM: Artificial Sequence
<220> FEATURE:
<223> OTHER INFORMATION: Synthetic

<400> SEQUENCE: 275

cagagcctcc tgcatagtaa tggatacaac tat                                  33


<210> SEQ ID NO 276
<211> LENGTH: 11
<212> TYPE: PRT
<213> ORGANISM: Artificial Sequence
<220> FEATURE:
<223> OTHER INFORMATION: Synthetic

<400> SEQUENCE: 276

Gln Ser Leu Leu His Ser Asn Gly Tyr Asn Tyr
1               5                   10


<210> SEQ ID NO 277
<211> LENGTH: 9
<212> TYPE: DNA
<213> ORGANISM: Artificial Sequence
<220> FEATURE:
<223> OTHER INFORMATION: Synthetic

<400> SEQUENCE: 277

ttgggtttt                                                              9


<210> SEQ ID NO 278
<211> LENGTH: 3
<212> TYPE: PRT
<213> ORGANISM: Artificial Sequence
<220> FEATURE:
<223> OTHER INFORMATION: Synthetic

<400> SEQUENCE: 278

Leu Gly Phe
1


<210> SEQ ID NO 279
<211> LENGTH: 27
<212> TYPE: DNA
<213> ORGANISM: Artificial Sequence
<220> FEATURE:
<223> OTHER INFORMATION: Synthetic

<400> SEQUENCE: 279

atgcaagctc tacaaactcc tctcact                                         27


<210> SEQ ID NO 280
<211> LENGTH: 9
<212> TYPE: PRT
<213> ORGANISM: Artificial Sequence
<220> FEATURE:
<223> OTHER INFORMATION: Synthetic

<400> SEQUENCE: 280

Met Gln Ala Leu Gln Thr Pro Leu Thr
1               5
```

<210> SEQ ID NO 281
<211> LENGTH: 381
<212> TYPE: DNA
<213> ORGANISM: Artificial Sequence
<220> FEATURE:
<223> OTHER INFORMATION: Synthetic

<400> SEQUENCE: 281
caggtgcagc tggtggagtc tgggggaggc gtggtccagc ctgggaggtc cctgagactc 60
tcctgtgcag tctctggatt caccttcagt agctatggca tgcactgggt ccgccaggct 120
ccaggcaagg ggctggagtg ggtggcagct atatcatatg atggaagtaa taaatactat 180
gtagactccg tgaagggccg attcaccatc tccagagaca attccaagaa aacgctgtat 240
ctgcaaatga acagcctgag agctgaggac acggctgtgt ataattgtgc gaaaaatatt 300
gtactagtga tgtatgatat agactatcac tactatggga tggacgtctg gggccaaggg 360
accacggtca ccgtctcctc a 381

<210> SEQ ID NO 282
<211> LENGTH: 127
<212> TYPE: PRT
<213> ORGANISM: Artificial Sequence
<220> FEATURE:
<223> OTHER INFORMATION: Synthetic

<400> SEQUENCE: 282

Gln Val Gln Leu Val Glu Ser Gly Gly Gly Val Val Gln Pro Gly Arg
1 5 10 15

Ser Leu Arg Leu Ser Cys Ala Val Ser Gly Phe Thr Phe Ser Ser Tyr
20 25 30

Gly Met His Trp Val Arg Gln Ala Pro Gly Lys Gly Leu Glu Trp Val
35 40 45

Ala Ala Ile Ser Tyr Asp Gly Ser Asn Lys Tyr Tyr Val Asp Ser Val
50 55 60

Lys Gly Arg Phe Thr Ile Ser Arg Asp Asn Ser Lys Lys Thr Leu Tyr
65 70 75 80

Leu Gln Met Asn Ser Leu Arg Ala Glu Asp Thr Ala Val Tyr Asn Cys
85 90 95

Ala Lys Asn Ile Val Leu Val Met Tyr Asp Ile Asp Tyr His Tyr Tyr
100 105 110

Gly Met Asp Val Trp Gly Gln Gly Thr Thr Val Thr Val Ser Ser
115 120 125

<210> SEQ ID NO 283
<211> LENGTH: 336
<212> TYPE: DNA
<213> ORGANISM: Artificial Sequence
<220> FEATURE:
<223> OTHER INFORMATION: Synthetic

<400> SEQUENCE: 283
gatattgtga tgactcagtc tccactctcc ctgcccgtca cccctggaga gccggcctcc 60
atctcctgca ggtctagtca gagcctcctg catagtaatg gatacaacta tttggattgg 120
tacctgcaga agccagggca gtctccacaa ctcctgatct atttgggttt taatcgggcc 180
tccggggtcc ctgacaggtt cagtggcagt ggatcaggca cagattttac actgaaaatc 240
agcagagtgg aggctgagga tgttggggtt tattactgca tgcaagctct acaaactcct 300
ctcactttcg gcggagggac caaggtggag atcaaa 336

<210> SEQ ID NO 284
<211> LENGTH: 112
<212> TYPE: PRT
<213> ORGANISM: Artificial Sequence
<220> FEATURE:
<223> OTHER INFORMATION: Synthetic

<400> SEQUENCE: 284

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

Asn Gly Tyr Asn Tyr Leu Asp Trp Tyr Leu Gln Lys Pro Gly Gln Ser
35 40 45

Pro Gln Leu Leu Ile Tyr Leu Gly Phe Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Ala
85 90 95

Leu Gln Thr Pro Leu Thr Phe Gly Gly Gly Thr Lys Val Glu Ile Lys
100 105 110

<210> SEQ ID NO 285
<211> LENGTH: 381
<212> TYPE: DNA
<213> ORGANISM: Artificial Sequence
<220> FEATURE:
<223> OTHER INFORMATION: Synthetic

<400> SEQUENCE: 285
caggtgcagc tggtggagtc tgggggaggc gtggtccagc ctgggaggtc cctgagactc 60
tcctgtgcag cctctggatt caccttcagt agctatggca tgcactgggt ccgccaggct 120
ccaggcaagg ggctggagtg ggtggcagtt atatcatatg atggaagtaa taaatactat 180
gcagactccg tgaagggccg attcaccatc tccagagaca attccaagaa cacgctgtat 240
ctgcaaatga acagcctgag agctgaggac acggctgtgt attactgtgc gaaaaatatt 300
gtactagtga tgtatgatat agactatcac tactatggga tggacgtctg gggcaaggg 360 accacggtca ccgtctcctc a 381

<210> SEQ ID NO 286
<211> LENGTH: 127
<212> TYPE: PRT
<213> ORGANISM: Artificial Sequence
<220> FEATURE:
<223> OTHER INFORMATION: Synthetic

<400> SEQUENCE: 286

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Val Ile Ser Tyr Asp Gly Ser Asn Lys Tyr Tyr Ala Asp Ser Val
50 55 60

-continued

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Ile Val Leu Val Met Tyr Asp Ile Asp Tyr His Tyr Tyr
            100                 105                 110

Gly Met Asp Val Trp Gly Gln Gly Thr Thr Val Thr Val Ser Ser
        115                 120                 125


<210> SEQ ID NO 287
<211> LENGTH: 336
<212> TYPE: DNA
<213> ORGANISM: Artificial Sequence
<220> FEATURE:
<223> OTHER INFORMATION: Synthetic

<400> SEQUENCE: 287

gatattgtga tgactcagtc tccactctcc ctgcccgtca cccctggaga gccggcctcc      60

atctcctgca ggtctagtca gagcctcctg catagtaatg gatacaacta tttggattgg     120

tacctgcaga agccagggca gtctccacag ctcctgatct atttgggttt taatcgggcc     180

tccggggtcc ctgacaggtt cagtggcagt ggatcaggca cagattttac actgaaaatc     240

agcagagtgg aggctgagga tgttggggtt tattactgca tgcaagctct acaaactcct     300

ctcactttcg gcggagggac caaggtggag atcaaa                               336


<210> SEQ ID NO 288
<211> LENGTH: 112
<212> TYPE: PRT
<213> ORGANISM: Artificial Sequence
<220> FEATURE:
<223> OTHER INFORMATION: Synthetic

<400> SEQUENCE: 288

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Phe Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110


<210> SEQ ID NO 289
<211> LENGTH: 372
<212> TYPE: DNA
<213> ORGANISM: Artificial Sequence
<220> FEATURE:
<223> OTHER INFORMATION: Synthetic

<400> SEQUENCE: 289

cagatcacct tgaaggagtc tggtcctacg ctggtaaaac ccacacagac cctcacgctg      60

acctgcacct tctctgggtt ctcactcagc gctagtggag tgggtgtggg ctggttccgt     120
```

```
cagcccccag gaaaggccct ggagtggctt gcactcattt attggaatga tgataagcgt    180

tacagcccat ctctaaagaa cagcctcacc atcaccaagg acacctccaa aaaccaggtg    240

gtccttacaa tgaccaacat ggaccctgtg gacacagcca catattactg tgcacacaga    300

atacatctat ggtcctactt ctactacggt atggacgtct ggggccaagg gaccacggtc    360

accgtctcct ca                                                        372
```

```
<210> SEQ ID NO 290
<211> LENGTH: 124
<212> TYPE: PRT
<213> ORGANISM: Artificial Sequence
<220> FEATURE:
<223> OTHER INFORMATION: Synthetic

<400> SEQUENCE: 290

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Ala Ser
            20                  25                  30

Gly Val Gly Val Gly Trp Phe Arg Gln Pro Pro Gly Lys Ala Leu Glu
        35                  40                  45

Trp Leu Ala Leu Ile Tyr Trp Asn Asp Asp Lys Arg Tyr Ser Pro Ser
    50                  55                  60

Leu Lys Asn Ser Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg Ile His Leu Trp Ser Tyr Phe Tyr Tyr Gly Met Asp
            100                 105                 110

Val Trp Gly Gln Gly Thr Thr Val Thr Val Ser Ser
        115                 120


<210> SEQ ID NO 291
<211> LENGTH: 30
<212> TYPE: DNA
<213> ORGANISM: Artificial Sequence
<220> FEATURE:
<223> OTHER INFORMATION: Synthetic

<400> SEQUENCE: 291

gggttctcac tcagcgctag tggagtgggt                                      30


<210> SEQ ID NO 292
<211> LENGTH: 10
<212> TYPE: PRT
<213> ORGANISM: Artificial Sequence
<220> FEATURE:
<223> OTHER INFORMATION: Synthetic

<400> SEQUENCE: 292

Gly Phe Ser Leu Ser Ala Ser Gly Val Gly
1               5                   10


<210> SEQ ID NO 293
<211> LENGTH: 21
<212> TYPE: DNA
<213> ORGANISM: Artificial Sequence
<220> FEATURE:
<223> OTHER INFORMATION: Synthetic

<400> SEQUENCE: 293
```

atttattgga atgatgataa g 21

<210> SEQ ID NO 294
<211> LENGTH: 7
<212> TYPE: PRT
<213> ORGANISM: Artificial Sequence
<220> FEATURE:
<223> OTHER INFORMATION: Synthetic

<400> SEQUENCE: 294

Ile Tyr Trp Asn Asp Asp Lys
1 5

<210> SEQ ID NO 295
<211> LENGTH: 48
<212> TYPE: DNA
<213> ORGANISM: Artificial Sequence
<220> FEATURE:
<223> OTHER INFORMATION: Synthetic

<400> SEQUENCE: 295
gcacacagaa tacatctatg gtcctacttc tactacggta tggacgtc 48

<210> SEQ ID NO 296
<211> LENGTH: 16
<212> TYPE: PRT
<213> ORGANISM: Artificial Sequence
<220> FEATURE:
<223> OTHER INFORMATION: Synthetic

<400> SEQUENCE: 296

Ala His Arg Ile His Leu Trp Ser Tyr Phe Tyr Tyr Gly Met Asp Val
1 5 10 15

<210> SEQ ID NO 297
<211> LENGTH: 336
<212> TYPE: DNA
<213> ORGANISM: Artificial Sequence
<220> FEATURE:
<223> OTHER INFORMATION: Synthetic

<400> SEQUENCE: 297
gatattgtga tgactcagtc tccactctcc ctgcccgtca cccctggaga gccggcctcc 60
atctcctgca ggtctagtca gactctcctg catagtaatg gatacaacta tttcgattgg 120
tacctgcaga agccagggca gtctccacag ctcctgatct atttgggttc taatcgggcc 180
tccggggtcc ctgacagatt cagtggcagt ggatcaggca cagattttac actgaaaatc 240
agcagagtgg aggctgagga tgttggaatt tattactgca tgcaagctct acaaactcct 300
ctcactttcg gcggagggac caaggtggag atcaga 336

<210> SEQ ID NO 298
<211> LENGTH: 112
<212> TYPE: PRT
<213> ORGANISM: Artificial Sequence
<220> FEATURE:
<223> OTHER INFORMATION: Synthetic

<400> SEQUENCE: 298

Asp Ile Val Met Thr Gln Ser Pro Leu Ser Leu Pro Val Thr Pro Gly
1 5 10 15

Glu Pro Ala Ser Ile Ser Cys Arg Ser Ser Gln Thr Leu Leu His Ser
20 25 30

Asn Gly Tyr Asn Tyr Phe Asp Trp Tyr Leu Gln Lys Pro Gly Gln Ser

```
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Leu Gln Thr Pro Leu Thr Phe Gly Gly Gly Thr Lys Val Glu Ile Arg
            100                 105                 110


<210> SEQ ID NO 299
<211> LENGTH: 33
<212> TYPE: DNA
<213> ORGANISM: Artificial Sequence
<220> FEATURE:
<223> OTHER INFORMATION: Synthetic

<400> SEQUENCE: 299

cagactctcc tgcatagtaa tggatacaac tat                                  33


<210> SEQ ID NO 300
<211> LENGTH: 11
<212> TYPE: PRT
<213> ORGANISM: Artificial Sequence
<220> FEATURE:
<223> OTHER INFORMATION: Synthetic

<400> SEQUENCE: 300

Gln Thr Leu Leu His Ser Asn Gly Tyr Asn Tyr
1               5                   10


<210> SEQ ID NO 301
<211> LENGTH: 9
<212> TYPE: DNA
<213> ORGANISM: Artificial Sequence
<220> FEATURE:
<223> OTHER INFORMATION: Synthetic

<400> SEQUENCE: 301

ttgggttct                                                              9


<210> SEQ ID NO 302
<211> LENGTH: 3
<212> TYPE: PRT
<213> ORGANISM: Artificial Sequence
<220> FEATURE:
<223> OTHER INFORMATION: Synthetic

<400> SEQUENCE: 302

Leu Gly Ser
1


<210> SEQ ID NO 303
<211> LENGTH: 27
<212> TYPE: DNA
<213> ORGANISM: Artificial Sequence
<220> FEATURE:
<223> OTHER INFORMATION: Synthetic

<400> SEQUENCE: 303

atgcaagctc tacaaactcc tctcact                                         27


<210> SEQ ID NO 304
<211> LENGTH: 9
```

<212> TYPE: PRT
<213> ORGANISM: Artificial Sequence
<220> FEATURE:
<223> OTHER INFORMATION: Synthetic

<400> SEQUENCE: 304

Met Gln Ala Leu Gln Thr Pro Leu Thr
1 5

<210> SEQ ID NO 305
<211> LENGTH: 372
<212> TYPE: DNA
<213> ORGANISM: Artificial Sequence
<220> FEATURE:
<223> OTHER INFORMATION: Synthetic

<400> SEQUENCE: 305
cagatcacct tgaaggagtc tggtcctacg ctggtaaaac ccacacagac cctcacgctg 60
acctgcacct tctctgggtt ctcactcagc gctagtggag tgggtgtggg ctggttccgt 120
cagcccccag gaaaggccct ggagtggctt gcactcattt attggaatga tgataagcgt 180
tacagcccat ctctaaagaa cagcctcacc atcaccaagg acacctccaa aaaccaggtg 240
gtccttacaa tgaccaacat ggaccctgtg gacacagcca catattactg tgcacacaga 300
atacatctat ggtcctactt ctactacggt atggacgtct ggggccaagg gaccacggtc 360
accgtctcct ca 372

<210> SEQ ID NO 306
<211> LENGTH: 124
<212> TYPE: PRT
<213> ORGANISM: Artificial Sequence
<220> FEATURE:
<223> OTHER INFORMATION: Synthetic

<400> SEQUENCE: 306

Gln Ile Thr Leu Lys Glu Ser Gly Pro Thr Leu Val Lys Pro Thr Gln
1 5 10 15

Thr Leu Thr Leu Thr Cys Thr Phe Ser Gly Phe Ser Leu Ser Ala Ser
20 25 30

Gly Val Gly Val Gly Trp Phe Arg Gln Pro Pro Gly Lys Ala Leu Glu
35 40 45

Trp Leu Ala Leu Ile Tyr Trp Asn Asp Asp Lys Arg Tyr Ser Pro Ser
50 55 60

Leu Lys Asn Ser Leu Thr Ile Thr Lys Asp Thr Ser Lys Asn Gln Val
65 70 75 80

Val Leu Thr Met Thr Asn Met Asp Pro Val Asp Thr Ala Thr Tyr Tyr
85 90 95

Cys Ala His Arg Ile His Leu Trp Ser Tyr Phe Tyr Tyr Gly Met Asp
100 105 110

Val Trp Gly Gln Gly Thr Thr Val Thr Val Ser Ser
115 120

<210> SEQ ID NO 307
<211> LENGTH: 336
<212> TYPE: DNA
<213> ORGANISM: Artificial Sequence
<220> FEATURE:
<223> OTHER INFORMATION: Synthetic

<400> SEQUENCE: 307
gatattgtga tgactcagtc tccactctcc ctgcccgtca cccctggaga gccggcctcc 60

```
atctcctgca ggtctagtca gactctcctg catagtaatg gatacaacta tttcgattgg    120

tacctgcaga agccagggca gtctccacag ctcctgatct atttgggttc taatcgggcc    180

tccggggtcc ctgacagatt cagtggcagt ggatcaggca cagattttac actgaaaatc    240

agcagagtgg aggctgagga tgttggaatt tattactgca tgcaagctct acaaactcct    300

ctcactttcg gcggagggac caaggtggag atcaaa                              336


<210> SEQ ID NO 308
<211> LENGTH: 112
<212> TYPE: PRT
<213> ORGANISM: Artificial Sequence
<220> FEATURE:
<223> OTHER INFORMATION: Synthetic

<400> SEQUENCE: 308

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Thr Leu Leu His Ser
            20                  25                  30

Asn Gly Tyr Asn Tyr Phe Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Leu Gln Thr Pro Leu Thr Phe Gly Gly Gly Thr Lys Val Glu Ile Lys
            100                 105                 110


<210> SEQ ID NO 309
<211> LENGTH: 372
<212> TYPE: DNA
<213> ORGANISM: Artificial Sequence
<220> FEATURE:
<223> OTHER INFORMATION: Synthetic

<400> SEQUENCE: 309

cagatcacct tgaaggagtc tggtcctacg ctggtgaaac ccacacagac cctcacgctg     60

acctgcacct tctctgggtt ctcactcagc gctagtggag tgggtgtggg ctggatccgt    120

cagcccccag gaaaggccct ggagtggctt gcactcattt attggaatga tgataagcgc    180

tacagcccat ctctgaagag caggctcacc atcaccaagg acacctccaa aaaccaggtg    240

gtccttacaa tgaccaacat ggaccctgtg gacacagcca catattactg tgcacacaga    300

atacatctat ggtcctactt ctactacggt atggacgtct gggggcaagg gaccacggtc    360

accgtctcct ca                                                        372


<210> SEQ ID NO 310
<211> LENGTH: 124
<212> TYPE: PRT
<213> ORGANISM: Artificial Sequence
<220> FEATURE:
<223> OTHER INFORMATION: Synthetic

<400> SEQUENCE: 310

Gln Ile Thr Leu Lys Glu Ser Gly Pro Thr Leu Val Lys Pro Thr Gln
1               5                   10                  15
```

```
Thr Leu Thr Leu Thr Cys Thr Phe Ser Gly Phe Ser Leu Ser Ala Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg Ile His Leu Trp Ser Tyr Phe Tyr Tyr Gly Met Asp
            100                 105                 110

Val Trp Gly Gln Gly Thr Thr Val Thr Val Ser Ser
        115                 120


<210> SEQ ID NO 311
<211> LENGTH: 336
<212> TYPE: DNA
<213> ORGANISM: Artificial Sequence
<220> FEATURE:
<223> OTHER INFORMATION: Synthetic

<400> SEQUENCE: 311

gatattgtga tgactcagtc tccactctcc ctgcccgtca cccctggaga gccggcctcc     60

atctcctgca ggtctagtca gactctcctg catagtaatg gatacaacta tttggattgg    120

tacctgcaga agccagggca gtctccacag ctcctgatct atttgggttc taatcgggcc    180

tccggggtcc ctgacaggtt cagtggcagt ggatcaggca cagattttac actgaaaatc    240

agcagagtgg aggctgagga tgttggggtt tattactgca tgcaagctct acaaactcct    300

ctcactttcg gcggagggac caaggtggag atcaaa                              336


<210> SEQ ID NO 312
<211> LENGTH: 112
<212> TYPE: PRT
<213> ORGANISM: Artificial Sequence
<220> FEATURE:
<223> OTHER INFORMATION: Synthetic

<400> SEQUENCE: 312

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Thr Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110


<210> SEQ ID NO 313
<211> LENGTH: 381
<212> TYPE: DNA
<213> ORGANISM: Artificial Sequence
```

<220> FEATURE:
<223> OTHER INFORMATION: Synthetic

<400> SEQUENCE: 313
caggttcagc tggtgcagtc tggacctgag gtgaagaacc ctggggcctc agtgaaggtc 60
tcctgcaagg cttctggtta cacctttacc acctatggta tcagttgggt acgacaggcc 120
cctggacaag ggcttgagtg gatgggatgg atcagcggtt acaatggtaa aacaaacgat 180
gcacagaagt tccaggacag agtcgccatg accacagaca catccacgag cacagcctac 240
atggagctga ggagcctgag atctgacgac acggccattt attactgttc gagagatcgt 300
ttagtagtac cacctgccct taattattcc tactacgtta tggacgtctg gggccaaggg 360
accacggtca ccgtctcctc a 381

<210> SEQ ID NO 314
<211> LENGTH: 127
<212> TYPE: PRT
<213> ORGANISM: Artificial Sequence
<220> FEATURE:
<223> OTHER INFORMATION: Synthetic

<400> SEQUENCE: 314

Gln Val Gln Leu Val Gln Ser Gly Pro Glu Val Lys Asn Pro Gly Ala
1 5 10 15

Ser Val Lys Val Ser Cys Lys Ala Ser Gly Tyr Thr Phe Thr Thr Tyr
20 25 30

Gly Ile Ser Trp Val Arg Gln Ala Pro Gly Gln Gly Leu Glu Trp Met
35 40 45

Gly Trp Ile Ser Gly Tyr Asn Gly Lys Thr Asn Asp Ala Gln Lys Phe
50 55 60

Gln Asp Arg Val Ala Met Thr Thr Asp Thr Ser Thr Ser Thr Ala Tyr
65 70 75 80

Met Glu Leu Arg Ser Leu Arg Ser Asp Asp Thr Ala Ile Tyr Tyr Cys
85 90 95

Ser Arg Asp Arg Leu Val Val Pro Pro Ala Leu Asn Tyr Ser Tyr Tyr
100 105 110

Val Met Asp Val Trp Gly Gln Gly Thr Thr Val Thr Val Ser Ser
115 120 125

<210> SEQ ID NO 315
<211> LENGTH: 24
<212> TYPE: DNA
<213> ORGANISM: Artificial Sequence
<220> FEATURE:
<223> OTHER INFORMATION: Synthetic

<400> SEQUENCE: 315
ggttacacct ttaccaccta tggt 24

<210> SEQ ID NO 316
<211> LENGTH: 8
<212> TYPE: PRT
<213> ORGANISM: Artificial Sequence
<220> FEATURE:
<223> OTHER INFORMATION: Synthetic

<400> SEQUENCE: 316

Gly Tyr Thr Phe Thr Thr Tyr Gly
1 5

<210> SEQ ID NO 317
<211> LENGTH: 24
<212> TYPE: DNA
<213> ORGANISM: Artificial Sequence
<220> FEATURE:
<223> OTHER INFORMATION: Synthetic

<400> SEQUENCE: 317
atcagcggtt acaatggtaa aaca 24

<210> SEQ ID NO 318
<211> LENGTH: 8
<212> TYPE: PRT
<213> ORGANISM: Artificial Sequence
<220> FEATURE:
<223> OTHER INFORMATION: Synthetic

<400> SEQUENCE: 318

Ile Ser Gly Tyr Asn Gly Lys Thr
1 5

<210> SEQ ID NO 319
<211> LENGTH: 60
<212> TYPE: DNA
<213> ORGANISM: Artificial Sequence
<220> FEATURE:
<223> OTHER INFORMATION: Synthetic

<400> SEQUENCE: 319
tcgagagatc gtttagtagt accacctgcc cttaattatt cctactacgt tatggacgtc 60

<210> SEQ ID NO 320
<211> LENGTH: 20
<212> TYPE: PRT
<213> ORGANISM: Artificial Sequence
<220> FEATURE:
<223> OTHER INFORMATION: Synthetic

<400> SEQUENCE: 320

Ser Arg Asp Arg Leu Val Val Pro Pro Ala Leu Asn Tyr Ser Tyr Tyr
1 5 10 15

Val Met Asp Val
20

<210> SEQ ID NO 321
<211> LENGTH: 336
<212> TYPE: DNA
<213> ORGANISM: Artificial Sequence
<220> FEATURE:
<223> OTHER INFORMATION: Synthetic

<400> SEQUENCE: 321
gatgttgtga tgactcagtc tccactctcc ctgcccgtca cccttggaca gccggcctcc 60
atctcctgca ggtctagtca aagcctcgta tacagtgatg gaaacaccta cttgaattgg 120
tctcagcaga ggccaggtca atctccaagg cgcctaattt ataaggtttc taaccgggac 180
tctggggtcc cagacagatt cagcggcagt gggtcaggca ctgatttcac actgaaaatc 240
agcagggtgg aggctgagga tgttggggtt tattactgca tgcaaggtac acactggccg 300
tacacttttg gccaggggac caagctggag atcaaa 336

<210> SEQ ID NO 322
<211> LENGTH: 112
<212> TYPE: PRT
<213> ORGANISM: Artificial Sequence
<220> FEATURE:
<223> OTHER INFORMATION: Synthetic

<400> SEQUENCE: 322

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Ser Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Tyr Thr Phe Gly Gln Gly Thr Lys Leu Glu Ile Lys
            100                 105                 110

<210> SEQ ID NO 323
<211> LENGTH: 33
<212> TYPE: DNA
<213> ORGANISM: Artificial Sequence
<220> FEATURE:
<223> OTHER INFORMATION: Synthetic

<400> SEQUENCE: 323
caaagcctcg tatacagtga tggaaacacc tac 33

<210> SEQ ID NO 324
<211> LENGTH: 11
<212> TYPE: PRT
<213> ORGANISM: Artificial Sequence
<220> FEATURE:
<223> OTHER INFORMATION: Synthetic

<400> SEQUENCE: 324

Gln Ser Leu Val Tyr Ser Asp Gly Asn Thr Tyr
1               5                   10

<210> SEQ ID NO 325
<211> LENGTH: 9
<212> TYPE: DNA
<213> ORGANISM: Artificial Sequence
<220> FEATURE:
<223> OTHER INFORMATION: Synthetic

<400> SEQUENCE: 325 aaggtttct 9

<210> SEQ ID NO 326
<211> LENGTH: 3
<212> TYPE: PRT
<213> ORGANISM: Artificial Sequence
<220> FEATURE:
<223> OTHER INFORMATION: Synthetic

<400> SEQUENCE: 326

Lys Val Ser
1

<210> SEQ ID NO 327
<211> LENGTH: 27

```
<212> TYPE: DNA
<213> ORGANISM: Artificial Sequence
<220> FEATURE:
<223> OTHER INFORMATION: Synthetic

<400> SEQUENCE: 327

atgcaaggta cacactggcc gtacact                                          27


<210> SEQ ID NO 328
<211> LENGTH: 9
<212> TYPE: PRT
<213> ORGANISM: Artificial Sequence
<220> FEATURE:
<223> OTHER INFORMATION: Synthetic

<400> SEQUENCE: 328

Met Gln Gly Thr His Trp Pro Tyr Thr
1               5


<210> SEQ ID NO 329
<211> LENGTH: 381
<212> TYPE: DNA
<213> ORGANISM: Artificial Sequence
<220> FEATURE:
<223> OTHER INFORMATION: Synthetic

<400> SEQUENCE: 329

caggttcagc tggtgcagtc tggacctgag gtgaagaacc ctggggcctc agtgaaggtc      60

tcctgcaagg cttctggtta cacctttacc acctatggta tcagttgggt acgacaggcc     120

cctggacaag ggcttgagtg gatgggatgg atcagcggtt acaatggtaa aacaaacgat     180

gcacagaagt tccaggacag agtcgccatg accacagaca catccacgag cacagcctac     240

atggagctga ggagcctgag atctgacgac acggccattt attactgttc gagagatcgt     300

ttagtagtac cacctgccct taattattcc tactacgtta tggacgtctg gggccaaggg     360

accacggtca ccgtctcctc a                                                381


<210> SEQ ID NO 330
<211> LENGTH: 127
<212> TYPE: PRT
<213> ORGANISM: Artificial Sequence
<220> FEATURE:
<223> OTHER INFORMATION: Synthetic

<400> SEQUENCE: 330

Gln Val Gln Leu Val Gln Ser Gly Pro Glu Val Lys Asn Pro Gly Ala
1               5                   10                  15

Ser Val Lys Val Ser Cys Lys Ala Ser Gly Tyr Thr Phe Thr Thr Tyr
            20                  25                  30

Gly Ile Ser Trp Val Arg Gln Ala Pro Gly Gln Gly Leu Glu Trp Met
        35                  40                  45

Gly Trp Ile Ser Gly Tyr Asn Gly Lys Thr Asn Asp Ala Gln Lys Phe
    50                  55                  60

Gln Asp Arg Val Ala Met Thr Thr Asp Thr Ser Thr Ser Thr Ala Tyr
65                  70                  75                  80

Met Glu Leu Arg Ser Leu Arg Ser Asp Asp Thr Ala Ile Tyr Tyr Cys
                85                  90                  95

Ser Arg Asp Arg Leu Val Val Pro Pro Ala Leu Asn Tyr Ser Tyr Tyr
            100                 105                 110

Val Met Asp Val Trp Gly Gln Gly Thr Thr Val Thr Val Ser Ser
        115                 120                 125
```

<210> SEQ ID NO 331
<211> LENGTH: 336
<212> TYPE: DNA
<213> ORGANISM: Artificial Sequence
<220> FEATURE:
<223> OTHER INFORMATION: Synthetic

<400> SEQUENCE: 331
gatgttgtga tgactcagtc tccactctcc ctgcccgtca cccttggaca gccggcctcc 60
atctcctgca ggtctagtca aagcctcgta tacagtgatg gaaacaccta cttgaattgg 120
tctcagcaga ggccaggtca atctccaagg cgcctaattt ataaggtttc taaccgggac 180
tctggggtcc cagacagatt cagcggcagt gggtcaggca ctgatttcac actgaaaatc 240
agcagggtgg aggctgagga tgttggggtt tattactgca tgcaaggtac acactggccg 300
tacacttttg gccaggggac caagctggag atcaaa 336

<210> SEQ ID NO 332
<211> LENGTH: 112
<212> TYPE: PRT
<213> ORGANISM: Artificial Sequence
<220> FEATURE:
<223> OTHER INFORMATION: Synthetic

<400> SEQUENCE: 332

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Leu Val Tyr Ser
20 25 30

Asp Gly Asn Thr Tyr Leu Asn Trp Ser Gln Gln Arg Pro Gly Gln Ser
35 40 45

Pro Arg Arg Leu Ile Tyr Lys Val Ser Asn Arg Asp Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Gly
85 90 95

Thr His Trp Pro Tyr Thr Phe Gly Gln Gly Thr Lys Leu Glu Ile Lys
100 105 110

<210> SEQ ID NO 333
<211> LENGTH: 381
<212> TYPE: DNA
<213> ORGANISM: Artificial Sequence
<220> FEATURE:
<223> OTHER INFORMATION: Synthetic

<400> SEQUENCE: 333
caggttcagc tggtgcagtc tggagctgag gtgaagaagc ctggggcctc agtgaaggtc 60
tcctgcaagg cttctggtta cacctttacc acctatggta tcagctgggt gcgacaggcc 120
cctggacaag ggcttgagtg gatgggatgg atcagcggtt acaatggtaa aacaaactat 180
gcacagaagc tccagggcag agtcaccatg accacagaca catccacgag cacagcctac 240
atggagctga ggagcctgag atctgacgac acggccgtgt attactgttc gagagatcgt 300
ttagtagtac cacctgccct taattattcc tactacgtta tggacgtctg gggcaaggg 360 accacggtca ccgtctcctc a 381

<210> SEQ ID NO 334
<211> LENGTH: 127
<212> TYPE: PRT
<213> ORGANISM: Artificial Sequence
<220> FEATURE:
<223> OTHER INFORMATION: Synthetic

<400> SEQUENCE: 334

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Gly Ile Ser Trp Val Arg Gln Ala Pro Gly Gln Gly Leu Glu Trp Met
        35                  40                  45

Gly Trp Ile Ser Gly Tyr Asn Gly Lys Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ser Arg Asp Arg Leu Val Val Pro Pro Ala Leu Asn Tyr Ser Tyr Tyr
            100                 105                 110

Val Met Asp Val Trp Gly Gln Gly Thr Thr Val Thr Val Ser Ser
        115                 120                 125
```

<210> SEQ ID NO 335
<211> LENGTH: 336
<212> TYPE: DNA
<213> ORGANISM: Artificial Sequence
<220> FEATURE:
<223> OTHER INFORMATION: Synthetic

<400> SEQUENCE: 335

```
gatgttgtga tgactcagtc tccactctcc ctgcccgtca cccttggaca gccggcctcc      60

atctcctgca ggtctagtca aagcctcgta tacagtgatg gaaacaccta cttgaattgg     120

tttcagcaga ggccaggcca atctccaagg cgcctaattt ataaggtttc taaccgggac     180

tctggggtcc cagacagatt cagcggcagt gggtcaggca ctgatttcac actgaaaatc     240

agcagggtgg aggctgagga tgttggggtt tattactgca tgcaaggtac acactggccg     300

tacacttttg gccaggggac caagctggag atcaaa                               336
```

<210> SEQ ID NO 336
<211> LENGTH: 112
<212> TYPE: PRT
<213> ORGANISM: Artificial Sequence
<220> FEATURE:
<223> OTHER INFORMATION: Synthetic

<400> SEQUENCE: 336

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80
```

```
Ser Arg Val Glu Ala Glu Asp Val Gly Val Tyr Tyr Cys Met Gln Gly
                85                  90                  95

Thr His Trp Pro Tyr Thr Phe Gly Gln Gly Thr Lys Leu Glu Ile Lys
            100                 105                 110


<210> SEQ ID NO 337
<211> LENGTH: 354
<212> TYPE: DNA
<213> ORGANISM: Artificial Sequence
<220> FEATURE:
<223> OTHER INFORMATION: Synthetic

<400> SEQUENCE: 337

gaggtgcagc tggtggagtc tgggggaggc ctggtcaagc ctgggggggtc cctgagactc      60

tcctgtgcag cctctggatt caccttcagt agctatagca tggactgggt ccgccaggct     120

ccagggaagg ggctggagtg ggtctcatcc attagtagta gtagtagtta catatactac     180

gcagactctg tgaagggccg attcaccatc tccagagaca ccgccaagaa ctcactgtat     240

ctgcaaatga acagcctgag agacgaggac acggctgttt attactgtgc gagagagggc     300

agtagcagac tttttgacta ctggggccag ggaaccctgg tcaccgtctc ctca           354


<210> SEQ ID NO 338
<211> LENGTH: 118
<212> TYPE: PRT
<213> ORGANISM: Artificial Sequence
<220> FEATURE:
<223> OTHER INFORMATION: Synthetic

<400> SEQUENCE: 338

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asp Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Thr Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Glu Gly Ser Ser Arg Leu Phe Asp Tyr Trp Gly Gln Gly Thr
            100                 105                 110

Leu Val Thr Val Ser Ser
        115


<210> SEQ ID NO 339
<211> LENGTH: 24
<212> TYPE: DNA
<213> ORGANISM: Artificial Sequence
<220> FEATURE:
<223> OTHER INFORMATION: Synthetic

<400> SEQUENCE: 339

ggattcacct tcagtagcta tagc                                             24


<210> SEQ ID NO 340
<211> LENGTH: 8
<212> TYPE: PRT
```

<213> ORGANISM: Artificial Sequence
<220> FEATURE:
<223> OTHER INFORMATION: Synthetic

<400> SEQUENCE: 340

Gly Phe Thr Phe Ser Ser Tyr Ser
1 5

<210> SEQ ID NO 341
<211> LENGTH: 24
<212> TYPE: DNA
<213> ORGANISM: Artificial Sequence
<220> FEATURE:
<223> OTHER INFORMATION: Synthetic

<400> SEQUENCE: 341
attagtagta gtagtagtta cata 24

<210> SEQ ID NO 342
<211> LENGTH: 8
<212> TYPE: PRT
<213> ORGANISM: Artificial Sequence
<220> FEATURE:
<223> OTHER INFORMATION: Synthetic

<400> SEQUENCE: 342

Ile Ser Ser Ser Ser Ser Tyr Ile
1 5

<210> SEQ ID NO 343
<211> LENGTH: 33
<212> TYPE: DNA
<213> ORGANISM: Artificial Sequence
<220> FEATURE:
<223> OTHER INFORMATION: Synthetic

<400> SEQUENCE: 343
gcgagagagg gcagtagcag actttttgac tac 33

<210> SEQ ID NO 344
<211> LENGTH: 11
<212> TYPE: PRT
<213> ORGANISM: Artificial Sequence
<220> FEATURE:
<223> OTHER INFORMATION: Synthetic

<400> SEQUENCE: 344

Ala Arg Glu Gly Ser Ser Arg Leu Phe Asp Tyr
1 5 10

<210> SEQ ID NO 345
<211> LENGTH: 321
<212> TYPE: DNA
<213> ORGANISM: Artificial Sequence
<220> FEATURE:
<223> OTHER INFORMATION: Synthetic

<400> SEQUENCE: 345
gacatccaga tgacccagtc tccttccacc ctgtctgcat ctgtaggaga cagagtcacc 60
atcacttgcc gggccagtca gagtattagt agctggttgg cctggtatca gcagagacca 120
gggaaagccc ctaagctcct gatctataag gcgtctagtt tagaaggtgg agtcccatca 180
aggttcagcg gcagtggatc tgggacagaa ttcactctca ccatcagcag cctgcagcct 240
gaggattttg caacttatta ctgccaacag tataatagtt attggtacac ttttggccag 300

-continued gggaccaagc tggagatcaa a 321

<210> SEQ ID NO 346
<211> LENGTH: 107
<212> TYPE: PRT
<213> ORGANISM: Artificial Sequence
<220> FEATURE:
<223> OTHER INFORMATION: Synthetic

<400> SEQUENCE: 346

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Arg Pro Gly Lys Ala Pro Lys Leu Leu Ile
        35                  40                  45

Tyr Lys Ala Ser Ser Leu Glu Gly Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Asn Ser Tyr Trp Tyr
                85                  90                  95

Thr Phe Gly Gln Gly Thr Lys Leu Glu Ile Lys
            100                 105
```

<210> SEQ ID NO 347
<211> LENGTH: 18
<212> TYPE: DNA
<213> ORGANISM: Artificial Sequence
<220> FEATURE:
<223> OTHER INFORMATION: Synthetic

<400> SEQUENCE: 347
cagagtatta gtagctgg 18

<210> SEQ ID NO 348
<211> LENGTH: 6
<212> TYPE: PRT
<213> ORGANISM: Artificial Sequence
<220> FEATURE:
<223> OTHER INFORMATION: Synthetic

<400> SEQUENCE: 348

```
Gln Ser Ile Ser Ser Trp
1               5
```

<210> SEQ ID NO 349
<211> LENGTH: 9
<212> TYPE: DNA
<213> ORGANISM: Artificial Sequence
<220> FEATURE:
<223> OTHER INFORMATION: Synthetic

<400> SEQUENCE: 349 aaggcgtct 9

<210> SEQ ID NO 350
<211> LENGTH: 3
<212> TYPE: PRT
<213> ORGANISM: Artificial Sequence
<220> FEATURE:
<223> OTHER INFORMATION: Synthetic

<400> SEQUENCE: 350

Lys Ala Ser
1

<210> SEQ ID NO 351
<211> LENGTH: 27
<212> TYPE: DNA
<213> ORGANISM: Artificial Sequence
<220> FEATURE:
<223> OTHER INFORMATION: Synthetic

<400> SEQUENCE: 351
caacagtata atagttattg gtacact 27

<210> SEQ ID NO 352
<211> LENGTH: 9
<212> TYPE: PRT
<213> ORGANISM: Artificial Sequence
<220> FEATURE:
<223> OTHER INFORMATION: Synthetic

<400> SEQUENCE: 352

Gln Gln Tyr Asn Ser Tyr Trp Tyr Thr
1 5

<210> SEQ ID NO 353
<211> LENGTH: 354
<212> TYPE: DNA
<213> ORGANISM: Artificial Sequence
<220> FEATURE:
<223> OTHER INFORMATION: Synthetic

<400> SEQUENCE: 353
gaggtgcagc tggtggagtc tgggggaggc ctggtcaagc ctggggggtc cctgagactc 60
tcctgtgcag cctctggatt caccttcagt agctatagca tggactgggt ccgccaggct 120
ccagggaagg ggctggagtg ggtctcatcc attagtagta gtagtagtta catatactac 180
gcagactctg tgaagggccg attcaccatc tccagagaca ccgccaagaa ctcactgtat 240
ctgcaaatga acagcctgag agacgaggac acggctgttt attactgtgc gagagagggc 300
agtagcagac tttttgacta ctggggccag ggaaccctgg tcaccgtctc ctca 354

<210> SEQ ID NO 354
<211> LENGTH: 118
<212> TYPE: PRT
<213> ORGANISM: Artificial Sequence
<220> FEATURE:
<223> OTHER INFORMATION: Synthetic

<400> SEQUENCE: 354

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

Ser Met Asp Trp Val Arg Gln Ala Pro Gly Lys Gly Leu Glu Trp Val
35 40 45

Ser Ser Ile Ser Ser Ser Ser Ser Tyr Ile Tyr Tyr Ala Asp Ser Val
50 55 60

Lys Gly Arg Phe Thr Ile Ser Arg Asp Thr Ala Lys Asn Ser Leu Tyr
65 70 75 80

Leu Gln Met Asn Ser Leu Arg Asp Glu Asp Thr Ala Val Tyr Tyr Cys
85 90 95

```
Ala Arg Glu Gly Ser Ser Arg Leu Phe Asp Tyr Trp Gly Gln Gly Thr
            100                 105                 110

Leu Val Thr Val Ser Ser
        115


<210> SEQ ID NO 355
<211> LENGTH: 321
<212> TYPE: DNA
<213> ORGANISM: Artificial Sequence
<220> FEATURE:
<223> OTHER INFORMATION: Synthetic

<400> SEQUENCE: 355

gacatccaga tgacccagtc tccttccacc ctgtctgcat ctgtaggaga cagagtcacc      60

atcacttgcc gggccagtca gagtattagt agctggttgg cctggtatca gcagagacca     120

gggaaagccc ctaagctcct gatctataag gcgtctagtt tagaaggtgg agtcccatca     180

aggttcagcg gcagtggatc tgggacagaa ttcactctca ccatcagcag cctgcagcct     240

gaggattttg caacttatta ctgccaacag tataatagtt attggtacac ttttggccag     300

gggaccaagc tggagatcaa a                                               321


<210> SEQ ID NO 356
<211> LENGTH: 107
<212> TYPE: PRT
<213> ORGANISM: Artificial Sequence
<220> FEATURE:
<223> OTHER INFORMATION: Synthetic

<400> SEQUENCE: 356

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Arg Pro Gly Lys Ala Pro Lys Leu Leu Ile
        35                  40                  45

Tyr Lys Ala Ser Ser Leu Glu Gly Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Asn Ser Tyr Trp Tyr
                85                  90                  95

Thr Phe Gly Gln Gly Thr Lys Leu Glu Ile Lys
            100                 105


<210> SEQ ID NO 357
<211> LENGTH: 354
<212> TYPE: DNA
<213> ORGANISM: Artificial Sequence
<220> FEATURE:
<223> OTHER INFORMATION: Synthetic

<400> SEQUENCE: 357

gaggtgcagc tggtggagtc tgggggaggc ctggtcaagc ctggggggtc cctgagactc      60

tcctgtgcag cctctggatt caccttcagt agctatagca tgaactgggt ccgccaggct     120

ccagggaagg ggctggagtg ggtctcatcc attagtagta gtagtagtta catatactac     180

gcagactcag tgaagggccg attcaccatc tccagagaca acgccaagaa ctcactgtat     240

ctgcaaatga acagcctgag agccgaggac acggctgtgt attactgtgc gagagagggc     300
```

agtagcagac tttttgacta ctggggccaa ggaaccctgg tcaccgtctc ctca 354

<210> SEQ ID NO 358
<211> LENGTH: 118
<212> TYPE: PRT
<213> ORGANISM: Artificial Sequence
<220> FEATURE:
<223> OTHER INFORMATION: Synthetic

<400> SEQUENCE: 358

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

Ser Met Asn Trp Val Arg Gln Ala Pro Gly Lys Gly Leu Glu Trp Val
35 40 45

Ser Ser Ile Ser Ser Ser Ser Ser Tyr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Glu Gly Ser Ser Arg Leu Phe Asp Tyr Trp Gly Gln Gly Thr
100 105 110

Leu Val Thr Val Ser Ser
115

<210> SEQ ID NO 359
<211> LENGTH: 321
<212> TYPE: DNA
<213> ORGANISM: Artificial Sequence
<220> FEATURE:
<223> OTHER INFORMATION: Synthetic

<400> SEQUENCE: 359
gacatccaga tgacccagtc tccttccacc ctgtctgcat ctgtaggaga cagagtcacc 60
atcacttgcc gggccagtca gagtattagt agctggttgg cctggtatca gcagaaacca 120
gggaaagccc ctaagctcct gatctataag gcgtctagtt tagaaagtgg ggtcccatca 180
aggttcagcg gcagtggatc tgggacagaa ttcactctca ccatcagcag cctgcagcct 240
gatgattttg caacttatta ctgccaacag tataatagtt attggtacac ttttggccag 300
gggaccaagc tggagatcaa a 321

<210> SEQ ID NO 360
<211> LENGTH: 107
<212> TYPE: PRT
<213> ORGANISM: Artificial Sequence
<220> FEATURE:
<223> OTHER INFORMATION: Synthetic

<400> SEQUENCE: 360

Asp Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Ser Ser Trp
20 25 30

Leu Ala Trp Tyr Gln Gln Lys Pro Gly Lys Ala Pro Lys Leu Leu Ile
35 40 45

Tyr Lys Ala Ser Ser Leu Glu Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Tyr Asn Ser Tyr Trp Tyr
85 90 95

Thr Phe Gly Gln Gly Thr Lys Leu Glu Ile Lys
100 105

<210> SEQ ID NO 361
<211> LENGTH: 384
<212> TYPE: DNA
<213> ORGANISM: Artificial Sequence
<220> FEATURE:
<223> OTHER INFORMATION: Synthetic

<400> SEQUENCE: 361
caggtgcacc tggtggagtc tgggggaggc ttggtcaagc ctggagggtc cctgagactc 60
tcctgtgcag cctctggatt caccttcagt gaccactaca tgagctggat ccgccaggct 120
ccagggaagg ggctggagtg gatttcatac attagtaatg atggtggtac caaatactat 180
gtggactctg tggagggccg attcatcatt tccagggaca acgccaagaa ctcattgtat 240
ctacatatga acagcctcag agccgacgac acggccgtgt attactgtgc gagagatcag 300
ggatatattg gctacgactc gtattattac tattcctacg gtatggacgt ctggggccaa 360
gggaccacgg tcaccgtcgc ctca 384

<210> SEQ ID NO 362
<211> LENGTH: 128
<212> TYPE: PRT
<213> ORGANISM: Artificial Sequence
<220> FEATURE:
<223> OTHER INFORMATION: Synthetic

<400> SEQUENCE: 362

Gln Val His Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asp His
20 25 30

Tyr Met Ser Trp Ile Arg Gln Ala Pro Gly Lys Gly Leu Glu Trp Ile
35 40 45

Ser Tyr Ile Ser Asn Asp Gly Gly Thr Lys Tyr Tyr Val Asp Ser Val
50 55 60

Glu Gly Arg Phe Ile Ile Ser Arg Asp Asn Ala Lys Asn Ser Leu Tyr
65 70 75 80

Leu His Met Asn Ser Leu Arg Ala Asp Asp Thr Ala Val Tyr Tyr Cys
85 90 95

Ala Arg Asp Gln Gly Tyr Ile Gly Tyr Asp Ser Tyr Tyr Tyr Tyr Ser
100 105 110

Tyr Gly Met Asp Val Trp Gly Gln Gly Thr Thr Val Thr Val Ala Ser
115 120 125

<210> SEQ ID NO 363
<211> LENGTH: 24
<212> TYPE: DNA
<213> ORGANISM: Artificial Sequence
<220> FEATURE:
<223> OTHER INFORMATION: Synthetic

<400> SEQUENCE: 363
ggattcacct tcagtgacca ctac 24

<210> SEQ ID NO 364
<211> LENGTH: 8
<212> TYPE: PRT
<213> ORGANISM: Artificial Sequence
<220> FEATURE:
<223> OTHER INFORMATION: Synthetic

<400> SEQUENCE: 364

Gly Phe Thr Phe Ser Asp His Tyr
1               5

<210> SEQ ID NO 365
<211> LENGTH: 24
<212> TYPE: DNA
<213> ORGANISM: Artificial Sequence
<220> FEATURE:
<223> OTHER INFORMATION: Synthetic

<400> SEQUENCE: 365
attagtaatg atggtggtac caaa 24

<210> SEQ ID NO 366
<211> LENGTH: 8
<212> TYPE: PRT
<213> ORGANISM: Artificial Sequence
<220> FEATURE:
<223> OTHER INFORMATION: Synthetic

<400> SEQUENCE: 366

Ile Ser Asn Asp Gly Gly Thr Lys
1               5

<210> SEQ ID NO 367
<211> LENGTH: 63
<212> TYPE: DNA
<213> ORGANISM: Artificial Sequence
<220> FEATURE:
<223> OTHER INFORMATION: Synthetic

<400> SEQUENCE: 367
gcgagagatc agggatatat tggctacgac tcgtattatt actattccta cggtatggac 60
gtc 63

<210> SEQ ID NO 368
<211> LENGTH: 21
<212> TYPE: PRT
<213> ORGANISM: Artificial Sequence
<220> FEATURE:
<223> OTHER INFORMATION: Synthetic

<400> SEQUENCE: 368

Ala Arg Asp Gln Gly Tyr Ile Gly Tyr Asp Ser Tyr Tyr Tyr Tyr Ser
1               5                   10                  15

Tyr Gly Met Asp Val
            20

<210> SEQ ID NO 369
<211> LENGTH: 321
<212> TYPE: DNA
<213> ORGANISM: Artificial Sequence
<220> FEATURE:
<223> OTHER INFORMATION: Synthetic

<400> SEQUENCE: 369

```
aaaattgtgt tgacgcagtc tccaggcacc ctgcctttgt ttccagggga aagagccacc      60

ctctcctgta gggccagtca gagtgttaac aacaaattct tagcctggta ccagcagaaa     120

tctggccagg ctcccaggct cctcatctat ggtgcatcca gcagggccac tggcatccca     180

gacaggttca gtggcagtgg gtctgggacc gacttcactc tcaccatcag cggactggag     240

cctgaagatt ttgaagtgta ttattgtcaa gtatatggta actcactcac tctcggcgga     300

gggaccaagg tggagatcaa g                                               321
```

```
<210> SEQ ID NO 370
<211> LENGTH: 107
<212> TYPE: PRT
<213> ORGANISM: Artificial Sequence
<220> FEATURE:
<223> OTHER INFORMATION: Synthetic

<400> SEQUENCE: 370

Lys Ile Val Leu Thr Gln Ser Pro Gly Thr Leu Pro Leu Phe Pro Gly
1               5                   10                  15

Glu Arg Ala Thr Leu Ser Cys Arg Ala Ser Gln Ser Val Asn Asn Lys
            20                  25                  30

Phe Leu Ala Trp Tyr Gln Gln Lys Ser Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Gly Leu Glu
65                  70                  75                  80

Pro Glu Asp Phe Glu Val Tyr Tyr Cys Gln Val Tyr Gly Asn Ser Leu
                85                  90                  95

Thr Leu Gly Gly Gly Thr Lys Val Glu Ile Lys
            100                 105
```

```
<210> SEQ ID NO 371
<211> LENGTH: 21
<212> TYPE: DNA
<213> ORGANISM: Artificial Sequence
<220> FEATURE:
<223> OTHER INFORMATION: Synthetic

<400> SEQUENCE: 371

cagagtgtta acaacaaatt c                                                21
```

```
<210> SEQ ID NO 372
<211> LENGTH: 7
<212> TYPE: PRT
<213> ORGANISM: Artificial Sequence
<220> FEATURE:
<223> OTHER INFORMATION: Synthetic

<400> SEQUENCE: 372

Gln Ser Val Asn Asn Lys Phe
1               5
```

```
<210> SEQ ID NO 373
<211> LENGTH: 9
<212> TYPE: DNA
<213> ORGANISM: Artificial Sequence
<220> FEATURE:
<223> OTHER INFORMATION: Synthetic

<400> SEQUENCE: 373

ggtgcatcc                                                               9
```

<210> SEQ ID NO 374
<211> LENGTH: 3
<212> TYPE: PRT
<213> ORGANISM: Artificial Sequence
<220> FEATURE:
<223> OTHER INFORMATION: Synthetic

<400> SEQUENCE: 374

Gly Ala Ser
1

<210> SEQ ID NO 375
<211> LENGTH: 24
<212> TYPE: DNA
<213> ORGANISM: Artificial Sequence
<220> FEATURE:
<223> OTHER INFORMATION: Synthetic

<400> SEQUENCE: 375
caagtatatg gtaactcact cact 24

<210> SEQ ID NO 376
<211> LENGTH: 8
<212> TYPE: PRT
<213> ORGANISM: Artificial Sequence
<220> FEATURE:
<223> OTHER INFORMATION: Synthetic

<400> SEQUENCE: 376

Gln Val Tyr Gly Asn Ser Leu Thr
1 5

<210> SEQ ID NO 377
<211> LENGTH: 384
<212> TYPE: DNA
<213> ORGANISM: Artificial Sequence
<220> FEATURE:
<223> OTHER INFORMATION: Synthetic

<400> SEQUENCE: 377
caggtgcagc tggtggagtc tgggggaggc ttggtcaagc ctggagggtc cctgagactc 60
tcctgtgcag cctctggatt caccttcagt gaccactaca tgagctggat ccgccaggct 120
ccagggaagg ggctggagtg gatttcatac attagtaatg atggtggtac caaatactat 180
gtggactctg tggagggccg attcatcatt tccagggaca acgccaagaa ctcattgtat 240
ctacatatga acagcctcag agccgacgac acggccgtgt attactgtgc gagagatcag 300
ggatatattg gctacgactc gtattattac tattcctacg gtatggacgt ctggggccaa 360
gggaccacgg tcaccgtctc ctca 384

<210> SEQ ID NO 378
<211> LENGTH: 128
<212> TYPE: PRT
<213> ORGANISM: Artificial Sequence
<220> FEATURE:
<223> OTHER INFORMATION: Synthetic

<400> SEQUENCE: 378

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asp His
20 25 30

-continued

```
Tyr Met Ser Trp Ile Arg Gln Ala Pro Gly Lys Gly Leu Glu Trp Ile
        35                  40                  45

Ser Tyr Ile Ser Asn Asp Gly Gly Thr Lys Tyr Tyr Val Asp Ser Val
    50                  55                  60

Glu Gly Arg Phe Ile Ile Ser Arg Asp Asn Ala Lys Asn Ser Leu Tyr
65                  70                  75                  80

Leu His Met Asn Ser Leu Arg Ala Asp Asp Thr Ala Val Tyr Tyr Cys
                85                  90                  95

Ala Arg Asp Gln Gly Tyr Ile Gly Tyr Asp Ser Tyr Tyr Tyr Tyr Ser
            100                 105                 110

Tyr Gly Met Asp Val Trp Gly Gln Gly Thr Thr Val Thr Val Ser Ser
        115                 120                 125


<210> SEQ ID NO 379
<211> LENGTH: 321
<212> TYPE: DNA
<213> ORGANISM: Artificial Sequence
<220> FEATURE:
<223> OTHER INFORMATION: Synthetic

<400> SEQUENCE: 379

gaaattgtgt tgacgcagtc tccaggcacc ctgcctttgt ttccaggggga aagagccacc      60

ctctcctgta gggccagtca gagtgttaac aacaaattct tagcctggta ccagcagaaa     120

tctggccagg ctcccaggct cctcatctat ggtgcatcca gcagggccac tggcatccca     180

gacaggttca gtggcagtgg gtctgggacc gacttcactc tcaccatcag cggactggag     240

cctgaagatt ttgaagtgta ttattgtcaa gtatatggta actcactcac tctcggcgga     300

gggaccaagg tggagatcaa a                                               321


<210> SEQ ID NO 380
<211> LENGTH: 107
<212> TYPE: PRT
<213> ORGANISM: Artificial Sequence
<220> FEATURE:
<223> OTHER INFORMATION: Synthetic

<400> SEQUENCE: 380

Glu Ile Val Leu Thr Gln Ser Pro Gly Thr Leu Pro Leu Phe Pro Gly
1               5                   10                  15

Glu Arg Ala Thr Leu Ser Cys Arg Ala Ser Gln Ser Val Asn Asn Lys
            20                  25                  30

Phe Leu Ala Trp Tyr Gln Gln Lys Ser Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Gly Leu Glu
65                  70                  75                  80

Pro Glu Asp Phe Glu Val Tyr Tyr Cys Gln Val Tyr Gly Asn Ser Leu
                85                  90                  95

Thr Leu Gly Gly Gly Thr Lys Val Glu Ile Lys
            100                 105


<210> SEQ ID NO 381
<211> LENGTH: 384
<212> TYPE: DNA
<213> ORGANISM: Artificial Sequence
<220> FEATURE:
<223> OTHER INFORMATION: Synthetic
```

<400> SEQUENCE: 381
caggtgcagc tggtggagtc tgggggaggc ttggtcaagc ctggagggtc cctgagactc 60
tcctgtgcag cctctggatt caccttcagt gaccactaca tgagctggat ccgccaggct 120
ccagggaagg ggctggagtg ggtttcatac attagtaatg atggtggtac caaatactac 180
gcagactctg tgaagggccg attcaccatc tccagggaca acgccaagaa ctcactgtat 240
ctgcaaatga acagcctgag agccgaggac acggccgtgt attactgtgc gagagatcag 300
ggatatattg gctacgactc gtattattac tattcctacg gtatggacgt ctgggggcaa 360
gggaccacgg tcaccgtctc ctca 384

<210> SEQ ID NO 382
<211> LENGTH: 128
<212> TYPE: PRT
<213> ORGANISM: Artificial Sequence
<220> FEATURE:
<223> OTHER INFORMATION: Synthetic

<400> SEQUENCE: 382

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asp His
20 25 30

Tyr Met Ser Trp Ile Arg Gln Ala Pro Gly Lys Gly Leu Glu Trp Val
35 40 45

Ser Tyr Ile Ser Asn Asp Gly Gly Thr Lys Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Asp Gln Gly Tyr Ile Gly Tyr Asp Ser Tyr Tyr Tyr Tyr Ser
100 105 110

Tyr Gly Met Asp Val Trp Gly Gln Gly Thr Thr Val Thr Val Ser Ser
115 120 125

<210> SEQ ID NO 383
<211> LENGTH: 321
<212> TYPE: DNA
<213> ORGANISM: Artificial Sequence
<220> FEATURE:
<223> OTHER INFORMATION: Synthetic

<400> SEQUENCE: 383
gaaattgtgt tgacgcagtc tccaggcacc ctgtctttgt ctccagggga aagagccacc 60
ctctcctgca gggccagtca gagtgttaac aacaaattct tagcctggta ccagcagaaa 120
cctggccagg ctcccaggct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcaa gtatatggta actcactcac tttcggcgga 300
gggaccaagg tggagatcaa a 321

<210> SEQ ID NO 384
<211> LENGTH: 107
<212> TYPE: PRT
<213> ORGANISM: Artificial Sequence
<220> FEATURE:
<223> OTHER INFORMATION: Synthetic

<400> SEQUENCE: 384

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Asn Asn Lys
20 25 30

Phe Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Val Tyr Gly Asn Ser Leu
85 90 95

Thr Phe Gly Gly Gly Thr Lys Val Glu Ile Lys
100 105

<210> SEQ ID NO 385
<211> LENGTH: 360
<212> TYPE: DNA
<213> ORGANISM: Artificial Sequence
<220> FEATURE:
<223> OTHER INFORMATION: Synthetic

<400> SEQUENCE: 385
gaggtgcaga aggtggagtc tgggggaggc ctggtcaagc cggggggtc cctgagactc 60 tcctgtacag cctctggatt caccttcagt acttataaca tgaattgggt ccgccaggct 120
ccagggaagg gactggagtg ggtctcatcc attaggagta gtagtaatta catatactac 180
gcagactcag tgaagggccg attcaccatc tccagagaca acgccaagaa ttcactgtat 240
ctgcaaatga acagcctgag agccgatgac acggctgtgt attactgtgc gagagatggc 300
agcagttggt acgactactc tgactactgg ggccagggaa ccctggtcac cgtctcctca 360

<210> SEQ ID NO 386
<211> LENGTH: 120
<212> TYPE: PRT
<213> ORGANISM: Artificial Sequence
<220> FEATURE:
<223> OTHER INFORMATION: Synthetic

<400> SEQUENCE: 386

Glu Val Gln Lys Val Glu Ser Gly Gly Gly Leu Val Lys Pro Gly Gly
1 5 10 15

Ser Leu Arg Leu Ser Cys Thr Ala Ser Gly Phe Thr Phe Ser Thr Tyr
20 25 30

Asn Met Asn Trp Val Arg Gln Ala Pro Gly Lys Gly Leu Glu Trp Val
35 40 45

Ser Ser Ile Arg Ser Ser Ser Asn Tyr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Asp Asp Thr Ala Val Tyr Tyr Cys
85 90 95

Ala Arg Asp Gly Ser Ser Trp Tyr Asp Tyr Ser Asp Tyr Trp Gly Gln
100 105 110

Gly Thr Leu Val Thr Val Ser Ser
115 120

<210> SEQ ID NO 387
<211> LENGTH: 24
<212> TYPE: DNA
<213> ORGANISM: Artificial Sequence
<220> FEATURE:
<223> OTHER INFORMATION: Synthetic

<400> SEQUENCE: 387
ggattcacct tcagtactta taac 24

<210> SEQ ID NO 388
<211> LENGTH: 8
<212> TYPE: PRT
<213> ORGANISM: Artificial Sequence
<220> FEATURE:
<223> OTHER INFORMATION: Synthetic

<400> SEQUENCE: 388

Gly Phe Thr Phe Ser Thr Tyr Asn
1 5

<210> SEQ ID NO 389
<211> LENGTH: 24
<212> TYPE: DNA
<213> ORGANISM: Artificial Sequence
<220> FEATURE:
<223> OTHER INFORMATION: Synthetic

<400> SEQUENCE: 389
attaggagta gtagtaatta cata 24

<210> SEQ ID NO 390
<211> LENGTH: 8
<212> TYPE: PRT
<213> ORGANISM: Artificial Sequence
<220> FEATURE:
<223> OTHER INFORMATION: Synthetic

<400> SEQUENCE: 390

Ile Arg Ser Ser Ser Asn Tyr Ile
1 5

<210> SEQ ID NO 391
<211> LENGTH: 39
<212> TYPE: DNA
<213> ORGANISM: Artificial Sequence
<220> FEATURE:
<223> OTHER INFORMATION: Synthetic

<400> SEQUENCE: 391
gcgagagatg gcagcagttg gtacgactac tctgactac 39

<210> SEQ ID NO 392
<211> LENGTH: 13
<212> TYPE: PRT
<213> ORGANISM: Artificial Sequence
<220> FEATURE:
<223> OTHER INFORMATION: Synthetic

<400> SEQUENCE: 392

Ala Arg Asp Gly Ser Ser Trp Tyr Asp Tyr Ser Asp Tyr
1 5 10

<210> SEQ ID NO 393
<211> LENGTH: 321

<212> TYPE: DNA
<213> ORGANISM: Artificial Sequence
<220> FEATURE:
<223> OTHER INFORMATION: Synthetic

<400> SEQUENCE: 393
gacatccaga tgacccagtc tccttccacc ctgtctgcat ctgtaggaga cagagtcacc 60
atcacttgcc gggccagtca gagtattagt agctggttgg cctggtatca acagatacca 120
gggaaagccc ctaaactcct gatctataag gcgtctagtt tagaaaatgg ggtcccatca 180
aggttcagcg gcagtggatc tgggacagaa ttcactctca tcatcagcag cctgcagcct 240
gatgattttg caacttatta ctgccaacag tatattagtt attctcggac gttcggccaa 300
gggaccaagg tggaaatcaa a 321

<210> SEQ ID NO 394
<211> LENGTH: 107
<212> TYPE: PRT
<213> ORGANISM: Artificial Sequence
<220> FEATURE:
<223> OTHER INFORMATION: Synthetic

<400> SEQUENCE: 394

Asp Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Ser Ser Trp
20 25 30

Leu Ala Trp Tyr Gln Gln Ile Pro Gly Lys Ala Pro Lys Leu Leu Ile
35 40 45

Tyr Lys Ala Ser Ser Leu Glu Asn Gly Val Pro Ser Arg Phe Ser Gly
50 55 60

Ser Gly Ser Gly Thr Glu Phe Thr Leu Ile Ile Ser Ser Leu Gln Pro
65 70 75 80

Asp Asp Phe Ala Thr Tyr Tyr Cys Gln Gln Tyr Ile Ser Tyr Ser Arg
85 90 95

Thr Phe Gly Gln Gly Thr Lys Val Glu Ile Lys
100 105

<210> SEQ ID NO 395
<211> LENGTH: 18
<212> TYPE: DNA
<213> ORGANISM: Artificial Sequence
<220> FEATURE:
<223> OTHER INFORMATION: Synthetic

<400> SEQUENCE: 395
cagagtatta gtagctgg 18

<210> SEQ ID NO 396
<211> LENGTH: 6
<212> TYPE: PRT
<213> ORGANISM: Artificial Sequence
<220> FEATURE:
<223> OTHER INFORMATION: Synthetic

<400> SEQUENCE: 396

Gln Ser Ile Ser Ser Trp
1 5

<210> SEQ ID NO 397
<211> LENGTH: 9
<212> TYPE: DNA

<213> ORGANISM: Artificial Sequence
<220> FEATURE:
<223> OTHER INFORMATION: Synthetic

<400> SEQUENCE: 397 aaggcgtct 9

<210> SEQ ID NO 398
<211> LENGTH: 3
<212> TYPE: PRT
<213> ORGANISM: Artificial Sequence
<220> FEATURE:
<223> OTHER INFORMATION: Synthetic

<400> SEQUENCE: 398

Lys Ala Ser
1

<210> SEQ ID NO 399
<211> LENGTH: 27
<212> TYPE: DNA
<213> ORGANISM: Artificial Sequence
<220> FEATURE:
<223> OTHER INFORMATION: Synthetic

<400> SEQUENCE: 399
caacagtata ttagttattc tcggacg 27

<210> SEQ ID NO 400
<211> LENGTH: 9
<212> TYPE: PRT
<213> ORGANISM: Artificial Sequence
<220> FEATURE:
<223> OTHER INFORMATION: Synthetic

<400> SEQUENCE: 400

Gln Gln Tyr Ile Ser Tyr Ser Arg Thr
1 5

<210> SEQ ID NO 401
<211> LENGTH: 360
<212> TYPE: DNA
<213> ORGANISM: Artificial Sequence
<220> FEATURE:
<223> OTHER INFORMATION: Synthetic

<400> SEQUENCE: 401
gaggtgcagc tggtggagtc tgggggaggc ctggtcaagc cggggggtc cctgagactc 60 tcctgtacag cctctggatt caccttcagt acttataaca tgaattgggt ccgccaggct 120
ccagggaagg gactggagtg ggtctcatcc attaggagta gtagtaatta catatactac 180
gcagactcag tgaagggccg attcaccatc tccagagaca acgccaagaa ttcactgtat 240
ctgcaaatga acagcctgag agccgatgac acggctgtgt attactgtgc gagagatggc 300
agcagttggt acgactactc tgactactgg ggccagggaa ccctggtcac cgtctcctca 360

<210> SEQ ID NO 402
<211> LENGTH: 120
<212> TYPE: PRT
<213> ORGANISM: Artificial Sequence
<220> FEATURE:
<223> OTHER INFORMATION: Synthetic

<400> SEQUENCE: 402

Glu Val Gln Leu Val Glu Ser Gly Gly Gly Leu Val Lys Pro Gly Gly

```
1               5                   10                  15

Ser Leu Arg Leu Ser Cys Thr Ala Ser Gly Phe Thr Phe Ser Thr Tyr
            20                  25                  30

Asn Met Asn Trp Val Arg Gln Ala Pro Gly Lys Gly Leu Glu Trp Val
        35                  40                  45

Ser Ser Ile Arg Ser Ser Ser Asn Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Asp Gly Ser Ser Trp Tyr Asp Tyr Ser Asp Tyr Trp Gly Gln
            100                 105                 110

Gly Thr Leu Val Thr Val Ser Ser
        115                 120
```

<210> SEQ ID NO 403
<211> LENGTH: 321
<212> TYPE: DNA
<213> ORGANISM: Artificial Sequence
<220> FEATURE:
<223> OTHER INFORMATION: Synthetic

<400> SEQUENCE: 403

```
gacatccaga tgacccagtc tccttccacc ctgtctgcat ctgtaggaga cagagtcacc      60

atcacttgcc gggccagtca gagtattagt agctggttgg cctggtatca acagatacca     120

gggaaagccc ctaaactcct gatctataag gcgtctagtt tagaaaatgg ggtcccatca     180

aggttcagcg gcagtggatc tgggacagaa ttcactctca tcatcagcag cctgcagcct     240

gatgattttg caacttatta ctgccaacag tatattagtt attctcggac gttcggccaa     300

gggaccaagg tggaaatcaa a                                                321
```

<210> SEQ ID NO 404
<211> LENGTH: 107
<212> TYPE: PRT
<213> ORGANISM: Artificial Sequence
<220> FEATURE:
<223> OTHER INFORMATION: Synthetic

<400> SEQUENCE: 404

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Ile Pro Gly Lys Ala Pro Lys Leu Leu Ile
        35                  40                  45

Tyr Lys Ala Ser Ser Leu Glu Asn Gly Val Pro Ser Arg Phe Ser Gly
    50                  55                  60

Ser Gly Ser Gly Thr Glu Phe Thr Leu Ile Ile Ser Ser Leu Gln Pro
65                  70                  75                  80

Asp Asp Phe Ala Thr Tyr Tyr Cys Gln Gln Tyr Ile Ser Tyr Ser Arg
                85                  90                  95

Thr Phe Gly Gln Gly Thr Lys Val Glu Ile Lys
            100                 105
```

<210> SEQ ID NO 405
<211> LENGTH: 360

<212> TYPE: DNA
<213> ORGANISM: Artificial Sequence
<220> FEATURE:
<223> OTHER INFORMATION: Synthetic

<400> SEQUENCE: 405
gaggtgcagc tggtggagtc tgggggaggc ctggtcaagc ctggggggtc cctgagactc 60
tcctgtgcag cctctggatt caccttcagt acttataaca tgaactgggt ccgccaggct 120
ccagggaagg ggctggagtg ggtctcatcc attaggagta gtagtaatta catatactac 180
gcagactcag tgaagggccg attcaccatc tccagagaca acgccaagaa ctcactgtat 240
ctgcaaatga acagcctgag agccgaggac acggctgtgt attactgtgc gagagatggc 300
agcagttggt acgactactc tgactactgg ggccaaggaa ccctggtcac cgtctcctca 360

<210> SEQ ID NO 406
<211> LENGTH: 120
<212> TYPE: PRT
<213> ORGANISM: Artificial Sequence
<220> FEATURE:
<223> OTHER INFORMATION: Synthetic

<400> SEQUENCE: 406

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Thr Tyr
20 25 30

Asn Met Asn Trp Val Arg Gln Ala Pro Gly Lys Gly Leu Glu Trp Val
35 40 45

Ser Ser Ile Arg Ser Ser Ser Asn Tyr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Asp Gly Ser Ser Trp Tyr Asp Tyr Ser Asp Tyr Trp Gly Gln
100 105 110

Gly Thr Leu Val Thr Val Ser Ser
115 120

<210> SEQ ID NO 407
<211> LENGTH: 321
<212> TYPE: DNA
<213> ORGANISM: Artificial Sequence
<220> FEATURE:
<223> OTHER INFORMATION: Synthetic

<400> SEQUENCE: 407
gacatccaga tgacccagtc tccttccacc ctgtctgcat ctgtaggaga cagagtcacc 60
atcacttgcc gggccagtca gagtattagt agctggttgg cctggtatca gcagaaacca 120
gggaaagccc ctaagctcct gatctataag gcgtctagtt tagaaagtgg ggtcccatca 180
aggttcagcg gcagtggatc tgggacagaa ttcactctca ccatcagcag cctgcagcct 240
gatgattttg caacttatta ctgccaacag tatattagtt attctcggac gttcggccaa 300
gggaccaagg tggaaatcaa a 321

<210> SEQ ID NO 408
<211> LENGTH: 107
<212> TYPE: PRT

```
<213> ORGANISM: Artificial Sequence
<220> FEATURE:
<223> OTHER INFORMATION: Synthetic

<400> SEQUENCE: 408

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ile Ser Tyr Ser Arg
                85                  90                  95

Thr Phe Gly Gln Gly Thr Lys Val Glu Ile Lys
            100                 105


<210> SEQ ID NO 409
<211> LENGTH: 360
<212> TYPE: DNA
<213> ORGANISM: Artificial Sequence
<220> FEATURE:
<223> OTHER INFORMATION: Synthetic

<400> SEQUENCE: 409

gaggtgcagc tggtggagtc tgggggaggc ctggtcaagc cggggggtc cctgagactc      60

tcctgtacag cctctggatt caccttcagt acttataaca tgaattgggt ccgccaggct     120

ccagggaagg gactggagtg ggtctcatcc attaggagta gtagtaatta catatactac     180

gcagactcag tgaagggccg attcaccatc tccagagaca acgccaagaa ttcactgtat     240

ctgcaaatga acagcctgag agccgatgac acggctgtgt attactgtgc gagagatggc     300

agcagttggt acgactactc tgactactgg ggccagggaa ccctggtcac cgtctcctca     360


<210> SEQ ID NO 410
<211> LENGTH: 120
<212> TYPE: PRT
<213> ORGANISM: Artificial Sequence
<220> FEATURE:
<223> OTHER INFORMATION: Synthetic

<400> SEQUENCE: 410

Glu Val Gln Leu Val Glu Ser Gly Gly Gly Leu Val Lys Pro Gly Gly
1               5                   10                  15

Ser Leu Arg Leu Ser Cys Thr Ala Ser Gly Phe Thr Phe Ser Thr Tyr
            20                  25                  30

Asn Met Asn Trp Val Arg Gln Ala Pro Gly Lys Gly Leu Glu Trp Val
        35                  40                  45

Ser Ser Ile Arg Ser Ser Ser Asn Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Asp Gly Ser Ser Trp Tyr Asp Tyr Ser Asp Tyr Trp Gly Gln
            100                 105                 110
```

Gly Thr Leu Val Thr Val Ser Ser
        115                 120

<210> SEQ ID NO 411
<211> LENGTH: 24
<212> TYPE: DNA
<213> ORGANISM: Artificial Sequence
<220> FEATURE:
<223> OTHER INFORMATION: Synthetic

<400> SEQUENCE: 411
ggattcacct tcagtactta taac 24

<210> SEQ ID NO 412
<211> LENGTH: 8
<212> TYPE: PRT
<213> ORGANISM: Artificial Sequence
<220> FEATURE:
<223> OTHER INFORMATION: Synthetic

<400> SEQUENCE: 412

Gly Phe Thr Phe Ser Thr Tyr Asn
1               5

<210> SEQ ID NO 413
<211> LENGTH: 24
<212> TYPE: DNA
<213> ORGANISM: Artificial Sequence
<220> FEATURE:
<223> OTHER INFORMATION: Synthetic

<400> SEQUENCE: 413
attaggagta gtagtaatta cata 24

<210> SEQ ID NO 414
<211> LENGTH: 8
<212> TYPE: PRT
<213> ORGANISM: Artificial Sequence
<220> FEATURE:
<223> OTHER INFORMATION: Synthetic

<400> SEQUENCE: 414

Ile Arg Ser Ser Ser Asn Tyr Ile
1               5

<210> SEQ ID NO 415
<211> LENGTH: 39
<212> TYPE: DNA
<213> ORGANISM: Artificial Sequence
<220> FEATURE:
<223> OTHER INFORMATION: Synthetic

<400> SEQUENCE: 415
gcgagagatg gcagcagttg gtacgactac tctgactac 39

<210> SEQ ID NO 416
<211> LENGTH: 13
<212> TYPE: PRT
<213> ORGANISM: Artificial Sequence
<220> FEATURE:
<223> OTHER INFORMATION: Synthetic

<400> SEQUENCE: 416

Ala Arg Asp Gly Ser Ser Trp Tyr Asp Tyr Ser Asp Tyr
1               5                   10

<210> SEQ ID NO 417
<211> LENGTH: 321
<212> TYPE: DNA
<213> ORGANISM: Artificial Sequence
<220> FEATURE:
<223> OTHER INFORMATION: Synthetic

<400> SEQUENCE: 417
gacatccaga tgacccagtc tccttccacc ctgtctgcat ctgtaggaga cagagtcacc 60
atcacttgcc gggccagtca gagtattagt agctggttgg cctggtatca acagatacca 120
gggaaagccc ctaaactcct gatctataag gcgtctagtt tagaaaatgg ggtcccatca 180
aggttcagcg gcagtggatc tgggacagaa ttcactctca tcatcagcag cctgcagcct 240
gatgattttg caacttatta ctgccaacag tatattagtt attctcggac gttcggccaa 300
gggaccaagg tggaaatcaa a 321

<210> SEQ ID NO 418
<211> LENGTH: 107
<212> TYPE: PRT
<213> ORGANISM: Artificial Sequence
<220> FEATURE:
<223> OTHER INFORMATION: Synthetic

<400> SEQUENCE: 418

Asp Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Ser Ser Trp
20 25 30

Leu Ala Trp Tyr Gln Gln Ile Pro Gly Lys Ala Pro Lys Leu Leu Ile
35 40 45

Tyr Lys Ala Ser Ser Leu Glu Asn Gly Val Pro Ser Arg Phe Ser Gly
50 55 60

Ser Gly Ser Gly Thr Glu Phe Thr Leu Ile Ile Ser Ser Leu Gln Pro
65 70 75 80

Asp Asp Phe Ala Thr Tyr Tyr Cys Gln Gln Tyr Ile Ser Tyr Ser Arg
85 90 95

Thr Phe Gly Gln Gly Thr Lys Val Glu Ile Lys
100 105

<210> SEQ ID NO 419
<211> LENGTH: 18
<212> TYPE: DNA
<213> ORGANISM: Artificial Sequence
<220> FEATURE:
<223> OTHER INFORMATION: Synthetic

<400> SEQUENCE: 419
cagagtatta gtagctgg 18

<210> SEQ ID NO 420
<211> LENGTH: 6
<212> TYPE: PRT
<213> ORGANISM: Artificial Sequence
<220> FEATURE:
<223> OTHER INFORMATION: Synthetic

<400> SEQUENCE: 420

Gln Ser Ile Ser Ser Trp
1 5

<210> SEQ ID NO 421
<211> LENGTH: 9
<212> TYPE: DNA
<213> ORGANISM: Artificial Sequence
<220> FEATURE:
<223> OTHER INFORMATION: Synthetic

<400> SEQUENCE: 421 aaggcgtct 9

<210> SEQ ID NO 422
<211> LENGTH: 3
<212> TYPE: PRT
<213> ORGANISM: Artificial Sequence
<220> FEATURE:
<223> OTHER INFORMATION: Synthetic

<400> SEQUENCE: 422

Lys Ala Ser
1

<210> SEQ ID NO 423
<211> LENGTH: 27
<212> TYPE: DNA
<213> ORGANISM: Artificial Sequence
<220> FEATURE:
<223> OTHER INFORMATION: Synthetic

<400> SEQUENCE: 423
caacagtata ttagttattc tcggacg 27

<210> SEQ ID NO 424
<211> LENGTH: 9
<212> TYPE: PRT
<213> ORGANISM: Artificial Sequence
<220> FEATURE:
<223> OTHER INFORMATION: Synthetic

<400> SEQUENCE: 424

Gln Gln Tyr Ile Ser Tyr Ser Arg Thr
1 5

<210> SEQ ID NO 425
<211> LENGTH: 360
<212> TYPE: DNA
<213> ORGANISM: Artificial Sequence
<220> FEATURE:
<223> OTHER INFORMATION: Synthetic

<400> SEQUENCE: 425
gaggtgcagc tggtggagtc tgggggaggc ctggtcaagc cggggggtc cctgagactc 60 tcctgtacag cctctggatt caccttcagt acttataaca tgaattgggt ccgccaggct 120
ccagggaagg gactggagtg ggtctcatcc attaggagta gtagtaatta catatactac 180
gcagactcag tgaagggccg attcaccatc tccagagaca acgccaagaa ttcactgtat 240
ctgcaaatga acagcctgag agccgatgac acggctgtgt attactgtgc gagagatggc 300
agcagttggt acgactactc tgactactgg ggccagggaa ccctggtcac cgtctcctca 360

<210> SEQ ID NO 426
<211> LENGTH: 120
<212> TYPE: PRT
<213> ORGANISM: Artificial Sequence
<220> FEATURE:
<223> OTHER INFORMATION: Synthetic

<400> SEQUENCE: 426

```
Glu Val Gln Leu Val Glu Ser Gly Gly Gly Leu Val Lys Pro Gly Gly
1               5                   10                  15

Ser Leu Arg Leu Ser Cys Thr Ala Ser Gly Phe Thr Phe Ser Thr Tyr
            20                  25                  30

Asn Met Asn Trp Val Arg Gln Ala Pro Gly Lys Gly Leu Glu Trp Val
        35                  40                  45

Ser Ser Ile Arg Ser Ser Ser Asn Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Asp Gly Ser Ser Trp Tyr Asp Tyr Ser Asp Tyr Trp Gly Gln
            100                 105                 110

Gly Thr Leu Val Thr Val Ser Ser
        115                 120
```

<210> SEQ ID NO 427
<211> LENGTH: 321
<212> TYPE: DNA
<213> ORGANISM: Artificial Sequence
<220> FEATURE:
<223> OTHER INFORMATION: Synthetic

<400> SEQUENCE: 427

```
gacatccaga tgacccagtc tccttccacc ctgtctgcat ctgtaggaga cagagtcacc     60

atcacttgcc gggccagtca gagtattagt agctggttgg cctggtatca acagatacca    120

gggaaagccc ctaaactcct gatctataag gcgtctagtt tagaaaatgg ggtcccatca    180

aggttcagcg gcagtggatc tgggacagaa ttcactctca tcatcagcag cctgcagcct    240

gatgattttg caacttatta ctgccaacag tatattagtt attctcggac gttcggccaa    300

gggaccaagg tggaaatcaa a                                              321
```

<210> SEQ ID NO 428
<211> LENGTH: 107
<212> TYPE: PRT
<213> ORGANISM: Artificial Sequence
<220> FEATURE:
<223> OTHER INFORMATION: Synthetic

<400> SEQUENCE: 428

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Ile Pro Gly Lys Ala Pro Lys Leu Leu Ile
        35                  40                  45

Tyr Lys Ala Ser Ser Leu Glu Asn Gly Val Pro Ser Arg Phe Ser Gly
    50                  55                  60

Ser Gly Ser Gly Thr Glu Phe Thr Leu Ile Ile Ser Ser Leu Gln Pro
65                  70                  75                  80

Asp Asp Phe Ala Thr Tyr Tyr Cys Gln Gln Tyr Ile Ser Tyr Ser Arg
                85                  90                  95

Thr Phe Gly Gln Gly Thr Lys Val Glu Ile Lys
            100                 105
```

<210> SEQ ID NO 429
<211> LENGTH: 360
<212> TYPE: DNA
<213> ORGANISM: Artificial Sequence
<220> FEATURE:
<223> OTHER INFORMATION: Synthetic

<400> SEQUENCE: 429
gaggtgcagc tggtggagtc tgggggaggc ctggtcaagc ctgggggggtc cctgagactc 60 tcctgtgcag cctctggatt caccttcagt acttataaca tgaactgggt ccgccaggct 120
ccagggaagg ggctggagtg ggtctcatcc attaggagta gtagtaatta catatactac 180
gcagactcag tgaagggccg attcaccatc tccagagaca acgccaagaa ctcactgtat 240
ctgcaaatga acagcctgag agccgaggac acggctgtgt attactgtgc gagagatggc 300
agcagttggt acgactactc tgactactgg ggccaaggaa ccctggtcac cgtctcctca 360

<210> SEQ ID NO 430
<211> LENGTH: 120
<212> TYPE: PRT
<213> ORGANISM: Artificial Sequence
<220> FEATURE:
<223> OTHER INFORMATION: Synthetic

<400> SEQUENCE: 430

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Asn Met Asn Trp Val Arg Gln Ala Pro Gly Lys Gly Leu Glu Trp Val
        35                  40                  45

Ser Ser Ile Arg Ser Ser Ser Asn Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Ser Trp Tyr Asp Tyr Ser Asp Tyr Trp Gly Gln
            100                 105                 110

Gly Thr Leu Val Thr Val Ser Ser
        115                 120

<210> SEQ ID NO 431
<211> LENGTH: 321
<212> TYPE: DNA
<213> ORGANISM: Artificial Sequence
<220> FEATURE:
<223> OTHER INFORMATION: Synthetic

<400> SEQUENCE: 431
gacatccaga tgacccagtc tccttccacc ctgtctgcat ctgtaggaga cagagtcacc 60
atcacttgcc gggccagtca gagtattagt agctggttgg cctggtatca gcagaaacca 120
gggaaagccc ctaagctcct gatctataag gcgtctagtt tagaaagtgg ggtcccatca 180
aggttcagcg gcagtggatc tgggacagaa ttcactctca ccatcagcag cctgcagcct 240
gatgattttg caacttatta ctgccaacag tatattagtt attctcggac gttcggccaa 300
gggaccaagg tggaaatcaa a 321

-continued

<210> SEQ ID NO 432
<211> LENGTH: 107
<212> TYPE: PRT
<213> ORGANISM: Artificial Sequence
<220> FEATURE:
<223> OTHER INFORMATION: Synthetic

<400> SEQUENCE: 432

Asp Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Ser Ser Trp
20 25 30

Leu Ala Trp Tyr Gln Gln Lys Pro Gly Lys Ala Pro Lys Leu Leu Ile
35 40 45

Tyr Lys Ala Ser Ser Leu Glu Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Tyr Ile Ser Tyr Ser Arg
85 90 95

Thr Phe Gly Gln Gly Thr Lys Val Glu Ile Lys
100 105

<210> SEQ ID NO 433
<211> LENGTH: 360
<212> TYPE: DNA
<213> ORGANISM: Artificial Sequence
<220> FEATURE:
<223> OTHER INFORMATION: Synthetic

<400> SEQUENCE: 433
gaggtgcagc tggtggagtc tgggggaggc ctggtcaagc cggggggtc cctgagactc 60 tcctgtacag cctctggatt caccttcagt acttataaca tgaattgggt ccgccaggct 120
ccagggaagg gactggagtg ggtctcatcc attaggagta gtagtaatta catatactac 180
gcagactcag tgaagggccg attcaccatc tccagagaca acgccaagag ttcactgtat 240
ctgcaaatga acagcctgag agccgaggac acggctgtgt attactgtgc gagagatggc 300
agcagttggt acgactactc tgactactgg ggccagggaa ccctggtcac cgtctcctca 360

<210> SEQ ID NO 434
<211> LENGTH: 120
<212> TYPE: PRT
<213> ORGANISM: Artificial Sequence
<220> FEATURE:
<223> OTHER INFORMATION: Synthetic

<400> SEQUENCE: 434

Glu Val Gln Leu Val Glu Ser Gly Gly Gly Leu Val Lys Pro Gly Gly
1 5 10 15

Ser Leu Arg Leu Ser Cys Thr Ala Ser Gly Phe Thr Phe Ser Thr Tyr
20 25 30

Asn Met Asn Trp Val Arg Gln Ala Pro Gly Lys Gly Leu Glu Trp Val
35 40 45

Ser Ser Ile Arg Ser Ser Ser Asn Tyr Ile Tyr Tyr Ala Asp Ser Val
50 55 60

Lys Gly Arg Phe Thr Ile Ser Arg Asp Asn Ala Lys Ser Ser Leu Tyr
65 70 75 80

Leu Gln Met Asn Ser Leu Arg Ala Glu Asp Thr Ala Val Tyr Tyr Cys
85 90 95

```
Ala Arg Asp Gly Ser Ser Trp Tyr Asp Tyr Ser Asp Tyr Trp Gly Gln
            100                 105                 110

Gly Thr Leu Val Thr Val Ser Ser
        115                 120


<210> SEQ ID NO 435
<211> LENGTH: 24
<212> TYPE: DNA
<213> ORGANISM: Artificial Sequence
<220> FEATURE:
<223> OTHER INFORMATION: Synthetic

<400> SEQUENCE: 435

ggattcacct tcagtactta taac                                            24


<210> SEQ ID NO 436
<211> LENGTH: 8
<212> TYPE: PRT
<213> ORGANISM: Artificial Sequence
<220> FEATURE:
<223> OTHER INFORMATION: Synthetic

<400> SEQUENCE: 436

Gly Phe Thr Phe Ser Thr Tyr Asn
1               5


<210> SEQ ID NO 437
<211> LENGTH: 24
<212> TYPE: DNA
<213> ORGANISM: Artificial Sequence
<220> FEATURE:
<223> OTHER INFORMATION: Synthetic

<400> SEQUENCE: 437

attaggagta gtagtaatta cata                                            24


<210> SEQ ID NO 438
<211> LENGTH: 8
<212> TYPE: PRT
<213> ORGANISM: Artificial Sequence
<220> FEATURE:
<223> OTHER INFORMATION: Synthetic

<400> SEQUENCE: 438

Ile Arg Ser Ser Ser Asn Tyr Ile
1               5


<210> SEQ ID NO 439
<211> LENGTH: 39
<212> TYPE: DNA
<213> ORGANISM: Artificial Sequence
<220> FEATURE:
<223> OTHER INFORMATION: Synthetic

<400> SEQUENCE: 439

gcgagagatg gcagcagttg gtacgactac tctgactac                            39


<210> SEQ ID NO 440
<211> LENGTH: 13
<212> TYPE: PRT
<213> ORGANISM: Artificial Sequence
<220> FEATURE:
<223> OTHER INFORMATION: Synthetic

<400> SEQUENCE: 440
```

```
Ala Arg Asp Gly Ser Ser Trp Tyr Asp Tyr Ser Asp Tyr
1               5                   10


<210> SEQ ID NO 441
<211> LENGTH: 321
<212> TYPE: DNA
<213> ORGANISM: Artificial Sequence
<220> FEATURE:
<223> OTHER INFORMATION: Synthetic

<400> SEQUENCE: 441

gacatccaga tgacccagtc tccttccacc ctgtctgcat ctgtaggaga cagagtcacc      60

atcacttgcc gggccagtca gagtattagt agctggttgg cctggtatca acaggtacca     120

gggaaagccc ctaaactcct gatctataag gcgtctagtt tagaaaatgg ggtcccatca     180

aggttcagcg gcagtggatc tgggacagaa ttcactctca tcatcagcag cctgcagcct     240

gatgattttg caacttatta ctgccaacag tatattagtt attctcggac gttcggccaa     300

gggaccaagg tggaaatcaa a                                               321


<210> SEQ ID NO 442
<211> LENGTH: 107
<212> TYPE: PRT
<213> ORGANISM: Artificial Sequence
<220> FEATURE:
<223> OTHER INFORMATION: Synthetic

<400> SEQUENCE: 442

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Val Pro Gly Lys Ala Pro Lys Leu Leu Ile
        35                  40                  45

Tyr Lys Ala Ser Ser Leu Glu Asn Gly Val Pro Ser Arg Phe Ser Gly
    50                  55                  60

Ser Gly Ser Gly Thr Glu Phe Thr Leu Ile Ile Ser Ser Leu Gln Pro
65                  70                  75                  80

Asp Asp Phe Ala Thr Tyr Tyr Cys Gln Gln Tyr Ile Ser Tyr Ser Arg
                85                  90                  95

Thr Phe Gly Gln Gly Thr Lys Val Glu Ile Lys
            100                 105


<210> SEQ ID NO 443
<211> LENGTH: 18
<212> TYPE: DNA
<213> ORGANISM: Artificial Sequence
<220> FEATURE:
<223> OTHER INFORMATION: Synthetic

<400> SEQUENCE: 443

cagagtatta gtagctgg                                                    18


<210> SEQ ID NO 444
<211> LENGTH: 6
<212> TYPE: PRT
<213> ORGANISM: Artificial Sequence
<220> FEATURE:
<223> OTHER INFORMATION: Synthetic

<400> SEQUENCE: 444

Gln Ser Ile Ser Ser Trp
```

1 5

<210> SEQ ID NO 445
<211> LENGTH: 9
<212> TYPE: DNA
<213> ORGANISM: Artificial Sequence
<220> FEATURE:
<223> OTHER INFORMATION: Synthetic

<400> SEQUENCE: 445 aaggcgtct 9

<210> SEQ ID NO 446
<211> LENGTH: 3
<212> TYPE: PRT
<213> ORGANISM: Artificial Sequence
<220> FEATURE:
<223> OTHER INFORMATION: Synthetic

<400> SEQUENCE: 446

Lys Ala Ser
1

<210> SEQ ID NO 447
<211> LENGTH: 27
<212> TYPE: DNA
<213> ORGANISM: Artificial Sequence
<220> FEATURE:
<223> OTHER INFORMATION: Synthetic

<400> SEQUENCE: 447
caacagtata ttagttattc tcggacg 27

<210> SEQ ID NO 448
<211> LENGTH: 9
<212> TYPE: PRT
<213> ORGANISM: Artificial Sequence
<220> FEATURE:
<223> OTHER INFORMATION: Synthetic

<400> SEQUENCE: 448

Gln Gln Tyr Ile Ser Tyr Ser Arg Thr
1 5

<210> SEQ ID NO 449
<211> LENGTH: 360
<212> TYPE: DNA
<213> ORGANISM: Artificial Sequence
<220> FEATURE:
<223> OTHER INFORMATION: Synthetic

<400> SEQUENCE: 449
gaggtgcagc tggtggagtc tgggggaggc ctggtcaagc cggggggtc cctgagactc 60 tcctgtacag cctctggatt caccttcagt acttataaca tgaattgggt ccgccaggct 120
ccagggaagg gactggagtg ggtctcatcc attaggagta gtagtaatta catatactac 180
gcagactcag tgaagggccg attcaccatc tccagagaca acgccaagag ttcactgtat 240
ctgcaaatga acagcctgag agccgaggac acggctgtgt attactgtgc gagagatggc 300
agcagttggt acgactactc tgactactgg ggccagggaa ccctggtcac cgtctcctca 360

<210> SEQ ID NO 450
<211> LENGTH: 120
<212> TYPE: PRT
<213> ORGANISM: Artificial Sequence
<220> FEATURE:
<223> OTHER INFORMATION: Synthetic

<400> SEQUENCE: 450

```
Glu Val Gln Leu Val Glu Ser Gly Gly Gly Leu Val Lys Pro Gly Gly
1               5                   10                  15

Ser Leu Arg Leu Ser Cys Thr Ala Ser Gly Phe Thr Phe Ser Thr Tyr
            20                  25                  30

Asn Met Asn Trp Val Arg Gln Ala Pro Gly Lys Gly Leu Glu Trp Val
        35                  40                  45

Ser Ser Ile Arg Ser Ser Ser Asn Tyr Ile Tyr Tyr Ala Asp Ser Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Ser Trp Tyr Asp Tyr Ser Asp Tyr Trp Gly Gln
            100                 105                 110

Gly Thr Leu Val Thr Val Ser Ser
        115                 120
```

<210> SEQ ID NO 451
<211> LENGTH: 321
<212> TYPE: DNA
<213> ORGANISM: Artificial Sequence
<220> FEATURE:
<223> OTHER INFORMATION: Synthetic

<400> SEQUENCE: 451

```
gacatccaga tgacccagtc tccttccacc ctgtctgcat ctgtaggaga cagagtcacc      60

atcacttgcc gggccagtca gagtattagt agctggttgg cctggtatca acaggtacca     120

gggaaagccc ctaaactcct gatctataag gcgtctagtt tagaaaatgg ggtcccatca     180

aggttcagcg gcagtggatc tgggacagaa ttcactctca tcatcagcag cctgcagcct     240

gatgattttg caacttatta ctgccaacag tatattagtt attctcggac gttcggccaa     300

gggaccaagg tggaaatcaa a                                               321
```

<210> SEQ ID NO 452
<211> LENGTH: 107
<212> TYPE: PRT
<213> ORGANISM: Artificial Sequence
<220> FEATURE:
<223> OTHER INFORMATION: Synthetic

<400> SEQUENCE: 452

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Val Pro Gly Lys Ala Pro Lys Leu Leu Ile
        35                  40                  45

Tyr Lys Ala Ser Ser Leu Glu Asn Gly Val Pro Ser Arg Phe Ser Gly
    50                  55                  60

Ser Gly Ser Gly Thr Glu Phe Thr Leu Ile Ile Ser Ser Leu Gln Pro
65                  70                  75                  80

Asp Asp Phe Ala Thr Tyr Tyr Cys Gln Gln Tyr Ile Ser Tyr Ser Arg
                85                  90                  95
```

Thr Phe Gly Gln Gly Thr Lys Val Glu Ile Lys
100 105

<210> SEQ ID NO 453
<211> LENGTH: 360
<212> TYPE: DNA
<213> ORGANISM: Artificial Sequence
<220> FEATURE:
<223> OTHER INFORMATION: Synthetic

<400> SEQUENCE: 453
gaggtgcagc tggtggagtc tgggggaggc ctggtcaagc ctggggggtc cctgagactc 60
tcctgtgcag cctctggatt caccttcagt acttataaca tgaactgggt ccgccaggct 120
ccagggaagg ggctggagtg ggtctcatcc attaggagta gtagtaatta catatactac 180
gcagactcag tgaagggccg attcaccatc tccagagaca acgccaagaa ctcactgtat 240
ctgcaaatga acagcctgag agccgaggac acggctgtgt attactgtgc gagagatggc 300
agcagttggt acgactactc tgactactgg ggccagggaa ccctggtcac cgtctcctca 360

<210> SEQ ID NO 454
<211> LENGTH: 120
<212> TYPE: PRT
<213> ORGANISM: Artificial Sequence
<220> FEATURE:
<223> OTHER INFORMATION: Synthetic

<400> SEQUENCE: 454

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Thr Tyr
20 25 30

Asn Met Asn Trp Val Arg Gln Ala Pro Gly Lys Gly Leu Glu Trp Val
35 40 45

Ser Ser Ile Arg Ser Ser Ser Asn Tyr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Asp Gly Ser Ser Trp Tyr Asp Tyr Ser Asp Tyr Trp Gly Gln
100 105 110

Gly Thr Leu Val Thr Val Ser Ser
115 120

<210> SEQ ID NO 455
<211> LENGTH: 321
<212> TYPE: DNA
<213> ORGANISM: Artificial Sequence
<220> FEATURE:
<223> OTHER INFORMATION: Synthetic

<400> SEQUENCE: 455
gacatccaga tgacccagtc tccttccacc ctgtctgcat ctgtaggaga cagagtcacc 60
atcacttgcc gggccagtca gagtattagt agctggttgg cctggtatca gcagaaacca 120
gggaaagccc ctaagctcct gatctataag gcgtctagtt tagaaagtgg ggtcccatca 180
aggttcagcg gcagtggatc tgggacagaa ttcactctca ccatcagcag cctgcagcct 240
gatgattttg caacttatta ctgccaacag tatattagtt attctcggac gttcggccaa 300
gggaccaagg tggaaatcaa a 321

<210> SEQ ID NO 456
<211> LENGTH: 107
<212> TYPE: PRT
<213> ORGANISM: Artificial Sequence
<220> FEATURE:
<223> OTHER INFORMATION: Synthetic

<400> SEQUENCE: 456

Asp Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Ser Ser Trp
20 25 30

Leu Ala Trp Tyr Gln Gln Lys Pro Gly Lys Ala Pro Lys Leu Leu Ile
35 40 45

Tyr Lys Ala Ser Ser Leu Glu Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Tyr Ile Ser Tyr Ser Arg
85 90 95

Thr Phe Gly Gln Gly Thr Lys Val Glu Ile Lys
100 105

<210> SEQ ID NO 457
<211> LENGTH: 360
<212> TYPE: DNA
<213> ORGANISM: Artificial Sequence
<220> FEATURE:
<223> OTHER INFORMATION: Synthetic

<400> SEQUENCE: 457
gaggtgcagc tggtggagtc tgggggaggc ctggtcaagc cgggggggtc cctgagactc 60
tcctgtacag cctctggatt caccttcagt acttataaca tgaattgggt ccgccaggct 120
ccagggaagg gactggagtg ggtctcatcc attaggagta gtagtaatta catatactac 180
gcagactcag tgaagggccg attcaccatc tccagagaca acgccaagaa ttcactgtat 240
ctgcaaatga acagcctgag agccgatgac acggctgtgt attactgtgc gagagatggc 300
agcagttggt acgactactc tgactactgg ggccagggaa ccctggtcac cgtctcctca 360

<210> SEQ ID NO 458
<211> LENGTH: 120
<212> TYPE: PRT
<213> ORGANISM: Artificial Sequence
<220> FEATURE:
<223> OTHER INFORMATION: Synthetic

<400> SEQUENCE: 458

Glu Val Gln Leu Val Glu Ser Gly Gly Gly Leu Val Lys Pro Gly Gly
1 5 10 15

Ser Leu Arg Leu Ser Cys Thr Ala Ser Gly Phe Thr Phe Ser Thr Tyr
20 25 30

Asn Met Asn Trp Val Arg Gln Ala Pro Gly Lys Gly Leu Glu Trp Val
35 40 45

Ser Ser Ile Arg Ser Ser Ser Asn Tyr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Asp Asp Thr Ala Val Tyr Tyr Cys
85 90 95

Ala Arg Asp Gly Ser Ser Trp Tyr Asp Tyr Ser Asp Tyr Trp Gly Gln
100 105 110

Gly Thr Leu Val Thr Val Ser Ser
115 120

<210> SEQ ID NO 459
<211> LENGTH: 24
<212> TYPE: DNA
<213> ORGANISM: Artificial Sequence
<220> FEATURE:
<223> OTHER INFORMATION: Synthetic

<400> SEQUENCE: 459
ggattcacct tcagtactta taac 24

<210> SEQ ID NO 460
<211> LENGTH: 8
<212> TYPE: PRT
<213> ORGANISM: Artificial Sequence
<220> FEATURE:
<223> OTHER INFORMATION: Synthetic

<400> SEQUENCE: 460

Gly Phe Thr Phe Ser Thr Tyr Asn
1 5

<210> SEQ ID NO 461
<211> LENGTH: 24
<212> TYPE: DNA
<213> ORGANISM: Artificial Sequence
<220> FEATURE:
<223> OTHER INFORMATION: Synthetic

<400> SEQUENCE: 461
attaggagta gtagtaatta cata 24

<210> SEQ ID NO 462
<211> LENGTH: 8
<212> TYPE: PRT
<213> ORGANISM: Artificial Sequence
<220> FEATURE:
<223> OTHER INFORMATION: Synthetic

<400> SEQUENCE: 462

Ile Arg Ser Ser Ser Asn Tyr Ile
1 5

<210> SEQ ID NO 463
<211> LENGTH: 39
<212> TYPE: DNA
<213> ORGANISM: Artificial Sequence
<220> FEATURE:
<223> OTHER INFORMATION: Synthetic

<400> SEQUENCE: 463
gcgagagatg gcagcagttg gtacgactac tctgactac 39

<210> SEQ ID NO 464
<211> LENGTH: 13
<212> TYPE: PRT
<213> ORGANISM: Artificial Sequence
<220> FEATURE:
<223> OTHER INFORMATION: Synthetic

<400> SEQUENCE: 464

Ala Arg Asp Gly Ser Ser Trp Tyr Asp Tyr Ser Asp Tyr
1               5                   10

<210> SEQ ID NO 465
<211> LENGTH: 321
<212> TYPE: DNA
<213> ORGANISM: Artificial Sequence
<220> FEATURE:
<223> OTHER INFORMATION: Synthetic

<400> SEQUENCE: 465
gacatccaga tgacccagtc tccttccacc ctgtctgcat ctgtaggaga cagagtcacc 60
atcacttgcc gggccagtca gagtattagt agctggttgg cctggtatca acagatacca 120
gggaaagccc ctaaactcct gatctataag gcgtctagtt tagaaaatgg ggtcccatca 180
aggttcagcg gcagtggatc tgggacagaa ttcactctca tcatcagcag cctgcagcct 240
gatgattttg caacttatta ctgccaacag tatattagtt attctcggac gttcggccaa 300
gggaccaagg tggaaatcaa a 321

<210> SEQ ID NO 466
<211> LENGTH: 107
<212> TYPE: PRT
<213> ORGANISM: Artificial Sequence
<220> FEATURE:
<223> OTHER INFORMATION: Synthetic

<400> SEQUENCE: 466

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Ile Pro Gly Lys Ala Pro Lys Leu Leu Ile
        35                  40                  45

Tyr Lys Ala Ser Ser Leu Glu Asn Gly Val Pro Ser Arg Phe Ser Gly
    50                  55                  60

Ser Gly Ser Gly Thr Glu Phe Thr Leu Ile Ile Ser Ser Leu Gln Pro
65                  70                  75                  80

Asp Asp Phe Ala Thr Tyr Tyr Cys Gln Gln Tyr Ile Ser Tyr Ser Arg
                85                  90                  95

Thr Phe Gly Gln Gly Thr Lys Val Glu Ile Lys
            100                 105

<210> SEQ ID NO 467
<211> LENGTH: 18
<212> TYPE: DNA
<213> ORGANISM: Artificial Sequence
<220> FEATURE:
<223> OTHER INFORMATION: Synthetic

<400> SEQUENCE: 467
cagagtatta gtagctgg 18

<210> SEQ ID NO 468
<211> LENGTH: 6
<212> TYPE: PRT
<213> ORGANISM: Artificial Sequence
<220> FEATURE:
<223> OTHER INFORMATION: Synthetic

<400> SEQUENCE: 468

Gln Ser Ile Ser Ser Trp
1 5

<210> SEQ ID NO 469
<211> LENGTH: 9
<212> TYPE: DNA
<213> ORGANISM: Artificial Sequence
<220> FEATURE:
<223> OTHER INFORMATION: Synthetic

<400> SEQUENCE: 469 aaggcgtct 9

<210> SEQ ID NO 470
<211> LENGTH: 3
<212> TYPE: PRT
<213> ORGANISM: Artificial Sequence
<220> FEATURE:
<223> OTHER INFORMATION: Synthetic

<400> SEQUENCE: 470

Lys Ala Ser
1

<210> SEQ ID NO 471
<211> LENGTH: 27
<212> TYPE: DNA
<213> ORGANISM: Artificial Sequence
<220> FEATURE:
<223> OTHER INFORMATION: Synthetic

<400> SEQUENCE: 471
caacagtata ttagttattc tcggacg 27

<210> SEQ ID NO 472
<211> LENGTH: 9
<212> TYPE: PRT
<213> ORGANISM: Artificial Sequence
<220> FEATURE:
<223> OTHER INFORMATION: Synthetic

<400> SEQUENCE: 472

Gln Gln Tyr Ile Ser Tyr Ser Arg Thr
1 5

<210> SEQ ID NO 473
<211> LENGTH: 360
<212> TYPE: DNA
<213> ORGANISM: Artificial Sequence
<220> FEATURE:
<223> OTHER INFORMATION: Synthetic

<400> SEQUENCE: 473
gaggtgcagc tggtggagtc tgggggaggc ctggtcaagc cggggggggtc cctgagactc 60 tcctgtacag cctctggatt caccttcagt acttataaca tgaattgggt ccgccaggct 120
ccagggaagg gactggagtg ggtctcatcc attaggagta gtagtaatta catatactac 180
gcagactcag tgaagggccg attcaccatc tccagagaca acgccaagaa ttcactgtat 240
ctgcaaatga acagcctgag agccgatgac acggctgtgt attactgtgc gagagatggc 300
agcagttggt acgactactc tgactactgg ggccagggaa ccctggtcac cgtctcctca 360

<210> SEQ ID NO 474

<211> LENGTH: 120
<212> TYPE: PRT
<213> ORGANISM: Artificial Sequence
<220> FEATURE:
<223> OTHER INFORMATION: Synthetic

<400> SEQUENCE: 474

```
Glu Val Gln Leu Val Glu Ser Gly Gly Gly Leu Val Lys Pro Gly Gly
1               5                   10                  15

Ser Leu Arg Leu Ser Cys Thr Ala Ser Gly Phe Thr Phe Ser Thr Tyr
            20                  25                  30

Asn Met Asn Trp Val Arg Gln Ala Pro Gly Lys Gly Leu Glu Trp Val
        35                  40                  45

Ser Ser Ile Arg Ser Ser Ser Asn Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Asp Gly Ser Ser Trp Tyr Asp Tyr Ser Asp Tyr Trp Gly Gln
            100                 105                 110

Gly Thr Leu Val Thr Val Ser Ser
        115                 120
```

<210> SEQ ID NO 475
<211> LENGTH: 321
<212> TYPE: DNA
<213> ORGANISM: Artificial Sequence
<220> FEATURE:
<223> OTHER INFORMATION: Synthetic

<400> SEQUENCE: 475

```
gacatccaga tgacccagtc tccttccacc ctgtctgcat ctgtaggaga cagagtcacc      60

atcacttgcc gggccagtca gagtattagt agctggttgg cctggtatca acagatacca     120

gggaaagccc ctaaactcct gatctataag gcgtctagtt tagaaaatgg ggtcccatca     180

aggttcagcg gcagtggatc tgggacagaa ttcactctca tcatcagcag cctgcagcct     240

gatgattttg caacttatta ctgccaacag tatattagtt attctcggac gttcggccaa     300

gggaccaagg tggaaatcaa a                                               321
```

<210> SEQ ID NO 476
<211> LENGTH: 107
<212> TYPE: PRT
<213> ORGANISM: Artificial Sequence
<220> FEATURE:
<223> OTHER INFORMATION: Synthetic

<400> SEQUENCE: 476

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Ile Pro Gly Lys Ala Pro Lys Leu Leu Ile
        35                  40                  45

Tyr Lys Ala Ser Ser Leu Glu Asn Gly Val Pro Ser Arg Phe Ser Gly
    50                  55                  60

Ser Gly Ser Gly Thr Glu Phe Thr Leu Ile Ile Ser Ser Leu Gln Pro
65                  70                  75                  80
```

```
Asp Asp Phe Ala Thr Tyr Tyr Cys Gln Gln Tyr Ile Ser Tyr Ser Arg
                85                  90                  95

Thr Phe Gly Gln Gly Thr Lys Val Glu Ile Lys
            100                 105
```

<210> SEQ ID NO 477
<211> LENGTH: 360
<212> TYPE: DNA
<213> ORGANISM: Artificial Sequence
<220> FEATURE:
<223> OTHER INFORMATION: Synthetic

<400> SEQUENCE: 477

```
gaggtgcagc tggtggagtc tgggggaggc ctggtcaagc ctggggggtc cctgagactc      60

tcctgtgcag cctctggatt caccttcagt acttataaca tgaactgggt ccgccaggct     120

ccagggaagg ggctggagtg ggtctcatcc attaggagta gtagtaatta catatactac     180

gcagactcag tgaagggccg attcaccatc tccagagaca acgccaagaa ctcactgtat     240

ctgcaaatga acagcctgag agccgaggac acggctgtgt attactgtgc gagagatggc     300

agcagttggt acgactactc tgactactgg ggccaaggaa ccctggtcac cgtctcctca     360
```

<210> SEQ ID NO 478
<211> LENGTH: 120
<212> TYPE: PRT
<213> ORGANISM: Artificial Sequence
<220> FEATURE:
<223> OTHER INFORMATION: Synthetic

<400> SEQUENCE: 478

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Asn Met Asn Trp Val Arg Gln Ala Pro Gly Lys Gly Leu Glu Trp Val
        35                  40                  45

Ser Ser Ile Arg Ser Ser Ser Asn Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Ser Trp Tyr Asp Tyr Ser Asp Tyr Trp Gly Gln
            100                 105                 110

Gly Thr Leu Val Thr Val Ser Ser
        115                 120
```

<210> SEQ ID NO 479
<211> LENGTH: 321
<212> TYPE: DNA
<213> ORGANISM: Artificial Sequence
<220> FEATURE:
<223> OTHER INFORMATION: Synthetic

<400> SEQUENCE: 479

```
gacatccaga tgacccagtc tccttccacc ctgtctgcat ctgtaggaga cagagtcacc      60

atcacttgcc gggccagtca gagtattagt agctggttgg cctggtatca gcagaaacca     120

gggaaagccc ctaagctcct gatctataag gcgtctagtt tagaaagtgg ggtcccatca     180

aggttcagcg gcagtggatc tgggacagaa ttcactctca ccatcagcag cctgcagcct     240
```

gatgattttg caacttatta ctgccaacag tatattagtt attctcggac gttcggccaa 300
gggaccaagg tggaaatcaa a 321

<210> SEQ ID NO 480
<211> LENGTH: 107
<212> TYPE: PRT
<213> ORGANISM: Artificial Sequence
<220> FEATURE:
<223> OTHER INFORMATION: Synthetic

<400> SEQUENCE: 480

Asp Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Ser Ser Trp
20 25 30

Leu Ala Trp Tyr Gln Gln Lys Pro Gly Lys Ala Pro Lys Leu Leu Ile
35 40 45

Tyr Lys Ala Ser Ser Leu Glu Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Tyr Ile Ser Tyr Ser Arg
85 90 95

Thr Phe Gly Gln Gly Thr Lys Val Glu Ile Lys
100 105

<210> SEQ ID NO 481
<211> LENGTH: 354
<212> TYPE: DNA
<213> ORGANISM: Artificial Sequence
<220> FEATURE:
<223> OTHER INFORMATION: Synthetic

<400> SEQUENCE: 481
gaggtgcaac tagtggagtc tgggggaggc ttggtacagc ctggggggtc cctgagactc 60
tcctgtgtag tctctggatt caccttcggt gactacgaca tgcactgggt ccgtcaagct 120
acaggaagag gtctggagtg ggtctcaggt attgctcctg ctggtgacac atcctataca 180
ggctccgtga agggccgatt caccatctcc agagagaatg ccaagaactc cttgcatctt 240
caaatgaaca gcctgacaac cggggacacg gctatatatt attgtgctag agaggatata 300
gcagtgcctg gttttgatta ctggggccag ggaaccctgg tcaccgtctc ctca 354

<210> SEQ ID NO 482
<211> LENGTH: 118
<212> TYPE: PRT
<213> ORGANISM: Artificial Sequence
<220> FEATURE:
<223> OTHER INFORMATION: Synthetic

<400> SEQUENCE: 482

Glu Val Gln Leu Val Glu Ser Gly Gly Gly Leu Val Gln Pro Gly Gly
1 5 10 15

Ser Leu Arg Leu Ser Cys Val Val Ser Gly Phe Thr Phe Gly Asp Tyr
20 25 30

Asp Met His Trp Val Arg Gln Ala Thr Gly Arg Gly Leu Glu Trp Val
35 40 45

Ser Gly Ile Ala Pro Ala Gly Asp Thr Ser Tyr Thr Gly Ser Val Lys
50 55 60

```
Gly Arg Phe Thr Ile Ser Arg Glu Asn Ala Lys Asn Ser Leu His Leu
65                  70                  75                  80

Gln Met Asn Ser Leu Thr Thr Gly Asp Thr Ala Ile Tyr Tyr Cys Ala
                85                  90                  95

Arg Glu Asp Ile Ala Val Pro Gly Phe Asp Tyr Trp Gly Gln Gly Thr
            100                 105                 110

Leu Val Thr Val Ser Ser
        115
```

<210> SEQ ID NO 483
<211> LENGTH: 24
<212> TYPE: DNA
<213> ORGANISM: Artificial Sequence
<220> FEATURE:
<223> OTHER INFORMATION: Synthetic

<400> SEQUENCE: 483
ggattcacct tcggtgacta cgac 24

<210> SEQ ID NO 484
<211> LENGTH: 8
<212> TYPE: PRT
<213> ORGANISM: Artificial Sequence
<220> FEATURE:
<223> OTHER INFORMATION: Synthetic

<400> SEQUENCE: 484

```
Gly Phe Thr Phe Gly Asp Tyr Asp
1               5
```

<210> SEQ ID NO 485
<211> LENGTH: 21
<212> TYPE: DNA
<213> ORGANISM: Artificial Sequence
<220> FEATURE:
<223> OTHER INFORMATION: Synthetic

<400> SEQUENCE: 485
attgctcctg ctggtgacac a 21

<210> SEQ ID NO 486
<211> LENGTH: 7
<212> TYPE: PRT
<213> ORGANISM: Artificial Sequence
<220> FEATURE:
<223> OTHER INFORMATION: Synthetic

<400> SEQUENCE: 486

```
Ile Ala Pro Ala Gly Asp Thr
1               5
```

<210> SEQ ID NO 487
<211> LENGTH: 36
<212> TYPE: DNA
<213> ORGANISM: Artificial Sequence
<220> FEATURE:
<223> OTHER INFORMATION: Synthetic

<400> SEQUENCE: 487
gctagagagg atatagcagt gcctggtttt gattac 36

<210> SEQ ID NO 488
<211> LENGTH: 12
<212> TYPE: PRT

<213> ORGANISM: Artificial Sequence
<220> FEATURE:
<223> OTHER INFORMATION: Synthetic

<400> SEQUENCE: 488

Ala Arg Glu Asp Ile Ala Val Pro Gly Phe Asp Tyr
1 5 10

<210> SEQ ID NO 489
<211> LENGTH: 324
<212> TYPE: DNA
<213> ORGANISM: Artificial Sequence
<220> FEATURE:
<223> OTHER INFORMATION: Synthetic

<400> SEQUENCE: 489
gaaatagtga tgacgcagtc tccagccacc ctgtctgtgt ctccagggga acgaggcacc 60
ctctcctgca gggccagtca gagtgttagc agcaacttag cctggtacca gcagaaacct 120
ggccaggctc ccagactcct catctatggt gcatccacga gggccactgg cttcccagcc 180
aggttcagtg gcagtgggtc tgggacagag ttcactctca ccatcagcag cctgcagtct 240
gaagattttg cagtttatta ctgtcagcag tataataagt ggcctccgtt cactttcggc 300
cctgggacca aagtggattt caaa 324

<210> SEQ ID NO 490
<211> LENGTH: 108
<212> TYPE: PRT
<213> ORGANISM: Artificial Sequence
<220> FEATURE:
<223> OTHER INFORMATION: Synthetic

<400> SEQUENCE: 490

Glu Ile Val Met Thr Gln Ser Pro Ala Thr Leu Ser Val Ser Pro Gly
1 5 10 15

Glu Arg Gly Thr Leu Ser Cys Arg Ala Ser Gln Ser Val Ser Ser Asn
20 25 30

Leu Ala Trp Tyr Gln Gln Lys Pro Gly Gln Ala Pro Arg Leu Leu Ile
35 40 45

Tyr Gly Ala Ser Thr Arg Ala Thr Gly Phe Pro Ala Arg Phe Ser Gly
50 55 60

Ser Gly Ser Gly Thr Glu Phe Thr Leu Thr Ile Ser Ser Leu Gln Ser
65 70 75 80

Glu Asp Phe Ala Val Tyr Tyr Cys Gln Gln Tyr Asn Lys Trp Pro Pro
85 90 95

Phe Thr Phe Gly Pro Gly Thr Lys Val Asp Phe Lys
100 105

<210> SEQ ID NO 491
<211> LENGTH: 18
<212> TYPE: DNA
<213> ORGANISM: Artificial Sequence
<220> FEATURE:
<223> OTHER INFORMATION: Synthetic

<400> SEQUENCE: 491
cagagtgtta gcagcaac 18

<210> SEQ ID NO 492
<211> LENGTH: 6
<212> TYPE: PRT
<213> ORGANISM: Artificial Sequence
<220> FEATURE:
<223> OTHER INFORMATION: Synthetic

<400> SEQUENCE: 492

Gln Ser Val Ser Ser Asn
1               5

<210> SEQ ID NO 493
<211> LENGTH: 9
<212> TYPE: DNA
<213> ORGANISM: Artificial Sequence
<220> FEATURE:
<223> OTHER INFORMATION: Synthetic

<400> SEQUENCE: 493 ggtgcatcc                                                                   9

<210> SEQ ID NO 494
<211> LENGTH: 3
<212> TYPE: PRT
<213> ORGANISM: Artificial Sequence
<220> FEATURE:
<223> OTHER INFORMATION: Synthetic

<400> SEQUENCE: 494

Gly Ala Ser
1

<210> SEQ ID NO 495
<211> LENGTH: 30
<212> TYPE: DNA
<213> ORGANISM: Artificial Sequence
<220> FEATURE:
<223> OTHER INFORMATION: Synthetic

<400> SEQUENCE: 495
cagcagtata ataagtggcc tccgttcact                                           30

<210> SEQ ID NO 496
<211> LENGTH: 10
<212> TYPE: PRT
<213> ORGANISM: Artificial Sequence
<220> FEATURE:
<223> OTHER INFORMATION: Synthetic

<400> SEQUENCE: 496

Gln Gln Tyr Asn Lys Trp Pro Pro Phe Thr
1               5                   10

<210> SEQ ID NO 497
<211> LENGTH: 354
<212> TYPE: DNA
<213> ORGANISM: Artificial Sequence
<220> FEATURE:
<223> OTHER INFORMATION: Synthetic

<400> SEQUENCE: 497
gaggtgcaac tagtggagtc tgggggaggc ttggtacagc ctggggggtc cctgagactc          60
tcctgtgtag tctctggatt caccttcggt gactacgaca tgcactgggt ccgtcaagct         120
acaggaagag gtctggagtg ggtctcaggt attgctcctg ctggtgacac atcctataca         180
ggctccgtga agggccgatt caccatctcc agagagaatg ccaagaactc cttgcatctt         240
caaatgaaca gcctgacaac cggggacacg gctatatatt attgtgctag agaggatata         300
gcagtgcctg gttttgatta ctggggccag ggaaccctgg tcaccgtctc ctca               354

<210> SEQ ID NO 498
<211> LENGTH: 118
<212> TYPE: PRT
<213> ORGANISM: Artificial Sequence
<220> FEATURE:
<223> OTHER INFORMATION: Synthetic

<400> SEQUENCE: 498

Glu Val Gln Leu Val Glu Ser Gly Gly Gly Leu Val Gln Pro Gly Gly
1               5                   10                  15

Ser Leu Arg Leu Ser Cys Val Val Ser Gly Phe Thr Phe Gly Asp Tyr
            20                  25                  30

Asp Met His Trp Val Arg Gln Ala Thr Gly Arg Gly Leu Glu Trp Val
        35                  40                  45

Ser Gly Ile Ala Pro Ala Gly Asp Thr Ser Tyr Thr Gly Ser Val Lys
    50                  55                  60

Gly Arg Phe Thr Ile Ser Arg Glu Asn Ala Lys Asn Ser Leu His Leu
65                  70                  75                  80

Gln Met Asn Ser Leu Thr Thr Gly Asp Thr Ala Ile Tyr Tyr Cys Ala
                85                  90                  95

Arg Glu Asp Ile Ala Val Pro Gly Phe Asp Tyr Trp Gly Gln Gly Thr
            100                 105                 110

Leu Val Thr Val Ser Ser
        115

<210> SEQ ID NO 499
<211> LENGTH: 324
<212> TYPE: DNA
<213> ORGANISM: Artificial Sequence
<220> FEATURE:
<223> OTHER INFORMATION: Synthetic

<400> SEQUENCE: 499
gaaatagtga tgacgcagtc tccagccacc ctgtctgtgt ctccagggga acgaggcacc 60
ctctcctgca gggccagtca gagtgttagc agcaacttag cctggtacca gcagaaacct 120
ggccaggctc ccagactcct catctatggt gcatccacga gggccactgg cttcccagcc 180
aggttcagtg gcagtgggtc tgggacagag ttcactctca ccatcagcag cctgcagtct 240
gaagattttg cagtttatta ctgtcagcag tataataagt ggcctccgtt cactttcggc 300
cctgggacca aagtggatat caaa 324

<210> SEQ ID NO 500
<211> LENGTH: 108
<212> TYPE: PRT
<213> ORGANISM: Artificial Sequence
<220> FEATURE:
<223> OTHER INFORMATION: Synthetic

<400> SEQUENCE: 500

Glu Ile Val Met Thr Gln Ser Pro Ala Thr Leu Ser Val Ser Pro Gly
1               5                   10                  15

Glu Arg Gly Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Phe Pro Ala Arg Phe Ser Gly
    50                  55                  60

```
Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Lys Trp Pro Pro
                85                  90                  95

Phe Thr Phe Gly Pro Gly Thr Lys Val Asp Ile Lys
            100                 105


<210> SEQ ID NO 501
<211> LENGTH: 354
<212> TYPE: DNA
<213> ORGANISM: Artificial Sequence
<220> FEATURE:
<223> OTHER INFORMATION: Synthetic

<400> SEQUENCE: 501

gaggtgcagc tggtggagtc tgggggaggc ttggtacagc ctggggggtc cctgagactc      60

tcctgtgcag cctctggatt caccttcggt gactacgaca tgcactgggt ccgccaagct     120

acaggaaaag gtctggagtg ggtctcagct attgctcctg ctggtgacac atactatcca     180

ggctccgtga agggccgatt caccatctcc agagaaaatg ccaagaactc cttgtatctt     240

caaatgaaca gcctgagagc cggggacacg gctgtgtatt actgtgctag agaggatata     300

gcagtgcctg gttttgatta ctggggccaa ggaaccctgg tcaccgtctc ctca           354


<210> SEQ ID NO 502
<211> LENGTH: 118
<212> TYPE: PRT
<213> ORGANISM: Artificial Sequence
<220> FEATURE:
<223> OTHER INFORMATION: Synthetic

<400> SEQUENCE: 502

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Asp Tyr
            20                  25                  30

Asp Met His Trp Val Arg Gln Ala Thr Gly Lys Gly Leu Glu Trp Val
        35                  40                  45

Ser Ala Ile Ala Pro Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Glu Asp Ile Ala Val Pro Gly Phe Asp Tyr Trp Gly Gln Gly Thr
            100                 105                 110

Leu Val Thr Val Ser Ser
        115


<210> SEQ ID NO 503
<211> LENGTH: 324
<212> TYPE: DNA
<213> ORGANISM: Artificial Sequence
<220> FEATURE:
<223> OTHER INFORMATION: Synthetic

<400> SEQUENCE: 503

gaaatagtga tgacgcagtc tccagccacc ctgtctgtgt ctccagggga aagagccacc      60

ctctcctgca gggccagtca gagtgttagc agcaacttag cctggtacca gcagaaacct     120
```

-continued

```
ggccaggctc ccaggctcct catctatggt gcatccacca gggccactgg tatcccagcc    180

aggttcagtg gcagtgggtc tgggacagag ttcactctca ccatcagcag cctgcagtct    240

gaagattttg cagtttatta ctgtcagcag tataataagt ggcctccgtt cactttcggc    300

cctgggacca aagtggatat caaa                                           324


<210> SEQ ID NO 504
<211> LENGTH: 108
<212> TYPE: PRT
<213> ORGANISM: Artificial Sequence
<220> FEATURE:
<223> OTHER INFORMATION: Synthetic

<400> SEQUENCE: 504

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Lys Trp Pro Pro
                85                  90                  95

Phe Thr Phe Gly Pro Gly Thr Lys Val Asp Ile Lys
            100                 105


<210> SEQ ID NO 505
<211> LENGTH: 378
<212> TYPE: DNA
<213> ORGANISM: Artificial Sequence
<220> FEATURE:
<223> OTHER INFORMATION: Synthetic

<400> SEQUENCE: 505

caaattctgc tggtgcaatc tggacctgag gtgaaggagc ctggggcctc agtgaaggtc     60

tcctgcaagg cttctggtta cacctttacc aactacgcta tcagctgggt gcgacaggtc    120

cctggacaag ggcttgagtg gatgggatgg gtcagcgctt acaatggtca cacaaactat    180

gcacatgaag tccagggcag agtcaccatg accacagaca catccacgac cacagcctac    240

atggagctga ggagcctgag atctgacgac acggccatgt attactgtgc gagagggggt    300

gtagtcgtgc cagttgctcc ccacttctac aacggtatgg acgtctgggg ccaagggacc    360

acggtcaccg tctcctca                                                  378


<210> SEQ ID NO 506
<211> LENGTH: 126
<212> TYPE: PRT
<213> ORGANISM: Artificial Sequence
<220> FEATURE:
<223> OTHER INFORMATION: Synthetic

<400> SEQUENCE: 506

Gln Ile Leu Leu Val Gln Ser Gly Pro Glu Val Lys Glu Pro Gly Ala
1               5                   10                  15

Ser Val Lys Val Ser Cys Lys Ala Ser Gly Tyr Thr Phe Thr Asn Tyr
            20                  25                  30
```

```
Ala Ile Ser Trp Val Arg Gln Val Pro Gly Gln Gly Leu Glu Trp Met
        35                  40                  45

Gly Trp Val Ser Ala Tyr Asn Gly His Thr Asn Tyr Ala His Glu Val
    50                  55                  60

Gln Gly Arg Val Thr Met Thr Thr Asp Thr Ser Thr Thr Thr Ala Tyr
65                  70                  75                  80

Met Glu Leu Arg Ser Leu Arg Ser Asp Asp Thr Ala Met Tyr Tyr Cys
                85                  90                  95

Ala Arg Gly Gly Val Val Val Pro Val Ala Pro His Phe Tyr Asn Gly
            100                 105                 110

Met Asp Val Trp Gly Gln Gly Thr Thr Val Thr Val Ser Ser
        115                 120                 125


<210> SEQ ID NO 507
<211> LENGTH: 24
<212> TYPE: DNA
<213> ORGANISM: Artificial Sequence
<220> FEATURE:
<223> OTHER INFORMATION: Synthetic

<400> SEQUENCE: 507

ggttacacct ttaccaacta cgct                                            24


<210> SEQ ID NO 508
<211> LENGTH: 8
<212> TYPE: PRT
<213> ORGANISM: Artificial Sequence
<220> FEATURE:
<223> OTHER INFORMATION: Synthetic

<400> SEQUENCE: 508

Gly Tyr Thr Phe Thr Asn Tyr Ala
1               5


<210> SEQ ID NO 509
<211> LENGTH: 24
<212> TYPE: DNA
<213> ORGANISM: Artificial Sequence
<220> FEATURE:
<223> OTHER INFORMATION: Synthetic

<400> SEQUENCE: 509

gtcagcgctt acaatggtca caca                                            24


<210> SEQ ID NO 510
<211> LENGTH: 8
<212> TYPE: PRT
<213> ORGANISM: Artificial Sequence
<220> FEATURE:
<223> OTHER INFORMATION: Synthetic

<400> SEQUENCE: 510

Val Ser Ala Tyr Asn Gly His Thr
1               5


<210> SEQ ID NO 511
<211> LENGTH: 57
<212> TYPE: DNA
<213> ORGANISM: Artificial Sequence
<220> FEATURE:
<223> OTHER INFORMATION: Synthetic

<400> SEQUENCE: 511

gcgagagggg gtgtagtcgt gccagttgct ccccacttct acaacggtat ggacgtc        57
```

<210> SEQ ID NO 512
<211> LENGTH: 19
<212> TYPE: PRT
<213> ORGANISM: Artificial Sequence
<220> FEATURE:
<223> OTHER INFORMATION: Synthetic

<400> SEQUENCE: 512

Ala Arg Gly Gly Val Val Val Pro Val Ala Pro His Phe Tyr Asn Gly
1 5 10 15

Met Asp Val

<210> SEQ ID NO 513
<211> LENGTH: 336
<212> TYPE: DNA
<213> ORGANISM: Artificial Sequence
<220> FEATURE:
<223> OTHER INFORMATION: Synthetic

<400> SEQUENCE: 513
gatattgtga tgactcagtt tccactctcc ctgcccgtca cccctggaga gccggcctcc 60
atctcctgca ggtctagtca gagcctcctg catattaatg aatacaacta tttggattgg 120
tacctaaaga agccagggca gtctccacag ctcctgatct atttgggttt taatcgggcc 180
tccggggtcc ctgacaggtt cagtggcagt ggatcaggca cagattttac actgaaaatc 240
agcagagtgg aggctgagga tgttggggtc tattactgca tgcaagctct tcaaactccg 300
tggacgttag gccaagggac caaggtggaa atcaaa 336

<210> SEQ ID NO 514
<211> LENGTH: 112
<212> TYPE: PRT
<213> ORGANISM: Artificial Sequence
<220> FEATURE:
<223> OTHER INFORMATION: Synthetic

<400> SEQUENCE: 514

Asp Ile Val Met Thr Gln Phe Pro Leu Ser Leu Pro Val Thr Pro Gly
1 5 10 15

Glu Pro Ala Ser Ile Ser Cys Arg Ser Ser Gln Ser Leu Leu His Ile
20 25 30

Asn Glu Tyr Asn Tyr Leu Asp Trp Tyr Leu Lys Lys Pro Gly Gln Ser
35 40 45

Pro Gln Leu Leu Ile Tyr Leu Gly Phe Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Ala
85 90 95

Leu Gln Thr Pro Trp Thr Leu Gly Gln Gly Thr Lys Val Glu Ile Lys
100 105 110

<210> SEQ ID NO 515
<211> LENGTH: 33
<212> TYPE: DNA
<213> ORGANISM: Artificial Sequence
<220> FEATURE:
<223> OTHER INFORMATION: Synthetic

<400> SEQUENCE: 515
cagagcctcc tgcatattaa tgaatacaac tat 33

<210> SEQ ID NO 516
<211> LENGTH: 11
<212> TYPE: PRT
<213> ORGANISM: Artificial Sequence
<220> FEATURE:
<223> OTHER INFORMATION: Synthetic

<400> SEQUENCE: 516

Gln Ser Leu Leu His Ile Asn Glu Tyr Asn Tyr
1 5 10

<210> SEQ ID NO 517
<211> LENGTH: 9
<212> TYPE: DNA
<213> ORGANISM: Artificial Sequence
<220> FEATURE:
<223> OTHER INFORMATION: Synthetic

<400> SEQUENCE: 517 ttgggtttt 9

<210> SEQ ID NO 518
<211> LENGTH: 3
<212> TYPE: PRT
<213> ORGANISM: Artificial Sequence
<220> FEATURE:
<223> OTHER INFORMATION: Synthetic

<400> SEQUENCE: 518

Leu Gly Phe
1

<210> SEQ ID NO 519
<211> LENGTH: 27
<212> TYPE: DNA
<213> ORGANISM: Artificial Sequence
<220> FEATURE:
<223> OTHER INFORMATION: Synthetic

<400> SEQUENCE: 519
atgcaagctc ttcaaactcc gtggacg 27

<210> SEQ ID NO 520
<211> LENGTH: 9
<212> TYPE: PRT
<213> ORGANISM: Artificial Sequence
<220> FEATURE:
<223> OTHER INFORMATION: Synthetic

<400> SEQUENCE: 520

Met Gln Ala Leu Gln Thr Pro Trp Thr
1 5

<210> SEQ ID NO 521
<211> LENGTH: 378
<212> TYPE: DNA
<213> ORGANISM: Artificial Sequence
<220> FEATURE:
<223> OTHER INFORMATION: Synthetic

<400> SEQUENCE: 521
caggttcagc tggtgcagtc tggacctgag gtgaaggagc ctggggcctc agtgaaggtc 60
tcctgcaagg cttctggtta cacctttacc aactacgcta tcagctgggt gcgacaggtc 120
cctggacaag ggcttgagtg gatgggatgg gtcagcgctt acaatggtca cacaaactat 180
gcacatgaag tccagggcag agtcaccatg accacagaca catccacgac cacagcctac 240
atggagctga ggagcctgag atctgacgac acggccatgt attactgtgc gagagggggt 300
gtagtcgtgc cagttgctcc ccacttctac aacggtatgg acgtctgggg ccaagggacc 360
acggtcaccg tctcctca 378

<210> SEQ ID NO 522
<211> LENGTH: 126
<212> TYPE: PRT
<213> ORGANISM: Artificial Sequence
<220> FEATURE:
<223> OTHER INFORMATION: Synthetic

<400> SEQUENCE: 522

Gln Val Gln Leu Val Gln Ser Gly Pro Glu Val Lys Glu Pro Gly Ala
1               5                   10                  15

Ser Val Lys Val Ser Cys Lys Ala Ser Gly Tyr Thr Phe Thr Asn Tyr
            20                  25                  30

Ala Ile Ser Trp Val Arg Gln Val Pro Gly Gln Gly Leu Glu Trp Met
        35                  40                  45

Gly Trp Val Ser Ala Tyr Asn Gly His Thr Asn Tyr Ala His Glu Val
    50                  55                  60

Gln Gly Arg Val Thr Met Thr Thr Asp Thr Ser Thr Thr Thr Ala Tyr
65                  70                  75                  80

Met Glu Leu Arg Ser Leu Arg Ser Asp Asp Thr Ala Met Tyr Tyr Cys
                85                  90                  95

Ala Arg Gly Gly Val Val Val Pro Val Ala Pro His Phe Tyr Asn Gly
            100                 105                 110

Met Asp Val Trp Gly Gln Gly Thr Thr Val Thr Val Ser Ser
        115                 120                 125

<210> SEQ ID NO 523
<211> LENGTH: 336
<212> TYPE: DNA
<213> ORGANISM: Artificial Sequence
<220> FEATURE:
<223> OTHER INFORMATION: Synthetic

<400> SEQUENCE: 523
gatattgtga tgactcagtc tccactctcc ctgcccgtca cccctggaga gccggcctcc 60
atctcctgca ggtctagtca gagcctcctg catattaatg aatacaacta tttggattgg 120
tacctaaaga agccagggca gtctccacag ctcctgatct atttgggttt taatcgggcc 180
tccggggtcc ctgacaggtt cagtggcagt ggatcaggca cagattttac actgaaaatc 240
agcagagtgg aggctgagga tgttggggtc tattactgca tgcaagctct tcaaactccg 300
tggacgttag gccaagggac caaggtggaa atcaaa 336

<210> SEQ ID NO 524
<211> LENGTH: 112
<212> TYPE: PRT
<213> ORGANISM: Artificial Sequence
<220> FEATURE:
<223> OTHER INFORMATION: Synthetic

<400> SEQUENCE: 524

Asp Ile Val Met Thr Gln Ser Pro Leu Ser Leu Pro Val Thr Pro Gly
1               5                   10                  15

-continued

```
Glu Pro Ala Ser Ile Ser Cys Arg Ser Ser Gln Ser Leu Leu His Ile
            20                  25                  30

Asn Glu Tyr Asn Tyr Leu Asp Trp Tyr Leu Lys Lys Pro Gly Gln Ser
        35                  40                  45

Pro Gln Leu Leu Ile Tyr Leu Gly Phe Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Leu Gly Gln Gly Thr Lys Val Glu Ile Lys
            100                 105                 110
```

<210> SEQ ID NO 525
<211> LENGTH: 378
<212> TYPE: DNA
<213> ORGANISM: Artificial Sequence
<220> FEATURE:
<223> OTHER INFORMATION: Synthetic

<400> SEQUENCE: 525

```
caggttcagc tggtgcagtc tggagctgag gtgaagaagc ctggggcctc agtgaaggtc      60

tcctgcaagg cttctggtta cacctttacc aactacgcta tcagctgggt gcgacaggcc     120

cctggacaag ggcttgagtg gatgggatgg gtcagcgctt acaatggtca cacaaactat     180

gcacagaagc tccagggcag agtcaccatg accacagaca catccacgag cacagcctac     240

atggagctga ggagcctgag atctgacgac acggccgtgt attactgtgc gagagggggt     300

gtagtcgtgc cagttgctcc ccacttctac aacggtatgg acgtctgggg gcaagggacc     360

acggtcaccg tctcctca                                                   378
```

<210> SEQ ID NO 526
<211> LENGTH: 126
<212> TYPE: PRT
<213> ORGANISM: Artificial Sequence
<220> FEATURE:
<223> OTHER INFORMATION: Synthetic

<400> SEQUENCE: 526

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Ala Ile Ser Trp Val Arg Gln Ala Pro Gly Gln Gly Leu Glu Trp Met
        35                  40                  45

Gly Trp Val Ser Ala Tyr Asn Gly His Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Val Val Val Pro Val Ala Pro His Phe Tyr Asn Gly
            100                 105                 110

Met Asp Val Trp Gly Gln Gly Thr Thr Val Thr Val Ser Ser
        115                 120                 125
```

<210> SEQ ID NO 527
<211> LENGTH: 336

<212> TYPE: DNA
<213> ORGANISM: Artificial Sequence
<220> FEATURE:
<223> OTHER INFORMATION: Synthetic

<400> SEQUENCE: 527
gatattgtga tgactcagtc tccactctcc ctgcccgtca cccctggaga gccggcctcc 60
atctcctgca ggtctagtca gagcctcctg catattaatg aatacaacta tttggattgg 120
tacctgcaga agccagggca gtctccacag ctcctgatct atttgggttc taatcgggcc 180
tccggggtcc ctgacaggtt cagtggcagt ggatcaggca cagattttac actgaaaatc 240
agcagagtgg aggctgagga tgttggggtt tattactgca tgcaagctct tcaaactccg 300
tggacgttcg gccaagggac caaggtggaa atcaaa 336

<210> SEQ ID NO 528
<211> LENGTH: 112
<212> TYPE: PRT
<213> ORGANISM: Artificial Sequence
<220> FEATURE:
<223> OTHER INFORMATION: Synthetic

<400> SEQUENCE: 528

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ile
20 25 30

Asn Glu Tyr Asn Tyr Leu Asp Trp Tyr Leu Gln Lys Pro Gly Gln Ser
35 40 45

Pro Gln Leu Leu Ile Tyr Leu Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Ala
85 90 95

Leu Gln Thr Pro Trp Thr Phe Gly Gln Gly Thr Lys Val Glu Ile Lys
100 105 110

<210> SEQ ID NO 529
<211> LENGTH: 351
<212> TYPE: DNA
<213> ORGANISM: Artificial Sequence
<220> FEATURE:
<223> OTHER INFORMATION: Synthetic

<400> SEQUENCE: 529
gaggtgcagc tggtggagtc tgggggaggc ttggtacagc ctggggggtc cctgagactc 60
tcctgtgcag cctctggatt caccctaagt agctacgaca tgcactgggt ccgccaagca 120
acaggaaaag gtctggagtg ggtctcagct attggcagta ctggtgacac atactataca 180
ggctccgtga tgggccgatt caccatctcc agagacgctg ccaaaaactc cttctatctt 240
gaaatgaaca gcctgagagt cggggacacg gctgtatatt actgtgcaag agagggaata 300
agaacaccct atgattattg gggccaggga gcccgggtca ccgtctcctc a 351

<210> SEQ ID NO 530
<211> LENGTH: 117
<212> TYPE: PRT
<213> ORGANISM: Artificial Sequence
<220> FEATURE:
<223> OTHER INFORMATION: Synthetic

<400> SEQUENCE: 530

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Leu Ser Ser Tyr
20 25 30

Asp Met His Trp Val Arg Gln Ala Thr Gly Lys Gly Leu Glu Trp Val
35 40 45

Ser Ala Ile Gly Ser Thr Gly Asp Thr Tyr Tyr Thr Gly Ser Val Met
50 55 60

Gly Arg Phe Thr Ile Ser Arg Asp Ala Ala Lys Asn Ser Phe Tyr Leu
65 70 75 80

Glu Met Asn Ser Leu Arg Val Gly Asp Thr Ala Val Tyr Tyr Cys Ala
85 90 95

Arg Glu Gly Ile Arg Thr Pro Tyr Asp Tyr Trp Gly Gln Gly Ala Arg
100 105 110

Val Thr Val Ser Ser
115

<210> SEQ ID NO 531
<211> LENGTH: 24
<212> TYPE: DNA
<213> ORGANISM: Artificial Sequence
<220> FEATURE:
<223> OTHER INFORMATION: Synthetic

<400> SEQUENCE: 531
ggattcaccc taagtagcta cgac 24

<210> SEQ ID NO 532
<211> LENGTH: 8
<212> TYPE: PRT
<213> ORGANISM: Artificial Sequence
<220> FEATURE:
<223> OTHER INFORMATION: Synthetic

<400> SEQUENCE: 532

Gly Phe Thr Leu Ser Ser Tyr Asp
1 5

<210> SEQ ID NO 533
<211> LENGTH: 21
<212> TYPE: DNA
<213> ORGANISM: Artificial Sequence
<220> FEATURE:
<223> OTHER INFORMATION: Synthetic

<400> SEQUENCE: 533
attggcagta ctggtgacac a 21

<210> SEQ ID NO 534
<211> LENGTH: 7
<212> TYPE: PRT
<213> ORGANISM: Artificial Sequence
<220> FEATURE:
<223> OTHER INFORMATION: Synthetic

<400> SEQUENCE: 534

Ile Gly Ser Thr Gly Asp Thr
1 5

<210> SEQ ID NO 535

<211> LENGTH: 33
<212> TYPE: DNA
<213> ORGANISM: Artificial Sequence
<220> FEATURE:
<223> OTHER INFORMATION: Synthetic

<400> SEQUENCE: 535
gcaagagagg gaataagaac accctatgat tat 33

<210> SEQ ID NO 536
<211> LENGTH: 11
<212> TYPE: PRT
<213> ORGANISM: Artificial Sequence
<220> FEATURE:
<223> OTHER INFORMATION: Synthetic

<400> SEQUENCE: 536

Ala Arg Glu Gly Ile Arg Thr Pro Tyr Asp Tyr
1               5                   10

<210> SEQ ID NO 537
<211> LENGTH: 324
<212> TYPE: DNA
<213> ORGANISM: Artificial Sequence
<220> FEATURE:
<223> OTHER INFORMATION: Synthetic

<400> SEQUENCE: 537
gaaatagtga tgacgcagtc tccagccacc ctgtctgtgt ctccagggga aagagccacc 60
ctctcctgca gggccagtca gagtgttagc agcaatgtag cctggtacca gcagaaacct 120
ggccaggctc ccaggctcct catctatggt gcatccacca gggccactgg tatcccagcc 180
aggttcagtg gcagtgggtc tgggacagaa ttcactctca ccatcagcag cctgcagtct 240
gaagattttg cagtttatta ctgtcagcag tataataatt ggcctccatt cactttcggc 300
cctgggacca aagtggatat caaa 324

<210> SEQ ID NO 538
<211> LENGTH: 108
<212> TYPE: PRT
<213> ORGANISM: Artificial Sequence
<220> FEATURE:
<223> OTHER INFORMATION: Synthetic

<400> SEQUENCE: 538

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Val Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Phe Thr Phe Gly Pro Gly Thr Lys Val Asp Ile Lys
            100                 105

<210> SEQ ID NO 539
<211> LENGTH: 18

<212> TYPE: DNA
<213> ORGANISM: Artificial Sequence
<220> FEATURE:
<223> OTHER INFORMATION: Synthetic

<400> SEQUENCE: 539
cagagtgtta gcagcaat 18

<210> SEQ ID NO 540
<211> LENGTH: 6
<212> TYPE: PRT
<213> ORGANISM: Artificial Sequence
<220> FEATURE:
<223> OTHER INFORMATION: Synthetic

<400> SEQUENCE: 540

Gln Ser Val Ser Ser Asn
1 5

<210> SEQ ID NO 541
<211> LENGTH: 9
<212> TYPE: DNA
<213> ORGANISM: Artificial Sequence
<220> FEATURE:
<223> OTHER INFORMATION: Synthetic

<400> SEQUENCE: 541 ggtgcatcc 9

<210> SEQ ID NO 542
<211> LENGTH: 3
<212> TYPE: PRT
<213> ORGANISM: Artificial Sequence
<220> FEATURE:
<223> OTHER INFORMATION: Synthetic

<400> SEQUENCE: 542

Gly Ala Ser
1

<210> SEQ ID NO 543
<211> LENGTH: 30
<212> TYPE: DNA
<213> ORGANISM: Artificial Sequence
<220> FEATURE:
<223> OTHER INFORMATION: Synthetic

<400> SEQUENCE: 543
cagcagtata ataattggcc tccattcact 30

<210> SEQ ID NO 544
<211> LENGTH: 10
<212> TYPE: PRT
<213> ORGANISM: Artificial Sequence
<220> FEATURE:
<223> OTHER INFORMATION: Synthetic

<400> SEQUENCE: 544

Gln Gln Tyr Asn Asn Trp Pro Pro Phe Thr
1 5 10

<210> SEQ ID NO 545
<211> LENGTH: 351
<212> TYPE: DNA
<213> ORGANISM: Artificial Sequence
<220> FEATURE:
<223> OTHER INFORMATION: Synthetic

<400> SEQUENCE: 545
gaggtgcagc tggtggagtc tgggggaggc ttggtacagc ctggggggtc cctgagactc 60
tcctgtgcag cctctggatt caccctaagt agctacgaca tgcactgggt ccgccaagca 120
acaggaaaag gtctggagtg ggtctcagct attggcagta ctggtgacac atactataca 180
ggctccgtga tgggccgatt caccatctcc agagacgctg ccaaaaactc cttctatctt 240
gaaatgaaca gcctgagagt cggggacacg gctgtatatt actgtgcaag agagggaata 300
agaacaccct atgattattg gggccaggga accctggtca ccgtctcctc a 351

<210> SEQ ID NO 546
<211> LENGTH: 117
<212> TYPE: PRT
<213> ORGANISM: Artificial Sequence
<220> FEATURE:
<223> OTHER INFORMATION: Synthetic

<400> SEQUENCE: 546

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Leu Ser Ser Tyr
20 25 30

Asp Met His Trp Val Arg Gln Ala Thr Gly Lys Gly Leu Glu Trp Val
35 40 45

Ser Ala Ile Gly Ser Thr Gly Asp Thr Tyr Tyr Thr Gly Ser Val Met
50 55 60

Gly Arg Phe Thr Ile Ser Arg Asp Ala Ala Lys Asn Ser Phe Tyr Leu
65 70 75 80

Glu Met Asn Ser Leu Arg Val Gly Asp Thr Ala Val Tyr Tyr Cys Ala
85 90 95

Arg Glu Gly Ile Arg Thr Pro Tyr Asp Tyr Trp Gly Gln Gly Thr Leu
100 105 110

Val Thr Val Ser Ser
115

<210> SEQ ID NO 547
<211> LENGTH: 324
<212> TYPE: DNA
<213> ORGANISM: Artificial Sequence
<220> FEATURE:
<223> OTHER INFORMATION: Synthetic

<400> SEQUENCE: 547
gaaatagtga tgacgcagtc tccagccacc ctgtctgtgt ctccagggga aagagccacc 60
ctctcctgca gggccagtca gagtgttagc agcaatgtag cctggtacca gcagaaacct 120
ggccaggctc ccaggctcct catctatggt gcatccacca gggccactgg tatcccagcc 180
aggttcagtg gcagtgggtc tgggacagaa ttcactctca ccatcagcag cctgcagtct 240
gaagattttg cagtttatta ctgtcagcag tataataatt ggcctccatt cactttcggc 300
cctgggacca aagtggatat caaa 324

<210> SEQ ID NO 548
<211> LENGTH: 108
<212> TYPE: PRT
<213> ORGANISM: Artificial Sequence
<220> FEATURE:
<223> OTHER INFORMATION: Synthetic

```
<400> SEQUENCE: 548

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Val Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Phe Thr Phe Gly Pro Gly Thr Lys Val Asp Ile Lys
            100                 105

<210> SEQ ID NO 549
<211> LENGTH: 351
<212> TYPE: DNA
<213> ORGANISM: Artificial Sequence
<220> FEATURE:
<223> OTHER INFORMATION: Synthetic

<400> SEQUENCE: 549

gaggtgcagc tggtggagtc tgggggaggc ttggtacagc ctggggggtc cctgagactc      60

tcctgtgcag cctctggatt caccctaagt agctacgaca tgcactgggt ccgccaagct     120

acaggaaaag gtctggagtg ggtctcagct attggcagta ctggtgacac atactatcca     180

ggctccgtga agggccgatt caccatctcc agagaaaatg ccaagaactc cttgtatctt     240

caaatgaaca gcctgagagc cggggacacg gctgtgtatt actgtgcaag agagggaata     300

agaacaccct atgattattg gggccaagga accctggtca ccgtctcctc a              351

<210> SEQ ID NO 550
<211> LENGTH: 117
<212> TYPE: PRT
<213> ORGANISM: Artificial Sequence
<220> FEATURE:
<223> OTHER INFORMATION: Synthetic

<400> SEQUENCE: 550

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
                20                  25                  30

Asp Met His Trp Val Arg Gln Ala Thr Gly Lys Gly Leu Glu Trp Val
            35                  40                  45

Ser Ala Ile Gly Ser Thr Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Glu Gly Ile Arg Thr Pro Tyr Asp Tyr Trp Gly Gln Gly Thr Leu
            100                 105                 110

Val Thr Val Ser Ser
            115
```

<210> SEQ ID NO 551
<211> LENGTH: 324
<212> TYPE: DNA
<213> ORGANISM: Artificial Sequence
<220> FEATURE:
<223> OTHER INFORMATION: Synthetic

<400> SEQUENCE: 551
gaaatagtga tgacgcagtc tccagccacc ctgtctgtgt ctccagggga aagagccacc 60
ctctcctgca gggccagtca gagtgttagc agcaatttag cctggtacca gcagaaacct 120
ggccaggctc ccaggctcct catctatggt gcatccacca gggccactgg tatcccagcc 180
aggttcagtg gcagtgggtc tgggacagag ttcactctca ccatcagcag cctgcagtct 240
gaagattttg cagtttatta ctgtcagcag tataataatt ggcctccatt cactttcggc 300
cctgggacca aagtggatat caaa 324

<210> SEQ ID NO 552
<211> LENGTH: 108
<212> TYPE: PRT
<213> ORGANISM: Artificial Sequence
<220> FEATURE:
<223> OTHER INFORMATION: Synthetic

<400> SEQUENCE: 552

Glu Ile Val Met Thr Gln Ser Pro Ala Thr Leu Ser Val Ser Pro Gly
1 5 10 15

Glu Arg Ala Thr Leu Ser Cys Arg Ala Ser Gln Ser Val Ser Ser Asn
20 25 30

Leu Ala Trp Tyr Gln Gln Lys Pro Gly Gln Ala Pro Arg Leu Leu Ile
35 40 45

Tyr Gly Ala Ser Thr Arg Ala Thr Gly Ile Pro Ala Arg Phe Ser Gly
50 55 60

Ser Gly Ser Gly Thr Glu Phe Thr Leu Thr Ile Ser Ser Leu Gln Ser
65 70 75 80

Glu Asp Phe Ala Val Tyr Tyr Cys Gln Gln Tyr Asn Asn Trp Pro Pro
85 90 95

Phe Thr Phe Gly Pro Gly Thr Lys Val Asp Ile Lys
100 105

<210> SEQ ID NO 553
<211> LENGTH: 351
<212> TYPE: DNA
<213> ORGANISM: Artificial Sequence
<220> FEATURE:
<223> OTHER INFORMATION: Synthetic

<400> SEQUENCE: 553
gaggtgcagc tggtggagtc tgggggaggc ttggtacagc ctgggggtc cctgagactc 60 tcctgtgcag cctctggatt caccctaagt agctacgaca tgcactgggt ccgccaagca 120
acaggaaaag gtctggagtg ggtctcagct attggcagta ctggtgacac atactataca 180
ggctccgtga tgggccgatt caccatctcc agagacgctg ccaaaaactc cttctatctt 240
gaaatgaaca gcctgagagt cggggacacg gctgtatatt actgtgcaag agagggaata 300
agaacaccct atgattattg gggccaggga gcccgggtca ccgtctcctc a 351

<210> SEQ ID NO 554
<211> LENGTH: 117
<212> TYPE: PRT

<213> ORGANISM: Artificial Sequence
<220> FEATURE:
<223> OTHER INFORMATION: Synthetic

<400> SEQUENCE: 554

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Leu Ser Ser Tyr
20 25 30

Asp Met His Trp Val Arg Gln Ala Thr Gly Lys Gly Leu Glu Trp Val
35 40 45

Ser Ala Ile Gly Ser Thr Gly Asp Thr Tyr Tyr Thr Gly Ser Val Met
50 55 60

Gly Arg Phe Thr Ile Ser Arg Asp Ala Ala Lys Asn Ser Phe Tyr Leu
65 70 75 80

Glu Met Asn Ser Leu Arg Val Gly Asp Thr Ala Val Tyr Tyr Cys Ala
85 90 95

Arg Glu Gly Ile Arg Thr Pro Tyr Asp Tyr Trp Gly Gln Gly Ala Arg
100 105 110

Val Thr Val Ser Ser
115

<210> SEQ ID NO 555
<211> LENGTH: 24
<212> TYPE: DNA
<213> ORGANISM: Artificial Sequence
<220> FEATURE:
<223> OTHER INFORMATION: Synthetic

<400> SEQUENCE: 555
ggattcaccc taagtagcta cgac 24

<210> SEQ ID NO 556
<211> LENGTH: 8
<212> TYPE: PRT
<213> ORGANISM: Artificial Sequence
<220> FEATURE:
<223> OTHER INFORMATION: Synthetic

<400> SEQUENCE: 556

Gly Phe Thr Leu Ser Ser Tyr Asp
1 5

<210> SEQ ID NO 557
<211> LENGTH: 21
<212> TYPE: DNA
<213> ORGANISM: Artificial Sequence
<220> FEATURE:
<223> OTHER INFORMATION: Synthetic

<400> SEQUENCE: 557
attggcagta ctggtgacac a 21

<210> SEQ ID NO 558
<211> LENGTH: 7
<212> TYPE: PRT
<213> ORGANISM: Artificial Sequence
<220> FEATURE:
<223> OTHER INFORMATION: Synthetic

<400> SEQUENCE: 558

Ile Gly Ser Thr Gly Asp Thr
1 5

<210> SEQ ID NO 559
<211> LENGTH: 33
<212> TYPE: DNA
<213> ORGANISM: Artificial Sequence
<220> FEATURE:
<223> OTHER INFORMATION: Synthetic

<400> SEQUENCE: 559
gcaagagagg gaataagaac accctatgat tat 33

<210> SEQ ID NO 560
<211> LENGTH: 11
<212> TYPE: PRT
<213> ORGANISM: Artificial Sequence
<220> FEATURE:
<223> OTHER INFORMATION: Synthetic

<400> SEQUENCE: 560

Ala Arg Glu Gly Ile Arg Thr Pro Tyr Asp Tyr
1 5 10

<210> SEQ ID NO 561
<211> LENGTH: 324
<212> TYPE: DNA
<213> ORGANISM: Artificial Sequence
<220> FEATURE:
<223> OTHER INFORMATION: Synthetic

<400> SEQUENCE: 561
gaaatagtga tgacgcagtc tccagccacc ctgtctgtgt ctccagggga aagagccacc 60
ctctcctgca gggccagtca gagtgttagc agcaatgtag cctggtacca gcagaaacct 120
ggccaggctc ccaggctcct catctatggt gcatccacca gggccactgg tatcccagcc 180
aggttcagtg gcagtgggtc tgggacagaa ttcactctca ccatcagcag cctgcagtct 240
gaagattttg cagtttatta ctgtcagcag tataataatt ggcctccatt cactttcggc 300
cctgggacca aagtggatat caaa 324

<210> SEQ ID NO 562
<211> LENGTH: 108
<212> TYPE: PRT
<213> ORGANISM: Artificial Sequence
<220> FEATURE:
<223> OTHER INFORMATION: Synthetic

<400> SEQUENCE: 562

Glu Ile Val Met Thr Gln Ser Pro Ala Thr Leu Ser Val Ser Pro Gly
1 5 10 15

Glu Arg Ala Thr Leu Ser Cys Arg Ala Ser Gln Ser Val Ser Ser Asn
20 25 30

Val Ala Trp Tyr Gln Gln Lys Pro Gly Gln Ala Pro Arg Leu Leu Ile
35 40 45

Tyr Gly Ala Ser Thr Arg Ala Thr Gly Ile Pro Ala Arg Phe Ser Gly
50 55 60

Ser Gly Ser Gly Thr Glu Phe Thr Leu Thr Ile Ser Ser Leu Gln Ser
65 70 75 80

Glu Asp Phe Ala Val Tyr Tyr Cys Gln Gln Tyr Asn Asn Trp Pro Pro
85 90 95

Phe Thr Phe Gly Pro Gly Thr Lys Val Asp Ile Lys
100 105

<210> SEQ ID NO 563
<211> LENGTH: 18
<212> TYPE: DNA
<213> ORGANISM: Artificial Sequence
<220> FEATURE:
<223> OTHER INFORMATION: Synthetic

<400> SEQUENCE: 563
cagagtgtta gcagcaat 18

<210> SEQ ID NO 564
<211> LENGTH: 6
<212> TYPE: PRT
<213> ORGANISM: Artificial Sequence
<220> FEATURE:
<223> OTHER INFORMATION: Synthetic

<400> SEQUENCE: 564

Gln Ser Val Ser Ser Asn
1 5

<210> SEQ ID NO 565
<211> LENGTH: 9
<212> TYPE: DNA
<213> ORGANISM: Artificial Sequence
<220> FEATURE:
<223> OTHER INFORMATION: Synthetic

<400> SEQUENCE: 565 ggtgcatcc 9

<210> SEQ ID NO 566
<211> LENGTH: 3
<212> TYPE: PRT
<213> ORGANISM: Artificial Sequence
<220> FEATURE:
<223> OTHER INFORMATION: Synthetic

<400> SEQUENCE: 566

Gly Ala Ser
1

<210> SEQ ID NO 567
<211> LENGTH: 30
<212> TYPE: DNA
<213> ORGANISM: Artificial Sequence
<220> FEATURE:
<223> OTHER INFORMATION: Synthetic

<400> SEQUENCE: 567
cagcagtata ataattggcc tccattcact 30

<210> SEQ ID NO 568
<211> LENGTH: 10
<212> TYPE: PRT
<213> ORGANISM: Artificial Sequence
<220> FEATURE:
<223> OTHER INFORMATION: Synthetic

<400> SEQUENCE: 568

Gln Gln Tyr Asn Asn Trp Pro Pro Phe Thr
1 5 10

<210> SEQ ID NO 569
<211> LENGTH: 351
<212> TYPE: DNA

<213> ORGANISM: Artificial Sequence
<220> FEATURE:
<223> OTHER INFORMATION: Synthetic

<400> SEQUENCE: 569
gaggtgcagc tggtggagtc tgggggaggc ttggtacagc ctggggggtc cctgagactc 60
tcctgtgcag cctctggatt caccctaagt agctacgaca tgcactgggt ccgccaagca 120
acaggaaaag gtctggagtg ggtctcagct attggcagta ctggtgacac atactataca 180
ggctccgtga tgggccgatt caccatctcc agagacgctg ccaaaaactc cttctatctt 240
gaaatgaaca gcctgagagt cggggacacg gctgtatatt actgtgcaag agagggaata 300
agaacaccct atgattattg gggccaggga accctggtca ccgtctcctc a 351

<210> SEQ ID NO 570
<211> LENGTH: 117
<212> TYPE: PRT
<213> ORGANISM: Artificial Sequence
<220> FEATURE:
<223> OTHER INFORMATION: Synthetic

<400> SEQUENCE: 570

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Leu Ser Ser Tyr
20 25 30

Asp Met His Trp Val Arg Gln Ala Thr Gly Lys Gly Leu Glu Trp Val
35 40 45

Ser Ala Ile Gly Ser Thr Gly Asp Thr Tyr Tyr Thr Gly Ser Val Met
50 55 60

Gly Arg Phe Thr Ile Ser Arg Asp Ala Ala Lys Asn Ser Phe Tyr Leu
65 70 75 80

Glu Met Asn Ser Leu Arg Val Gly Asp Thr Ala Val Tyr Tyr Cys Ala
85 90 95

Arg Glu Gly Ile Arg Thr Pro Tyr Asp Tyr Trp Gly Gln Gly Thr Leu
100 105 110

Val Thr Val Ser Ser
115

<210> SEQ ID NO 571
<211> LENGTH: 324
<212> TYPE: DNA
<213> ORGANISM: Artificial Sequence
<220> FEATURE:
<223> OTHER INFORMATION: Synthetic

<400> SEQUENCE: 571
gaaatagtga tgacgcagtc tccagccacc ctgtctgtgt ctccagggga aagagccacc 60
ctctcctgca gggccagtca gagtgttagc agcaatgtag cctggtacca gcagaaacct 120
ggccaggctc ccaggctcct catctatggt gcatccacca gggccactgg tatcccagcc 180
aggttcagtg gcagtgggtc tgggacagaa ttcactctca ccatcagcag cctgcagtct 240
gaagattttg cagtttatta ctgtcagcag tataataatt ggcctccatt cactttcggc 300
cctgggacca aagtggatat caaa 324

<210> SEQ ID NO 572
<211> LENGTH: 108
<212> TYPE: PRT
<213> ORGANISM: Artificial Sequence
<220> FEATURE:
<223> OTHER INFORMATION: Synthetic

<400> SEQUENCE: 572

Glu Ile Val Met Thr Gln Ser Pro Ala Thr Leu Ser Val Ser Pro Gly
1 5 10 15

Glu Arg Ala Thr Leu Ser Cys Arg Ala Ser Gln Ser Val Ser Ser Asn
20 25 30

Val Ala Trp Tyr Gln Gln Lys Pro Gly Gln Ala Pro Arg Leu Leu Ile
35 40 45

Tyr Gly Ala Ser Thr Arg Ala Thr Gly Ile Pro Ala Arg Phe Ser Gly
50 55 60

Ser Gly Ser Gly Thr Glu Phe Thr Leu Thr Ile Ser Ser Leu Gln Ser
65 70 75 80

Glu Asp Phe Ala Val Tyr Tyr Cys Gln Gln Tyr Asn Asn Trp Pro Pro
85 90 95

Phe Thr Phe Gly Pro Gly Thr Lys Val Asp Ile Lys
100 105

<210> SEQ ID NO 573
<211> LENGTH: 351
<212> TYPE: DNA
<213> ORGANISM: Artificial Sequence
<220> FEATURE:
<223> OTHER INFORMATION: Synthetic

<400> SEQUENCE: 573
gaggtgcagc tggtggagtc tgggggaggc ttggtacagc ctgggggtc cctgagactc 60 tcctgtgcag cctctggatt caccctaagt agctacgaca tgcactgggt ccgccaagct 120
acaggaaaag gtctggagtg ggtctcagct attggcagta ctggtgacac atactatcca 180
ggctccgtga agggccgatt caccatctcc agagaaaatg ccaagaactc cttgtatctt 240
caaatgaaca gcctgagagc cggggacacg gctgtgtatt actgtgcaag agagggaata 300
agaacaccct atgattattg gggccaagga accctggtca ccgtctcctc a 351

<210> SEQ ID NO 574
<211> LENGTH: 117
<212> TYPE: PRT
<213> ORGANISM: Artificial Sequence
<220> FEATURE:
<223> OTHER INFORMATION: Synthetic

<400> SEQUENCE: 574

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Leu Ser Ser Tyr
20 25 30

Asp Met His Trp Val Arg Gln Ala Thr Gly Lys Gly Leu Glu Trp Val
35 40 45

Ser Ala Ile Gly Ser Thr Gly Asp Thr Tyr Tyr Pro Gly Ser Val Lys
50 55 60

Gly Arg Phe Thr Ile Ser Arg Glu Asn Ala Lys Asn Ser Leu Tyr Leu
65 70 75 80

Gln Met Asn Ser Leu Arg Ala Gly Asp Thr Ala Val Tyr Tyr Cys Ala
85 90 95

Arg Glu Gly Ile Arg Thr Pro Tyr Asp Tyr Trp Gly Gln Gly Thr Leu
100 105 110

Val Thr Val Ser Ser
115

<210> SEQ ID NO 575
<211> LENGTH: 324
<212> TYPE: DNA
<213> ORGANISM: Artificial Sequence
<220> FEATURE:
<223> OTHER INFORMATION: Synthetic

<400> SEQUENCE: 575
gaaatagtga tgacgcagtc tccagccacc ctgtctgtgt ctccagggga aagagccacc 60
ctctcctgca gggccagtca gagtgttagc agcaatttag cctggtacca gcagaaacct 120
ggccaggctc ccaggctcct catctatggt gcatccacca gggccactgg tatcccagcc 180
aggttcagtg gcagtgggtc tgggacagag ttcactctca ccatcagcag cctgcagtct 240
gaagattttg cagtttatta ctgtcagcag tataataatt ggcctccatt cactttcggc 300
cctgggacca aagtggatat caaa 324

<210> SEQ ID NO 576
<211> LENGTH: 108
<212> TYPE: PRT
<213> ORGANISM: Artificial Sequence
<220> FEATURE:
<223> OTHER INFORMATION: Synthetic

<400> SEQUENCE: 576

Glu Ile Val Met Thr Gln Ser Pro Ala Thr Leu Ser Val Ser Pro Gly
1 5 10 15

Glu Arg Ala Thr Leu Ser Cys Arg Ala Ser Gln Ser Val Ser Ser Asn
20 25 30

Leu Ala Trp Tyr Gln Gln Lys Pro Gly Gln Ala Pro Arg Leu Leu Ile
35 40 45

Tyr Gly Ala Ser Thr Arg Ala Thr Gly Ile Pro Ala Arg Phe Ser Gly
50 55 60

Ser Gly Ser Gly Thr Glu Phe Thr Leu Thr Ile Ser Ser Leu Gln Ser
65 70 75 80

Glu Asp Phe Ala Val Tyr Tyr Cys Gln Gln Tyr Asn Asn Trp Pro Pro
85 90 95

Phe Thr Phe Gly Pro Gly Thr Lys Val Asp Ile Lys
100 105

<210> SEQ ID NO 577
<211> LENGTH: 363
<212> TYPE: DNA
<213> ORGANISM: Artificial Sequence
<220> FEATURE:
<223> OTHER INFORMATION: Synthetic

<400> SEQUENCE: 577
gaagtgcagc tggtggagtc tgggggaggc ttggtacagc ctggcaggtc cctgagactc 60
tcctgtgcag cctctggatt cacctttgat gattatgcca tgcactgggt ccggcaagct 120
ccagggaagg gcctggagtg ggtctcaggt attaattgga acagtggtag cataggctat 180
gcggactctg tgaagggccg attcaccatc tccagagaca acgccaagca ctccctgtat 240
ctgcaaatga acagtctgag acctgaggac acggccttgt attactgtgt aaaagaggtg 300
actacgggat actactacgg tatggacgtc tggggccaag ggaccacggt caccgtctcc 360
tca 363

<210> SEQ ID NO 578
<211> LENGTH: 121
<212> TYPE: PRT
<213> ORGANISM: Artificial Sequence
<220> FEATURE:
<223> OTHER INFORMATION: Synthetic

<400> SEQUENCE: 578

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Asn Trp Asn Ser Gly Ser Ile Gly Tyr Ala Asp Ser Val
    50                  55                  60

Lys Gly Arg Phe Thr Ile Ser Arg Asp Asn Ala Lys His Ser Leu Tyr
65                  70                  75                  80

Leu Gln Met Asn Ser Leu Arg Pro Glu Asp Thr Ala Leu Tyr Tyr Cys
                85                  90                  95

Val Lys Glu Val Thr Thr Gly Tyr Tyr Tyr Gly Met Asp Val Trp Gly
            100                 105                 110

Gln Gly Thr Thr Val Thr Val Ser Ser
        115                 120
```

<210> SEQ ID NO 579
<211> LENGTH: 24
<212> TYPE: DNA
<213> ORGANISM: Artificial Sequence
<220> FEATURE:
<223> OTHER INFORMATION: Synthetic

<400> SEQUENCE: 579
ggattcacct ttgatgatta tgcc 24

<210> SEQ ID NO 580
<211> LENGTH: 8
<212> TYPE: PRT
<213> ORGANISM: Artificial Sequence
<220> FEATURE:
<223> OTHER INFORMATION: Synthetic

<400> SEQUENCE: 580

```
Gly Phe Thr Phe Asp Asp Tyr Ala
1               5
```

<210> SEQ ID NO 581
<211> LENGTH: 24
<212> TYPE: DNA
<213> ORGANISM: Artificial Sequence
<220> FEATURE:
<223> OTHER INFORMATION: Synthetic

<400> SEQUENCE: 581
attaattgga acagtggtag cata 24

<210> SEQ ID NO 582
<211> LENGTH: 8
<212> TYPE: PRT
<213> ORGANISM: Artificial Sequence
<220> FEATURE:
<223> OTHER INFORMATION: Synthetic

<400> SEQUENCE: 582

Ile Asn Trp Asn Ser Gly Ser Ile
1 5

<210> SEQ ID NO 583
<211> LENGTH: 42
<212> TYPE: DNA
<213> ORGANISM: Artificial Sequence
<220> FEATURE:
<223> OTHER INFORMATION: Synthetic

<400> SEQUENCE: 583
gtaaaagagg tgactacggg atactactac ggtatggacg tc 42

<210> SEQ ID NO 584
<211> LENGTH: 14
<212> TYPE: PRT
<213> ORGANISM: Artificial Sequence
<220> FEATURE:
<223> OTHER INFORMATION: Synthetic

<400> SEQUENCE: 584

Val Lys Glu Val Thr Thr Gly Tyr Tyr Tyr Gly Met Asp Val
1 5 10

<210> SEQ ID NO 585
<211> LENGTH: 321
<212> TYPE: DNA
<213> ORGANISM: Artificial Sequence
<220> FEATURE:
<223> OTHER INFORMATION: Synthetic

<400> SEQUENCE: 585
gacatccagt tgacccagtc tccatccttc ctgtctgcat ctgtaggaga cagagtcacc 60
atcacttgct gggccagtca gggcattagc agttatttag cctggtatca gaaaaaacca 120
gggaaagccc ctaacctcct gatctatgat gcatccactt tgcaaagtgg ggtcccatca 180
aggttcagcg gcagtggatc tgggacagaa ttcactctca cactcagcag cctgcagcct 240
gaagattttg caacttatta ctgtcaacag cttaatattt acccattcac tttcggccct 300
gggaccaaag tggatatcaa a 321

<210> SEQ ID NO 586
<211> LENGTH: 107
<212> TYPE: PRT
<213> ORGANISM: Artificial Sequence
<220> FEATURE:
<223> OTHER INFORMATION: Synthetic

<400> SEQUENCE: 586

Asp Ile Gln Leu Thr Gln Ser Pro Ser Phe Leu Ser Ala Ser Val Gly
1 5 10 15

Asp Arg Val Thr Ile Thr Cys Trp Ala Ser Gln Gly Ile Ser Ser Tyr
20 25 30

Leu Ala Trp Tyr Gln Lys Lys Pro Gly Lys Ala Pro Asn Leu Leu Ile
35 40 45

Tyr Asp Ala Ser Thr Leu Gln Ser Gly Val Pro Ser Arg Phe Ser Gly
50 55 60

Ser Gly Ser Gly Thr Glu Phe Thr Leu Thr Leu Ser Ser Leu Gln Pro
65 70 75 80

Glu Asp Phe Ala Thr Tyr Tyr Cys Gln Gln Leu Asn Ile Tyr Pro Phe 85 90 95

Thr Phe Gly Pro Gly Thr Lys Val Asp Ile Lys
100 105

<210> SEQ ID NO 587
<211> LENGTH: 18
<212> TYPE: DNA
<213> ORGANISM: Artificial Sequence
<220> FEATURE:
<223> OTHER INFORMATION: Synthetic

<400> SEQUENCE: 587
cagggcatta gcagttat 18

<210> SEQ ID NO 588
<211> LENGTH: 6
<212> TYPE: PRT
<213> ORGANISM: Artificial Sequence
<220> FEATURE:
<223> OTHER INFORMATION: Synthetic

<400> SEQUENCE: 588

Gln Gly Ile Ser Ser Tyr
1 5

<210> SEQ ID NO 589
<211> LENGTH: 9
<212> TYPE: DNA
<213> ORGANISM: Artificial Sequence
<220> FEATURE:
<223> OTHER INFORMATION: Synthetic

<400> SEQUENCE: 589 gatgcatcc 9

<210> SEQ ID NO 590
<211> LENGTH: 3
<212> TYPE: PRT
<213> ORGANISM: Artificial Sequence
<220> FEATURE:
<223> OTHER INFORMATION: Synthetic

<400> SEQUENCE: 590

Asp Ala Ser
1

<210> SEQ ID NO 591
<211> LENGTH: 27
<212> TYPE: DNA
<213> ORGANISM: Artificial Sequence
<220> FEATURE:
<223> OTHER INFORMATION: Synthetic

<400> SEQUENCE: 591
caacagctta atatttaccc attcact 27

<210> SEQ ID NO 592
<211> LENGTH: 9
<212> TYPE: PRT
<213> ORGANISM: Artificial Sequence
<220> FEATURE:
<223> OTHER INFORMATION: Synthetic

<400> SEQUENCE: 592

Gln Gln Leu Asn Ile Tyr Pro Phe Thr
1 5

<210> SEQ ID NO 593
<211> LENGTH: 363
<212> TYPE: DNA
<213> ORGANISM: Artificial Sequence
<220> FEATURE:
<223> OTHER INFORMATION: Synthetic

<400> SEQUENCE: 593
gaagtgcagc tggtggagtc tgggggaggc ttggtacagc ctggcaggtc cctgagactc 60
tcctgtgcag cctctggatt cacctttgat gattatgcca tgcactgggt ccggcaagct 120
ccagggaagg gcctggagtg ggtctcaggt attaattgga acagtggtag cataggctat 180
gcggactctg tgaagggccg attcaccatc tccagagaca acgccaagca ctccctgtat 240
ctgcaaatga acagtctgag acctgaggac acggccttgt attactgtgt aaaagaggtg 300
actacgggat actactacgg tatggacgtc tggggccaag ggaccacggt caccgtctcc 360
tca 363

<210> SEQ ID NO 594
<211> LENGTH: 121
<212> TYPE: PRT
<213> ORGANISM: Artificial Sequence
<220> FEATURE:
<223> OTHER INFORMATION: Synthetic

<400> SEQUENCE: 594

Glu Val Gln Leu Val Glu Ser Gly Gly Gly Leu Val Gln Pro Gly Arg
1 5 10 15

Ser Leu Arg Leu Ser Cys Ala Ala Ser Gly Phe Thr Phe Asp Asp Tyr
20 25 30

Ala Met His Trp Val Arg Gln Ala Pro Gly Lys Gly Leu Glu Trp Val
35 40 45

Ser Gly Ile Asn Trp Asn Ser Gly Ser Ile Gly Tyr Ala Asp Ser Val
50 55 60

Lys Gly Arg Phe Thr Ile Ser Arg Asp Asn Ala Lys His Ser Leu Tyr
65 70 75 80

Leu Gln Met Asn Ser Leu Arg Pro Glu Asp Thr Ala Leu Tyr Tyr Cys
85 90 95

Val Lys Glu Val Thr Thr Gly Tyr Tyr Tyr Gly Met Asp Val Trp Gly
100 105 110

Gln Gly Thr Thr Val Thr Val Ser Ser
115 120

<210> SEQ ID NO 595
<211> LENGTH: 321
<212> TYPE: DNA
<213> ORGANISM: Artificial Sequence
<220> FEATURE:
<223> OTHER INFORMATION: Synthetic

<400> SEQUENCE: 595
gacatccagt tgacccagtc tccatccttc ctgtctgcat ctgtaggaga cagagtcacc 60
atcacttgct gggccagtca gggcattagc agttatttag cctggtatca gaaaaaacca 120
gggaaagccc ctaacctcct gatctatgat gcatccactt tgcaaagtgg ggtcccatca 180
aggttcagcg gcagtggatc tgggacagaa ttcactctca cactcagcag cctgcagcct 240
gaagattttg caacttatta ctgtcaacag cttaatattt acccattcac tttcggccct 300
gggaccaaag tggatatcaa a 321

<210> SEQ ID NO 596
<211> LENGTH: 107
<212> TYPE: PRT
<213> ORGANISM: Artificial Sequence
<220> FEATURE:
<223> OTHER INFORMATION: Synthetic

<400> SEQUENCE: 596

Asp Ile Gln Leu Thr Gln Ser Pro Ser Phe Leu Ser Ala Ser Val Gly
1 5 10 15

Asp Arg Val Thr Ile Thr Cys Trp Ala Ser Gln Gly Ile Ser Ser Tyr
20 25 30

Leu Ala Trp Tyr Gln Lys Lys Pro Gly Lys Ala Pro Asn Leu Leu Ile
35 40 45

Tyr Asp Ala Ser Thr Leu Gln Ser Gly Val Pro Ser Arg Phe Ser Gly
50 55 60

Ser Gly Ser Gly Thr Glu Phe Thr Leu Thr Leu Ser Ser Leu Gln Pro
65 70 75 80

Glu Asp Phe Ala Thr Tyr Tyr Cys Gln Gln Leu Asn Ile Tyr Pro Phe
85 90 95

Thr Phe Gly Pro Gly Thr Lys Val Asp Ile Lys
100 105

<210> SEQ ID NO 597
<211> LENGTH: 363
<212> TYPE: DNA
<213> ORGANISM: Artificial Sequence
<220> FEATURE:
<223> OTHER INFORMATION: Synthetic

<400> SEQUENCE: 597
gaagtgcagc tggtggagtc tgggggaggc ttggtacagc ctggcaggtc cctgagactc 60
tcctgtgcag cctctggatt cacctttgat gattatgcca tgcactgggt ccggcaagct 120
ccagggaagg gcctggagtg ggtctcaggt attaattgga acagtggtag cataggctat 180
gcggactctg tgaagggccg attcaccatc tccagagaca acgccaagaa ctccctgtat 240
ctgcaaatga acagtctgag agctgaggac acggccttgt attactgtgt aaaagaggtg 300
actacgggat actactacgg tatggacgtc tgggggcaag ggaccacggt caccgtctcc 360
tca 363

<210> SEQ ID NO 598
<211> LENGTH: 121
<212> TYPE: PRT
<213> ORGANISM: Artificial Sequence
<220> FEATURE:
<223> OTHER INFORMATION: Synthetic

<400> SEQUENCE: 598

Glu Val Gln Leu Val Glu Ser Gly Gly Gly Leu Val Gln Pro Gly Arg
1 5 10 15

Ser Leu Arg Leu Ser Cys Ala Ala Ser Gly Phe Thr Phe Asp Asp Tyr
20 25 30

Ala Met His Trp Val Arg Gln Ala Pro Gly Lys Gly Leu Glu Trp Val
35 40 45

Ser Gly Ile Asn Trp Asn Ser Gly Ser Ile Gly Tyr Ala Asp Ser Val
50 55 60

```
Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Glu Val Thr Thr Gly Tyr Tyr Tyr Gly Met Asp Val Trp Gly
            100                 105                 110

Gln Gly Thr Thr Val Thr Val Ser Ser
        115                 120


<210> SEQ ID NO 599
<211> LENGTH: 321
<212> TYPE: DNA
<213> ORGANISM: Artificial Sequence
<220> FEATURE:
<223> OTHER INFORMATION: Synthetic

<400> SEQUENCE: 599

gacatccagt tgacccagtc tccatccttc ctgtctgcat ctgtaggaga cagagtcacc      60

atcacttgcc gggccagtca gggcattagc agttatttag cctggtatca gcaaaaacca     120

gggaaagccc ctaagctcct gatctatgat gcatccactt tgcaaagtgg ggtcccatca     180

aggttcagcg gcagtggatc tgggacagaa ttcactctca caatcagcag cctgcagcct     240

gaagattttg caacttatta ctgtcaacag cttaatattt acccattcac tttcggccct     300

gggaccaaag tggatatcaa a                                               321


<210> SEQ ID NO 600
<211> LENGTH: 107
<212> TYPE: PRT
<213> ORGANISM: Artificial Sequence
<220> FEATURE:
<223> OTHER INFORMATION: Synthetic

<400> SEQUENCE: 600

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ile Tyr Pro Phe
                85                  90                  95

Thr Phe Gly Pro Gly Thr Lys Val Asp Ile Lys
            100                 105


<210> SEQ ID NO 601
<211> LENGTH: 366
<212> TYPE: DNA
<213> ORGANISM: Artificial Sequence
<220> FEATURE:
<223> OTHER INFORMATION: Synthetic

<400> SEQUENCE: 601

gaggtgcagt tgttggagtc tgggggaggc ttggtacagc ctggggggtc cctgagactc      60

tcctgtgcag cctctggatt cacgtttagt agctatgcca tgaactgggt ccgccaggct     120
```

ccagggaagg ggctggattg ggtctcaggt atcagtggta atggtggtag cacctactac 180
gcagactccg tgaagggccg gttcaccatc tccagagaca tttccaagaa cacgctgtat 240
gtgcaaatgc acagcctgag agtcgaggac acggccgttt actactgtgc gaaagcccgt 300
tattacgatt tttggggggg gaatttcgat ctctggggcc gtggcaccca ggtcactgtc 360
tcctca 366

<210> SEQ ID NO 602
<211> LENGTH: 122
<212> TYPE: PRT
<213> ORGANISM: Artificial Sequence
<220> FEATURE:
<223> OTHER INFORMATION: Synthetic

<400> SEQUENCE: 602

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Asn Trp Val Arg Gln Ala Pro Gly Lys Gly Leu Asp Trp Val
35 40 45

Ser Gly Ile Ser Gly Asn Gly Gly Ser Thr Tyr Tyr Ala Asp Ser Val
50 55 60

Lys Gly Arg Phe Thr Ile Ser Arg Asp Ile Ser Lys Asn Thr Leu Tyr
65 70 75 80

Val Gln Met His Ser Leu Arg Val Glu Asp Thr Ala Val Tyr Tyr Cys
85 90 95

Ala Lys Ala Arg Tyr Tyr Asp Phe Trp Gly Gly Asn Phe Asp Leu Trp
100 105 110

Gly Arg Gly Thr Gln Val Thr Val Ser Ser
115 120

<210> SEQ ID NO 603
<211> LENGTH: 24
<212> TYPE: DNA
<213> ORGANISM: Artificial Sequence
<220> FEATURE:
<223> OTHER INFORMATION: Synthetic

<400> SEQUENCE: 603
ggattcacgt ttagtagcta tgcc 24

<210> SEQ ID NO 604
<211> LENGTH: 8
<212> TYPE: PRT
<213> ORGANISM: Artificial Sequence
<220> FEATURE:
<223> OTHER INFORMATION: Synthetic

<400> SEQUENCE: 604

Gly Phe Thr Phe Ser Ser Tyr Ala
1 5

<210> SEQ ID NO 605
<211> LENGTH: 24
<212> TYPE: DNA
<213> ORGANISM: Artificial Sequence
<220> FEATURE:
<223> OTHER INFORMATION: Synthetic

<400> SEQUENCE: 605
atcagtggta atggtggtag cacc 24

<210> SEQ ID NO 606
<211> LENGTH: 8
<212> TYPE: PRT
<213> ORGANISM: Artificial Sequence
<220> FEATURE:
<223> OTHER INFORMATION: Synthetic

<400> SEQUENCE: 606

Ile Ser Gly Asn Gly Gly Ser Thr
1 5

<210> SEQ ID NO 607
<211> LENGTH: 45
<212> TYPE: DNA
<213> ORGANISM: Artificial Sequence
<220> FEATURE:
<223> OTHER INFORMATION: Synthetic

<400> SEQUENCE: 607
gcgaaagccc gttattacga tttttggggg gggaatttcg atctc 45

<210> SEQ ID NO 608
<211> LENGTH: 15
<212> TYPE: PRT
<213> ORGANISM: Artificial Sequence
<220> FEATURE:
<223> OTHER INFORMATION: Synthetic

<400> SEQUENCE: 608

Ala Lys Ala Arg Tyr Tyr Asp Phe Trp Gly Gly Asn Phe Asp Leu
1 5 10 15

<210> SEQ ID NO 609
<211> LENGTH: 324
<212> TYPE: DNA
<213> ORGANISM: Artificial Sequence
<220> FEATURE:
<223> OTHER INFORMATION: Synthetic

<400> SEQUENCE: 609
gaaattgtgt tgacgcagtc tccaggcacc ctgtctttgt ctccagggga aagagccacc 60
ctctcctgca gggccagtca gagtgttagc atcaggtact tagcctggta tcagcagaaa 120
cctggccagg ctcccaggct cctcatctat ggtgcatcca gcagggccac tggcatccca 180
gacaggttca gtgtcagtgt gtctgggaca gacttcactc tcaccatcac tagactggag 240
cctgaagatt ttgcagtcta ttactgtcag caatatggta gttcaccgct cactttcggc 300
ggagggacca aggtggagat caaa 324

<210> SEQ ID NO 610
<211> LENGTH: 108
<212> TYPE: PRT
<213> ORGANISM: Artificial Sequence
<220> FEATURE:
<223> OTHER INFORMATION: Synthetic

<400> SEQUENCE: 610

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ile Arg
20 25 30

Tyr Leu Ala Trp Tyr Gln Gln Lys Pro Gly Gln Ala Pro Arg Leu Leu 35 40 45

Ile Tyr Gly Ala Ser Ser Arg Ala Thr Gly Ile Pro Asp Arg Phe Ser
50 55 60

Val Ser Val Ser Gly Thr Asp Phe Thr Leu Thr Ile Thr Arg Leu Glu
65 70 75 80

Pro Glu Asp Phe Ala Val Tyr Tyr Cys Gln Gln Tyr Gly Ser Ser Pro
85 90 95

Leu Thr Phe Gly Gly Gly Thr Lys Val Glu Ile Lys
100 105

<210> SEQ ID NO 611
<211> LENGTH: 21
<212> TYPE: DNA
<213> ORGANISM: Artificial Sequence
<220> FEATURE:
<223> OTHER INFORMATION: Synthetic

<400> SEQUENCE: 611
cagagtgtta gcatcaggta c 21

<210> SEQ ID NO 612
<211> LENGTH: 7
<212> TYPE: PRT
<213> ORGANISM: Artificial Sequence
<220> FEATURE:
<223> OTHER INFORMATION: Synthetic

<400> SEQUENCE: 612

Gln Ser Val Ser Ile Arg Tyr
1 5

<210> SEQ ID NO 613
<211> LENGTH: 9
<212> TYPE: DNA
<213> ORGANISM: Artificial Sequence
<220> FEATURE:
<223> OTHER INFORMATION: Synthetic

<400> SEQUENCE: 613 ggtgcatcc 9

<210> SEQ ID NO 614
<211> LENGTH: 3
<212> TYPE: PRT
<213> ORGANISM: Artificial Sequence
<220> FEATURE:
<223> OTHER INFORMATION: Synthetic

<400> SEQUENCE: 614

Gly Ala Ser
1

<210> SEQ ID NO 615
<211> LENGTH: 27
<212> TYPE: DNA
<213> ORGANISM: Artificial Sequence
<220> FEATURE:
<223> OTHER INFORMATION: Synthetic

<400> SEQUENCE: 615
cagcaatatg gtagttcacc gctcact 27

<210> SEQ ID NO 616
<211> LENGTH: 9

<212> TYPE: PRT
<213> ORGANISM: Artificial Sequence
<220> FEATURE:
<223> OTHER INFORMATION: Synthetic

<400> SEQUENCE: 616

Gln Gln Tyr Gly Ser Ser Pro Leu Thr
1               5

<210> SEQ ID NO 617
<211> LENGTH: 366
<212> TYPE: DNA
<213> ORGANISM: Artificial Sequence
<220> FEATURE:
<223> OTHER INFORMATION: Synthetic

<400> SEQUENCE: 617
gaggtgcagt tgttggagtc tgggggaggc ttggtacagc ctggggggtc cctgagactc 60
tcctgtgcag cctctggatt cacgtttagt agctatgcca tgaactgggt ccgccaggct 120
ccagggaagg ggctggattg ggtctcaggt atcagtggta atggtggtag cacctactac 180
gcagactccg tgaagggccg gttcaccatc tccagagaca tttccaagaa cacgctgtat 240
gtgcaaatgc acagcctgag agtcgaggac acggccgttt actactgtgc gaaagcccgt 300
tattacgatt tttggggggg gaatttcgat ctctggggcc gtggcaccct ggtcactgtc 360
tcctca 366

<210> SEQ ID NO 618
<211> LENGTH: 122
<212> TYPE: PRT
<213> ORGANISM: Artificial Sequence
<220> FEATURE:
<223> OTHER INFORMATION: Synthetic

<400> SEQUENCE: 618

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Asp Trp Val
        35                  40                  45

Ser Gly Ile Ser Gly Asn Gly Gly Ser Thr Tyr Tyr Ala Asp Ser Val
    50                  55                  60

Lys Gly Arg Phe Thr Ile Ser Arg Asp Ile Ser Lys Asn Thr Leu Tyr
65                  70                  75                  80

Val Gln Met His Ser Leu Arg Val Glu Asp Thr Ala Val Tyr Tyr Cys
                85                  90                  95

Ala Lys Ala Arg Tyr Tyr Asp Phe Trp Gly Gly Asn Phe Asp Leu Trp
            100                 105                 110

Gly Arg Gly Thr Leu Val Thr Val Ser Ser
        115                 120

<210> SEQ ID NO 619
<211> LENGTH: 324
<212> TYPE: DNA
<213> ORGANISM: Artificial Sequence
<220> FEATURE:
<223> OTHER INFORMATION: Synthetic

<400> SEQUENCE: 619
gaaattgtgt tgacgcagtc tccaggcacc ctgtctttgt ctccagggga aagagccacc 60

-continued

```
ctctcctgca gggccagtca gagtgttagc atcaggtact tagcctggta tcagcagaaa    120

cctggccagg ctcccaggct cctcatctat ggtgcatcca gcagggccac tggcatccca    180

gacaggttca gtgtcagtgt gtctgggaca gacttcactc tcaccatcac tagactggag    240

cctgaagatt ttgcagtcta ttactgtcag caatatggta gttcaccgct cactttcggc    300

ggagggacca aggtggagat caaa                                            324
```

<210> SEQ ID NO 620
<211> LENGTH: 108
<212> TYPE: PRT
<213> ORGANISM: Artificial Sequence
<220> FEATURE:
<223> OTHER INFORMATION: Synthetic

<400> SEQUENCE: 620

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ile Arg
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Val Ser Val Ser Gly Thr Asp Phe Thr Leu Thr Ile Thr Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
            100                 105
```

<210> SEQ ID NO 621
<211> LENGTH: 366
<212> TYPE: DNA
<213> ORGANISM: Artificial Sequence
<220> FEATURE:
<223> OTHER INFORMATION: Synthetic

<400> SEQUENCE: 621

```
gaggtgcagc tgttggagtc tgggggaggc ttggtacagc ctggggggtc cctgagactc     60

tcctgtgcag cctctggatt cacgtttagt agctatgcca tgagctgggt ccgccaggct    120

ccagggaagg ggctggagtg ggtctcagct atcagtggta atggtggtag cacctactac    180

gcagactccg tgaagggccg gttcaccatc tccagagaca attccaagaa cacgctgtat    240

ctgcaaatga acagcctgag agccgaggac acggccgtat attactgtgc gaaagcccgt    300

tattacgatt tttggggggg gaatttcgat ctctggggcc gtggcaccct ggtcactgtc    360

tcctca                                                                366
```

<210> SEQ ID NO 622
<211> LENGTH: 122
<212> TYPE: PRT
<213> ORGANISM: Artificial Sequence
<220> FEATURE:
<223> OTHER INFORMATION: Synthetic

<400> SEQUENCE: 622

```
Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Asn Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Arg Tyr Tyr Asp Phe Trp Gly Gly Asn Phe Asp Leu Trp
            100                 105                 110

Gly Arg Gly Thr Leu Val Thr Val Ser Ser
        115                 120


<210> SEQ ID NO 623
<211> LENGTH: 324
<212> TYPE: DNA
<213> ORGANISM: Artificial Sequence
<220> FEATURE:
<223> OTHER INFORMATION: Synthetic

<400> SEQUENCE: 623

gaaattgtgt tgacgcagtc tccaggcacc ctgtctttgt ctccagggga aagagccacc      60

ctctcctgca gggccagtca gagtgttagc atcaggtact tagcctggta ccagcagaaa     120

cctggccagg ctcccaggct cctcatctat ggtgcatcca gcagggccac tggcatccca     180

gacaggttca gtggcagtgg gtctgggaca gacttcactc tcaccatcag cagactggag     240

cctgaagatt ttgcagtgta ttactgtcag caatatggta gttcaccgct cactttcggc     300

ggagggacca aggtggagat caaa                                            324


<210> SEQ ID NO 624
<211> LENGTH: 108
<212> TYPE: PRT
<213> ORGANISM: Artificial Sequence
<220> FEATURE:
<223> OTHER INFORMATION: Synthetic

<400> SEQUENCE: 624

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ile Arg
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
            100                 105


<210> SEQ ID NO 625
<211> LENGTH: 381
<212> TYPE: DNA
<213> ORGANISM: Artificial Sequence
```

<220> FEATURE:
<223> OTHER INFORMATION: Synthetic

<400> SEQUENCE: 625
caggttcagc tggtgcagtc tggacctgag gtgaagaacc ctggggcctc agtgaaggtc 60
tcctgcaagg cttctggtta cacctttacc acctatggta tcagttgggt acgacaggcc 120
cctggacaag ggcttgagtg gatgggatgg atcagcggtt acaatggtaa aacaaacgat 180
gcacagaagt tccaggacag agtcgccatg accacagaca catccacgag cacagcctac 240
atggagctga ggagcctgag atctgacgac acggccattt attactgttc gagagatcgt 300
ttagtagtac cacctgccct ttattattcc tactacgtta tggacgtctg gggccaaggg 360
accacggtca ccgtctcctc a 381

<210> SEQ ID NO 626
<211> LENGTH: 127
<212> TYPE: PRT
<213> ORGANISM: Artificial Sequence
<220> FEATURE:
<223> OTHER INFORMATION: Synthetic

<400> SEQUENCE: 626

Gln Val Gln Leu Val Gln Ser Gly Pro Glu Val Lys Asn Pro Gly Ala
1 5 10 15

Ser Val Lys Val Ser Cys Lys Ala Ser Gly Tyr Thr Phe Thr Thr Tyr
20 25 30

Gly Ile Ser Trp Val Arg Gln Ala Pro Gly Gln Gly Leu Glu Trp Met
35 40 45

Gly Trp Ile Ser Gly Tyr Asn Gly Lys Thr Asn Asp Ala Gln Lys Phe
50 55 60

Gln Asp Arg Val Ala Met Thr Thr Asp Thr Ser Thr Ser Thr Ala Tyr
65 70 75 80

Met Glu Leu Arg Ser Leu Arg Ser Asp Asp Thr Ala Ile Tyr Tyr Cys
85 90 95

Ser Arg Asp Arg Leu Val Val Pro Pro Ala Leu Tyr Tyr Ser Tyr Tyr
100 105 110

Val Met Asp Val Trp Gly Gln Gly Thr Thr Val Thr Val Ser Ser
115 120 125

<210> SEQ ID NO 627
<211> LENGTH: 24
<212> TYPE: DNA
<213> ORGANISM: Artificial Sequence
<220> FEATURE:
<223> OTHER INFORMATION: Synthetic

<400> SEQUENCE: 627
ggttacacct ttaccaccta tggt 24

<210> SEQ ID NO 628
<211> LENGTH: 8
<212> TYPE: PRT
<213> ORGANISM: Artificial Sequence
<220> FEATURE:
<223> OTHER INFORMATION: Synthetic

<400> SEQUENCE: 628

Gly Tyr Thr Phe Thr Thr Tyr Gly
1 5

<210> SEQ ID NO 629
<211> LENGTH: 24
<212> TYPE: DNA
<213> ORGANISM: Artificial Sequence
<220> FEATURE:
<223> OTHER INFORMATION: Synthetic

<400> SEQUENCE: 629
atcagcggtt acaatggtaa aaca 24

<210> SEQ ID NO 630
<211> LENGTH: 8
<212> TYPE: PRT
<213> ORGANISM: Artificial Sequence
<220> FEATURE:
<223> OTHER INFORMATION: Synthetic

<400> SEQUENCE: 630

Ile Ser Gly Tyr Asn Gly Lys Thr
1 5

<210> SEQ ID NO 631
<211> LENGTH: 60
<212> TYPE: DNA
<213> ORGANISM: Artificial Sequence
<220> FEATURE:
<223> OTHER INFORMATION: Synthetic

<400> SEQUENCE: 631
tcgagagatc gtttagtagt accacctgcc ctttattatt cctactacgt tatggacgtc 60

<210> SEQ ID NO 632
<211> LENGTH: 20
<212> TYPE: PRT
<213> ORGANISM: Artificial Sequence
<220> FEATURE:
<223> OTHER INFORMATION: Synthetic

<400> SEQUENCE: 632

Ser Arg Asp Arg Leu Val Val Pro Pro Ala Leu Tyr Tyr Ser Tyr Tyr
1 5 10 15

Val Met Asp Val
20

<210> SEQ ID NO 633
<211> LENGTH: 336
<212> TYPE: DNA
<213> ORGANISM: Artificial Sequence
<220> FEATURE:
<223> OTHER INFORMATION: Synthetic

<400> SEQUENCE: 633
gatgttgtga tgactcagtc tccactctcc ctgcccgtca cccttggaca gccggcctcc 60
atctcctgca ggtctagtca aagcctcgta tacagtgatg gaaacaccta cttgaattgg 120
tttcagcaga ggccaggtca atctccaagg cgcctaattt ataaggtttc taaccgggac 180
tctggggtcc cagacagatt cagcggcagt gggtcaggca ctgatttcac actgaaaatc 240
agcagggtgg aggctgagga tgttggggtt tattactgca tgcaaggtac acactggccg 300
tacacttttg gccaggggac caagctggag atcaaa 336

<210> SEQ ID NO 634
<211> LENGTH: 112
<212> TYPE: PRT
<213> ORGANISM: Artificial Sequence
<220> FEATURE:
<223> OTHER INFORMATION: Synthetic

<400> SEQUENCE: 634

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Leu Val Tyr Ser
20 25 30

Asp Gly Asn Thr Tyr Leu Asn Trp Phe Gln Gln Arg Pro Gly Gln Ser
35 40 45

Pro Arg Arg Leu Ile Tyr Lys Val Ser Asn Arg Asp Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Gly
85 90 95

Thr His Trp Pro Tyr Thr Phe Gly Gln Gly Thr Lys Leu Glu Ile Lys
100 105 110

<210> SEQ ID NO 635
<211> LENGTH: 33
<212> TYPE: DNA
<213> ORGANISM: Artificial Sequence
<220> FEATURE:
<223> OTHER INFORMATION: Synthetic

<400> SEQUENCE: 635
caaagcctcg tatacagtga tggaaacacc tac 33

<210> SEQ ID NO 636
<211> LENGTH: 11
<212> TYPE: PRT
<213> ORGANISM: Artificial Sequence
<220> FEATURE:
<223> OTHER INFORMATION: Synthetic

<400> SEQUENCE: 636

Gln Ser Leu Val Tyr Ser Asp Gly Asn Thr Tyr
1 5 10

<210> SEQ ID NO 637
<211> LENGTH: 9
<212> TYPE: DNA
<213> ORGANISM: Artificial Sequence
<220> FEATURE:
<223> OTHER INFORMATION: Synthetic

<400> SEQUENCE: 637 aaggtttct 9

<210> SEQ ID NO 638
<211> LENGTH: 3
<212> TYPE: PRT
<213> ORGANISM: Artificial Sequence
<220> FEATURE:
<223> OTHER INFORMATION: Synthetic

<400> SEQUENCE: 638

Lys Val Ser
1

<210> SEQ ID NO 639
<211> LENGTH: 27

<212> TYPE: DNA
<213> ORGANISM: Artificial Sequence
<220> FEATURE:
<223> OTHER INFORMATION: Synthetic

<400> SEQUENCE: 639
atgcaaggta cacactggcc gtacact 27

<210> SEQ ID NO 640
<211> LENGTH: 9
<212> TYPE: PRT
<213> ORGANISM: Artificial Sequence
<220> FEATURE:
<223> OTHER INFORMATION: Synthetic

<400> SEQUENCE: 640

Met Gln Gly Thr His Trp Pro Tyr Thr
1 5

<210> SEQ ID NO 641
<211> LENGTH: 381
<212> TYPE: DNA
<213> ORGANISM: Artificial Sequence
<220> FEATURE:
<223> OTHER INFORMATION: Synthetic

<400> SEQUENCE: 641
caggttcagc tggtgcagtc tggacctgag gtgaagaacc ctggggcctc agtgaaggtc 60
tcctgcaagg cttctggtta cacctttacc acctatggta tcagttgggt acgacaggcc 120
cctggacaag ggcttgagtg gatgggatgg atcagcggtt acaatggtaa aacaaacgat 180
gcacagaagt tccaggacag agtcgccatg accacagaca catccacgag cacagcctac 240
atggagctga ggagcctgag atctgacgac acggccattt attactgttc gagagatcgt 300
ttagtagtac cacctgccct ttattattcc tactacgtta tggacgtctg gggccaaggg 360
accacggtca ccgtctcctc a 381

<210> SEQ ID NO 642
<211> LENGTH: 127
<212> TYPE: PRT
<213> ORGANISM: Artificial Sequence
<220> FEATURE:
<223> OTHER INFORMATION: Synthetic

<400> SEQUENCE: 642

Gln Val Gln Leu Val Gln Ser Gly Pro Glu Val Lys Asn Pro Gly Ala
1 5 10 15

Ser Val Lys Val Ser Cys Lys Ala Ser Gly Tyr Thr Phe Thr Thr Tyr
20 25 30

Gly Ile Ser Trp Val Arg Gln Ala Pro Gly Gln Gly Leu Glu Trp Met
35 40 45

Gly Trp Ile Ser Gly Tyr Asn Gly Lys Thr Asn Asp Ala Gln Lys Phe
50 55 60

Gln Asp Arg Val Ala Met Thr Thr Asp Thr Ser Thr Ser Thr Ala Tyr
65 70 75 80

Met Glu Leu Arg Ser Leu Arg Ser Asp Asp Thr Ala Ile Tyr Tyr Cys
85 90 95

Ser Arg Asp Arg Leu Val Val Pro Pro Ala Leu Tyr Tyr Ser Tyr Tyr
100 105 110

Val Met Asp Val Trp Gly Gln Gly Thr Thr Val Thr Val Ser Ser
115 120 125

<210> SEQ ID NO 643
<211> LENGTH: 336
<212> TYPE: DNA
<213> ORGANISM: Artificial Sequence
<220> FEATURE:
<223> OTHER INFORMATION: Synthetic

<400> SEQUENCE: 643
gatgttgtga tgactcagtc tccactctcc ctgcccgtca cccttggaca gccggcctcc 60
atctcctgca ggtctagtca aagcctcgta tacagtgatg gaaacaccta cttgaattgg 120
tttcagcaga ggccaggtca atctccaagg cgcctaattt ataaggtttc taaccgggac 180
tctggggtcc cagacagatt cagcggcagt gggtcaggca ctgatttcac actgaaaatc 240
agcagggtgg aggctgagga tgttggggtt tattactgca tgcaaggtac acactggccg 300
tacacttttg gccaggggac caagctggag atcaaa 336

<210> SEQ ID NO 644
<211> LENGTH: 112
<212> TYPE: PRT
<213> ORGANISM: Artificial Sequence
<220> FEATURE:
<223> OTHER INFORMATION: Synthetic

<400> SEQUENCE: 644

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Leu Val Tyr Ser
20 25 30

Asp Gly Asn Thr Tyr Leu Asn Trp Phe Gln Gln Arg Pro Gly Gln Ser
35 40 45

Pro Arg Arg Leu Ile Tyr Lys Val Ser Asn Arg Asp Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Gly
85 90 95

Thr His Trp Pro Tyr Thr Phe Gly Gln Gly Thr Lys Leu Glu Ile Lys
100 105 110

<210> SEQ ID NO 645
<211> LENGTH: 381
<212> TYPE: DNA
<213> ORGANISM: Artificial Sequence
<220> FEATURE:
<223> OTHER INFORMATION: Synthetic

<400> SEQUENCE: 645
caggttcagc tggtgcagtc tggagctgag gtgaagaagc ctggggcctc agtgaaggtc 60
tcctgcaagg cttctggtta cacctttacc acctatggta tcagctgggt gcgacaggcc 120
cctggacaag ggcttgagtg gatgggatgg atcagcggtt acaatggtaa aacaaactat 180
gcacagaagc tccagggcag agtcaccatg accacagaca catccacgag cacagcctac 240
atggagctga ggagcctgag atctgacgac acggccgtgt attactgttc gagagatcgt 300
ttagtagtac cacctgccct ttattattcc tactacgtta tggacgtctg ggggcaaggg 360
accacggtca ccgtctcctc a 381

<210> SEQ ID NO 646
<211> LENGTH: 127
<212> TYPE: PRT
<213> ORGANISM: Artificial Sequence
<220> FEATURE:
<223> OTHER INFORMATION: Synthetic

<400> SEQUENCE: 646

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Gly Ile Ser Trp Val Arg Gln Ala Pro Gly Gln Gly Leu Glu Trp Met
        35                  40                  45

Gly Trp Ile Ser Gly Tyr Asn Gly Lys Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ser Arg Asp Arg Leu Val Val Pro Pro Ala Leu Tyr Tyr Ser Tyr Tyr
            100                 105                 110

Val Met Asp Val Trp Gly Gln Gly Thr Thr Val Thr Val Ser Ser
        115                 120                 125
```

<210> SEQ ID NO 647
<211> LENGTH: 336
<212> TYPE: DNA
<213> ORGANISM: Artificial Sequence
<220> FEATURE:
<223> OTHER INFORMATION: Synthetic

<400> SEQUENCE: 647

```
gatgttgtga tgactcagtc tccactctcc ctgcccgtca cccttggaca gccggcctcc      60

atctcctgca ggtctagtca aagcctcgta tacagtgatg gaaacaccta cttgaattgg     120

tttcagcaga ggccaggcca atctccaagg cgcctaattt ataaggtttc taaccgggac     180

tctggggtcc cagacagatt cagcggcagt gggtcaggca ctgatttcac actgaaaatc     240

agcagggtgg aggctgagga tgttggggtt tattactgca tgcaaggtac acactggccg     300

tacacttttg gccaggggac caagctggag atcaaa                               336
```

<210> SEQ ID NO 648
<211> LENGTH: 112
<212> TYPE: PRT
<213> ORGANISM: Artificial Sequence
<220> FEATURE:
<223> OTHER INFORMATION: Synthetic

<400> SEQUENCE: 648

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80
```

Ser Arg Val Glu Ala Glu Asp Val Gly Val Tyr Tyr Cys Met Gln Gly
                85                  90                  95

Thr His Trp Pro Tyr Thr Phe Gly Gln Gly Thr Lys Leu Glu Ile Lys
            100                 105                 110

<210> SEQ ID NO 649
<211> LENGTH: 381
<212> TYPE: DNA
<213> ORGANISM: Artificial Sequence
<220> FEATURE:
<223> OTHER INFORMATION: Synthetic

<400> SEQUENCE: 649
caggttcagc tggtgcagtc tggacctgag gtgaagaacc ctggggcctc agtgaaggtc 60
tcctgcaagg cttctggtta cacctttacc acctatggta tcagttgggt acgacaggcc 120
cctggacaag ggcttgagtg gatgggatgg atcagcggtt acaatggtaa aacaaacgat 180
gcacagaagt tccaggacag agtcgccatg accacagaca catccacgag cacagcctac 240
atggagctga ggagcctgag atctgacgac acggccattt attactgttc gagagatcgt 300
ttagtagtac cacctgccct taattattac tactacgtta tggacgtctg ggccaaggg 360 accacggtca ccgtctcctc a 381

<210> SEQ ID NO 650
<211> LENGTH: 127
<212> TYPE: PRT
<213> ORGANISM: Artificial Sequence
<220> FEATURE:
<223> OTHER INFORMATION: Synthetic

<400> SEQUENCE: 650

Gln Val Gln Leu Val Gln Ser Gly Pro Glu Val Lys Asn Pro Gly Ala
1               5                   10                  15

Ser Val Lys Val Ser Cys Lys Ala Ser Gly Tyr Thr Phe Thr Thr Tyr
            20                  25                  30

Gly Ile Ser Trp Val Arg Gln Ala Pro Gly Gln Gly Leu Glu Trp Met
        35                  40                  45

Gly Trp Ile Ser Gly Tyr Asn Gly Lys Thr Asn Asp Ala Gln Lys Phe
    50                  55                  60

Gln Asp Arg Val Ala Met Thr Thr Asp Thr Ser Thr Ser Thr Ala Tyr
65                  70                  75                  80

Met Glu Leu Arg Ser Leu Arg Ser Asp Asp Thr Ala Ile Tyr Tyr Cys
                85                  90                  95

Ser Arg Asp Arg Leu Val Val Pro Pro Ala Leu Asn Tyr Tyr Tyr Tyr
            100                 105                 110

Val Met Asp Val Trp Gly Gln Gly Thr Thr Val Thr Val Ser Ser
        115                 120                 125

<210> SEQ ID NO 651
<211> LENGTH: 24
<212> TYPE: DNA
<213> ORGANISM: Artificial Sequence
<220> FEATURE:
<223> OTHER INFORMATION: Synthetic

<400> SEQUENCE: 651
ggttacacct ttaccaccta tggt 24

<210> SEQ ID NO 652

<211> LENGTH: 8
<212> TYPE: PRT
<213> ORGANISM: Artificial Sequence
<220> FEATURE:
<223> OTHER INFORMATION: Synthetic

<400> SEQUENCE: 652

Gly Tyr Thr Phe Thr Thr Tyr Gly
1 5

<210> SEQ ID NO 653
<211> LENGTH: 24
<212> TYPE: DNA
<213> ORGANISM: Artificial Sequence
<220> FEATURE:
<223> OTHER INFORMATION: Synthetic

<400> SEQUENCE: 653
atcagcggtt acaatggtaa aaca 24

<210> SEQ ID NO 654
<211> LENGTH: 8
<212> TYPE: PRT
<213> ORGANISM: Artificial Sequence
<220> FEATURE:
<223> OTHER INFORMATION: Synthetic

<400> SEQUENCE: 654

Ile Ser Gly Tyr Asn Gly Lys Thr
1 5

<210> SEQ ID NO 655
<211> LENGTH: 60
<212> TYPE: DNA
<213> ORGANISM: Artificial Sequence
<220> FEATURE:
<223> OTHER INFORMATION: Synthetic

<400> SEQUENCE: 655
tcgagagatc gtttagtagt accacctgcc cttaattatt actactacgt tatggacgtc 60

<210> SEQ ID NO 656
<211> LENGTH: 20
<212> TYPE: PRT
<213> ORGANISM: Artificial Sequence
<220> FEATURE:
<223> OTHER INFORMATION: Synthetic

<400> SEQUENCE: 656

Ser Arg Asp Arg Leu Val Val Pro Pro Ala Leu Asn Tyr Tyr Tyr Tyr
1 5 10 15

Val Met Asp Val
20

<210> SEQ ID NO 657
<211> LENGTH: 336
<212> TYPE: DNA
<213> ORGANISM: Artificial Sequence
<220> FEATURE:
<223> OTHER INFORMATION: Synthetic

<400> SEQUENCE: 657
gatgttgtga tgactcagtc tccactctcc ctgcccgtca cccttggaca gccggcctcc 60
atctcctgca ggtctagtca aagcctcgta tacagtgatg gaaacaccta cttgaattgg 120
tttcagcaga ggccaggtca atctccaagg cgcctaattt ataaggtttc taaccgggac 180
tctggggtcc cagacagatt cagcggcagt gggtcaggca ctgatttcac actgaaaatc 240
agcagggtgg aggctgagga tgttggggtt tattactgca tgcaaggtac acactggccg 300
tacacttttg gccaggggac caagctggag atcaaa 336

<210> SEQ ID NO 658
<211> LENGTH: 112
<212> TYPE: PRT
<213> ORGANISM: Artificial Sequence
<220> FEATURE:
<223> OTHER INFORMATION: Synthetic

<400> SEQUENCE: 658

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Leu Val Tyr Ser
20 25 30

Asp Gly Asn Thr Tyr Leu Asn Trp Phe Gln Gln Arg Pro Gly Gln Ser
35 40 45

Pro Arg Arg Leu Ile Tyr Lys Val Ser Asn Arg Asp Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Gly
85 90 95

Thr His Trp Pro Tyr Thr Phe Gly Gln Gly Thr Lys Leu Glu Ile Lys
100 105 110

<210> SEQ ID NO 659
<211> LENGTH: 33
<212> TYPE: DNA
<213> ORGANISM: Artificial Sequence
<220> FEATURE:
<223> OTHER INFORMATION: Synthetic

<400> SEQUENCE: 659
caaagcctcg tatacagtga tggaaacacc tac 33

<210> SEQ ID NO 660
<211> LENGTH: 11
<212> TYPE: PRT
<213> ORGANISM: Artificial Sequence
<220> FEATURE:
<223> OTHER INFORMATION: Synthetic

<400> SEQUENCE: 660

Gln Ser Leu Val Tyr Ser Asp Gly Asn Thr Tyr
1 5 10

<210> SEQ ID NO 661
<211> LENGTH: 9
<212> TYPE: DNA
<213> ORGANISM: Artificial Sequence
<220> FEATURE:
<223> OTHER INFORMATION: Synthetic

<400> SEQUENCE: 661 aaggtttct 9

<210> SEQ ID NO 662
<211> LENGTH: 3
<212> TYPE: PRT

<213> ORGANISM: Artificial Sequence
<220> FEATURE:
<223> OTHER INFORMATION: Synthetic

<400> SEQUENCE: 662

Lys Val Ser
1

<210> SEQ ID NO 663
<211> LENGTH: 27
<212> TYPE: DNA
<213> ORGANISM: Artificial Sequence
<220> FEATURE:
<223> OTHER INFORMATION: Synthetic

<400> SEQUENCE: 663
atgcaaggta cacactggcc gtacact 27

<210> SEQ ID NO 664
<211> LENGTH: 9
<212> TYPE: PRT
<213> ORGANISM: Artificial Sequence
<220> FEATURE:
<223> OTHER INFORMATION: Synthetic

<400> SEQUENCE: 664

Met Gln Gly Thr His Trp Pro Tyr Thr
1 5

<210> SEQ ID NO 665
<211> LENGTH: 381
<212> TYPE: DNA
<213> ORGANISM: Artificial Sequence
<220> FEATURE:
<223> OTHER INFORMATION: Synthetic

<400> SEQUENCE: 665
caggttcagc tggtgcagtc tggacctgag gtgaagaacc ctggggcctc agtgaaggtc 60
tcctgcaagg cttctggtta cacctttacc acctatggta tcagttgggt acgacaggcc 120
cctggacaag ggcttgagtg gatgggatgg atcagcggtt acaatggtaa aacaaacgat 180
gcacagaagt tccaggacag agtcgccatg accacagaca catccacgag cacagcctac 240
atggagctga ggagcctgag atctgacgac acggccattt attactgttc gagagatcgt 300
ttagtagtac cacctgccct taattattac tactacgtta tggacgtctg gggccaaggg 360
accacggtca ccgtctcctc a 381

<210> SEQ ID NO 666
<211> LENGTH: 127
<212> TYPE: PRT
<213> ORGANISM: Artificial Sequence
<220> FEATURE:
<223> OTHER INFORMATION: Synthetic

<400> SEQUENCE: 666

Gln Val Gln Leu Val Gln Ser Gly Pro Glu Val Lys Asn Pro Gly Ala
1 5 10 15

Ser Val Lys Val Ser Cys Lys Ala Ser Gly Tyr Thr Phe Thr Thr Tyr
20 25 30

Gly Ile Ser Trp Val Arg Gln Ala Pro Gly Gln Gly Leu Glu Trp Met
35 40 45

Gly Trp Ile Ser Gly Tyr Asn Gly Lys Thr Asn Asp Ala Gln Lys Phe
50 55 60

Gln Asp Arg Val Ala Met Thr Thr Asp Thr Ser Thr Ser Thr Ala Tyr
65 70 75 80

Met Glu Leu Arg Ser Leu Arg Ser Asp Asp Thr Ala Ile Tyr Tyr Cys
85 90 95

Ser Arg Asp Arg Leu Val Val Pro Pro Ala Leu Asn Tyr Tyr Tyr Tyr
100 105 110

Val Met Asp Val Trp Gly Gln Gly Thr Thr Val Thr Val Ser Ser
115 120 125

<210> SEQ ID NO 667
<211> LENGTH: 336
<212> TYPE: DNA
<213> ORGANISM: Artificial Sequence
<220> FEATURE:
<223> OTHER INFORMATION: Synthetic

<400> SEQUENCE: 667
gatgttgtga tgactcagtc tccactctcc ctgcccgtca cccttggaca gccggcctcc 60
atctcctgca ggtctagtca aagcctcgta tacagtgatg gaaacaccta cttgaattgg 120
tttcagcaga ggccaggtca atctccaagg cgcctaattt ataaggtttc taaccgggac 180
tctggggtcc cagacagatt cagcggcagt gggtcaggca ctgatttcac actgaaaatc 240
agcagggtgg aggctgagga tgttggggtt tattactgca tgcaaggtac acactggccg 300
tacacttttg gccaggggac caagctggag atcaaa 336

<210> SEQ ID NO 668
<211> LENGTH: 112
<212> TYPE: PRT
<213> ORGANISM: Artificial Sequence
<220> FEATURE:
<223> OTHER INFORMATION: Synthetic

<400> SEQUENCE: 668

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Leu Val Tyr Ser
20 25 30

Asp Gly Asn Thr Tyr Leu Asn Trp Phe Gln Gln Arg Pro Gly Gln Ser
35 40 45

Pro Arg Arg Leu Ile Tyr Lys Val Ser Asn Arg Asp Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Gly
85 90 95

Thr His Trp Pro Tyr Thr Phe Gly Gln Gly Thr Lys Leu Glu Ile Lys
100 105 110

<210> SEQ ID NO 669
<211> LENGTH: 381
<212> TYPE: DNA
<213> ORGANISM: Artificial Sequence
<220> FEATURE:
<223> OTHER INFORMATION: Synthetic

<400> SEQUENCE: 669
caggttcagc tggtgcagtc tggagctgag gtgaagaagc ctggggcctc agtgaaggtc 60
tcctgcaagg cttctggtta cacctttacc acctatggta tcagctgggt gcgacaggcc 120

```
cctggacaag ggcttgagtg gatgggatgg atcagcggtt acaatggtaa aacaaactat    180

gcacagaagc tccagggcag agtcaccatg accacagaca catccacgag cacagcctac    240

atggagctga ggagcctgag atctgacgac acggccgtgt attactgttc gagagatcgt    300

ttagtagtac cacctgccct taattattac tactacgtta tggacgtctg gggcaaggg    360

accacggtca ccgtctcctc a                                              381


<210> SEQ ID NO 670
<211> LENGTH: 127
<212> TYPE: PRT
<213> ORGANISM: Artificial Sequence
<220> FEATURE:
<223> OTHER INFORMATION: Synthetic

<400> SEQUENCE: 670

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Gly Ile Ser Trp Val Arg Gln Ala Pro Gly Gln Gly Leu Glu Trp Met
        35                  40                  45

Gly Trp Ile Ser Gly Tyr Asn Gly Lys Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ser Arg Asp Arg Leu Val Val Pro Pro Ala Leu Asn Tyr Tyr Tyr Tyr
            100                 105                 110

Val Met Asp Val Trp Gly Gln Gly Thr Thr Val Thr Val Ser Ser
        115                 120                 125


<210> SEQ ID NO 671
<211> LENGTH: 336
<212> TYPE: DNA
<213> ORGANISM: Artificial Sequence
<220> FEATURE:
<223> OTHER INFORMATION: Synthetic

<400> SEQUENCE: 671

gatgttgtga tgactcagtc tccactctcc ctgcccgtca cccttggaca gccggcctcc     60

atctcctgca ggtctagtca aagcctcgta tacagtgatg gaaacaccta cttgaattgg    120

tttcagcaga ggccaggcca atctccaagg cgcctaattt ataaggtttc taaccgggac    180

tctggggtcc cagacagatt cagcggcagt gggtcaggca ctgatttcac actgaaaatc    240

agcagggtgg aggctgagga tgttggggtt tattactgca tgcaaggtac acactggccg    300

tacacttttg gccaggggac caagctggag atcaaa                              336


<210> SEQ ID NO 672
<211> LENGTH: 112
<212> TYPE: PRT
<213> ORGANISM: Artificial Sequence
<220> FEATURE:
<223> OTHER INFORMATION: Synthetic

<400> SEQUENCE: 672

Asp Val Val Met Thr Gln Ser Pro Leu Ser Leu Pro Val Thr Leu Gly
1               5                   10                  15
```

```
Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Tyr Thr Phe Gly Gln Gly Thr Lys Leu Glu Ile Lys
            100                 105                 110


<210> SEQ ID NO 673
<211> LENGTH: 381
<212> TYPE: DNA
<213> ORGANISM: Artificial Sequence
<220> FEATURE:
<223> OTHER INFORMATION: Synthetic

<400> SEQUENCE: 673

caggttcagc tggtgcagtc tggacctgag gtgaagaacc ctggggcctc agtgaaggtc      60

tcctgcaagg cttctggtta cacctttacc acctatggta tcagttgggt acgacaggcc     120

cctggacaag ggcttgagtg gatgggatgg atcagcggtt acaatggtaa aacaaacgat     180

gcacagaagt tccaggacag agtcgccatg accacagaca catccacgag cacagcctac     240

atggagctga ggagcctgag atctgacgac acggccattt attactgttc gagagatcgt     300

ttagtagtac cacctgccct ttattattac tactacgtta tggacgtctg gggccaaggg     360

accacggtca ccgtctcctc a                                                381


<210> SEQ ID NO 674
<211> LENGTH: 127
<212> TYPE: PRT
<213> ORGANISM: Artificial Sequence
<220> FEATURE:
<223> OTHER INFORMATION: Synthetic

<400> SEQUENCE: 674

Gln Val Gln Leu Val Gln Ser Gly Pro Glu Val Lys Asn Pro Gly Ala
1               5                   10                  15

Ser Val Lys Val Ser Cys Lys Ala Ser Gly Tyr Thr Phe Thr Thr Tyr
            20                  25                  30

Gly Ile Ser Trp Val Arg Gln Ala Pro Gly Gln Gly Leu Glu Trp Met
        35                  40                  45

Gly Trp Ile Ser Gly Tyr Asn Gly Lys Thr Asn Asp Ala Gln Lys Phe
    50                  55                  60

Gln Asp Arg Val Ala Met Thr Thr Asp Thr Ser Thr Ser Thr Ala Tyr
65                  70                  75                  80

Met Glu Leu Arg Ser Leu Arg Ser Asp Asp Thr Ala Ile Tyr Tyr Cys
                85                  90                  95

Ser Arg Asp Arg Leu Val Val Pro Pro Ala Leu Tyr Tyr Tyr Tyr Tyr
            100                 105                 110

Val Met Asp Val Trp Gly Gln Gly Thr Thr Val Thr Val Ser Ser
        115                 120                 125


<210> SEQ ID NO 675
```

<211> LENGTH: 24
<212> TYPE: DNA
<213> ORGANISM: Artificial Sequence
<220> FEATURE:
<223> OTHER INFORMATION: Synthetic

<400> SEQUENCE: 675
ggttacacct ttaccaccta tggt 24

<210> SEQ ID NO 676
<211> LENGTH: 8
<212> TYPE: PRT
<213> ORGANISM: Artificial Sequence
<220> FEATURE:
<223> OTHER INFORMATION: Synthetic

<400> SEQUENCE: 676

Gly Tyr Thr Phe Thr Thr Tyr Gly
1 5

<210> SEQ ID NO 677
<211> LENGTH: 24
<212> TYPE: DNA
<213> ORGANISM: Artificial Sequence
<220> FEATURE:
<223> OTHER INFORMATION: Synthetic

<400> SEQUENCE: 677
atcagcggtt acaatggtaa aaca 24

<210> SEQ ID NO 678
<211> LENGTH: 8
<212> TYPE: PRT
<213> ORGANISM: Artificial Sequence
<220> FEATURE:
<223> OTHER INFORMATION: Synthetic

<400> SEQUENCE: 678

Ile Ser Gly Tyr Asn Gly Lys Thr
1 5

<210> SEQ ID NO 679
<211> LENGTH: 60
<212> TYPE: DNA
<213> ORGANISM: Artificial Sequence
<220> FEATURE:
<223> OTHER INFORMATION: Synthetic

<400> SEQUENCE: 679
tcgagagatc gtttagtagt accacctgcc ctttattatt actactacgt tatggacgtc 60

<210> SEQ ID NO 680
<211> LENGTH: 20
<212> TYPE: PRT
<213> ORGANISM: Artificial Sequence
<220> FEATURE:
<223> OTHER INFORMATION: Synthetic

<400> SEQUENCE: 680

Ser Arg Asp Arg Leu Val Val Pro Pro Ala Leu Tyr Tyr Tyr Tyr Tyr
1 5 10 15

Val Met Asp Val
20

<210> SEQ ID NO 681
<211> LENGTH: 336

<212> TYPE: DNA
<213> ORGANISM: Artificial Sequence
<220> FEATURE:
<223> OTHER INFORMATION: Synthetic

<400> SEQUENCE: 681
gatgttgtga tgactcagtc tccactctcc ctgcccgtca cccttggaca gccggcctcc 60
atctcctgca ggtctagtca aagcctcgta tacagtgatg gaaacaccta cttgaattgg 120
tttcagcaga ggccaggtca atctccaagg cgcctaattt ataaggtttc taaccgggac 180
tctggggtcc cagacagatt cagcggcagt gggtcaggca ctgatttcac actgaaaatc 240
agcagggtgg aggctgagga tgttggggtt tattactgca tgcaaggtac acactggccg 300
tacacttttg gccaggggac caagctggag atcaaa 336

<210> SEQ ID NO 682
<211> LENGTH: 112
<212> TYPE: PRT
<213> ORGANISM: Artificial Sequence
<220> FEATURE:
<223> OTHER INFORMATION: Synthetic

<400> SEQUENCE: 682

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Leu Val Tyr Ser
20 25 30

Asp Gly Asn Thr Tyr Leu Asn Trp Phe Gln Gln Arg Pro Gly Gln Ser
35 40 45

Pro Arg Arg Leu Ile Tyr Lys Val Ser Asn Arg Asp Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Gly
85 90 95

Thr His Trp Pro Tyr Thr Phe Gly Gln Gly Thr Lys Leu Glu Ile Lys
100 105 110

<210> SEQ ID NO 683
<211> LENGTH: 33
<212> TYPE: DNA
<213> ORGANISM: Artificial Sequence
<220> FEATURE:
<223> OTHER INFORMATION: Synthetic

<400> SEQUENCE: 683
caaagcctcg tatacagtga tggaaacacc tac 33

<210> SEQ ID NO 684
<211> LENGTH: 11
<212> TYPE: PRT
<213> ORGANISM: Artificial Sequence
<220> FEATURE:
<223> OTHER INFORMATION: Synthetic

<400> SEQUENCE: 684

Gln Ser Leu Val Tyr Ser Asp Gly Asn Thr Tyr
1 5 10

<210> SEQ ID NO 685
<211> LENGTH: 9
<212> TYPE: DNA

<213> ORGANISM: Artificial Sequence
<220> FEATURE:
<223> OTHER INFORMATION: Synthetic

<400> SEQUENCE: 685 aaggtttct 9

<210> SEQ ID NO 686
<211> LENGTH: 3
<212> TYPE: PRT
<213> ORGANISM: Artificial Sequence
<220> FEATURE:
<223> OTHER INFORMATION: Synthetic

<400> SEQUENCE: 686

Lys Val Ser
1

<210> SEQ ID NO 687
<211> LENGTH: 27
<212> TYPE: DNA
<213> ORGANISM: Artificial Sequence
<220> FEATURE:
<223> OTHER INFORMATION: Synthetic

<400> SEQUENCE: 687
atgcaaggta cacactggcc gtacact 27

<210> SEQ ID NO 688
<211> LENGTH: 9
<212> TYPE: PRT
<213> ORGANISM: Artificial Sequence
<220> FEATURE:
<223> OTHER INFORMATION: Synthetic

<400> SEQUENCE: 688

Met Gln Gly Thr His Trp Pro Tyr Thr
1 5

<210> SEQ ID NO 689
<211> LENGTH: 381
<212> TYPE: DNA
<213> ORGANISM: Artificial Sequence
<220> FEATURE:
<223> OTHER INFORMATION: Synthetic

<400> SEQUENCE: 689
caggttcagc tggtgcagtc tggacctgag gtgaagaacc ctggggcctc agtgaaggtc 60
tcctgcaagg cttctggtta cacctttacc acctatggta tcagttgggt acgacaggcc 120
cctggacaag ggcttgagtg gatgggatgg atcagcggtt acaatggtaa aacaaacgat 180
gcacagaagt tccaggacag agtcgccatg accacagaca catccacgag cacagcctac 240
atggagctga ggagcctgag atctgacgac acggccattt attactgttc gagagatcgt 300
ttagtagtac cacctgccct ttattattac tactacgtta tggacgtctg gggccaaggg 360
accacggtca ccgtctcctc a 381

<210> SEQ ID NO 690
<211> LENGTH: 127
<212> TYPE: PRT
<213> ORGANISM: Artificial Sequence
<220> FEATURE:
<223> OTHER INFORMATION: Synthetic

<400> SEQUENCE: 690

Gln Val Gln Leu Val Gln Ser Gly Pro Glu Val Lys Asn Pro Gly Ala
1 5 10 15

Ser Val Lys Val Ser Cys Lys Ala Ser Gly Tyr Thr Phe Thr Thr Tyr
20 25 30

Gly Ile Ser Trp Val Arg Gln Ala Pro Gly Gln Gly Leu Glu Trp Met
35 40 45

Gly Trp Ile Ser Gly Tyr Asn Gly Lys Thr Asn Asp Ala Gln Lys Phe
50 55 60

Gln Asp Arg Val Ala Met Thr Thr Asp Thr Ser Thr Ser Thr Ala Tyr
65 70 75 80

Met Glu Leu Arg Ser Leu Arg Ser Asp Asp Thr Ala Ile Tyr Tyr Cys
85 90 95

Ser Arg Asp Arg Leu Val Val Pro Pro Ala Leu Tyr Tyr Tyr Tyr Tyr
100 105 110

Val Met Asp Val Trp Gly Gln Gly Thr Thr Val Thr Val Ser Ser
115 120 125

<210> SEQ ID NO 691
<211> LENGTH: 336
<212> TYPE: DNA
<213> ORGANISM: Artificial Sequence
<220> FEATURE:
<223> OTHER INFORMATION: Synthetic

<400> SEQUENCE: 691
gatgttgtga tgactcagtc tccactctcc ctgcccgtca cccttggaca gccggcctcc 60
atctcctgca ggtctagtca aagcctcgta tacagtgatg gaaacaccta cttgaattgg 120
tttcagcaga ggccaggtca atctccaagg cgcctaattt ataaggtttc taaccgggac 180
tctggggtcc cagacagatt cagcggcagt gggtcaggca ctgatttcac actgaaaatc 240
agcagggtgg aggctgagga tgttggggtt tattactgca tgcaaggtac acactggccg 300
tacacttttg gccaggggac caagctggag atcaaa 336

<210> SEQ ID NO 692
<211> LENGTH: 112
<212> TYPE: PRT
<213> ORGANISM: Artificial Sequence
<220> FEATURE:
<223> OTHER INFORMATION: Synthetic

<400> SEQUENCE: 692

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Leu Val Tyr Ser
20 25 30

Asp Gly Asn Thr Tyr Leu Asn Trp Phe Gln Gln Arg Pro Gly Gln Ser
35 40 45

Pro Arg Arg Leu Ile Tyr Lys Val Ser Asn Arg Asp Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Gly
85 90 95

Thr His Trp Pro Tyr Thr Phe Gly Gln Gly Thr Lys Leu Glu Ile Lys
100 105 110

<210> SEQ ID NO 693
<211> LENGTH: 381
<212> TYPE: DNA
<213> ORGANISM: Artificial Sequence
<220> FEATURE:
<223> OTHER INFORMATION: Synthetic

<400> SEQUENCE: 693
caggttcagc tggtgcagtc tggagctgag gtgaagaagc ctggggcctc agtgaaggtc 60
tcctgcaagg cttctggtta cacctttacc acctatggta tcagctgggt gcgacaggcc 120
cctggacaag ggcttgagtg gatgggatgg atcagcggtt acaatggtaa aacaaactat 180
gcacagaagc tccagggcag agtcaccatg accacagaca catccacgag cacagcctac 240
atggagctga ggagcctgag atctgacgac acggccgtgt attactgttc gagagatcgt 300
ttagtagtac cacctgccct ttattattac tactacgtta tggacgtctg gggcaaggg 360 accacggtca ccgtctcctc a 381

<210> SEQ ID NO 694
<211> LENGTH: 127
<212> TYPE: PRT
<213> ORGANISM: Artificial Sequence
<220> FEATURE:
<223> OTHER INFORMATION: Synthetic

<400> SEQUENCE: 694

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Thr Tyr
20 25 30

Gly Ile Ser Trp Val Arg Gln Ala Pro Gly Gln Gly Leu Glu Trp Met
35 40 45

Gly Trp Ile Ser Gly Tyr Asn Gly Lys Thr Asn Tyr Ala Gln Lys Leu
50 55 60

Gln Gly Arg Val Thr Met Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ser Arg Asp Arg Leu Val Val Pro Pro Ala Leu Tyr Tyr Tyr Tyr Tyr
100 105 110

Val Met Asp Val Trp Gly Gln Gly Thr Thr Val Thr Val Ser Ser
115 120 125

<210> SEQ ID NO 695
<211> LENGTH: 336
<212> TYPE: DNA
<213> ORGANISM: Artificial Sequence
<220> FEATURE:
<223> OTHER INFORMATION: Synthetic

<400> SEQUENCE: 695
gatgttgtga tgactcagtc tccactctcc ctgcccgtca cccttggaca gccggcctcc 60
atctcctgca ggtctagtca aagcctcgta tacagtgatg gaaacaccta cttgaattgg 120
tttcagcaga ggccaggcca atctccaagg cgcctaattt ataaggtttc taaccgggac 180
tctggggtcc cagacagatt cagcggcagt gggtcaggca ctgatttcac actgaaaatc 240
agcagggtgg aggctgagga tgttggggtt tattactgca tgcaaggtac acactggccg 300
tacacttttg gccaggggac caagctggag atcaaa 336

<210> SEQ ID NO 696
<211> LENGTH: 112
<212> TYPE: PRT
<213> ORGANISM: Artificial Sequence
<220> FEATURE:
<223> OTHER INFORMATION: Synthetic

<400> SEQUENCE: 696

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Tyr Thr Phe Gly Gln Gly Thr Lys Leu Glu Ile Lys
            100                 105                 110
```

<210> SEQ ID NO 697
<211> LENGTH: 384
<212> TYPE: DNA
<213> ORGANISM: Artificial Sequence
<220> FEATURE:
<223> OTHER INFORMATION: Synthetic

<400> SEQUENCE: 697

```
caggtgcacc tggtggagtc tgggggaggc ttggtcaagc ctggagggtc cctgagactc      60

tcctgtgcag cctctggatt caccttcagt gaccactaca tgagctggat ccgccaggct     120

ccagggaagg ggctggagtg gatttcatac attagtaatg atggtggtac caaatactat     180

gtggactctg tggagggccg attcatcatt tccagggaca acgccaagaa ctcattgtat     240

ctacatatga acagcctcag agccgacgac acggccgtgt attactgtgc gagagatcag     300

ggatatattg gctacgactc gtattattac tattcctacg gtatggacgt ctggggccaa     360

gggaccacgg tcaccgtcgc ctca                                            384
```

<210> SEQ ID NO 698
<211> LENGTH: 128
<212> TYPE: PRT
<213> ORGANISM: Artificial Sequence
<220> FEATURE:
<223> OTHER INFORMATION: Synthetic

<400> SEQUENCE: 698

```
Gln Val His Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp His
            20                  25                  30

Tyr Met Ser Trp Ile Arg Gln Ala Pro Gly Lys Gly Leu Glu Trp Ile
        35                  40                  45

Ser Tyr Ile Ser Asn Asp Gly Gly Thr Lys Tyr Tyr Val Asp Ser Val
    50                  55                  60

Glu Gly Arg Phe Ile Ile Ser Arg Asp Asn Ala Lys Asn Ser Leu Tyr
65                  70                  75                  80
```

Leu His Met Asn Ser Leu Arg Ala Asp Asp Thr Ala Val Tyr Tyr Cys
85 90 95

Ala Arg Asp Gln Gly Tyr Ile Gly Tyr Asp Ser Tyr Tyr Tyr Tyr Ser
100 105 110

Tyr Gly Met Asp Val Trp Gly Gln Gly Thr Thr Val Thr Val Ala Ser
115 120 125

<210> SEQ ID NO 699
<211> LENGTH: 24
<212> TYPE: DNA
<213> ORGANISM: Artificial Sequence
<220> FEATURE:
<223> OTHER INFORMATION: Synthetic

<400> SEQUENCE: 699
ggattcacct tcagtgacca ctac 24

<210> SEQ ID NO 700
<211> LENGTH: 8
<212> TYPE: PRT
<213> ORGANISM: Artificial Sequence
<220> FEATURE:
<223> OTHER INFORMATION: Synthetic

<400> SEQUENCE: 700

Gly Phe Thr Phe Ser Asp His Tyr
1 5

<210> SEQ ID NO 701
<211> LENGTH: 24
<212> TYPE: DNA
<213> ORGANISM: Artificial Sequence
<220> FEATURE:
<223> OTHER INFORMATION: Synthetic

<400> SEQUENCE: 701
attagtaatg atggtggtac caaa 24

<210> SEQ ID NO 702
<211> LENGTH: 8
<212> TYPE: PRT
<213> ORGANISM: Artificial Sequence
<220> FEATURE:
<223> OTHER INFORMATION: Synthetic

<400> SEQUENCE: 702

Ile Ser Asn Asp Gly Gly Thr Lys
1 5

<210> SEQ ID NO 703
<211> LENGTH: 63
<212> TYPE: DNA
<213> ORGANISM: Artificial Sequence
<220> FEATURE:
<223> OTHER INFORMATION: Synthetic

<400> SEQUENCE: 703
gcgagagatc agggatatat tggctacgac tcgtattatt actattccta cggtatggac 60
gtc 63

<210> SEQ ID NO 704
<211> LENGTH: 21
<212> TYPE: PRT
<213> ORGANISM: Artificial Sequence
<220> FEATURE:
<223> OTHER INFORMATION: Synthetic

<400> SEQUENCE: 704

Ala Arg Asp Gln Gly Tyr Ile Gly Tyr Asp Ser Tyr Tyr Tyr Tyr Ser
1 5 10 15

Tyr Gly Met Asp Val
20

<210> SEQ ID NO 705
<211> LENGTH: 321
<212> TYPE: DNA
<213> ORGANISM: Artificial Sequence
<220> FEATURE:
<223> OTHER INFORMATION: Synthetic

<400> SEQUENCE: 705
aaaattgtgt tgacgcagtc tccaggcacc ctgcctttgt ttccagggga aagagccacc 60
ctctcctgta gggccagtca gagtgttaac aacaaattct tagcctggta ccagcagaaa 120
tctggccagg ctcccaggct cctcatctat ggtgcatcca gcagggccac tggcatccca 180
gacaggttca gtggcagtgg gtctgggacc gacttcactc tcaccatcag cggactggag 240
cctgaagatt ttgaagtgta ttattgtcaa gtatatggta actcactcac tttcggcgga 300
gggaccaagg tggagatcaa g 321

<210> SEQ ID NO 706
<211> LENGTH: 107
<212> TYPE: PRT
<213> ORGANISM: Artificial Sequence
<220> FEATURE:
<223> OTHER INFORMATION: Synthetic

<400> SEQUENCE: 706

Lys Ile Val Leu Thr Gln Ser Pro Gly Thr Leu Pro Leu Phe Pro Gly
1 5 10 15

Glu Arg Ala Thr Leu Ser Cys Arg Ala Ser Gln Ser Val Asn Asn Lys
20 25 30

Phe Leu Ala Trp Tyr Gln Gln Lys Ser Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Gly Leu Glu
65 70 75 80

Pro Glu Asp Phe Glu Val Tyr Tyr Cys Gln Val Tyr Gly Asn Ser Leu
85 90 95

Thr Phe Gly Gly Gly Thr Lys Val Glu Ile Lys
100 105

<210> SEQ ID NO 707
<211> LENGTH: 21
<212> TYPE: DNA
<213> ORGANISM: Artificial Sequence
<220> FEATURE:
<223> OTHER INFORMATION: Synthetic

<400> SEQUENCE: 707
cagagtgtta acaacaaatt c 21

<210> SEQ ID NO 708
<211> LENGTH: 7

<212> TYPE: PRT
<213> ORGANISM: Artificial Sequence
<220> FEATURE:
<223> OTHER INFORMATION: Synthetic

<400> SEQUENCE: 708

Gln Ser Val Asn Asn Lys Phe
1               5

<210> SEQ ID NO 709
<211> LENGTH: 9
<212> TYPE: DNA
<213> ORGANISM: Artificial Sequence
<220> FEATURE:
<223> OTHER INFORMATION: Synthetic

<400> SEQUENCE: 709 ggtgcatcc 9

<210> SEQ ID NO 710
<211> LENGTH: 3
<212> TYPE: PRT
<213> ORGANISM: Artificial Sequence
<220> FEATURE:
<223> OTHER INFORMATION: Synthetic

<400> SEQUENCE: 710

Gly Ala Ser
1

<210> SEQ ID NO 711
<211> LENGTH: 24
<212> TYPE: DNA
<213> ORGANISM: Artificial Sequence
<220> FEATURE:
<223> OTHER INFORMATION: Synthetic

<400> SEQUENCE: 711
caagtatatg gtaactcact cact 24

<210> SEQ ID NO 712
<211> LENGTH: 8
<212> TYPE: PRT
<213> ORGANISM: Artificial Sequence
<220> FEATURE:
<223> OTHER INFORMATION: Synthetic

<400> SEQUENCE: 712

Gln Val Tyr Gly Asn Ser Leu Thr
1               5

<210> SEQ ID NO 713
<211> LENGTH: 384
<212> TYPE: DNA
<213> ORGANISM: Artificial Sequence
<220> FEATURE:
<223> OTHER INFORMATION: Synthetic

<400> SEQUENCE: 713
caggtgcagc tggtggagtc tgggggaggc ttggtcaagc ctggagggtc cctgagactc 60
tcctgtgcag cctctggatt caccttcagt gaccactaca tgagctggat ccgccaggct 120
ccagggaagg ggctggagtg gatttcatac attagtaatg atggtggtac caaatactat 180
gtggactctg tggagggccg attcatcatt tccagggaca acgccaagaa ctcattgtat 240
ctacatatga acagcctcag agccgacgac acggccgtgt attactgtgc gagagatcag 300
ggatatattg gctacgactc gtattattac tattcctacg gtatggacgt ctggggccaa 360
gggaccacgg tcaccgtctc ctca 384

<210> SEQ ID NO 714
<211> LENGTH: 128
<212> TYPE: PRT
<213> ORGANISM: Artificial Sequence
<220> FEATURE:
<223> OTHER INFORMATION: Synthetic

<400> SEQUENCE: 714

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asp His
20 25 30

Tyr Met Ser Trp Ile Arg Gln Ala Pro Gly Lys Gly Leu Glu Trp Ile
35 40 45

Ser Tyr Ile Ser Asn Asp Gly Gly Thr Lys Tyr Tyr Val Asp Ser Val
50 55 60

Glu Gly Arg Phe Ile Ile Ser Arg Asp Asn Ala Lys Asn Ser Leu Tyr
65 70 75 80

Leu His Met Asn Ser Leu Arg Ala Asp Asp Thr Ala Val Tyr Tyr Cys
85 90 95

Ala Arg Asp Gln Gly Tyr Ile Gly Tyr Asp Ser Tyr Tyr Tyr Tyr Ser
100 105 110

Tyr Gly Met Asp Val Trp Gly Gln Gly Thr Thr Val Thr Val Ser Ser
115 120 125

<210> SEQ ID NO 715
<211> LENGTH: 321
<212> TYPE: DNA
<213> ORGANISM: Artificial Sequence
<220> FEATURE:
<223> OTHER INFORMATION: Synthetic

<400> SEQUENCE: 715
gaaattgtgt tgacgcagtc tccaggcacc ctgcctttgt ttccagggga aagagccacc 60
ctctcctgta gggccagtca gagtgttaac aacaaattct tagcctggta ccagcagaaa 120
tctggccagg ctcccaggct cctcatctat ggtgcatcca gcagggccac tggcatccca 180
gacaggttca gtggcagtgg gtctgggacc gacttcactc tcaccatcag cggactggag 240
cctgaagatt ttgaagtgta ttattgtcaa gtatatggta actcactcac tttcggcgga 300
gggaccaagg tggagatcaa a 321

<210> SEQ ID NO 716
<211> LENGTH: 107
<212> TYPE: PRT
<213> ORGANISM: Artificial Sequence
<220> FEATURE:
<223> OTHER INFORMATION: Synthetic

<400> SEQUENCE: 716

Glu Ile Val Leu Thr Gln Ser Pro Gly Thr Leu Pro Leu Phe Pro Gly
1 5 10 15

Glu Arg Ala Thr Leu Ser Cys Arg Ala Ser Gln Ser Val Asn Asn Lys
20 25 30

Phe Leu Ala Trp Tyr Gln Gln Lys Ser Gly Gln Ala Pro Arg Leu Leu
35 40 45

```
Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Gly Leu Glu
65                  70                  75                  80

Pro Glu Asp Phe Glu Val Tyr Tyr Cys Gln Val Tyr Gly Asn Ser Leu
                85                  90                  95

Thr Phe Gly Gly Gly Thr Lys Val Glu Ile Lys
            100                 105
```

<210> SEQ ID NO 717
<211> LENGTH: 384
<212> TYPE: DNA
<213> ORGANISM: Artificial Sequence
<220> FEATURE:
<223> OTHER INFORMATION: Synthetic

<400> SEQUENCE: 717

```
caggtgcagc tggtggagtc tgggggaggc ttggtcaagc ctggagggtc cctgagactc     60

tcctgtgcag cctctggatt caccttcagt gaccactaca tgagctggat ccgccaggct    120

ccagggaagg ggctggagtg ggtttcatac attagtaatg atggtggtac caaatactac    180

gcagactctg tgaagggccg attcaccatc tccagggaca acgccaagaa ctcactgtat    240

ctgcaaatga acagcctgag agccgaggac acggccgtgt attactgtgc gagagatcag    300

ggatatattg gctacgactc gtattattac tattcctacg gtatggacgt ctgggggcaa    360

gggaccacgg tcaccgtctc ctca                                           384
```

<210> SEQ ID NO 718
<211> LENGTH: 128
<212> TYPE: PRT
<213> ORGANISM: Artificial Sequence
<220> FEATURE:
<223> OTHER INFORMATION: Synthetic

<400> SEQUENCE: 718

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp His
            20                  25                  30

Tyr Met Ser Trp Ile Arg Gln Ala Pro Gly Lys Gly Leu Glu Trp Val
        35                  40                  45

Ser Tyr Ile Ser Asn Asp Gly Gly Thr Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Gly Tyr Ile Gly Tyr Asp Ser Tyr Tyr Tyr Tyr Ser
            100                 105                 110

Tyr Gly Met Asp Val Trp Gly Gln Gly Thr Thr Val Thr Val Ser Ser
        115                 120                 125
```

<210> SEQ ID NO 719
<211> LENGTH: 321
<212> TYPE: DNA
<213> ORGANISM: Artificial Sequence
<220> FEATURE:
<223> OTHER INFORMATION: Synthetic

<400> SEQUENCE: 719
gaaattgtgt tgacgcagtc tccaggcacc ctgtctttgt ctccagggga aagagccacc 60
ctctcctgca gggccagtca gagtgttaac aacaaattct tagcctggta ccagcagaaa 120
cctggccagg ctcccaggct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcaa gtatatggta actcactcac tttcggcgga 300
gggaccaagg tggagatcaa a 321

<210> SEQ ID NO 720
<211> LENGTH: 107
<212> TYPE: PRT
<213> ORGANISM: Artificial Sequence
<220> FEATURE:
<223> OTHER INFORMATION: Synthetic

<400> SEQUENCE: 720

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Asn Asn Lys
20 25 30

Phe Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Val Tyr Gly Asn Ser Leu
85 90 95

Thr Phe Gly Gly Gly Thr Lys Val Glu Ile Lys
100 105

<210> SEQ ID NO 721
<211> LENGTH: 378
<212> TYPE: DNA
<213> ORGANISM: Artificial Sequence
<220> FEATURE:
<223> OTHER INFORMATION: Synthetic

<400> SEQUENCE: 721
caaattctgc tggtgcaatc tggacctgag gtgaaggagc ctggggcctc agtgaaggtc 60
tcctgcaagg cttctggtta cacctttacc aactacgcta tcagctgggt gcgacaggtc 120
cctggacaag ggcttgagtg gatgggatgg gtcagcgctt acaatggtca cacaaactat 180
gcacatgaag tccagggcag agtcaccatg accacagaca catccacgac cacagcctac 240
atggagctga ggagcctgag atctgacgac acggccatgt attactgtgc gagagggggt 300
gtagtcgtgc cagttgctcc ccacttctac aacggtatgg acgtctgggg ccaagggacc 360
acggtcaccg tctcctca 378

<210> SEQ ID NO 722
<211> LENGTH: 126
<212> TYPE: PRT
<213> ORGANISM: Artificial Sequence
<220> FEATURE:
<223> OTHER INFORMATION: Synthetic

<400> SEQUENCE: 722

```
Gln Ile Leu Leu Val Gln Ser Gly Pro Glu Val Lys Glu Pro Gly Ala
1               5                   10                  15

Ser Val Lys Val Ser Cys Lys Ala Ser Gly Tyr Thr Phe Thr Asn Tyr
            20                  25                  30

Ala Ile Ser Trp Val Arg Gln Val Pro Gly Gln Gly Leu Glu Trp Met
        35                  40                  45

Gly Trp Val Ser Ala Tyr Asn Gly His Thr Asn Tyr Ala His Glu Val
    50                  55                  60

Gln Gly Arg Val Thr Met Thr Thr Asp Thr Ser Thr Thr Thr Ala Tyr
65                  70                  75                  80

Met Glu Leu Arg Ser Leu Arg Ser Asp Asp Thr Ala Met Tyr Tyr Cys
                85                  90                  95

Ala Arg Gly Gly Val Val Val Pro Val Ala Pro His Phe Tyr Asn Gly
            100                 105                 110

Met Asp Val Trp Gly Gln Gly Thr Thr Val Thr Val Ser Ser
        115                 120                 125
```

<210> SEQ ID NO 723
<211> LENGTH: 24
<212> TYPE: DNA
<213> ORGANISM: Artificial Sequence
<220> FEATURE:
<223> OTHER INFORMATION: Synthetic

<400> SEQUENCE: 723
ggttacacct ttaccaacta cgct 24

<210> SEQ ID NO 724
<211> LENGTH: 8
<212> TYPE: PRT
<213> ORGANISM: Artificial Sequence
<220> FEATURE:
<223> OTHER INFORMATION: Synthetic

<400> SEQUENCE: 724

```
Gly Tyr Thr Phe Thr Asn Tyr Ala
1               5
```

<210> SEQ ID NO 725
<211> LENGTH: 24
<212> TYPE: DNA
<213> ORGANISM: Artificial Sequence
<220> FEATURE:
<223> OTHER INFORMATION: Synthetic

<400> SEQUENCE: 725
gtcagcgctt acaatggtca caca 24

<210> SEQ ID NO 726
<211> LENGTH: 8
<212> TYPE: PRT
<213> ORGANISM: Artificial Sequence
<220> FEATURE:
<223> OTHER INFORMATION: Synthetic

<400> SEQUENCE: 726

```
Val Ser Ala Tyr Asn Gly His Thr
1               5
```

<210> SEQ ID NO 727
<211> LENGTH: 57
<212> TYPE: DNA
<213> ORGANISM: Artificial Sequence
<220> FEATURE:
<223> OTHER INFORMATION: Synthetic

<400> SEQUENCE: 727
gcgagagggg gtgtagtcgt gccagttgct ccccacttct acaacggtat ggacgtc 57

<210> SEQ ID NO 728
<211> LENGTH: 19
<212> TYPE: PRT
<213> ORGANISM: Artificial Sequence
<220> FEATURE:
<223> OTHER INFORMATION: Synthetic

<400> SEQUENCE: 728

Ala Arg Gly Gly Val Val Val Pro Val Ala Pro His Phe Tyr Asn Gly
1 5 10 15

Met Asp Val

<210> SEQ ID NO 729
<211> LENGTH: 336
<212> TYPE: DNA
<213> ORGANISM: Artificial Sequence
<220> FEATURE:
<223> OTHER INFORMATION: Synthetic

<400> SEQUENCE: 729
gatattgtga tgactcagtt tccactctcc ctgcccgtca cccctggaga gccggcctcc 60
atctcctgca ggtctagtca gagcctcctg catattaatg aatacaacta tttggattgg 120
tacctaaaga agccagggca gtctccacag ctcctgatct atttgggttt taatcgggcc 180
tccggggtcc ctgacaggtt cagtggcagt ggatcaggca cagattttac actgaaaatc 240
agcagagtgg aggctgagga tgttggggtc tattactgca tgcaagctct tcaaactccg 300
tggacgttcg gccaagggac caaggtggaa atcaaa 336

<210> SEQ ID NO 730
<211> LENGTH: 112
<212> TYPE: PRT
<213> ORGANISM: Artificial Sequence
<220> FEATURE:
<223> OTHER INFORMATION: Synthetic

<400> SEQUENCE: 730

Asp Ile Val Met Thr Gln Phe Pro Leu Ser Leu Pro Val Thr Pro Gly
1 5 10 15

Glu Pro Ala Ser Ile Ser Cys Arg Ser Ser Gln Ser Leu Leu His Ile
20 25 30

Asn Glu Tyr Asn Tyr Leu Asp Trp Tyr Leu Lys Lys Pro Gly Gln Ser
35 40 45

Pro Gln Leu Leu Ile Tyr Leu Gly Phe Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Ala
85 90 95

Leu Gln Thr Pro Trp Thr Phe Gly Gln Gly Thr Lys Val Glu Ile Lys
100 105 110

<210> SEQ ID NO 731
<211> LENGTH: 33
<212> TYPE: DNA

<213> ORGANISM: Artificial Sequence
<220> FEATURE:
<223> OTHER INFORMATION: Synthetic

<400> SEQUENCE: 731
cagagcctcc tgcatattaa tgaatacaac tat 33

<210> SEQ ID NO 732
<211> LENGTH: 11
<212> TYPE: PRT
<213> ORGANISM: Artificial Sequence
<220> FEATURE:
<223> OTHER INFORMATION: Synthetic

<400> SEQUENCE: 732

Gln Ser Leu Leu His Ile Asn Glu Tyr Asn Tyr
1 5 10

<210> SEQ ID NO 733
<211> LENGTH: 9
<212> TYPE: DNA
<213> ORGANISM: Artificial Sequence
<220> FEATURE:
<223> OTHER INFORMATION: Synthetic

<400> SEQUENCE: 733 ttgggtttt 9

<210> SEQ ID NO 734
<211> LENGTH: 3
<212> TYPE: PRT
<213> ORGANISM: Artificial Sequence
<220> FEATURE:
<223> OTHER INFORMATION: Synthetic

<400> SEQUENCE: 734

Leu Gly Phe
1

<210> SEQ ID NO 735
<211> LENGTH: 27
<212> TYPE: DNA
<213> ORGANISM: Artificial Sequence
<220> FEATURE:
<223> OTHER INFORMATION: Synthetic

<400> SEQUENCE: 735
atgcaagctc ttcaaactcc gtggacg 27

<210> SEQ ID NO 736
<211> LENGTH: 9
<212> TYPE: PRT
<213> ORGANISM: Artificial Sequence
<220> FEATURE:
<223> OTHER INFORMATION: Synthetic

<400> SEQUENCE: 736

Met Gln Ala Leu Gln Thr Pro Trp Thr
1 5

<210> SEQ ID NO 737
<211> LENGTH: 378
<212> TYPE: DNA
<213> ORGANISM: Artificial Sequence
<220> FEATURE:
<223> OTHER INFORMATION: Synthetic

<400> SEQUENCE: 737
caggttcagc tggtgcagtc tggacctgag gtgaaggagc ctggggcctc agtgaaggtc 60
tcctgcaagg cttctggtta cacctttacc aactacgcta tcagctgggt gcgacaggtc 120
cctggacaag ggcttgagtg gatgggatgg gtcagcgctt acaatggtca cacaaactat 180
gcacatgaag tccagggcag agtcaccatg accacagaca catccacgac cacagcctac 240
atggagctga ggagcctgag atctgacgac acggccatgt attactgtgc gagagggggt 300
gtagtcgtgc cagttgctcc ccacttctac aacggtatgg acgtctgggg ccaagggacc 360
acggtcaccg tctcctca 378

<210> SEQ ID NO 738
<211> LENGTH: 126
<212> TYPE: PRT
<213> ORGANISM: Artificial Sequence
<220> FEATURE:
<223> OTHER INFORMATION: Synthetic

<400> SEQUENCE: 738

Gln Val Gln Leu Val Gln Ser Gly Pro Glu Val Lys Glu Pro Gly Ala
1 5 10 15

Ser Val Lys Val Ser Cys Lys Ala Ser Gly Tyr Thr Phe Thr Asn Tyr
20 25 30

Ala Ile Ser Trp Val Arg Gln Val Pro Gly Gln Gly Leu Glu Trp Met
35 40 45

Gly Trp Val Ser Ala Tyr Asn Gly His Thr Asn Tyr Ala His Glu Val
50 55 60

Gln Gly Arg Val Thr Met Thr Thr Asp Thr Ser Thr Thr Thr Ala Tyr
65 70 75 80

Met Glu Leu Arg Ser Leu Arg Ser Asp Asp Thr Ala Met Tyr Tyr Cys
85 90 95

Ala Arg Gly Gly Val Val Val Pro Val Ala Pro His Phe Tyr Asn Gly
100 105 110

Met Asp Val Trp Gly Gln Gly Thr Thr Val Thr Val Ser Ser
115 120 125

<210> SEQ ID NO 739
<211> LENGTH: 336
<212> TYPE: DNA
<213> ORGANISM: Artificial Sequence
<220> FEATURE:
<223> OTHER INFORMATION: Synthetic

<400> SEQUENCE: 739
gatattgtga tgactcagtc tccactctcc ctgcccgtca cccctggaga gccggcctcc 60
atctcctgca ggtctagtca gagcctcctg catattaatg aatacaacta tttggattgg 120
tacctaaaga agccagggca gtctccacag ctcctgatct atttgggttt taatcgggcc 180
tccggggtcc ctgacaggtt cagtggcagt ggatcaggca cagattttac actgaaaatc 240
agcagagtgg aggctgagga tgttggggtc tattactgca tgcaagctct tcaaactccg 300
tggacgttcg gccaagggac caaggtggaa atcaaa 336

<210> SEQ ID NO 740
<211> LENGTH: 112
<212> TYPE: PRT
<213> ORGANISM: Artificial Sequence
<220> FEATURE:
<223> OTHER INFORMATION: Synthetic

<400> SEQUENCE: 740

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ile
            20                  25                  30

Asn Glu Tyr Asn Tyr Leu Asp Trp Tyr Leu Lys Lys Pro Gly Gln Ser
        35                  40                  45

Pro Gln Leu Leu Ile Tyr Leu Gly Phe Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110

<210> SEQ ID NO 741
<211> LENGTH: 378
<212> TYPE: DNA
<213> ORGANISM: Artificial Sequence
<220> FEATURE:
<223> OTHER INFORMATION: Synthetic

<400> SEQUENCE: 741
caggttcagc tggtgcagtc tggagctgag gtgaagaagc ctggggcctc agtgaaggtc      60
tcctgcaagg cttctggtta cacctttacc aactacgcta tcagctgggt gcgacaggcc     120
cctggacaag ggcttgagtg gatgggatgg gtcagcgctt acaatggtca cacaaactat     180
gcacagaagc tccagggcag agtcaccatg accacagaca catccacgag cacagcctac     240
atggagctga ggagcctgag atctgacgac acggccgtgt attactgtgc gagagggggt     300
gtagtcgtgc cagttgctcc ccacttctac aacggtatgg acgtctgggg gcaagggacc     360
acggtcaccg tctcctca                                                   378

<210> SEQ ID NO 742
<211> LENGTH: 126
<212> TYPE: PRT
<213> ORGANISM: Artificial Sequence
<220> FEATURE:
<223> OTHER INFORMATION: Synthetic

<400> SEQUENCE: 742

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Ala Ile Ser Trp Val Arg Gln Ala Pro Gly Gln Gly Leu Glu Trp Met
        35                  40                  45

Gly Trp Val Ser Ala Tyr Asn Gly His Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Val Val Val Pro Val Ala Pro His Phe Tyr Asn Gly
            100                 105                 110

```
Met Asp Val Trp Gly Gln Gly Thr Thr Val Thr Val Ser Ser
        115                 120                 125


<210> SEQ ID NO 743
<211> LENGTH: 336
<212> TYPE: DNA
<213> ORGANISM: Artificial Sequence
<220> FEATURE:
<223> OTHER INFORMATION: Synthetic

<400> SEQUENCE: 743

gatattgtga tgactcagtc tccactctcc ctgcccgtca cccctggaga gccggcctcc      60

atctcctgca ggtctagtca gagcctcctg catattaatg aatacaacta tttggattgg     120

tacctgcaga agccagggca gtctccacag ctcctgatct atttgggttc taatcgggcc     180

tccggggtcc ctgacaggtt cagtggcagt ggatcaggca cagattttac actgaaaatc     240

agcagagtgg aggctgagga tgttggggtt tattactgca tgcaagctct tcaaactccg     300

tggacgttcg gccaagggac caaggtggaa atcaaa                               336


<210> SEQ ID NO 744
<211> LENGTH: 112
<212> TYPE: PRT
<213> ORGANISM: Artificial Sequence
<220> FEATURE:
<223> OTHER INFORMATION: Synthetic

<400> SEQUENCE: 744

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ile
            20                  25                  30

Asn Glu Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110


<210> SEQ ID NO 745
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(8)
<223> OTHER INFORMATION: Xaa = Any amino acid

<400> SEQUENCE: 745

Xaa Xaa Xaa Xaa Xaa Xaa Xaa Xaa
1               5


<210> SEQ ID NO 746
<211> LENGTH: 8
<212> TYPE: PRT
<213> ORGANISM: Artificial Sequence
<220> FEATURE:
```

<223> OTHER INFORMATION: Synthetic
<220> FEATURE:
<221> NAME/KEY: VARIANT
<222> LOCATION: (1)...(8)
<223> OTHER INFORMATION: Xaa - Any amino acid

<400> SEQUENCE: 746

Xaa Xaa Xaa Xaa Xaa Xaa Xaa Xaa
1 5

<210> SEQ ID NO 747
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(20)
<223> OTHER INFORMATION: Xaa = Any amino acid

<400> SEQUENCE: 747

Xaa Xaa Xaa Xaa Xaa Xaa Xaa Xaa Xaa Xaa Xaa Xaa Xaa Xaa Xaa Xaa
1 5 10 15

Xaa Xaa Xaa Xaa
20

<210> SEQ ID NO 748
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(12)
<223> OTHER INFORMATION: Xaa = Any amino acid

<400> SEQUENCE: 748

Xaa Xaa Xaa Xaa Xaa Xaa Xaa Xaa Xaa Xaa Xaa Xaa
1 5 10

<210> SEQ ID NO 749
<211> LENGTH: 3
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(3)
<223> OTHER INFORMATION: Xaa = Any amino acid

<400> SEQUENCE: 749

Xaa Xaa Xaa
1

<210> SEQ ID NO 750
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(9)
<223> OTHER INFORMATION: Xaa = Any amino acid

<400> SEQUENCE: 750

```
Xaa Xaa Xaa Xaa Xaa Xaa Xaa Xaa Xaa
1               5


<210> SEQ ID NO 751
<211> LENGTH: 330
<212> TYPE: PRT
<213> ORGANISM: Artificial Sequence
<220> FEATURE:
<223> OTHER INFORMATION: Synthetic

<400> SEQUENCE: 751

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 752
<211> LENGTH: 327
```

-continued

<212> TYPE: PRT
<213> ORGANISM: Artificial Sequence
<220> FEATURE:
<223> OTHER INFORMATION: Synthetic

<400> SEQUENCE: 752

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 753
<211> LENGTH: 327
<212> TYPE: PRT
<213> ORGANISM: Artificial Sequence
<220> FEATURE:
<223> OTHER INFORMATION: Synthetic

<400> SEQUENCE: 753

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 754
<211> LENGTH: 2076
<212> TYPE: DNA
<213> ORGANISM: Homo sapiens

<400> SEQUENCE: 754

```
atgggcaccg tcagctccag gcggtcctgg tggccgctgc cactgctgct gctgctgctg      60

ctgctcctgg gtcccgcggg cgcccgtgcg caggaggacg aggacggcga ctacgaggag     120

ctggtgctag ccttgcgttc cgaggaggac ggcctggccg aagcacccga gcacggaacc     180

acagccacct tccaccgctg cgccaaggat ccgtggaggt tgcctggcac ctacgtggtg     240
```

```
gtgctgaagg aggagaccca cctctcgcag tcagagcgca ctgcccgccg cctgcaggcc    300
caggctgccc gccggggata cctcaccaag atcctgcatg tcttccatgg ccttcttcct    360
ggcttcctgg tgaagatgag tggcgacctg ctggagctgg ccttgaagtt gccccatgtc    420
gactacatcg aggaggactc ctctgtcttt gcccagagca tcccgtggaa cctggagcgg    480
attacccctc cacggtaccg ggcggatgaa taccagcccc ccgacggagg cagcctggtg    540
gaggtgtatc tcctagacac cagcatacag agtgaccacc gggaaatcga gggcagggtc    600
atggtcaccg acttcgagaa tgtgcccgag gaggacggga cccgcttcca cagacaggcc    660
agcaagtgtg acagtcatgg cacccacctg gcaggggtgg tcagcggccg ggatgccggc    720
gtggccaagg gtgccagcat gcgcagcctg cgcgtgctca actgccaagg gaagggcacg    780
gttagcggca ccctcatagg cctggagttt attcggaaaa gccagctggt ccagcctgtg    840
gggccactgg tggtgctgct gcccctggcg ggtgggtaca gccgcgtcct caacgccgcc    900
tgccagcgcc tggcgagggc tggggtcgtg ctggtcaccg ctgccggcaa cttccgggac    960
gatgcctgcc tctactcccc agcctcagct cccgaggtca tcacagttgg ggccaccaat   1020
gcccaggacc agccggtgac cctggggact ttggggacca actttggccg ctgtgtggac   1080
ctctttgccc caggggagga catcattggt gcctccagcg actgcagcac ctgctttgtg   1140
tcacagagtg ggacatcaca ggctgctgcc cacgtggctg gcattgcagc catgatgctg   1200
tctgccgagc cggagctcac cctggccgag ttgaggcaga gactgatcca cttctctgcc   1260
aaagatgtca tcaatgaggc ctggttccct gaggaccagc gggtactgac ccccaacctg   1320
gtggccgccc tgccccccag cacccatggg gcaggttggc agctgttttg caggactgtg   1380
tggtcagcac actcggggcc tacacggatg gccacagcca tcgcccgctg cgccccagat   1440
gaggagctgc tgagctgctc cagtttctcc aggagtggga agcggcgggg cgagcgcatg   1500
gaggcccaag gggggcaagct ggtctgccgg gcccacaacg cttttggggg tgagggtgtc   1560
tacgccattg ccaggtgctg cctgctaccc caggccaact gcagcgtcca cacagctcca   1620
ccagctgagg ccagcatggg gacccgtgtc cactgccacc aacagggcca cgtcctcaca   1680
ggctgcagct cccactggga ggtggaggac cttggcaccc acaagccgcc tgtgctgagg   1740
ccacgaggtc agcccaacca gtgcgtgggc cacagggagg ccagcatcca cgcttcctgc   1800
tgccatgccc caggtctgga atgcaaagtc aaggagcatg gaatcccggc ccctcaggag   1860
caggtgaccg tggcctgcga ggagggctgg accctgactg gctgcagtgc cctccctggg   1920
acctcccacg tcctgggggc ctacgccgta gacaacacgt gtgtagtcag gagccgggac   1980
gtcagcacta caggcagcac cagcgaagag gccgtgacag ccgttgccat ctgctgccgg   2040
agccggcacc tggcgcaggc ctcccaggag ctccag                             2076
```

<210> SEQ ID NO 755
<211> LENGTH: 692
<212> TYPE: PRT
<213> ORGANISM: Homo sapiens

<400> SEQUENCE: 755

```
Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45
```

-continued

```
Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
    370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
    450                 455                 460
```

Ser Gly Pro Thr Arg Met Ala Thr Ala Ile Ala Arg Cys Ala Pro Asp
465 470 475 480

Glu Glu Leu Leu Ser Cys Ser Ser Phe Ser Arg Ser Gly Lys Arg Arg
485 490 495

Gly Glu Arg Met Glu Ala Gln Gly Gly Lys Leu Val Cys Arg Ala His
500 505 510

Asn Ala Phe Gly Gly Glu Gly Val Tyr Ala Ile Ala Arg Cys Cys Leu
515 520 525

Leu Pro Gln Ala Asn Cys Ser Val His Thr Ala Pro Pro Ala Glu Ala
530 535 540

Ser Met Gly Thr Arg Val His Cys His Gln Gln Gly His Val Leu Thr
545 550 555 560

Gly Cys Ser Ser His Trp Glu Val Glu Asp Leu Gly Thr His Lys Pro
565 570 575

Pro Val Leu Arg Pro Arg Gly Gln Pro Asn Gln Cys Val Gly His Arg
580 585 590

Glu Ala Ser Ile His Ala Ser Cys Cys His Ala Pro Gly Leu Glu Cys
595 600 605

Lys Val Lys Glu His Gly Ile Pro Ala Pro Gln Glu Gln Val Thr Val
610 615 620

Ala Cys Glu Glu Gly Trp Thr Leu Thr Gly Cys Ser Ala Leu Pro Gly
625 630 635 640

Thr Ser His Val Leu Gly Ala Tyr Ala Val Asp Asn Thr Cys Val Val
645 650 655

Arg Ser Arg Asp Val Ser Thr Thr Gly Ser Thr Ser Glu Glu Ala Val
660 665 670

Thr Ala Val Ala Ile Cys Cys Arg Ser Arg His Leu Ala Gln Ala Ser
675 680 685

Gln Glu Leu Gln
690

<210> SEQ ID NO 756
<211> LENGTH: 692
<212> TYPE: PRT
<213> ORGANISM: Macaca mulata

<400> SEQUENCE: 756

Met Gly Thr Val Ser Ser Arg Arg Ser Trp Trp Pro Leu Pro Leu Pro
1 5 10 15

Leu Leu Leu Leu Leu Leu Leu Gly Pro Ala Gly Ala Arg Ala Gln Glu
20 25 30

Asp Glu Asp Gly Asp Tyr Glu Glu Leu Val Leu Ala Leu Arg Ser Glu
35 40 45

Glu Asp Gly Leu Ala Asp Ala Pro Glu His Gly Ala Thr Ala Thr Phe
50 55 60

His Arg Cys Ala Lys Asp Pro Trp Arg Leu Pro Gly Thr Tyr Val Val
65 70 75 80

Val Leu Lys Glu Glu Thr His Arg Ser Gln Ser Glu Arg Thr Ala Arg
85 90 95

Arg Leu Gln Ala Gln Ala Ala Arg Arg Gly Tyr Leu Thr Lys Ile Leu
100 105 110

His Val Phe His His Leu Leu Pro Gly Phe Leu Val Lys Met Ser Gly
115 120 125

Asp Leu Leu Glu Leu Ala Leu Lys Leu Pro His Val Asp Tyr Ile Glu
130 135 140

```
Glu Asp Ser Ser Val Phe Ala Gln Ser Ile Pro Trp Asn Leu Glu Arg
145                 150                 155                 160

Ile Thr Pro Ala Arg Tyr Arg Ala Asp Glu Tyr Gln Pro Pro Lys Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Ser Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Gly Leu Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Phe Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Arg Ser Gly
    370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Arg Ala Gly Trp Gln Leu Phe Cys Arg Thr Val Trp Ser Ala His
    450                 455                 460

Ser Gly Pro Thr Arg Met Ala Thr Ala Val Ala Arg Cys Ala Gln Asp
465                 470                 475                 480

Glu Glu Leu Leu Ser Cys Ser Ser Phe Ser Arg Ser Gly Lys Arg Arg
                485                 490                 495

Gly Glu Arg Ile Glu Ala Gln Gly Gly Lys Arg Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Val Asn Cys Ser Val His Thr Ala Pro Pro Ala Gly Ala
    530                 535                 540

Ser Met Gly Thr Arg Val His Cys His Gln Gln Gly His Val Leu Thr
545                 550                 555                 560
```

-continued

```
Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Ile Val
    610                 615                 620

Ala Cys Glu Asp Gly Trp Thr Leu Thr Gly Cys Ser Pro Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Lys Glu Ala Val
            660                 665                 670

Ala Ala Val Ala Ile Cys Cys Arg Ser Arg His Leu Val Gln Ala Ser
        675                 680                 685

Gln Glu Leu Gln
    690


<210> SEQ ID NO 757
<211> LENGTH: 694
<212> TYPE: PRT
<213> ORGANISM: Mus muscular

<400> SEQUENCE: 757

Met Gly Thr His Cys Ser Ala Trp Leu Arg Trp Pro Leu Leu Pro Leu
1               5                   10                  15

Leu Pro Pro Leu Leu Leu Leu Leu Leu Leu Leu Cys Pro Thr Gly Ala
            20                  25                  30

Gly Ala Gln Asp Glu Asp Gly Asp Tyr Glu Glu Leu Met Leu Ala Leu
        35                  40                  45

Pro Ser Gln Glu Asp Gly Leu Ala Asp Glu Ala Ala His Val Ala Thr
    50                  55                  60

Ala Thr Phe Arg Arg Cys Ser Lys Glu Ala Trp Arg Leu Pro Gly Thr
65                  70                  75                  80

Tyr Ile Val Val Leu Met Glu Glu Thr Gln Arg Leu Gln Ile Glu Gln
                85                  90                  95

Thr Ala His Arg Leu Gln Thr Arg Ala Ala Arg Arg Gly Tyr Val Ile
            100                 105                 110

Lys Val Leu His Ile Phe Tyr Asp Leu Phe Pro Gly Phe Leu Val Lys
        115                 120                 125

Met Ser Ser Asp Leu Leu Gly Leu Ala Leu Lys Leu Pro His Val Glu
    130                 135                 140

Tyr Ile Glu Glu Asp Ser Phe Val Phe Ala Gln Ser Ile Pro Trp Asn
145                 150                 155                 160

Leu Glu Arg Ile Ile Pro Ala Trp His Gln Thr Glu Glu Asp Arg Ser
                165                 170                 175

Pro Asp Gly Ser Ser Gln Val Glu Val Tyr Leu Leu Asp Thr Ser Ile
            180                 185                 190

Gln Gly Ala His Arg Glu Ile Glu Gly Arg Val Thr Ile Thr Asp Phe
        195                 200                 205

Asn Ser Val Pro Glu Glu Asp Gly Thr Arg Phe His Arg Gln Ala Ser
    210                 215                 220

Lys Cys Asp Ser His Gly Thr His Leu Ala Gly Val Val Ser Gly Arg
225                 230                 235                 240
```

```
Asp Ala Gly Val Ala Lys Gly Thr Ser Leu His Ser Leu Arg Val Leu
                245                 250                 255

Asn Cys Gln Gly Lys Gly Thr Val Ser Gly Thr Leu Ile Gly Leu Glu
            260                 265                 270

Phe Ile Arg Lys Ser Gln Leu Ile Gln Pro Ser Gly Pro Leu Val Val
        275                 280                 285

Leu Leu Pro Leu Ala Gly Gly Tyr Ser Arg Ile Leu Asn Ala Ala Cys
    290                 295                 300

Arg His Leu Ala Arg Thr Gly Val Val Leu Val Ala Ala Ala Gly Asn
305                 310                 315                 320

Phe Arg Asp Asp Ala Cys Leu Tyr Ser Pro Ala Ser Ala Pro Glu Val
                325                 330                 335

Ile Thr Val Gly Ala Thr Asn Ala Gln Asp Gln Pro Val Thr Leu Gly
            340                 345                 350

Thr Leu Gly Thr Asn Phe Gly Arg Cys Val Asp Leu Phe Ala Pro Gly
        355                 360                 365

Lys Asp Ile Ile Gly Ala Ser Ser Asp Cys Ser Thr Cys Phe Met Ser
    370                 375                 380

Gln Ser Gly Thr Ser Gln Ala Ala Ala His Val Ala Gly Ile Val Ala
385                 390                 395                 400

Arg Met Leu Ser Arg Glu Pro Thr Leu Thr Leu Ala Glu Leu Arg Gln
                405                 410                 415

Arg Leu Ile His Phe Ser Thr Lys Asp Val Ile Asn Met Ala Trp Phe
            420                 425                 430

Pro Glu Asp Gln Gln Val Leu Thr Pro Asn Leu Val Ala Thr Leu Pro
        435                 440                 445

Pro Ser Thr His Glu Thr Gly Gly Gln Leu Leu Cys Arg Thr Val Trp
    450                 455                 460

Ser Ala His Ser Gly Pro Thr Arg Thr Ala Thr Ala Thr Ala Arg Cys
465                 470                 475                 480

Ala Pro Glu Glu Glu Leu Leu Ser Cys Ser Ser Phe Ser Arg Ser Gly
                485                 490                 495

Arg Arg Arg Gly Asp Trp Ile Glu Ala Ile Gly Gly Gln Gln Val Cys
            500                 505                 510

Lys Ala Leu Asn Ala Phe Gly Gly Glu Gly Val Tyr Ala Val Ala Arg
        515                 520                 525

Cys Cys Leu Val Pro Arg Ala Asn Cys Ser Ile His Asn Thr Pro Ala
    530                 535                 540

Ala Arg Ala Gly Leu Glu Thr His Val His Cys His Gln Lys Asp His
545                 550                 555                 560

Val Leu Thr Gly Cys Ser Phe His Trp Glu Val Glu Asp Leu Ser Val
                565                 570                 575

Arg Arg Gln Pro Ala Leu Arg Ser Arg Arg Gln Pro Gly Gln Cys Val
            580                 585                 590

Gly His Gln Ala Ala Ser Val Tyr Ala Ser Cys Cys His Ala Pro Gly
        595                 600                 605

Leu Glu Cys Lys Ile Lys Glu His Gly Ile Ser Gly Pro Ser Glu Gln
    610                 615                 620

Val Thr Val Ala Cys Glu Ala Gly Trp Thr Leu Thr Gly Cys Asn Val
625                 630                 635                 640

Leu Pro Gly Ala Ser Leu Thr Leu Gly Ala Tyr Ser Val Asp Asn Leu
                645                 650                 655
```

Cys Val Ala Arg Val His Asp Thr Ala Arg Ala Asp Arg Thr Ser Gly
660 665 670

Glu Ala Thr Val Ala Ala Ala Ile Cys Cys Arg Ser Arg Pro Ser Ala
675 680 685

Lys Ala Ser Trp Val Gln
690

<210> SEQ ID NO 758
<211> LENGTH: 653
<212> TYPE: PRT
<213> ORGANISM: Homo sapiens

<400> SEQUENCE: 758

Glu Phe Arg Cys His Asp Gly Lys Cys Ile Ser Arg Gln Phe Val Cys
1 5 10 15

Asp Ser Asp Arg Asp Cys Leu Asp Gly Ser Asp Glu Ala Ser Cys Pro
20 25 30

Val Leu Thr Cys Gly Pro Ala Ser Phe Gln Cys Asn Ser Ser Thr Cys
35 40 45

Ile Pro Gln Leu Trp Ala Cys Asp Asn Asp Pro Asp Cys Glu Asp Gly
50 55 60

Ser Asp Glu Trp Pro Gln Arg Cys Arg Gly Leu Tyr Val Phe Gln Gly
65 70 75 80

Asp Ser Ser Pro Cys Ser Ala Phe Glu Phe His Cys Leu Ser Gly Glu
85 90 95

Cys Ile His Ser Ser Trp Arg Cys Asp Gly Gly Pro Asp Cys Lys Asp
100 105 110

Lys Ser Asp Glu Glu Asn Cys Ala Val Ala Thr Cys Arg Pro Asp Glu
115 120 125

Phe Gln Cys Ser Asp Gly Asn Cys Ile His Gly Ser Arg Gln Cys Asp
130 135 140

Arg Glu Tyr Asp Cys Lys Asp Met Ser Asp Glu Val Gly Cys Val Asn
145 150 155 160

Val Thr Leu Cys Glu Gly Pro Asn Lys Phe Lys Cys His Ser Gly Glu
165 170 175

Cys Ile Thr Leu Asp Lys Val Cys Asn Met Ala Arg Asp Cys Arg Asp
180 185 190

Trp Ser Asp Glu Pro Ile Lys Glu Cys Gly Thr Asn Glu Cys Leu Asp
195 200 205

Asn Asn Gly Gly Cys Ser His Val Cys Asn Asp Leu Lys Ile Gly Tyr
210 215 220

Glu Cys Leu Cys Pro Asp Gly Phe Gln Leu Val Ala Gln Arg Arg Cys
225 230 235 240

Glu Asp Ile Asp Glu Cys Gln Asp Pro Asp Thr Cys Ser Gln Leu Cys
245 250 255

Val Asn Leu Glu Gly Gly Tyr Lys Cys Gln Cys Glu Glu Gly Phe Gln
260 265 270

Leu Asp Pro His Thr Lys Ala Cys Lys Ala Val Gly Ser Ile Ala Tyr
275 280 285

Leu Phe Phe Thr Asn Arg His Glu Val Arg Lys Met Thr Leu Asp Arg
290 295 300

Ser Glu Tyr Thr Ser Leu Ile Pro Asn Leu Arg Asn Val Val Ala Leu
305 310 315 320

Asp Thr Glu Val Ala Ser Asn Arg Ile Tyr Trp Ser Asp Leu Ser Gln
325 330 335

Arg Met Ile Cys Ser Thr Gln Leu Asp Arg Ala His Gly Val Ser Ser
340 345 350

Tyr Asp Thr Val Ile Ser Arg Asp Ile Gln Ala Pro Asp Gly Leu Ala
355 360 365

Val Asp Trp Ile His Ser Asn Ile Tyr Trp Thr Asp Ser Val Leu Gly
370 375 380

Thr Val Ser Val Ala Asp Thr Lys Gly Val Lys Arg Lys Thr Leu Phe
385 390 395 400

Arg Glu Asn Gly Ser Lys Pro Arg Ala Ile Val Val Asp Pro Val His
405 410 415

Gly Phe Met Tyr Trp Thr Asp Trp Gly Thr Pro Ala Lys Ile Lys Lys
420 425 430

Gly Gly Leu Asn Gly Val Asp Ile Tyr Ser Leu Val Thr Glu Asn Ile
435 440 445

Gln Trp Pro Asn Gly Ile Thr Leu Asp Leu Leu Ser Gly Arg Leu Tyr
450 455 460

Trp Val Asp Ser Lys Leu His Ser Ile Ser Ser Ile Asp Val Asn Gly
465 470 475 480

Gly Asn Arg Lys Thr Ile Leu Glu Asp Glu Lys Arg Leu Ala His Pro
485 490 495

Phe Ser Leu Ala Val Phe Glu Asp Lys Val Phe Trp Thr Asp Ile Ile
500 505 510

Asn Glu Ala Ile Phe Ser Ala Asn Arg Leu Thr Gly Ser Asp Val Asn
515 520 525

Leu Leu Ala Glu Asn Leu Leu Ser Pro Glu Asp Met Val Leu Phe His
530 535 540

Asn Leu Thr Gln Pro Arg Gly Val Asn Trp Cys Glu Arg Thr Thr Leu
545 550 555 560

Ser Asn Gly Gly Cys Gln Tyr Leu Cys Leu Pro Ala Pro Gln Ile Asn
565 570 575

Pro His Ser Pro Lys Phe Thr Cys Ala Cys Pro Asp Gly Met Leu Leu
580 585 590

Ala Arg Asp Met Arg Ser Cys Leu Thr Glu Ala Glu Ala Ala Val Ala
595 600 605

Thr Gln Glu Thr Ser Thr Val Arg Leu Lys Val Ser Ser Thr Ala Val
610 615 620

Arg Thr Gln His Thr Thr Thr Arg Pro Val Pro Asp Thr Ser Arg Leu
625 630 635 640

Pro Gly Ala Thr Pro Gly Leu Thr Thr Val Glu Ile Val
645 650

<210> SEQ ID NO 759
<211> LENGTH: 753
<212> TYPE: PRT
<213> ORGANISM: Homo sapiens

<400> SEQUENCE: 759

Met Glu Arg Arg Ala Trp Ser Leu Gln Cys Thr Ala Phe Val Leu Phe
1 5 10 15

Cys Ala Trp Cys Ala Leu Asn Ser Ala Lys Ala Lys Arg Gln Phe Val
20 25 30

Asn Glu Trp Ala Ala Glu Ile Pro Gly Gly Pro Glu Ala Ala Ser Ala
35 40 45

Ile Ala Glu Glu Leu Gly Tyr Asp Leu Leu Gly Gln Ile Gly Ser Leu

-continued

```
    50                  55                  60

Glu Asn His Tyr Leu Phe Lys His Lys Asn His Pro Arg Arg Ser Arg
65                  70                  75                  80

Arg Ser Ala Phe His Ile Thr Lys Arg Leu Ser Asp Asp Asp Arg Val
                85                  90                  95

Ile Trp Ala Glu Gln Gln Tyr Glu Lys Glu Arg Ser Lys Arg Ser Ala
            100                 105                 110

Leu Arg Asp Ser Ala Leu Asn Leu Phe Asn Asp Pro Met Trp Asn Gln
        115                 120                 125

Gln Trp Tyr Leu Gln Asp Thr Arg Met Thr Ala Ala Leu Pro Lys Leu
    130                 135                 140

Asp Leu His Val Ile Pro Val Trp Gln Lys Gly Ile Thr Gly Lys Gly
145                 150                 155                 160

Val Val Ile Thr Val Leu Asp Asp Gly Leu Glu Trp Asn His Thr Asp
                165                 170                 175

Ile Tyr Ala Asn Tyr Asp Pro Glu Ala Ser Tyr Asp Phe Asn Asp Asn
            180                 185                 190

Asp His Asp Pro Phe Pro Arg Tyr Asp Pro Thr Asn Glu Asn Lys His
        195                 200                 205

Gly Thr Arg Cys Ala Gly Glu Ile Ala Met Gln Ala Asn Asn His Lys
    210                 215                 220

Cys Gly Val Gly Val Ala Tyr Asn Ser Lys Val Gly Gly Ile Arg Met
225                 230                 235                 240

Leu Asp Gly Ile Val Thr Asp Ala Ile Glu Ala Ser Ser Ile Gly Phe
                245                 250                 255

Asn Pro Gly His Val Asp Ile Tyr Ser Ala Ser Trp Gly Pro Asn Asp
            260                 265                 270

Asp Gly Lys Thr Val Glu Gly Pro Gly Arg Leu Ala Gln Lys Ala Phe
        275                 280                 285

Glu Tyr Gly Val Lys Gln Gly Arg Gln Gly Lys Gly Ser Ile Phe Val
    290                 295                 300

Trp Ala Ser Gly Asn Gly Gly Arg Gln Gly Asp Asn Cys Asp Cys Asp
305                 310                 315                 320

Gly Tyr Thr Asp Ser Ile Tyr Thr Ile Ser Ile Ser Ser Ala Ser Gln
                325                 330                 335

Gln Gly Leu Ser Pro Trp Tyr Ala Glu Lys Cys Ser Ser Thr Leu Ala
            340                 345                 350

Thr Ser Tyr Ser Ser Gly Asp Tyr Thr Asp Gln Arg Ile Thr Ser Ala
        355                 360                 365

Asp Leu His Asn Asp Cys Thr Glu Thr His Thr Gly Thr Ser Ala Ser
    370                 375                 380

Ala Pro Leu Ala Ala Gly Ile Phe Ala Leu Ala Leu Glu Ala Asn Pro
385                 390                 395                 400

Asn Leu Thr Trp Arg Asp Met Gln His Leu Val Val Trp Thr Ser Glu
                405                 410                 415

Tyr Asp Pro Leu Ala Asn Asn Pro Gly Trp Lys Lys Asn Gly Ala Gly
            420                 425                 430

Leu Met Val Asn Ser Arg Phe Gly Phe Gly Leu Leu Asn Ala Lys Ala
        435                 440                 445

Leu Val Asp Leu Ala Asp Pro Arg Thr Trp Arg Ser Val Pro Glu Lys
    450                 455                 460

Lys Glu Cys Val Val Lys Asp Asn Asp Phe Glu Pro Arg Ala Leu Lys
465                 470                 475                 480
```

```
Ala Asn Gly Glu Val Ile Ile Glu Ile Pro Thr Arg Ala Cys Glu Gly
                485                 490                 495

Gln Glu Asn Ala Ile Lys Ser Leu Glu His Val Gln Phe Glu Ala Thr
            500                 505                 510

Ile Glu Tyr Ser Arg Arg Gly Asp Leu His Val Thr Leu Thr Ser Ala
        515                 520                 525

Ala Gly Thr Ser Thr Val Leu Leu Ala Glu Arg Glu Arg Asp Thr Ser
    530                 535                 540

Pro Asn Gly Phe Lys Asn Trp Asp Phe Met Ser Val His Thr Trp Gly
545                 550                 555                 560

Glu Asn Pro Ile Gly Thr Trp Thr Leu Arg Ile Thr Asp Met Ser Gly
                565                 570                 575

Arg Ile Gln Asn Glu Gly Arg Ile Val Asn Trp Lys Leu Ile Leu His
            580                 585                 590

Gly Thr Ser Ser Gln Pro Glu His Met Lys Gln Pro Arg Val Tyr Thr
        595                 600                 605

Ser Tyr Asn Thr Val Gln Asn Asp Arg Arg Gly Val Glu Lys Met Val
    610                 615                 620

Asp Pro Gly Glu Glu Gln Pro Thr Gln Glu Asn Pro Lys Glu Asn Thr
625                 630                 635                 640

Leu Val Ser Lys Ser Pro Ser Ser Ser Ser Val Gly Gly Arg Arg Asp
                645                 650                 655

Glu Leu Glu Glu Gly Ala Pro Ser Gln Ala Met Leu Arg Leu Leu Gln
            660                 665                 670

Ser Ala Phe Ser Lys Asn Ser Pro Pro Lys Gln Ser Pro Lys Lys Ser
        675                 680                 685

Pro Ser Ala Lys Leu Asn Ile Pro Tyr Glu Asn Phe Tyr Glu Ala Leu
    690                 695                 700

Glu Lys Leu Asn Lys Pro Ser Gln Leu Lys Asp Ser Glu Asp Ser Leu
705                 710                 715                 720

Tyr Asn Asp Tyr Val Asp Val Phe Tyr Asn Thr Lys Pro Tyr Lys His
                725                 730                 735

Arg Asp Asp Arg Leu Leu Gln Ala Leu Val Asp Ile Leu Asn Glu Glu
            740                 745                 750

Asn


<210> SEQ ID NO 760
<211> LENGTH: 785
<212> TYPE: PRT
<213> ORGANISM: Homo sapiens

<400> SEQUENCE: 760

Met Pro Lys Gly Arg Gln Lys Val Pro His Leu Asp Ala Pro Leu Gly
1               5                   10                  15

Leu Pro Thr Cys Leu Trp Leu Glu Leu Ala Gly Leu Phe Leu Leu Val
            20                  25                  30

Pro Trp Val Met Gly Leu Ala Gly Thr Gly Gly Pro Asp Gly Gln Gly
        35                  40                  45

Thr Gly Gly Pro Ser Trp Ala Val His Leu Glu Ser Leu Glu Gly Asp
    50                  55                  60

Gly Glu Glu Glu Thr Leu Glu Gln Gln Ala Asp Ala Leu Ala Gln Ala
65                  70                  75                  80

Ala Gly Leu Val Asn Ala Gly Arg Ile Gly Glu Leu Gln Gly His Tyr
                85                  90                  95
```

```
Leu Phe Val Gln Pro Ala Gly His Arg Pro Ala Leu Glu Val Glu Ala
            100                 105                 110

Ile Arg Gln Gln Val Glu Ala Val Leu Ala Gly His Glu Ala Val Arg
        115                 120                 125

Trp His Ser Glu Gln Arg Leu Leu Arg Arg Ala Lys Arg Ser Val His
    130                 135                 140

Phe Asn Asp Pro Lys Tyr Pro Gln Gln Trp His Leu Asn Asn Arg Arg
145                 150                 155                 160

Ser Pro Gly Arg Asp Ile Asn Val Thr Gly Val Trp Glu Arg Asn Val
                165                 170                 175

Thr Gly Arg Gly Val Thr Val Val Val Val Asp Asp Gly Val Glu His
            180                 185                 190

Thr Ile Gln Asp Ile Ala Pro Asn Tyr Ser Pro Glu Gly Ser Tyr Asp
        195                 200                 205

Leu Asn Ser Asn Asp Pro Asp Pro Met Pro His Pro Asp Val Glu Asn
    210                 215                 220

Gly Asn His His Gly Thr Arg Cys Ala Gly Glu Ile Ala Ala Val Pro
225                 230                 235                 240

Asn Asn Ser Phe Cys Ala Val Gly Val Ala Tyr Gly Ser Arg Ile Ala
                245                 250                 255

Gly Ile Arg Val Leu Asp Gly Pro Leu Thr Asp Ser Met Glu Ala Val
            260                 265                 270

Ala Phe Asn Lys His Tyr Gln Ile Asn Asp Ile Tyr Ser Cys Ser Trp
        275                 280                 285

Gly Pro Asp Asp Asp Gly Lys Thr Val Asp Gly Pro His Gln Leu Gly
    290                 295                 300

Lys Ala Ala Leu Gln His Gly Val Ile Ala Gly Arg Gln Gly Phe Gly
305                 310                 315                 320

Ser Ile Phe Val Val Ala Ser Gly Asn Gly Gly Gln His Asn Asp Asn
                325                 330                 335

Cys Asn Tyr Asp Gly Tyr Ala Asn Ser Ile Tyr Thr Val Thr Ile Gly
            340                 345                 350

Ala Val Asp Glu Glu Gly Arg Met Pro Phe Tyr Ala Glu Glu Cys Ala
        355                 360                 365

Ser Met Leu Ala Val Thr Phe Ser Gly Gly Asp Lys Met Leu Arg Ser
    370                 375                 380

Ile Val Thr Thr Asp Trp Asp Leu Gln Lys Gly Thr Gly Cys Thr Glu
385                 390                 395                 400

Gly His Thr Gly Thr Ser Ala Ala Ala Pro Leu Ala Ala Gly Met Ile
                405                 410                 415

Ala Leu Met Leu Gln Val Arg Pro Cys Leu Thr Trp Arg Asp Val Gln
            420                 425                 430

His Ile Ile Val Phe Thr Ala Thr Arg Tyr Glu Asp Arg Arg Ala Glu
        435                 440                 445

Trp Val Thr Asn Glu Ala Gly Phe Ser His Ser His Gln His Gly Phe
    450                 455                 460

Gly Leu Leu Asn Ala Trp Arg Leu Val Asn Ala Ala Lys Ile Trp Thr
465                 470                 475                 480

Ser Val Pro Tyr Leu Ala Ser Tyr Val Ser Pro Val Leu Lys Glu Asn
                485                 490                 495

Lys Ala Ile Pro Gln Ser Pro Arg Ser Leu Glu Val Leu Trp Asn Val
            500                 505                 510
```

Ser Arg Met Asp Leu Glu Met Ser Gly Leu Lys Thr Leu Glu His Val
515 520 525

Ala Val Thr Val Ser Ile Thr His Pro Arg Arg Gly Ser Leu Glu Leu
530 535 540

Lys Leu Phe Cys Pro Ser Gly Met Met Ser Leu Ile Gly Ala Pro Arg
545 550 555 560

Ser Met Asp Ser Asp Pro Asn Gly Phe Asn Asp Trp Thr Phe Ser Thr
565 570 575

Val Arg Cys Trp Gly Glu Arg Ala Arg Gly Thr Tyr Arg Leu Val Ile
580 585 590

Arg Asp Val Gly Asp Glu Ser Phe Gln Val Gly Ile Leu Arg Gln Trp
595 600 605

Gln Leu Thr Leu Tyr Gly Ser Val Trp Ser Ala Val Asp Ile Arg Asp
610 615 620

Arg Gln Arg Leu Leu Glu Ser Ala Met Ser Gly Lys Tyr Leu His Asp
625 630 635 640

Asp Phe Ala Leu Pro Cys Pro Pro Gly Leu Lys Ile Pro Glu Glu Asp
645 650 655

Gly Tyr Thr Ile Thr Pro Asn Thr Leu Lys Thr Leu Val Leu Val Gly
660 665 670

Cys Phe Thr Val Phe Trp Thr Val Tyr Tyr Met Leu Glu Val Tyr Leu
675 680 685

Ser Gln Arg Asn Val Ala Ser Asn Gln Val Cys Arg Ser Gly Pro Cys
690 695 700

His Trp Pro His Arg Ser Arg Lys Ala Lys Glu Glu Gly Thr Glu Leu
705 710 715 720

Glu Ser Val Pro Leu Cys Ser Ser Lys Asp Pro Asp Glu Val Glu Thr
725 730 735

Glu Ser Arg Gly Pro Pro Thr Thr Ser Asp Leu Leu Ala Pro Asp Leu
740 745 750

Leu Glu Gln Gly Asp Trp Ser Leu Ser Gln Asn Lys Ser Ala Leu Asp
755 760 765

Cys Pro His Gln His Leu Asp Val Pro His Gly Lys Glu Glu Gln Ile
770 775 780

Cys
785

<210> SEQ ID NO 761
<211> LENGTH: 692
<212> TYPE: PRT
<213> ORGANISM: Macaca fascicularis

<400> SEQUENCE: 761

Met Gly Thr Val Ser Ser Arg Arg Ser Trp Trp Pro Leu Pro Leu Pro
1 5 10 15

Leu Leu Leu Leu Leu Leu Leu Gly Pro Ala Gly Ala Arg Ala Gln Glu
20 25 30

Asp Glu Asp Gly Asp Tyr Glu Glu Leu Val Leu Ala Leu Arg Ser Glu
35 40 45

Glu Asp Gly Leu Ala Asp Ala Pro Glu His Gly Ala Thr Ala Thr Phe
50 55 60

His Arg Cys Ala Lys Asp Pro Trp Arg Leu Pro Gly Thr Tyr Val Val
65 70 75 80

Val Leu Lys Glu Glu Thr His Arg Ser Gln Ser Glu Arg Thr Ala Arg
85 90 95

```
Arg Leu Gln Ala Gln Ala Ala Arg Arg Gly Tyr Leu Thr Lys Ile Leu
            100                 105                 110

His Val Phe His His Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Ala Arg Tyr Arg Ala Asp Glu Tyr Gln Pro Pro Lys Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Ser Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Gly Leu Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Phe Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Arg Ser Gly
    370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Arg Ala Gly Trp Gln Leu Phe Cys Arg Thr Val Trp Ser Ala His
    450                 455                 460

Ser Gly Pro Thr Arg Met Ala Thr Ala Val Ala Arg Cys Ala Gln Asp
465                 470                 475                 480

Glu Glu Leu Leu Ser Cys Ser Ser Phe Ser Arg Ser Gly Lys Arg Arg
                485                 490                 495

Gly Glu Arg Ile Glu Ala Gln Gly Gly Lys Arg Val Cys Arg Ala His
            500                 505                 510
```

```
Asn Ala Phe Gly Gly Glu Gly Val Tyr Ala Ile Ala Arg Cys Cys Leu
        515                 520                 525

Leu Pro Gln Val Asn Cys Ser Val His Thr Ala Pro Pro Ala Gly Ala
    530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Ile Val
    610                 615                 620

Ala Cys Glu Asp Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Glu Ala Val
            660                 665                 670

Ala Ala Val Ala Ile Cys Cys Arg Ser Arg His Leu Val Gln Ala Ser
        675                 680                 685

Gln Glu Leu Gln
    690
```

<210> SEQ ID NO 762
<211> LENGTH: 698
<212> TYPE: PRT
<213> ORGANISM: Mesocricetus auratus

<400> SEQUENCE: 762

```
Met Gly Thr Ser Cys Ser Ala Arg Pro Arg Trp Leu Leu Ser Pro Leu
1               5                   10                  15

Leu Leu Leu Leu Leu Leu Leu Arg Tyr Met Gly Ala Ser Ala Gln Asp
            20                  25                  30

Glu Asp Ala Glu Tyr Glu Glu Leu Met Leu Thr Leu Gln Ser Gln Asp
        35                  40                  45

Asp Gly Leu Ala Asp Glu Thr Asp Glu Ala Pro Gln Gly Ala Thr Ala
    50                  55                  60

Ala Phe His Arg Cys Pro Glu Glu Ala Trp Arg Val Pro Gly Thr Tyr
65                  70                  75                  80

Ile Val Met Leu Ala Glu Glu Ala Gln Trp Val His Ile Glu Gln Thr
                85                  90                  95

Met His Arg Leu Gln Thr Gln Ala Ala Arg Arg Gly Tyr Val Ile Lys
            100                 105                 110

Ile Gln His Ile Phe Tyr Asp Phe Leu Pro Ala Phe Val Val Lys Met
        115                 120                 125

Ser Ser Asp Leu Leu Asp Leu Ala Leu Lys Leu Pro His Val Lys Tyr
    130                 135                 140

Ile Glu Glu Asp Ser Leu Val Phe Ala Gln Ser Ile Pro Trp Asn Leu
145                 150                 155                 160

Asp Arg Ile Ile Pro Ala Gly Arg Gln Ala Gln Glu Tyr Ser Ser Ser
                165                 170                 175

Arg Lys Val Pro Ser Gly Ser Gly Gln Val Glu Val Tyr Leu Leu Asp
            180                 185                 190
```

```
Thr Ser Ile Gln Ser Asp His Arg Glu Ile Glu Gly Arg Val Thr Val
        195                 200                 205

Thr Asp Phe Asn Ser Val Pro Glu Glu Asp Gly Thr Arg Phe His Arg
    210                 215                 220

Gln Ala Ser Lys Cys Asp Ser His Gly Thr His Leu Ala Gly Val Val
225                 230                 235                 240

Ser Gly Arg Asp Ala Gly Val Ala Lys Gly Thr Ile Leu His Gly Leu
                245                 250                 255

Arg Val Leu Asn Cys Gln Gly Lys Gly Ile Val Ser Gly Ile Leu Thr
            260                 265                 270

Gly Leu Glu Phe Ile Trp Lys Ser Gln Leu Met Gln Pro Ser Gly Pro
        275                 280                 285

Gln Val Val Leu Leu Pro Leu Ala Gly Arg Tyr Ser Arg Val Leu Asn
    290                 295                 300

Thr Ala Cys Gln His Leu Ala Arg Thr Gly Val Val Leu Val Ala Ala
305                 310                 315                 320

Ala Gly Asn Phe Arg Asp Asp Ala Cys Leu Tyr Ser Pro Ala Ser Ala
                325                 330                 335

Pro Glu Val Ile Thr Val Gly Ala Thr Asp Val Gln Asp Gln Pro Val
            340                 345                 350

Thr Leu Gly Thr Leu Gly Thr Asn Phe Gly Arg Cys Val Asp Leu Phe
        355                 360                 365

Ala Pro Gly Lys Asp Ile Ile Gly Ala Ser Ser Asp Cys Ser Ala Cys
    370                 375                 380

Phe Met Ser Gln Ser Gly Thr Ser Gln Ala Ala Ala His Val Ala Gly
385                 390                 395                 400

Ile Val Ala Met Met Leu Thr Leu Glu Pro Glu Leu Thr Leu Thr Glu
                405                 410                 415

Leu Arg Gln Arg Leu Ile His Phe Ser Thr Lys Asp Ala Ile Asn Met
            420                 425                 430

Ala Trp Phe Pro Glu Asp Gln Arg Val Leu Thr Pro Asn Leu Val Ala
        435                 440                 445

Thr Leu Pro Pro Ser Thr His Gly Thr Gly Gly Gln Leu Leu Cys Arg
    450                 455                 460

Thr Val Trp Ser Ala His Ser Gly Pro Thr Arg Ala Ala Thr Ala Thr
465                 470                 475                 480

Ala Arg Cys Ala Pro Gly Glu Glu Leu Leu Ser Cys Ser Ser Phe Ser
                485                 490                 495

Arg Ser Gly Arg Arg Arg Gly Asp Arg Ile Glu Ala Ala Gly Thr Gln
            500                 505                 510

Gln Val Cys Lys Ala Leu Asn Ala Phe Gly Gly Glu Gly Val Tyr Ala
        515                 520                 525

Val Ala Arg Cys Cys Leu Leu Pro Arg Ala Asn Cys Ser Ile His Thr
    530                 535                 540

Thr Pro Ala Ala Arg Thr Ser Leu Glu Thr His Ala His Cys His Gln
545                 550                 555                 560

Lys Asp His Val Leu Thr Gly Cys Ser Leu His Trp Glu Val Glu Gly
                565                 570                 575

Ile Gly Val Gln Pro Leu Ala Val Leu Arg Ser Arg His Gln Pro Gly
            580                 585                 590

Gln Cys Thr Gly His Arg Glu Ala Ser Val His Ala Ser Cys Cys His
        595                 600                 605
```

```
Ala Pro Gly Leu Glu Cys Lys Ile Lys Glu His Gly Ile Ser Gly Pro
    610                 615                 620

Ala Glu Gln Val Thr Val Ala Cys Glu Ala Gly Trp Thr Leu Thr Gly
625                 630                 635                 640

Cys Asn Val Leu Pro Gly Ala Phe Ile Thr Leu Gly Ala Tyr Ala Val
                645                 650                 655

Asp Asn Thr Cys Val Ala Arg Ser Arg Val Thr Asp Thr Ala Gly Arg
            660                 665                 670

Thr Gly Glu Glu Ala Thr Val Ala Ala Ala Ile Cys Cys Arg Asn Arg
        675                 680                 685

Pro Ser Ala Lys Ala Ser Trp Val His Gln
    690                 695


<210> SEQ ID NO 763
<211> LENGTH: 691
<212> TYPE: PRT
<213> ORGANISM: Rattus norvegicus

<400> SEQUENCE: 763

Met Gly Ile Arg Cys Ser Thr Trp Leu Arg Trp Pro Leu Ser Pro Gln
1               5                   10                  15

Leu Leu Leu Leu Leu Leu Leu Cys Pro Thr Gly Ser Arg Ala Gln Asp
            20                  25                  30

Glu Asp Gly Asp Tyr Glu Glu Leu Met Leu Ala Leu Pro Ser Gln Glu
        35                  40                  45

Asp Ser Leu Val Asp Glu Ala Ser His Val Ala Thr Ala Thr Phe Arg
    50                  55                  60

Arg Cys Ser Lys Glu Ala Trp Arg Leu Pro Gly Thr Tyr Val Val Val
65                  70                  75                  80

Leu Met Glu Glu Thr Gln Arg Leu Gln Val Glu Gln Thr Ala His Arg
                85                  90                  95

Leu Gln Thr Trp Ala Ala Arg Arg Gly Tyr Val Ile Lys Val Leu His
            100                 105                 110

Val Phe Tyr Asp Leu Phe Pro Gly Phe Leu Val Lys Met Ser Ser Asp
        115                 120                 125

Leu Leu Gly Leu Ala Leu Lys Leu Pro His Val Glu Tyr Ile Glu Glu
    130                 135                 140

Asp Ser Leu Val Phe Ala Gln Ser Ile Pro Trp Asn Leu Glu Arg Ile
145                 150                 155                 160

Ile Pro Ala Trp Gln Gln Thr Glu Glu Asp Ser Ser Pro Asp Gly Ser
                165                 170                 175

Ser Gln Val Glu Val Tyr Leu Leu Asp Thr Ser Ile Gln Ser Gly His
            180                 185                 190

Arg Glu Ile Glu Gly Arg Val Thr Ile Thr Asp Phe Asn Ser Val Pro
        195                 200                 205

Glu Glu Asp Gly Thr Arg Phe His Arg Gln Ala Ser Lys Cys Asp Ser
    210                 215                 220

His Gly Thr His Leu Ala Gly Val Val Ser Gly Arg Asp Ala Gly Val
225                 230                 235                 240

Ala Lys Gly Thr Ser Leu His Ser Leu Arg Val Leu Asn Cys Gln Gly
                245                 250                 255

Lys Gly Thr Val Ser Gly Thr Leu Ile Gly Leu Glu Phe Ile Arg Lys
            260                 265                 270

Ser Gln Leu Ile Gln Pro Ser Gly Pro Leu Val Val Leu Leu Pro Leu
        275                 280                 285
```

```
Ala Gly Gly Tyr Ser Arg Ile Leu Asn Thr Ala Cys Gln Arg Leu Ala
    290                 295                 300

Arg Thr Gly Val Val Leu Val Ala Ala Ala Gly Asn Phe Arg Asp Asp
305                 310                 315                 320

Ala Cys Leu Tyr Ser Pro Ala Ser Ala Pro Glu Val Ile Thr Val Gly
                325                 330                 335

Ala Thr Asn Ala Gln Asp Gln Pro Val Thr Leu Gly Thr Leu Gly Thr
            340                 345                 350

Asn Phe Gly Arg Cys Val Asp Leu Phe Ala Pro Gly Lys Asp Ile Ile
        355                 360                 365

Gly Ala Ser Ser Asp Cys Ser Thr Cys Tyr Met Ser Gln Ser Gly Thr
    370                 375                 380

Ser Gln Ala Ala Ala His Val Ala Gly Ile Val Ala Met Met Leu Asn
385                 390                 395                 400

Arg Asp Pro Ala Leu Thr Leu Ala Glu Leu Arg Gln Arg Leu Ile Leu
                405                 410                 415

Phe Ser Thr Lys Asp Val Ile Asn Met Ala Trp Phe Pro Glu Asp Gln
            420                 425                 430

Arg Val Leu Thr Pro Asn Arg Val Ala Thr Leu Pro Pro Ser Thr Gln
        435                 440                 445

Glu Thr Gly Gly Gln Leu Leu Cys Arg Thr Val Trp Ser Ala His Ser
    450                 455                 460

Gly Pro Thr Arg Thr Ala Thr Ala Thr Ala Arg Cys Ala Pro Glu Glu
465                 470                 475                 480

Glu Leu Leu Ser Cys Ser Ser Phe Ser Arg Ser Gly Arg Arg Arg Gly
                485                 490                 495

Asp Arg Ile Glu Ala Ile Gly Gly Gln Gln Val Cys Lys Ala Leu Asn
            500                 505                 510

Ala Phe Gly Gly Glu Gly Val Tyr Ala Val Ala Arg Cys Cys Leu Leu
        515                 520                 525

Pro Arg Val Asn Cys Ser Ile His Asn Thr Pro Ala Ala Arg Ala Gly
    530                 535                 540

Pro Gln Thr Pro Val His Cys His Gln Lys Asp His Val Leu Thr Gly
545                 550                 555                 560

Cys Ser Phe His Trp Glu Val Glu Asn Leu Arg Ala Gln Gln Gln Pro
                565                 570                 575

Leu Leu Arg Ser Arg His Gln Pro Gly Gln Cys Val Gly His Gln Glu
            580                 585                 590

Ala Ser Val His Ala Ser Cys Cys His Ala Pro Gly Leu Glu Cys Lys
        595                 600                 605

Ile Lys Glu His Gly Ile Ala Gly Pro Ala Glu Gln Val Thr Val Ala
    610                 615                 620

Cys Glu Ala Gly Trp Thr Leu Thr Gly Cys Asn Val Leu Pro Gly Ala
625                 630                 635                 640

Ser Leu Pro Leu Gly Ala Tyr Ser Val Asp Asn Val Cys Val Ala Arg
                645                 650                 655

Ile Arg Asp Ala Gly Arg Ala Asp Arg Thr Ser Glu Glu Ala Thr Val
            660                 665                 670

Ala Ala Ala Ile Cys Cys Arg Ser Arg Pro Ser Ala Lys Ala Ser Trp
        675                 680                 685

Val His Gln
    690
```